(12) United States Patent
Lee et al.

(10) Patent No.: US 11,549,116 B2
(45) Date of Patent: *Jan. 10, 2023

(54) NUCLEIC ACID MOLECULES COMPRISING A VARIANT INC CODING STRAND

(71) Applicant: CJ CheilJedang Corporation, Seoul (KR)

(72) Inventors: Ji Sun Lee, Incheon (KR); Dong Eun Chang, Framingham, MA (US); Sang Jun Kim, Gyeonggi-do (KR); So Young Kim, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 599 days.

This patent is subject to a terminal disclaimer.

(21) Appl. No.: 16/534,132

(22) Filed: Aug. 7, 2019

(65) Prior Publication Data
US 2020/0048642 A1 Feb. 13, 2020

Related U.S. Application Data

(60) Provisional application No. 62/715,571, filed on Aug. 7, 2018.

(51) Int. Cl.
*C12N 15/70* (2006.01)

(52) U.S. Cl.
CPC .......... *C12N 15/70* (2013.01); *C12N 2830/42* (2013.01)

(58) Field of Classification Search
CPC .... C12N 15/70; C12N 2830/42; C12N 15/69; C12N 15/63; C12N 9/1247; C12N 2800/101; C12Y 207/07006
See application file for complete search history.

(56) References Cited

U.S. PATENT DOCUMENTS

2020/0048619 A1* 2/2020 Lee ........................ C12P 19/34

OTHER PUBLICATIONS

Adrio, et al., "Recombinant organisms for production of industrial products", Bioengineered Bugs, vol. 1, Issue 2, pp. 116-131, Mar./Apr. 2010.
Chamberlin, et al., "A Quantitative Assay for Bacterial RNA Polymerases", The Journal of Biological Chemistry, vol. 254, No. 20, pp. 10061-10069, Oct. 25, 1979.
Ederth, et al., "Origin-specific reduction of ColE1 plasmid copy number due to mutations in a distinct region of the *Escherichia coli* RNA polymerase", Mol Genet Genomics, vol. 267, pp. 587-592, Jun. 4, 2002, DOI 10.1007/s00438-002-0689-y.
Genbank, AP001918.1; *Escherichia coli* K-12 plasmid F DNA, complete sequence—Nucleotide—NCBI, pp. 1-57, Sep. 29, 2018.
Genbank, CP011496.1; *Escherichia coli* strain NCM3722 plasmid F, complete sequence—Nucleotide—NCBI, pp. 1-37, Sep. 2, 2015.
Genbank, CP018801.1; *Escherichia coli* strain tolC-chromosome, complete genome, p. 1, Jan. 3, 2017.
Kato, et al., "Evolution of the Replication Regions of Incla and IncFII Plasmids by Exchanging Their Replication Control Systems", DNA Research 1, vol. 1, No. 5, pp. 201-212, Sep. 12, 1994.
Lee, et al., "A Mutation of the RNA Polymerase β' Subunit (rpoC) Confers Cephalosporin Resistance in Bacillus subtilis", Antimicrobial Agents and Chemotherapy, vol. 57, No. 1, pp. 56-65, Jan. 2013.
Mukhopadhyay, et al., "The RNA Polymerase "Switch Region" Is a Target for Inhibitors", Cell, vol. 135, pp. 295-307, Oct. 17, 2008.
Pagotto, et al., "Multiple Origins and Replication Proteins Influence Biological Properties of β-Lactamase-Producing Plasmids from Neisseria gonorrhoeae", Journal of Bacteriology, vol. 183, No. 19, pp. 5472-5481, Oct. 2001, 0021-9193/01 DOI: 10.1128/JB.183.19.5472-5481.2001.
Petersen, et al., "A Missense Mutation in the ropC Gene Affects Chromosomal Replication Control in *Escherichia coli*", Journal of Bacteriology, vol. 173, No. 16, pp. 5200-5206, Aug. 1991, 0021-9193/165200-07.
Rand, et al., "Genome sequence and analysis of *Escherichia coli* production strain LS5218"; Metabolic Engineering Communications, vol. 5, pp. 78-83, 2017.
Saadi, et al., Nucleotide Sequence analysis of RepFIC, a Basic Replicon Present in IncFI Plasmids P307 and F, and Its Relation to the RepA Replicon of Inc FII Plasmids, Journal of Bacteriology, vol. 169, No. 5, pp. 1836-1846, May 1987, 0021-9193/051836-11.
Shintani, et al., "Genomics of microbial plasmids: classification and identification based on replication and transfer systems and host taxonomy", Frontiers in Microbiology, vol. 6, Article 242, pp. 1-16, Mar. 31, 2015.
Stead, et al., "RNAsnap™: a rapid, quantitative and inexpensive, method for isolating total RNA from bacteria", Nucleic Acids Research, vol. 40, No. 20, pp. 1-9, e156, Jul. 19, 2012, doi:10.1093/nar/gks680.

* cited by examiner

*Primary Examiner* — Iqbal H Chowdhury
(74) *Attorney, Agent, or Firm* — Seed IP Law Group LLP

(57) ABSTRACT

A nucleic acid molecule comprising a variant inc coding strand is disclosed as a regulator of plasmid copy number. Also disclosed is a replicon comprising the nucleic acid molecule, a promoter, and an origin of replication. Also disclosed is a vector comprising the replicon. Also disclosed is a recombinant microorganism comprising the vector.

25 Claims, 18 Drawing Sheets

Specification includes a Sequence Listing.

Multiple sequence alignment of DNA sequences of coding strands for *inc* RNAs

```
P307_RepFIC            ------ATAGCTGAATTGTTGGCTATACGGTTTAAGTGGACCCCGGTAATCTTCTCCTC 53
F_plasmid_RepFIC       ------ATAGCTGAATTGTTGGCTATACGGTTTAAGTGGATCCCGGTAATCTTCTCCTC 53
E._coli_strain_tolC    ------ATAGCTGAATTGTTGGCTATACGGTTTAAGTGGATCCCGGTAATCTTCTCCTC 53
E._coli_strain_K12     TCCCCGCATAGCTGAATTGTTGGCTATACGGTTTAAGTGGATCCCGGTAATCTTCTCCTC 60
E._coli_NCM3722        TCCCCGCATAGCTGAATTGTTGGCTATACGGTTTAAGTGGATCCCGGTAATCTTCTCCTC 60
                             ********************************* **************

P307_RepFIC            GTCGCCAAAACTAGATGAAGATTATCGGGTTTTTTTGCTT  91 (SEQ ID NO: 23, nt 8-98)
F_plasmid_RepFIC       GTCGCCAAAACTAGATGAAGATTATCGGGTTTTTTGCTT   91 (SEQ ID NO: 21, nt 8-98)
E._coli_strain_tolC    GTCGCCAAAACTAGATGAAGATTATCGGGTTTTTTGCTT   91 (SEQ ID NO: 21, nt 8-98)
E._coli_strain_K12     GTCGCCAAAACTAGATGAAGATTATCGGGTTTT------   93 (SEQ ID NO: 21, nt 1-93)
E._coli_NCM3722        GTCGCCAAAACTAGATGAAGATTATCGGGTTTTTTGCTT   98 (SEQ ID NO: 19)
                      ***** *********************************  ****
```

FIG. 1

Differences in DNA sequences of coding strands for *inc* RNAs

```
P307_RepFIC           ATAGCTGAATTGTTGGCTATACGGTTTAAGTGGACCCCGGTAATCTTCCTC 53
F_plasmid_RepFIC      -------------------------------------------------- 53
E._coli_strain_tolC   ----------------------------------T--------------- 53
E._coli_strain_K12    TCCCCGC---------------------------T--------------- 60
E._coli_NCM3722       TCCCCGC---------------------------T--------------- 60
Central_domain                                          CCCGGTAATCTTCTCCTC 18

P307_RepFIC           GTCGCCAAACTAGAGATGAAGAGATTATCGGGTTTTTTGCTT 91  (SEQ ID NO: 23, nt 8-98)
F_plasmid_RepFIC      ------C--------------------------G-----TGCTT 91  (SEQ ID NO: 21, nt 8-98)
E._coli_strain_tolC   ------C--------------------------G-----TGCTT 91  (SEQ ID NO: 21, nt 8-98)
E._coli_strain_K12    ------C--------------------------G-------    93  (SEQ ID NO: 21, nt 1-93)
E._coli_NCM3722       ------A--------------------------G-----TGCTT 98  (SEQ ID NO: 19)
Central_domain        GTCGC                                         23  (SEQ ID NO: 23, nt 43-65)
```

FIG. 2

Sequence alignment of DNA sequences of coding strands for
inc RNA of *Escherichia coli* strain NCM3722 and a variant *inc* RNA

```
E._coli_NCM3722   TCCCCGCATAGCTGAATTGTTGGCTATACGGTTTAAGTGGATCCCGGTAATCTTTCCTC 60
Variant           TCCCCGCATAGCTGAATTGTTGGCTATACGGTTTAAGTGGATCCCGGTAATCTTTCCTT 60
                  ********************************************************* *

E._coli_NCM3722   GTCGCAAAACTAGATGAAGATTATCGGGGTTTTTGCTT 98  (SEQ ID NO: 19)
Variant           GTCGCAAAACTAGATGAAGATTATCGGGGTTTTTGCTT 98  (SEQ ID NO: 17)
                  *************************************
```

FIG. 3

Differences in DNA sequences of coding strands for
*inc* RNA of *Escherichia coli* strain NCM3722 and a variant *inc* RNA

```
E._coli_NCM3722      TCCCCGCATAGCTGAATTGTTGGCTATACGGTTTAAGTGGATCCCGGTAATCTTTCCTC 60
Variant              ---------------------------------------------------------T 60
Var_Central-domain                                                     CCCGGTAATCTTTCCTT 18

E._coli_NCM3722      GTCGCAAAACTAGATGAAGATTATCGGGGTTTTTGCTT 98  (SEQ ID NO: 19)
Variant              ------------------------------------- 98  (SEQ ID NO: 17)
Var_Central-domain   GTCGC                                 23  (SEQ ID NO: 15)
```

FIG. 4

Multiple sequence alignment of an N-terminal domain of RpoC proteins

```
sp|Q8RQE8.1|RPOC_THET8   ---------------MKKEVRKVRIALASPEKIR-SWSYGEVKKPETINYRTLKPERDGLF  45
BAH99075.1               --MNELMKILGQTGQAMTFDQIKIQLASPEQIR-SWSYGEIKKPETINYRTFKPERDGLF  57
sp|Q5F5R6.1|RPOC_NEIG1   MNLLNLFNPLQTAGMEEEFDAIKIGIASPETIR-SWSYGEVKKPETINYRTFKPERDGLF  59
sp|Q5X865.1|RPOC_LEGPA   ---MSDLLGILKQQGQSEEFDAIKIALASPELIR-SWSYGEVKKPETINYRTFKPERDGLF  57
sp|Q9HWC9.1|RPOC_PSEAE   ---MKDLLNLLKNQGQIEEFDAIRIGLASPEMIR-SWSFGEVKKPETINYPTFKPERDGLF  57
sp|Q9KV29.1|RPOC_VIBCH   ---MKDLLNFLKAQHKTEEFDAIKIGLASPDMIR-SWSFGEVKKPETINYRTFKPERDGLF  57
sp|P0A8T7.1|RPOC_ECOLI   ---MKDLLKFLKAQTKTEEFDAIKIALASPDMIR-SWSFGEVKKPETINYRTFKPERDGLF  57
sp|P0A2R4.1|RPOC_SALTY   ---MKDLLKFLKAQTKTEEFDAIKIALASPDMIR-SWSFGEVKKPETINYRTFKPERDGLF  57
EDN79927.1               ---------------MLDAKTFDSLKITLATGDDIA-EWSHGEVKKPETINYRTLKPEKDGLF  47
sp|Q8CJT1.1|RPOC_STRCO   ---------------MLDVNFFDELRIGLATADDIR-QWSHGEVKKPETINYRTLKPEKDGLF  47
sp|Q6NJF6.1|RPOC_CORDI   ---------------MIDVNFFDELRIGLATADDIR-RWSKGEVKKPETINYRTLKPEKDGLF  47
sp|A5U053.1|RPOC_MYCTA   ---------------MLDVNFFDELRIGLATAEDIR-QWSYGEVKKPETINYRTLKPERDGLF  47
CBH49656.1               ---------------MLDVNFFDELRIGLATAEDIR-NWSYGEVKKPETINYRTLKPEKDGLF  47
sp|O84316.1|RPOC_CHLTR   --MFREGSRDDAALVKEGLEDKLEIGIASDVTIRDKWSCGEIKKPETINYPTFKPEKGGLF  59
sp|A7FZ76.1|RPOC_CLOB1   ---------------MFELNNFDALQIGLASPEKIR-EWSRGEVKKPETINYRTLKPERDGLF  47
sp|P37871.4|RPOC_BACSU   ---------------MLDVNNFEYMNIGLASPDKIR-SWSFGEVKKPETINYRTLKPEKDGLF  47
sp|Q97NQ8.1|RPOC_STRPN   ---------------MVDVNREKSMQITLASPSKVR-SWSYGEVKKPETINYRTLKPEREGLF  47
sp|Q82Z41.1|RPOC_ENTFA   ---------------MIDVNKFESMQIGLASPEKIR-SWSYGEVKKPETINYRTLKPEREGLF  47
sp|Q03PV0.1|RPOC_LACBA   ---------------MVDVNKFESMQIGLASPDKIR-SWSYGEVKKPETINYRTLKPEKDGLF  47
                                         :  :*:            ****:*:*********:****  ***
```

FIG. 7

Multiple sequence alignment of a central domain of RpoC proteins

```
sp|Q8RQE8.1|RPOC_THET8    APTLHRLGIQAFQPVLVEGQSIQLHPLVCEAFNADFDGDQMAVHVPLSSFAQEAERIQML 764
BAH99075.1                APTLHRLGIQAFEPVLVEGPILIEGKAIQLHPLVCTAFNADFDGDQMAVHVPLSLEAQLEARVLMM 486
sp|Q5F5R6.1|RPOC_NEIG1    APTLHRLGIQAFEPILIEGKAIQLHPLVCAAFNADFDGDQMAVHVPLSLEAQMEARTIML 487
sp|Q5X865.1|RPOC_LEGPA    APTLHRLGIQAFEPVLIEGKAIQLHPLVCTAYNADFDGDQMAVHVPLTLEAQLEARSLMM 485
sp|Q9HWC9.1|RPOC_PSEAE    APTLHRLGIQAFEPVLIEGKAIQLHPLVCAAYNADFDGDQMAVHVPLTTLEAQLEARALMM 485
sp|Q9KV29.1|RPOC_VIBCH    APTLHRLGIQAFEPVLIEGKAIQLHPLVCAAYNADFDGDQMAVHVPLTLEAQLEARTLMM 485
sp|P0A8T7.1|RPOC_ECOLI    APTLHRLGIQAFEPVLIEGKAIQLHPLVCAAYNADFDGDQMAVHVPLTLEAQLEARALMM 485
sp|P0A2R4.1|RPOC_SALTY    APTLHRLGIQAFEPVLIEGKAIQLHPLVCAAYNADFDGDQMAVHVPLTLEAQLEARALMM 485
EDN79927.1                APTLHRLGIQAFEPQLIEGKAIQLHPLACGAFNADFDGDQMAVHLPLGAEAQAEARIIML 560
sp|Q8CJT1.1|RPOC_STRCO    APTLHRLGIQAFEPQLVEGKAIQIHPLVCTAFNADFDGDQMAVHLPLSAEAQAEARIIML 560
sp|Q6NJF6.1|RPOC_CORDI    APTLHRLGIQAFEPKLVEGKAIQLHPLACEAFNADFDGDQMAVHLPLSAEAQAEARIIML 560
sp|A5U053.1|RPOC_MYCTA    APTLHRLGIQAFEPMLVEGKAIQLHPLVCEAFNADFDGDQMAVHLPLSAEAQAEARIIML 560
CBH49656.1                APTLHRLGIQAFEPQLVEGKAIQLHPLVCEAFNADFDGDQMAVHLPLSAEAQAEARIIML 560
sp|O84316.1|RPOC_CHLTR    APTLHRLGIQAFEPVLIEGKAIRVHPLVCAAFNADFDGDQMAVHPLSIEAQLEAKVLMM 488
sp|A7FZ76.1|RPOC_CLOB1    APTLHRLGIQAFQPVLVEGRAIKLHPLVPLSVEAQAEARFLML 475
sp|P37871.4|RPOC_BACSU    APTLHRLGIQAFEPTLVEGRAIRLHPLVCTAYNADFDGDQMAVHVPLSAEAQAEARIIML 474
sp|Q97NQ8.1|RPOC_STRPN    APTLHRLGIQAFEPVLIDGKALRLHPLVCEAYNADFDGDQMAIHVPLSEEAQAEARIIML 475
sp|Q8Z241.1|RPOC_ENTFA    APTLHRLGIQAFEPVLVEGRAIRLHPLVCEAYNADFDGDQMAVHVPLNEEAQAEARMLML 474
sp|Q03PV0.1|RPOC_LACBA    APTLHRLGIQAFEPVLVSGKAMRLHPLACEAYNADFDGDQMAIHVPLSDEAQAEARILML 475
                          ********:*    *:.:::;:***.*:  * :***.*****.**: *** ***:***
```

FIG. 8

Multiple sequence alignment of a C-terminal domain of RpoC proteins

```
sp|Q8RQE8.1|RPOC_THET8    MMKYVEVTDPGDSRLLEGQVLEKWDVEALNERLIAEGKTPVAWKPLLMGVTKSALSTKSW  1434
BAH99075.1                MLQKVEILEPGDTTYLIGETVDRIEFFAENAKCLKAGERPAQGMPVLQGITKASLSTDSF  1324
sp|Q5F5R6.1|RPOC_NEIG1    MLRVNIADAGETGFITGEQVERGDVMAANEKALEEGKEPARYENILLGITKASLSTDSF   1322
sp|Q5X865.1|RPOC_LEGPA    MLRKRVITFAGDSKFLVGEQVEESAMLQENDKLLAEGKQIARGTPILLGITKASLATESF  1312
sp|Q9HWC9.1|RPOC_PSEAE    MLRKVEVSESGDSSFIKGDQVELTQVLEENEQLGTEDKFPAKYERVLLGITKASLSTESF  1319
sp|Q9KV29.1|RPOC_VIBCH    MLRKCTITFAGDSEFLPGETVEYSQVKIANRKLVEEGKEPARFERELLGITKASLATESF  1318
sp|P0A8T7.1|RPOC_ECOLI    MLRKATIVNAGSSDFLEGEQVEYSRVKIANRELEANGKVGATYSRDLLGITKASLATESF  1319
sp|P0A2R4.1|RPOC_SALTY    MLRKATIESAGSSDFLEGEQVEYSRVKIANRELEANGKVGATFSRDLLGITKASLATESF  1319
EDN79927.1                MLRRVTILEPGDTTFMPGELVDRMAYLTQNRRVAAEGGQPASGRQMLGITKASLATDSW   1207
sp|Q8CJT1.1|RPOC_STRCO    MLRRVTIIESGDAELLPGELVERTKFETENRRVVQEGGHPASGRPQLMGITKASLATESW  1203
sp|Q6NJF6.1|RPOC_CORDI    MLRRGTVIESGSTEFLPGTLVDLSEAKAANAEAALANGGQPAELRSEIMGITKASLATESW  1242
sp|A5U053.1|RPOC_MYCTA    MLRRVTIIDSGSTEFLPGSLIDRAEFEAENRRVVAEGGEPAAGRPVLMGITKASLATDSW  1220
CBH49656.1                MLRRVTIIDSGSTEFLPGSLVERAEFEASNRRVVAEGGEPAAGRPVLMGITKASLATDSW  1221
sp|O84316.1|RPOC_CHLTR    MLQKVRITDPGDTTLLFGEDVDKKEFYEENRRTEEDGGKPAQAVPVLLGITKASLGTESF  1322
sp|A7FZ76.1|RPOC_CLOB1    MTRKIKIEDSGDTELLPGTMIDVFDFEEANRELLEKGGEPAVGRIALLGITKAALATDSF  1109
sp|P37871.4|RPOC_BACSU    MLRKVRVIDAGDTDVLPGTLLDIHQFTEANKKVLLEGNRPATGRPVLLGITKASLETDSF  1133
sp|Q97NQ8.1|RPOC_STRPN    MLRKVRVMDPGDTDLLMGTLMDINDFTDANKDVLIAGGVPATGRPVLMGITKASLETNSF  1135
sp|Q82241.1|RPOC_ENTFA    MLRKIRVMDPGDTEILPGTLMDIAEFKDRNYDTLVAGGVPATSRPVLLGITKASLETNSF  1134
sp|Q03PV0.1|RPOC_LACBA    MLRKVRIMDPGDTDVLPGTLMDIQDFFRRANYQTLIDGGIAATARPVLIGITKAALETNSF 1136
                          *  :    .  .      .  :.  .        .        .   : ** :;:* *:
```

FIG. 9A

Multiple sequence alignment of a C-terminal domain of RpoC proteins

```
sp|Q8RQE8.1|RPOC_THET8   LSAASFQNTTHVLTEAAIAGKKDELIGLKENVLLGRLIPAGTGSDFVRFTQVVDQKTLKA  1494
BAH99075.1               ISAASFQETTRVLTEAATAGKVDKLMGLKENVIVGRLIPAGTGSVMKRLRAIAAEQDRQR  1384
sp|Q5F5R6.1|RPOC_NEIG1   ISAASFQETTRVLTEAAIMGKQDELRGLKENVIVGRLIPAGTGLTYHRSRHQQWQGVEQE  1382
sp|Q5X865.1|RPOC_LEGPA   ISAASFQETTRVLTEAAVSGKVDELRGLKENVMVGRLIPAGTGYTYHQSRKAKRAPAAAG  1372
sp|Q9HWC9.1|RPOC_PSEAE   ISAASFQETTRVLTEAAVTGKRDFLRGLKENVVVGRLIPAGTGLAYHSERKQRDLGKPQ   1379
sp|Q9KV29.1|RPOC_VIBCH   ISAASFQETTRVLTEAAVSGKRDDLRGLKENVIVGRLIPAGTGFAYHQDRQAKRAQEQQG  1378
sp|P0A8T7.1|RPOC_ECOLI   ISAASFQETTRVLTEAAVAGKRDELRGLKENVIVGRLIPAGTGYAHQDRMRRRAAGEAP   1379
sp|P0A2R4.1|RPOC_SALTY   ISAASFQETTRVLTEAAVAGKRDELRGLKENVIVGRLIPAGTGYAHQDRMRRRAAGEQP   1379
EDN79927.1               ISAASFQETTKVLTEAAMNGKSDSLVGLKENVIIGKLIPAGTGLSRYNDVIVEPTAEAMA  1267
sp|Q8CJT1.1|RPOC_STRCO   LSAASFQETTRVLTDAAINAKSDSLIGLKENVIIGKLIPAGTGLSRYNIRVEPTEEAKA   1263
sp|Q6NJF6.1|RPOC_CORDI   ISAASFQETTRVLTDAAINKRSDKLIGLKENVIIGKLIPAGTGISRYRNISVKPTEAARN  1302
sp|A5U053.1|RPOC_MYCTA   ISAASFQETTRVLTDAAINCRSDKLNGLKENVIIGKLIPAGTGINRYRNIAVQPTEEARA  1280
CBH49656.1               ISAASFQETTRVLTDAAINCRSDKLIGLKENVIIGKLIPAGTGINRYRNIQVQPTEEARA  1281
sp|O84316.1|RPOC_CHLTR   ISAASFQDTTRVLTDAACSSKTDYLLGFKENVIMGHMIPGGTGFDTHKRIKQHLEKEQED  1382
sp|A7FZ76.1|RPOC_CLOB1   ISAASFQETTRVLTDAAIKGKIDPLLGLKENVIIGLKIIPAGTGMTRYRSIQINTDDENIE 1169
sp|P37871.4|RPOC_BACSU   ISAASFQETTRVLTDAAIKGKRDELLGLKENVIIGKLVPAGTGMKYRKVKPVSNVQPTD   1193
sp|Q97NQ8.1|RPOC_STRPN   ISAASFQETTRVLTDAAIRGKKDHLLGLKENVIGKIIPAGTGMARYRNLEPHAVNEEEY   1195
sp|Q82Z41.1|RPOC_ENTFA   ISAASFQETTRVLTDAAIRGKKDPLLGLKENVIIGKIIPAGTGMARYRNMEPKEVGV-AS  1193
sp|Q03PV0.1|RPOC_LACBA   LSAASFQETTRVLTDAAIRGKNDPLVGLKENVIIGKLIPAGTGMPDYRQIKPKEVGGTST  1196
                         :******:;**:******;;**  *  * *:*****;;**:;*::**.*:***
```

FIG. 9B

Sequence alignment of N-terminal domain of RpoC proteins of *Escherichia coli* and variant

```
sp|P0A8T7.1|RPOC_ECOLI    KPETINYRT 48
Variant                    KPETINYCT 48
                           ******* *
```

FIG. 10

Differences in N-terminal domain of RpoC proteins of *Escherichia coli* and variant

```
sp|P0A8T7.1|RPOC_ECOLI    KPETINYRT 48
Variant                   -------C- 48
```

FIG. 11

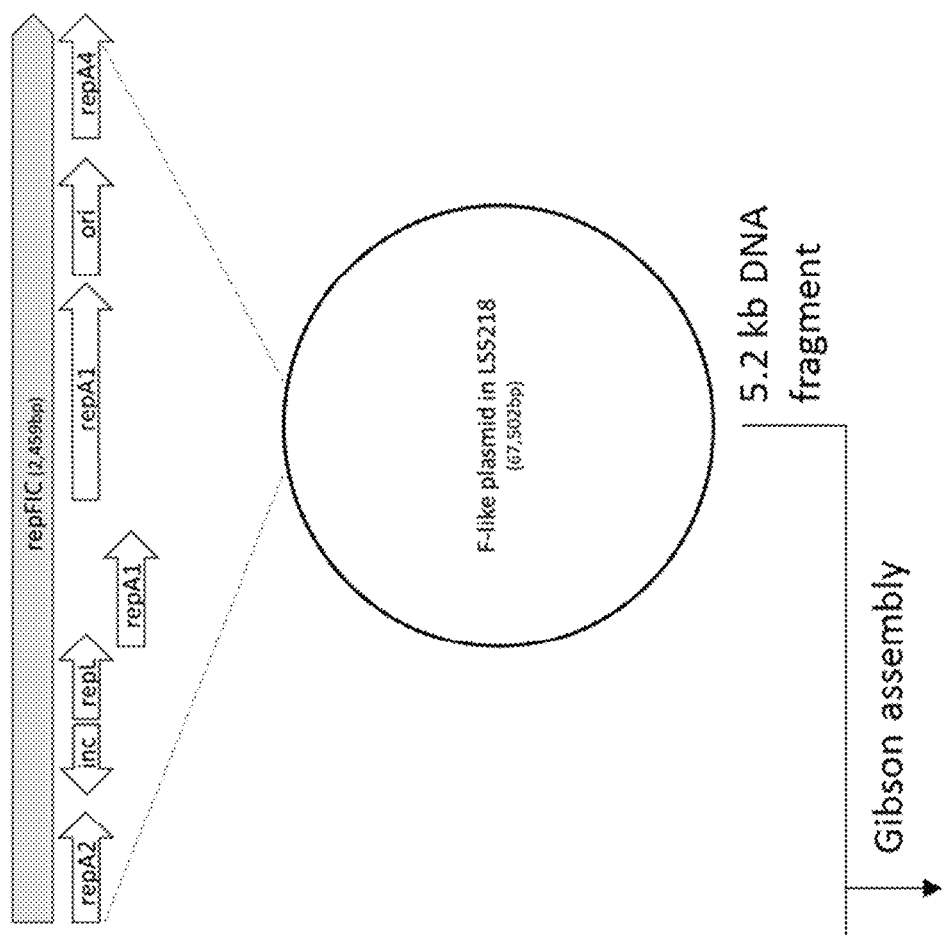
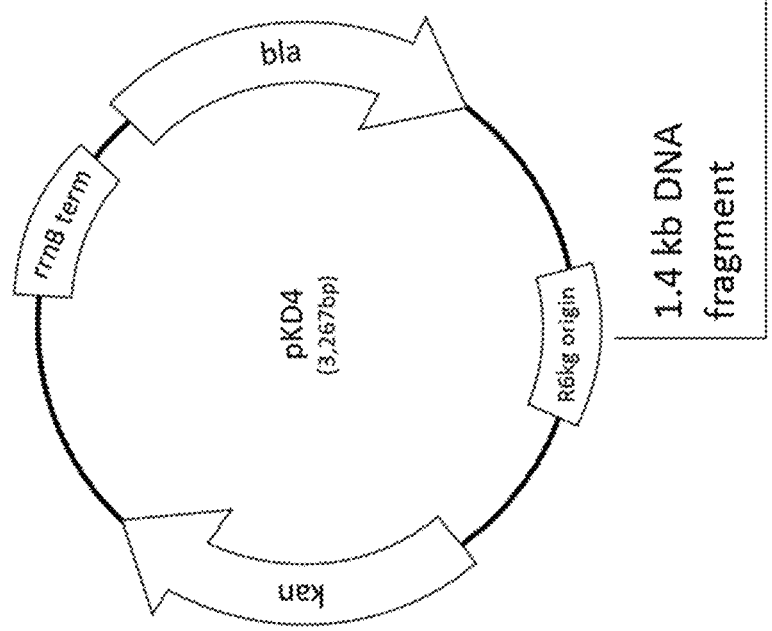
FIG. 13A

SEQUENCE LISTING

```
<160> NUMBER OF SEQ ID NOS: 69

<210> SEQ ID NO 1
<211> LENGTH: 2459
<212> TYPE: DNA
<213> ORGANISM: Escherichia coli

<400> SEQUENCE: 1
atgtcgcaga cagaaaatgc agtgacttcc tcatcaggta acaagcgtgc ataccggaaa        60
ggtaaccctg ttccggccag agagaggcaa agggcttctc tagctcgcag aagcaacact       120
cataaggctt ttcatgcggt tatccaggcc cggttaaaag acaggctgag tgaactggca       180
gatgaggaag gtattaccca ggcgcagatg cttgaaaaac tgattgaatc agagctgaaa       240
cgcagagcga ctttgtaaat attcacattc ttgcttatct caggcgtgag tgatagattg       300
ctgatcgttt aaggaatttt gtggctggcc acgccataag gtggcaggga actggttctg       360
atgtggattt acaggagcca gaaaagcaaa aaccccgata atcttcatct agttttgcga       420
```

```
cgaggagaag attaccggga tccacttaaa ccgtatagcc aacaattcag ctatgcgggg      480
agtatagtta tatgcccgga aaagttcaag acttctttct gtgctcactc cttctgtgca      540
ttgtaagtgc aggatggtgt ggctaatcat gaaacacatt cagtaatagc gggtgggatt      600
gaatcagatc ttcacattga ttccagcaag tatcctcacc cgttttgcag ccttctccag      660
aaaagggctc attttgactc cttcaagcat ctgatcttca tcagaggttt gcttgtaata      720
gcgcatggca aacgtaaaaa taaaatcagc gcgtcgatgg ttagttttta tgtttccctc      780
gtacaagtaa tgtgcgcaca ctacatccct gatacgaaca aagttaactt atctgttaaa      840
gagctttcag tttgtagtgg aggttcatac actcgtgttt ggagagccct caaaactctt      900
gataatgatc ttcatctcat cgcttttgat ggaggaacca tctggttcag accagatatg      960
ttcgaaactt tacgtgtcgg cccagacgag ctagttgccg cccgtaggag ggggaatagt     1020
gttggagggg gacatggctg atctccttca aaaatactat tcacaggtta aaacccgaa      1080 tccggtgttc acacccgtg aaggtgccgg aacgctgaag ttctgcgaaa aactgatgga      1140
aaaggcggtg ggcttcacct cccgttttga tttcgccatt catgtggcac atgctcgttc     1200
gaagggactg cgtcggcgca tgccaccggt actgcgtcgc cgggctattg atgcgctgct     1260
gcaggggctg tgttttcact atgacccgct ggccaaccgc gtccagtgct ccatcactac     1320
gctggccatt gagtgcggac tggcgacgga gtctgctgcc ggaaaactct ccatcacccg     1380
ggccacccga gccttgacgt tccttgcaga gctgggactg attacctacc agacggaata     1440
tgatccgctt atcgggtgct acattccgac cgatatcacg ttcacaccgg cgctatttgc     1500
cgcccttgat gtgtctgagg atgcagtggt tgctgcgcgc cgcagtcgtg ttgaatggga     1560
aaacagacag cgcaaaaagc agggactgga taccctgggt atggatgaac tgatagcgaa     1620
agcctggcgt tttgtgcgtg agcgtttccg cagttaccag acagagctta agtcccgtgg     1680
aataaagcgt gcccgtgcgc gtcgtgatgc gaacagggaa cgtcaggata tcgtcaccct     1740
ggtgaaacgg cagctgacgc gtgaaatctc ggaaggcgc ttcactgcca atcgtgaggc     1800
ggtaaaacgc gaagtggagc gtcgtgtgaa agatcgcatg attctgtcac gtaaccgtaa     1860
ttacagccgc ctggccacag cttccccctg aaagtgacct cctctgaata atccggcccg     1920
caccggaggc atctgcacgc ctgaagcctg tcggcgaaca aaaaaacagc accgcataca     1980
aaaaacaacc tcatcatcca ccttcaggtg catccggtcc ctcctgtttt tgatacaaaa     2040
cacgcctcac agacgaggaa ttttgcttat ccacatttaa ctgcaaggga cttccccata     2100
aggttacaac cgttcatgtc ataaagcgcc atccgccagc cttacagggt gcaatgtatc     2160
ttttaaacac ctgtttatat ctcctttaaa ctacttaact acattcattt aaaaagaaaa     2220
cctattcact gcctgtcctg tggacagaca ggtatgcacc tcccaccgca gcggcgggc      2280 cccgaccgga gccactttaa ttacaacact cagatacaac caccagaaaa accccggtcc     2340
cgcgcagaac tgaaaccaca aagccccccc tcataactga aaagcggccc cgccccggcc     2400
caaagggccg aacagagtc gcttttaatt atgaatgttg taactacaca gcatcatcg      2459
```

<210> SEQ ID NO 2
<211> LENGTH: 35
<212> TYPE: DNA
<213> ORGANISM: Artificial Sequence
<220> FEATURE:
<223> OTHER INFORMATION: Synthetic construct inc primer

<400> SEQUENCE: 2
ttccggaagt gtgaggcggc cgcacttgtg tataa                                35

<210> SEQ ID NO 3
<211> LENGTH: 35
<212> TYPE: DNA
<213> ORGANISM: Artificial Sequence
<220> FEATURE:
<223> OTHER INFORMATION: Synthetic construct inc primer

<400> SEQUENCE: 3
gtcgacaagc tttacgcggc cagatctgat caaga                          35

<210> SEQ ID NO 4
<211> LENGTH: 35
<212> TYPE: DNA
<213> ORGANISM: Artificial Sequence
<220> FEATURE:
<223> OTHER INFORMATION: Synthetic construct kanamycin primer

<400> SEQUENCE: 4
atcagatctg gccgcgtaaa gcttgtcgac gaatt                          35

<210> SEQ ID NO 5
<211> LENGTH: 35
<212> TYPE: DNA
<213> ORGANISM: Artificial Sequence
<220> FEATURE:
<223> OTHER INFORMATION: Synthetic construct kanamycin primer

<400> SEQUENCE: 5
cacaagtgcg gccgcctcac acttccggaa agcgg                          35

<210> SEQ ID NO 6
<211> LENGTH: 98
<212> TYPE: DNA
<213> ORGANISM: Artificial Sequence
<220> FEATURE:
<223> OTHER INFORMATION: Synthetic construct inc + copA including
      variation

<400> SEQUENCE: 6
aagcaaaaac cccgataatc ttcatctagt tttgcgacaa ggagaagatt accgggatcc    60
acttaaaccg tatagccaac aattcagcta tgcgggga                           98

<210> SEQ ID NO 7
<211> LENGTH: 20
<212> TYPE: DNA
<213> ORGANISM: Artificial Sequence
<220> FEATURE:
<223> OTHER INFORMATION: Synthetic construct variant primer

<400> SEQUENCE: 7
tcttctcctt gtcgcaaaac                                           20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct variant primer

<400> SEQUENCE: 8
gttttgcgac aaggagaaga                                           20

<210> SEQ ID NO 9
<211> LENGTH: 100

```
<212> TYPE: DNA
<213> ORGANISM: Artificial Sequence
<220> FEATURE:
<223> OTHER INFORMATION: Synthetic construct mini F plasmid primer

<400> SEQUENCE: 9
atctcaggcg tgagtgatag attgctgatc gtttaaggaa ttttgtgtaa cttcgtataa      60
tgtatgctat acgaagttat ggaataggaa cttcatttaa                           100

<210> SEQ ID NO 10
<211> LENGTH: 200
<212> TYPE: DNA
<213> ORGANISM: Artificial Sequence
<220> FEATURE:
<223> OTHER INFORMATION: Synthetic construct mini F plasmid primer

<400> SEQUENCE: 10
tgaattgttg gctatacggt ttaagtggat cccggtaatc ttctccttgt cgcaaaacta      60
gatgaagatt atcggggttt ttgcttttct ggctcctgta aatccacatc agaaccagtt    120
ccctgccacc ttatggcgtg gccagcataa cttcgtatag catacattat acgaagttat    180
ggcgcgccta cctgtgacgg                                                200

<210> SEQ ID NO 11
<211> LENGTH: 20
<212> TYPE: DNA
<213> ORGANISM: Artificial Sequence
<220> FEATURE:
<223> OTHER INFORMATION: Synthetic construct repFIC primer

<400> SEQUENCE: 11
cgggtgggat tgaatcagat                                                 20

<210> SEQ ID NO 12
<211> LENGTH: 21
<212> TYPE: DNA
<213> ORGANISM: Artificial Sequence
<220> FEATURE:
<223> OTHER INFORMATION: Synthetic construct repFIC primer

<400> SEQUENCE: 12
tacgtttgcc atgcgctatt a                                               21

<210> SEQ ID NO 13
<211> LENGTH: 20
<212> TYPE: DNA
<213> ORGANISM: Artificial Sequence
<220> FEATURE:
<223> OTHER INFORMATION: Synthetic construct LacZ primer

<400> SEQUENCE: 13
ccttactgcc gcctgttttg                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct LacZ primer

<400> SEQUENCE: 14
ccactggtgt gggccataat                                                 20

<210> SEQ ID NO 15
```

```
<211> LENGTH: 23
<212> TYPE: DNA
<213> ORGANISM: Artificial Sequence
<220> FEATURE:
<223> OTHER INFORMATION: Synthetic construct inc central domain coding
      strand with inc variant

<400> SEQUENCE: 15
cccggtaatc ttctccttgt cgc                                             23

<210> SEQ ID NO 16
<211> LENGTH: 23
<212> TYPE: DNA
<213> ORGANISM: Artificial Sequence
<220> FEATURE:
<223> OTHER INFORMATION: Synthetic construct inc central domain
      noncoding strand with inc variant

<400> SEQUENCE: 16
gcgacaagga agagattacc ggg                                             23

<210> SEQ ID NO 17
<211> LENGTH: 98
<212> TYPE: DNA
<213> ORGANISM: Artificial Sequence
<220> FEATURE:
<223> OTHER INFORMATION: Synthetic construct Escherichia coli NCM3722 F
      plasmid coding strand with inc variant

<400> SEQUENCE: 17
tccccgcata gctgaattgt tggctatacg gtttaagtgg atcccggtaa tcttctcctt     60
gtcgcaaaac tagatgaaga ttatcggggt ttttgctt                             98

<210> SEQ ID NO 18
<211> LENGTH: 98
<212> TYPE: DNA
<213> ORGANISM: Artificial Sequence
<220> FEATURE:
<223> OTHER INFORMATION: Synthetic construct Escherichia coli NCM3722 F
      plasmid noncoding strand with inc variant

<400> SEQUENCE: 18
aagcaaaaac cccgataatc ttcatctagt tttgcgacaa ggagaagatt accgggatcc     60
acttaaaccg tatagccaac aattcagcta tgcgggga                             98

<210> SEQ ID NO 19
<211> LENGTH: 98
<212> TYPE: DNA
<213> ORGANISM: Escherichia coli

<400> SEQUENCE: 19
tccccgcata gctgaattgt tggctatacg gtttaagtgg atcccggtaa tcttctcctc     60
gtcgcaaaac tagatgaaga ttatcggggt ttttgctt                             98

<210> SEQ ID NO 20
<211> LENGTH: 98
<212> TYPE: DNA
<213> ORGANISM: Escherichia coli

<400> SEQUENCE: 20
aagcaaaaac cccgataatc ttcatctagt tttgcgacga ggagaagatt accgggatcc     60
acttaaaccg tatagccaac aattcagcta tgcgggga                             98
```

```
<210> SEQ ID NO 21
<211> LENGTH: 98
<212> TYPE: DNA
<213> ORGANISM: Escherichia coli

<400> SEQUENCE: 21
tccccgcata gctgaattgt tggctatacg gtttaagtgg atcccggtaa tcttctcctc     60
gtcgccaaac tagatgaaga ttatcggggt ttttgctt                            98

<210> SEQ ID NO 22
<211> LENGTH: 98
<212> TYPE: DNA
<213> ORGANISM: Escherichia coli

<400> SEQUENCE: 22
aagcaaaaac cccgataatc ttcatctagt ttggcgacga ggagaagatt accgggatcc     60
acttaaaccg tatagccaac aattcagcta tgcgggga                            98

<210> SEQ ID NO 23
<211> LENGTH: 98
<212> TYPE: DNA
<213> ORGANISM: Escherichia coli

<400> SEQUENCE: 23
tccccgcata gctgaattgt tggctatacg gtttaagtgg accccggtaa tcttctcctc     60
gtcgccaaac tagatgaaga ttatcgggtt ttttgctt                            98

<210> SEQ ID NO 24
<211> LENGTH: 98
<212> TYPE: DNA
<213> ORGANISM: Escherichia coli

<400> SEQUENCE: 24
aagcaaaaaa cccgataatc ttcatctagt ttggcgacga ggagaagatt accggggtcc     60
acttaaaccg tatagccaac aattcagcta tgcgggga                            98

<210> SEQ ID NO 25
<211> LENGTH: 20
<212> TYPE: DNA
<213> ORGANISM: Artificial Sequence
<220> FEATURE:
<223> OTHER INFORMATION: Synthetic construct rrsH primer

<400> SEQUENCE: 25
gcataacgtc gcaagaccaa                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct rrsH primer

<400> SEQUENCE: 26
gtgagccgtt accccaccta                                                20

<210> SEQ ID NO 27
<211> LENGTH: 20
<212> TYPE: DNA
<213> ORGANISM: Artificial Sequence
<220> FEATURE:
<223> OTHER INFORMATION: Synthetic construct repFIA primer
```

<400> SEQUENCE: 27
atggctcagg catcgtctct                                       20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct repFIA primer

<400> SEQUENCE: 28
agaggcgcat tggagttctg                                       20

<210> SEQ ID NO 29
<211> LENGTH: 98
<212> TYPE: DNA
<213> ORGANISM: Artificial Sequence
<220> FEATURE:
<223> OTHER INFORMATION: Synthetic construct other Escherichia coli
      coding strand with inc variant

<400> SEQUENCE: 29
tccccgcata gctgaattgt tggctatacg gtttaagtgg atcccggtaa tcttctcctt    60
gtcgccaaac tagatgaaga ttatcggggt ttttgctt                            98

<210> SEQ ID NO 30
<211> LENGTH: 98
<212> TYPE: DNA
<213> ORGANISM: Artificial Sequence
<220> FEATURE:
<223> OTHER INFORMATION: Synthetic construct other Escherichia coli
      noncoding strand with inc variant

<400> SEQUENCE: 30
aagcaaaaac cccgataatc ttcatctagt ttggcgacaa ggagaagatt accgggatcc    60
acttaaaccg tatagccaac aattcagcta tgcgggga                            98

<210> SEQ ID NO 31
<211> LENGTH: 98
<212> TYPE: DNA
<213> ORGANISM: Artificial Sequence
<220> FEATURE:
<223> OTHER INFORMATION: Synthetic construct Escherichia coli P307
      plasmid coding strand with inc variant

<400> SEQUENCE: 31
tccccgcata gctgaattgt tggctatacg gtttaagtgg accccggtaa tcttctcctt    60
gtcgccaaac tagatgaaga ttatcgggtt ttttgctt                            98

<210> SEQ ID NO 32
<211> LENGTH: 98
<212> TYPE: DNA
<213> ORGANISM: Artificial Sequence
<220> FEATURE:
<223> OTHER INFORMATION: Synthetic construct Escherichia coli P307
      plasmid noncoding strand with inc variant

<400> SEQUENCE: 32
aagcaaaaaa cccgataatc ttcatctagt ttggcgacaa ggagaagatt accggggtcc    60
acttaaaccg tatagccaac aattcagcta tgcgggga                            98

<210> SEQ ID NO 33
<211> LENGTH: 4224

<212> TYPE: DNA
<213> ORGANISM: Artificial Sequence
<220> FEATURE:
<223> OTHER INFORMATION: Synthetic construct modified rpoC

<400> SEQUENCE: 33

```
gtgaaagatt tattaaagtt tctgaaagcg cagactaaaa ccgaagagtt tgatgcgatc      60
aaaattgctc tggcttcgcc agacatgatc cgttcatggt ctttcggtga agttaaaaag    120
ccggaaacca tcaactactg tacgttcaaa ccagaacgtg acggcctttt ctgcgcccgt    180
atctttgggc cggtaaaaga ttacgagtgc ctgtgcggta agtacaagcg cctgaaacac    240
cgtggcgtca tctgtgagaa gtgcggcgtt gaagtgaccc agactaaagt acgccgtgag    300
cgtatgggcc acatcgaact ggcttccccg actgcgcaca tctggttcct gaaatcgctg    360
ccgtcccgta tcggtctgct gctcgatatg ccgctgcgcg atatcgaacg cgtactgtac    420
tttgaatcct atgtggttat cgaaggcggt atgaccaacc tggaacgtca gcagatcctg    480
actgaagagc agtatctgga cgcgctggaa gagttcggtg acgaattcga cgcgaagatg    540
ggggcggaag caatccaggc tctgctgaag agcatggatc tggagcaaga gtgcgaacag    600
ctgcgtgaag agctgaacga aaccaactcc gaaaccaagc gtaaaaagct gaccaagcgt    660
atcaaactgc tggaagcgtt cgttcagtct ggtaacaaac cagagtggat gatcctgacc    720
gttctgccgg tactgccgcc agatctgcgt ccgctggttc cgctggatgg tggtcgtttc    780
gcgacttctg acctgaacga tctgtatcgt cgcgtcatta accgtaacaa ccgtctgaaa    840
cgtctgctgg atcggctgcg ccggacatc atcgtacgta acgaaaaacg tatgctgcag    900
gaagcggtag acgccctgct ggataacggt cgtcgcggtc gtgcgatcac cggttctaac    960
aagcgtcctc tgaaatcttt ggccgacatg atcaaaggta acagggtcg tttccgtcag   1020
aacctgctcg gtaagcgtgt tgactactcc ggtcgttctg taatcaccgt aggtccatac   1080
ctgcgtctgc atcagtgcgg tctgccgaag aaaatggcac tggagctgtt caaaccgttc   1140
atctacggca agctggaact gcgtggtctt gctaccacca ttaaagctgc gaagaaaatg   1200
gttgagcgcg aagaagctgt cgtttgggat atcctggacg aagttatccg gaacacccg   1260
gtactgctga accgtgcacc gactctgcac cgtctgggta tccaggcatt tgaaccggta   1320
ctgatcgaag gtaaagctat ccagctgcac ccgctggttt gtgcggcata taacgccgac   1380
ttcgatggtg accagatggc tgttcacgta ccgctgacgc tggaagccca gctggaagcg   1440
cgtgcgctga tgatgtctac caacaacatc ctgtccccgg cgaacggcga accaatcatc   1500
gttccgtctc aggacgttgt actgggtctg tactacatga cccgtgactg tgttaacgcc   1560
aaaggcgaag gcatggtgct gactggcccg aaagaagcag aacgtctgta tcgctctggt   1620
ctggcttctc tgcatgcgcg cgttaaagtg cgtatcaccg agtatgaaaa agatgctaac   1680
ggtgaattag tagcgaaaac cagcctgaaa gacacgactg ttggccgtgc cattctgtgg   1740
atgattgtac cgaaaggtct gccttactcc atcgtcaacc aggcgctggg taaaaaagca   1800
atctccaaaa tgctgaacac ctgctaccgc attctcggtc tgaaaccgac cgttattttt   1860
gcggaccaga tcatgtacac cggcttcgcc tatgcagcgc gttctggtgc atctgttggt   1920
atcgatgaca tggtcatccc ggagaagaaa cacgaaatca tctccgaggc agaagcagaa   1980
gttgctgaaa ttcaggagca gttccagtct ggtctggtaa ctgcgggcga acgctacaac   2040
aaagttatcg atatctgggc tgcggcgaac gatcgtgtat ccaaagcgat gatggataac   2100
ctgcaaactg aaaccgtgat taaccgtgac ggtcaggaag agaagcaggt ttccttcaac   2160
```

```
agcatctaca tgatggccga ctccggtgcg cgtggttctg cggcacagat tcgtcagctt   2220
gctggtatgc gtggtctgat ggcgaagccg atggctcca tcatcgaaac gccaatcacc   2280
gcgaacttcc gtgaaggtct gaacgtactc cagtacttca tctccaccca cggtgctcgt   2340
aaaggtctgg cggataccgc actgaaaact gcgaactccg gttacctgac tcgtcgtctg   2400
gttgacgtgg cgcaggacct ggtggttacc gaagacgatt gtggtaccca tgaaggtatc   2460
atgatgactc cggttatcga gggtggtgac gttaaagagc cgctgcgcga tcgcgtactg   2520
ggtcgtgtaa ctgctgaaga cgttctgaag ccgggtactg ctgatatcct cgttccgcgc   2580
aacacgctgc tgcacgaaca gtggtgtgac ctgctggaag agaactctgt cgacgcggtt   2640
aaagtacgtt ctgttgtatc ttgtgacacc gactttggtg tatgtgcgca ctgctacggt   2700
cgtgacctgg cgcgtggcca catcatcaac aaggtgaag caatcggtgt atcgcggca   2760 cagtccatcg gtgaaccggg tacacagctg accatgcgta cgttccacat cggtggtgcg   2820
gcatctcgtg cggctgctga atccagcatc caagtgaaaa acaaaggtag catcaagctc   2880
agcaacgtga agtcggttgt gaactccagc ggtaaactgg ttatcacttc ccgtaatact   2940
gaactgaaac tgatcgacga attcggtcgt actaaagaaa gctacaaagt accttacggt   3000
gcggtactgg cgaaaggcga tggcgaacag gttgctggcg cgaaaccgt tgcaaactgg   3060 gacccgcaca ccatgccggt tatcaccgaa gtaagcggtt ttgtacgctt tactgacatg   3120
atcgacggcc agaccattac gcgtcagacc gacgaactga ccggtctgtc ttcgctggtg   3180
gttctggatt ccgcagaacg taccgcaggt ggtaaagatc tgcgtccggc actgaaaatc   3240
gttgatgctc agggtaacga cgttctgatc ccaggtaccg atatgccagc gcagtacttc   3300
ctgccgggta aagcgattgt tcagctggaa gatggcgtac agatcagctc tggtgacacc   3360
ctggcgcgta ttccgcagga atccggcggt accaaggaca tcaccggtgg tctgccgcgc   3420
gttgcggacc tgttcgaagc acgtcgtccg aaagagccgg caatcctggc tgaaatcagc   3480
ggtatcgttt ccttcggtaa agaaaccaaa ggtaaacgtc gtctggttat cacccccggta   3540 gacggtagcg atccgtacga agagatgatt ccgaaatggc gtcagctcaa cgtgttcgaa   3600
ggtgaacgtg tagaacgtgg tgacgtaatt tccgacggtc cggaagcgcc gcacgacatt   3660
ctgcgtctgc gtggtgttca tgctgttact cgttacatcg ttaacgaagt acaggacgta   3720
taccgtctgc agggcgttaa gattaacgat aaacacatcg aagttatcgt tcgtcagatg   3780
ctgcgtaaag ctaccatcgt taacgcgggt agctccgact tcctggaagg cgaacaggtt   3840
gaatactctc gcgtcaagat cgcaaaccgc gaactgaag cgaacggcaa agtgggtgca   3900
acttactccc gcgatctgct gggtatcacc aaagcgtctc tggcaaccga gtccttcatc   3960
tccgcggcat cgttccagga gaccactcgc gtgctgaccg aagcagccgt tgcgggcaaa   4020
cgcgacgaac tgcgcggcct gaaagagaac gttatcgtgg gtcgtctgat cccggcaggt   4080
accggttacg cgtaccacca ggatcgtatg cgtcgccgtg ctgcgggtga agctccggct   4140
gcaccgcagg tgactgcaga agacgcatct gccagcctgg cagaactgct gaacgcaggt   4200
ctgggcggtt ctgataacga gtaa                                          4224
```

<210> SEQ ID NO 34
<211> LENGTH: 1407
<212> TYPE: PRT
<213> ORGANISM: Artificial Sequence
<220> FEATURE:
<223> OTHER INFORMATION: Synthetic construct modified RpoC

<400> SEQUENCE: 34

```
Val Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
            20                  25                  30

Trp Ser Phe Gly Glu Val Lys Lys Pro Glu Thr Ile Asn Tyr Cys Thr
        35                  40                  45

Phe Lys Pro Glu Arg Asp Gly Leu Phe Cys Ala Arg Ile Phe Gly Pro
    50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
            100                 105                 110

His Ile Trp Phe Leu Lys Ser Leu Pro Ser Arg Ile Gly Leu Leu Leu
        115                 120                 125

Asp Met Pro Leu Arg Asp Ile Glu Arg Val Leu Tyr Phe Glu Ser Tyr
    130                 135                 140

Val Val Ile Glu Gly Gly Met Thr Asn Leu Glu Arg Gln Gln Ile Leu
145                 150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
            180                 185                 190

Asp Leu Glu Gln Glu Cys Glu Gln Leu Arg Glu Glu Leu Asn Glu Thr
        195                 200                 205

Asn Ser Glu Thr Lys Arg Lys Lys Leu Thr Lys Arg Ile Lys Leu Leu
    210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Asp Leu Ala Ala Pro
        275                 280                 285

Asp Ile Ile Val Arg Asn Glu Lys Arg Met Leu Gln Glu Ala Val Asp
    290                 295                 300

Ala Leu Leu Asp Asn Gly Arg Arg Gly Arg Ala Ile Thr Gly Ser Asn
305                 310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
            340                 345                 350

Ser Val Ile Thr Val Gly Pro Tyr Leu Arg Leu His Gln Cys Gly Leu
        355                 360                 365

Pro Lys Lys Met Ala Leu Glu Leu Phe Lys Pro Phe Ile Tyr Gly Lys
    370                 375                 380

Leu Glu Leu Arg Gly Leu Ala Thr Thr Ile Lys Ala Ala Lys Lys Met
385                 390                 395                 400

Val Glu Arg Glu Glu Ala Val Val Trp Asp Ile Leu Asp Glu Val Ile
                405                 410                 415
```

```
Arg Glu His Pro Val Leu Leu Asn Arg Ala Pro Thr Leu His Arg Leu
            420                 425                 430

Gly Ile Gln Ala Phe Glu Pro Val Leu Ile Glu Gly Lys Ala Ile Gln
        435                 440                 445

Leu His Pro Leu Val Cys Ala Ala Tyr Asn Ala Asp Phe Asp Gly Asp
    450                 455                 460

Gln Met Ala Val His Val Pro Leu Thr Leu Glu Ala Gln Leu Glu Ala
465                 470                 475                 480

Arg Ala Leu Met Met Ser Thr Asn Asn Ile Leu Ser Pro Ala Asn Gly
                485                 490                 495

Glu Pro Ile Ile Val Pro Ser Gln Asp Val Val Leu Gly Leu Tyr Tyr
            500                 505                 510

Met Thr Arg Asp Cys Val Asn Ala Lys Gly Glu Gly Met Val Leu Thr
        515                 520                 525

Gly Pro Lys Glu Ala Glu Arg Leu Tyr Arg Ser Gly Leu Ala Ser Leu
    530                 535                 540

His Ala Arg Val Lys Val Arg Ile Thr Glu Tyr Glu Lys Asp Ala Asn
545                 550                 555                 560

Gly Glu Leu Val Ala Lys Thr Ser Leu Lys Asp Thr Thr Val Gly Arg
                565                 570                 575

Ala Ile Leu Trp Met Ile Val Pro Lys Gly Leu Pro Tyr Ser Ile Val
            580                 585                 590

Asn Gln Ala Leu Gly Lys Lys Ala Ile Ser Lys Met Leu Asn Thr Cys
        595                 600                 605

Tyr Arg Ile Leu Gly Leu Lys Pro Thr Val Ile Phe Ala Asp Gln Ile
    610                 615                 620

Met Tyr Thr Gly Phe Ala Tyr Ala Ala Arg Ser Gly Ala Ser Val Gly
625                 630                 635                 640

Ile Asp Asp Met Val Ile Pro Glu Lys Lys His Glu Ile Ile Ser Glu
                645                 650                 655

Ala Glu Ala Glu Val Ala Glu Ile Gln Glu Gln Phe Gln Ser Gly Leu
            660                 665                 670

Val Thr Ala Gly Glu Arg Tyr Asn Lys Val Ile Asp Ile Trp Ala Ala
        675                 680                 685

Ala Asn Asp Arg Val Ser Lys Ala Met Met Asp Asn Leu Gln Thr Glu
    690                 695                 700

Thr Val Ile Asn Arg Asp Gly Gln Glu Glu Lys Gln Val Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
        755                 760                 765

Val Leu Gln Tyr Phe Ile Ser Thr His Gly Ala Arg Lys Gly Leu Ala
    770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Asp Cys Gly Thr
                805                 810                 815

His Glu Gly Ile Met Met Thr Pro Val Ile Glu Gly Gly Asp Val Lys
            820                 825                 830

Glu Pro Leu Arg Asp Arg Val Leu Gly Arg Val Thr Ala Glu Asp Val
```

-continued

```
            835                 840                 845
Leu Lys Pro Gly Thr Ala Asp Ile Leu Val Pro Arg Asn Thr Leu Leu
    850                 855                 860

His Glu Gln Trp Cys Asp Leu Leu Glu Glu Asn Ser Val Asp Ala Val
865                 870                 875                 880

Lys Val Arg Ser Val Ser Cys Asp Thr Asp Phe Gly Val Cys Ala
                885                 890                 895

His Cys Tyr Gly Arg Asp Leu Ala Arg Gly His Ile Ile Asn Lys Gly
                900                 905                 910

Glu Ala Ile Gly Val Ile Ala Ala Gln Ser Ile Gly Glu Pro Gly Thr
                915                 920                 925

Gln Leu Thr Met Arg Thr Phe His Ile Gly Gly Ala Ala Ser Arg Ala
    930                 935                 940

Ala Ala Glu Ser Ser Ile Gln Val Lys Asn Lys Gly Ser Ile Lys Leu
945                 950                 955                 960

Ser Asn Val Lys Ser Val Val Asn Ser Ser Gly Lys Leu Val Ile Thr
                965                 970                 975

Ser Arg Asn Thr Glu Leu Lys Leu Ile Asp Glu Phe Gly Arg Thr Lys
                980                 985                 990

Glu Ser Tyr Lys Val Pro Tyr Gly Ala Val Leu Ala Lys Gly Asp Gly
                995                1000                1005

Glu Gln Val Ala Gly Gly Glu Thr Val Ala Asn Trp Asp Pro His
    1010                1015                1020

Thr Met Pro Val Ile Thr Glu Val Ser Gly Phe Val Arg Phe Thr
    1025                1030                1035

Asp Met Ile Asp Gly Gln Thr Ile Thr Arg Gln Thr Asp Glu Leu
    1040                1045                1050

Thr Gly Leu Ser Ser Leu Val Val Leu Asp Ser Ala Glu Arg Thr
    1055                1060                1065

Ala Gly Gly Lys Asp Leu Arg Pro Ala Leu Lys Ile Val Asp Ala
    1070                1075                1080

Gln Gly Asn Asp Val Leu Ile Pro Gly Thr Asp Met Pro Ala Gln
    1085                1090                1095

Tyr Phe Leu Pro Gly Lys Ala Ile Val Gln Leu Glu Asp Gly Val
    1100                1105                1110

Gln Ile Ser Ser Gly Asp Thr Leu Ala Arg Ile Pro Gln Glu Ser
    1115                1120                1125

Gly Gly Thr Lys Asp Ile Thr Gly Gly Leu Pro Arg Val Ala Asp
    1130                1135                1140

Leu Phe Glu Ala Arg Arg Pro Lys Glu Pro Ala Ile Leu Ala Glu
    1145                1150                1155

Ile Ser Gly Ile Val Ser Phe Gly Lys Glu Thr Lys Gly Lys Arg
    1160                1165                1170

Arg Leu Val Ile Thr Pro Val Asp Gly Ser Asp Pro Tyr Glu Glu
    1175                1180                1185

Met Ile Pro Lys Trp Arg Gln Leu Asn Val Phe Glu Gly Glu Arg
    1190                1195                1200

Val Glu Arg Gly Asp Val Ile Ser Asp Gly Pro Glu Ala Pro His
    1205                1210                1215

Asp Ile Leu Arg Leu Arg Gly Val His Ala Val Thr Arg Tyr Ile
    1220                1225                1230

Val Asn Glu Val Gln Asp Val Tyr Arg Leu Gln Gly Val Lys Ile
    1235                1240                1245
```

Asn Asp Lys His Ile Glu Val Ile Val Arg Gln Met Leu Arg Lys
1250                1255                1260

Ala Thr Ile Val Asn Ala Gly Ser Ser Asp Phe Leu Glu Gly Glu
1265                1270                1275

Gln Val Glu Tyr Ser Arg Val Lys Ile Ala Asn Arg Glu Leu Glu
1280                1285                1290

Ala Asn Gly Lys Val Gly Ala Thr Tyr Ser Arg Asp Leu Leu Gly
1295                1300                1305

Ile Thr Lys Ala Ser Leu Ala Thr Glu Ser Phe Ile Ser Ala Ala
1310                1315                1320

Ser Phe Gln Glu Thr Thr Arg Val Leu Thr Glu Ala Ala Val Ala
1325                1330                1335

Gly Lys Arg Asp Glu Leu Arg Gly Leu Lys Glu Asn Val Ile Val
1340                1345                1350

Gly Arg Leu Ile Pro Ala Gly Thr Gly Tyr Ala Tyr His Gln Asp
1355                1360                1365

Arg Met Arg Arg Ala Ala Gly Glu Ala Pro Ala Ala Pro Gln
1370                1375                1380

Val Thr Ala Glu Asp Ala Ser Ala Ser Leu Ala Glu Leu Leu Asn
1385                1390                1395

Ala Gly Leu Gly Gly Ser Asp Asn Glu
1400                1405

<210> SEQ ID NO 35
<211> LENGTH: 36
<212> TYPE: DNA
<213> ORGANISM: Artificial Sequence
<220> FEATURE:
<223> OTHER INFORMATION: Synthetic construct rpoC primer

<400> SEQUENCE: 35
ctgcaggaat tcgatcggtt cttacagcct ggttac        36

<210> SEQ ID NO 36
<211> LENGTH: 20
<212> TYPE: DNA
<213> ORGANISM: Artificial Sequence
<220> FEATURE:
<223> OTHER INFORMATION: Synthetic construct rpoC primer

<400> SEQUENCE: 36
gaacgtacag tagttgatgg        20

<210> SEQ ID NO 37
<211> LENGTH: 20
<212> TYPE: DNA
<213> ORGANISM: Artificial Sequence
<220> FEATURE:
<223> OTHER INFORMATION: Synthetic construct rpoC primer

<400> SEQUENCE: 37
ccatcaacta ctgtacgttc        20

<210> SEQ ID NO 38
<211> LENGTH: 36
<212> TYPE: DNA
<213> ORGANISM: Artificial Sequence
<220> FEATURE:
<223> OTHER INFORMATION: Synthetic construct rpoC primer

<400> SEQUENCE: 38

<210> SEQ ID NO 39
<211> LENGTH: 4224
<212> TYPE: DNA
<213> ORGANISM: Escherichia coli

<400> SEQUENCE: 39

```
gtcgactagc gtgatcttgg tttcggagtt ggtttc                              36
```

<210> SEQ ID NO 39
<211> LENGTH: 4224
<212> TYPE: DNA
<213> ORGANISM: Escherichia coli

<400> SEQUENCE: 39

```
gtgaaagatt tattaaagtt tctgaaagcg cagactaaaa ccgaagagtt tgatgcgatc      60
aaaattgctc tggcttcgcc agacatgatc cgttcatggt ctttcggtga agttaaaaag    120
ccggaaacca tcaactaccg tacgttcaaa ccagaacgtg acggcctttt ctgcgcccgt    180
atctttgggc cggtaaaaga ttacgagtgc ctgtgcggta agtacaagcg cctgaaacac    240
cgtggcgtca tctgtgagaa gtgcggcgtt gaagtgaccc agactaaagt acgccgtgag    300
cgtatgggcc acatcgaact ggcttccccg actgcgcaca tctggttcct gaaatcgctg    360
ccgtcccgta tcggtctgct gctcgatatg ccgctgcgcg atatcgaacg cgtactgtac    420
tttgaatcct atgtggttat cgaaggcggt atgaccaacc tggaacgtca gcagatcctg    480
actgaagagc agtatctgga cgcgctggaa gagttcggtg acgaattcga cgcgaagatg    540
ggggcggaag caatccaggc tctgctgaag agcatggatc tggagcaaga gtgcgaacag    600
ctgcgtgaag agctgaacga aaccaactcc gaaaccaagc gtaaaaagct gaccaagcgt    660
atcaaactgc tggaagcgtt cgttcagtct ggtaacaaac agagtggat gatcctgacc    720
gttctgccgg tactgccgcc agatctgcgt ccgctggttc cgctggatgg tggtcgtttc    780
gcgacttctg acctgaacga tctgtatcgt cgcgtcatta accgtaacaa ccgtctgaaa    840
cgtctgctgg atctggctgc gccggacatc atcgtacgta acgaaaaacg tatgctgcag    900
gaagcggtag acgccctgct ggataacggt cgtcgcggtc gtgcgatcac cggttctaac    960
aagcgtcctc tgaaatcttt ggccgacatg atcaaaggta acagggtcg tttccgtcag   1020
aacctgctcg gtaagcgtgt tgactactcc ggtcgttctg taatcaccgt aggtccatac   1080
ctgcgtctgc atcagtgcgg tctgccgaag aaaatggcac tggagctgtt caaaccgttc   1140
atctacggca agctggaact gcgtggtctt gctaccacca ttaaagctgc gaagaaaatg   1200
gttgagcgcg aagaagctgt cgtttgggat atcctggacg aagttatccg gaacacccg   1260
gtactgctga accgtgcacc gactctgcac cgtctgggta tccaggcatt tgaaccggta   1320
ctgatcgaag gtaaagctat ccagctgcac ccgctggttt gtgcggcata aacgccgac   1380
ttcgatggtg accagatggc tgttcacgta ccgctgacgc tggaagccca gctgaagcg   1440
cgtgcgctga tgatgtctac caacaacatc ctgtccccgg cgaacggcga accaatcatc   1500
gttccgtctc aggacgttgt actgggtctg tactacatga cccgtgactg tgttaacgcc   1560
aaaggcgaag gcatggtgct gactggcccg aaagaagcag aacgtctgta tcgctctggt   1620
ctggcttctc tgcatgcgcg cgttaaagtg cgtatcaccg agtatgaaaa agatgctaac   1680
ggtgaattag tagcgaaaac cagcctgaaa gacacgactg ttggccgtgc cattctgtgg   1740
atgattgtac cgaaaggtct gccttactcc atcgtcaacc aggcgctggg taaaaaagca   1800
atctccaaaa tgctgaacac ctgctaccgc attctcggtc tgaaaccgac cgttattttt   1860
gcggaccaga tcatgtacac cggcttcgcc tatgcagcgc gttctggtgc atctgttggt   1920
atcgatgaca tggtcatccc ggagaagaaa cacgaaatca tctccgaggc agaagcagaa   1980
gttgctgaaa ttcaggagca gttccagtct ggtctggtaa ctgcgggcga acgctacaac   2040
```

```
aaagttatcg atatctgggc tgcggcgaac gatcgtgtat ccaaagcgat gatggataac    2100
ctgcaaactg aaaccgtgat taaccgtgac ggtcaggaag agaagcaggt ttccttcaac    2160
agcatctaca tgatggccga ctccggtgcg cgtggttctg cggcacagat tcgtcagctt    2220
gctggtatgc gtggtctgat ggcgaagccg gatggctcca tcatcgaaac gccaatcacc    2280
gcgaacttcc gtgaaggtct gaacgtactc cagtacttca tctccaccca cggtgctcgt    2340
aaaggtctgg cggataccgc actgaaaact gcgaactccg gttacctgac tcgtcgtctg    2400
gttgacgtgg cgcaggacct ggtggttacc gaagacgatt gtggtaccca tgaaggtatc    2460
atgatgactc cggttatcga gggtggtgac gttaaagagc cgctgcgcga tcgcgtactg    2520
ggtcgtgtaa ctgctgaaga cgttctgaag ccgggtactg ctgatatcct cgttccgcgc    2580
aacacgctgc tgcacgaaca gtggtgtgac ctgctggaag agaactctgt cgacgcggtt    2640
aaagtacgtt ctgttgtatc ttgtgacacc gactttggtg tatgtgcgca ctgctacggt    2700
cgtgacctgg cgcgtggcca catcatcaac aagggtgaag caatcggtgt tatcgcggca    2760
cagtccatcg gtgaaccggg tacacagctg accatgcgta cgttccacat cggtggtgcg    2820
gcatctcgtg cggctgctga atccagcatc caagtgaaaa acaaaggtag catcaagctc    2880
agcaacgtga agtcggttgt gaactccagc ggtaaactgg ttatcacttc ccgtaatact    2940
gaactgaaac tgatcgacga attcggtcgt actaaagaaa gctacaaagt accttacggt    3000
gcggtactgg cgaaaggcga tggcgaacag gttgctggcg gcgaaaccgt tgcaaactgg    3060
gacccgcaca ccatgccggt tatcaccgaa gtaagcggtt ttgtacgctt tactgacatg    3120
atcgacggcc agaccattac gcgtcagacc gacgaactga ccgtctgtc ttcgctggtg    3180 gttctggatt ccgcagaacg taccgcaggt ggtaaagatc tgcgtccggc actgaaaatc    3240
gttgatgctc agggtaacga cgttctgatc ccaggtaccg atatgccagc gcagtacttc    3300
ctgccgggta aagcgattgt tcagctggaa gatggcgtac agatcagctc tggtgacacc    3360
ctggcgcgta ttccgcagga atccggcggt accaaggaca tcaccggtgg tctgccgcgc    3420
gttgcggacc tgttcgaagc acgtcgtccg aaagagccgg caatcctggc tgaaatcagc    3480
ggtatcgttt ccttcggtaa agaaaccaaa ggtaaacgtc gtctggttat caccccggta    3540
gacggtagcg atccgtacga agagatgatt ccgaaatggc gtcagctcaa cgtgttcgaa    3600
ggtgaacgtg tagaacgtgg tgacgtaatt tccgacggtc cggaagcgcc gcacgacatt    3660
ctgcgtctgc gtggtgttca tgctgttact cgttacatcg ttaacgaagt acaggacgta    3720
taccgtctgc agggcgttaa gattaacgat aaacacatcg aagttatcgt tcgtcagatg    3780
ctgcgtaaag ctaccatcgt taacgcgggt agctccgact tcctggaagg cgaacaggtt    3840
gaatactctc gcgtcaagat cgcaaaccgc gaactgaaag cgaacggcaa agtgggtgca    3900
acttactccc gcgatctgct gggtatcacc aaagcgtctc tggcaaccga gtccttcatc    3960
tccgcggcat cgttccagga gaccactcgc gtgctgaccg aagcagccgt tgcgggcaaa    4020
cgcgacgaac tgcgcggcct gaaagagaac gttatcgtgg gtcgtctgat cccggcaggt    4080
accggttacg cgtaccacca ggatcgtatg cgtcgccgtg ctgcgggtga agctccggct    4140
gcaccgcagg tgactgcaga agacgcatct gccagcctgg cagaactgct gaacgcaggt    4200
ctgggcggtt ctgataacga gtaa                                           4224

<210> SEQ ID NO 40
<211> LENGTH: 20
<212> TYPE: DNA
<213> ORGANISM: Artificial Sequence
```

```
<220> FEATURE:
<223> OTHER INFORMATION: Synthetic construct pJSL47 primer

<400> SEQUENCE: 40
gagcgtccgg taaccgttgg                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic construct pJSL47 primer

<400> SEQUENCE: 41
gtcaggatca tccactctgg                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic construct kanamycin primer

<400> SEQUENCE: 42
gcagccgatt gtctgttgtg                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct kanamycin primer

<400> SEQUENCE: 43
atggattgca cgcaggttct                                               20

<210> SEQ ID NO 44
<211> LENGTH: 1407
<212> TYPE: PRT
<213> ORGANISM: Escherichia coli

<400> SEQUENCE: 44
```

Met Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
                20                  25                  30

Trp Ser Phe Gly Glu Val Lys Lys Pro Glu Thr Ile Asn Tyr Arg Thr
            35                  40                  45

Phe Lys Pro Glu Arg Asp Gly Leu Phe Cys Ala Arg Ile Phe Gly Pro
        50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
                100                 105                 110

His Ile Trp Phe Leu Lys Ser Leu Pro Ser Arg Ile Gly Leu Leu Leu
            115                 120                 125

Asp Met Pro Leu Arg Asp Ile Glu Arg Val Leu Tyr Phe Glu Ser Tyr
        130                 135                 140

Val Val Ile Glu Gly Gly Met Thr Asn Leu Glu Arg Gln Gln Ile Leu

```
            145                 150                 155                 160
Thr Glu Glu Gln Tyr Leu Asp Ala Leu Glu Glu Phe Gly Asp Glu Phe
                    165                 170                 175

Asp Ala Lys Met Gly Ala Glu Ala Ile Gln Ala Leu Leu Lys Ser Met
                    180                 185                 190

Asp Leu Glu Gln Glu Cys Glu Gln Leu Arg Glu Glu Leu Asn Glu Thr
                    195                 200                 205

Asn Ser Glu Thr Lys Arg Lys Lys Leu Thr Lys Arg Ile Lys Leu Leu
            210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                    245                 250                 255

Gly Gly Arg Phe Ala Thr Ser Asp Leu Asn Asp Leu Tyr Arg Arg Val
                    260                 265                 270

Ile Asn Arg Asn Asn Arg Leu Lys Arg Leu Leu Asp Leu Ala Ala Pro
            275                 280                 285

Asp Ile Ile Val Arg Asn Glu Lys Arg Met Leu Gln Glu Ala Val Asp
            290                 295                 300

Ala Leu Leu Asp Asn Gly Arg Arg Gly Arg Ala Ile Thr Gly Ser Asn
305                 310                 315                 320

Lys Arg Pro Leu Lys Ser Leu Ala Asp Met Ile Lys Gly Lys Gln Gly
                    325                 330                 335

Arg Phe Arg Gln Asn Leu Leu Gly Lys Arg Val Asp Tyr Ser Gly Arg
                    340                 345                 350

Ser Val Ile Thr Val Gly Pro Tyr Leu Arg Leu His Gln Cys Gly Leu
            355                 360                 365

Pro Lys Lys Met Ala Leu Glu Leu Phe Lys Pro Phe Ile Tyr Gly Lys
            370                 375                 380

Leu Glu Leu Arg Gly Leu Ala Thr Thr Ile Lys Ala Ala Lys Lys Met
385                 390                 395                 400

Val Glu Arg Glu Glu Ala Val Val Trp Asp Ile Leu Asp Glu Val Ile
                    405                 410                 415

Arg Glu His Pro Val Leu Leu Asn Arg Ala Pro Thr Leu His Arg Leu
                    420                 425                 430

Gly Ile Gln Ala Phe Glu Pro Val Leu Ile Glu Gly Lys Ala Ile Gln
                    435                 440                 445

Leu His Pro Leu Val Cys Ala Ala Tyr Asn Ala Asp Phe Asp Gly Asp
            450                 455                 460

Gln Met Ala Val His Val Pro Leu Thr Leu Glu Ala Gln Leu Glu Ala
465                 470                 475                 480

Arg Ala Leu Met Met Ser Thr Asn Asn Ile Leu Ser Pro Ala Asn Gly
                    485                 490                 495

Glu Pro Ile Ile Val Pro Ser Gln Asp Val Val Leu Gly Leu Tyr Tyr
                    500                 505                 510

Met Thr Arg Asp Cys Val Asn Ala Lys Gly Glu Gly Met Val Leu Thr
                    515                 520                 525

Gly Pro Lys Glu Ala Glu Arg Leu Tyr Arg Ser Gly Leu Ala Ser Leu
            530                 535                 540

His Ala Arg Val Lys Val Arg Ile Thr Glu Tyr Glu Lys Asp Ala Asn
545                 550                 555                 560

Gly Glu Leu Val Ala Lys Thr Ser Leu Lys Asp Thr Thr Val Gly Arg
                    565                 570                 575
```

```
Ala Ile Leu Trp Met Ile Val Pro Lys Gly Leu Pro Tyr Ser Ile Val
            580                 585                 590

Asn Gln Ala Leu Gly Lys Lys Ala Ile Ser Lys Met Leu Asn Thr Cys
        595                 600                 605

Tyr Arg Ile Leu Gly Leu Lys Pro Thr Val Ile Phe Ala Asp Gln Ile
    610                 615                 620

Met Tyr Thr Gly Phe Ala Tyr Ala Ala Arg Ser Gly Ala Ser Val Gly
625                 630                 635                 640

Ile Asp Asp Met Val Ile Pro Glu Lys Lys His Glu Ile Ile Ser Glu
                645                 650                 655

Ala Glu Ala Glu Val Ala Glu Ile Gln Glu Gln Phe Gln Ser Gly Leu
            660                 665                 670

Val Thr Ala Gly Glu Arg Tyr Asn Lys Val Ile Asp Ile Trp Ala Ala
        675                 680                 685

Ala Asn Asp Arg Val Ser Lys Ala Met Met Asp Asn Leu Gln Thr Glu
    690                 695                 700

Thr Val Ile Asn Arg Asp Gly Gln Glu Glu Lys Gln Val Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
        755                 760                 765

Val Leu Gln Tyr Phe Ile Ser Thr His Gly Ala Arg Lys Gly Leu Ala
    770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Cys Gly Thr
                805                 810                 815

His Glu Gly Ile Met Met Thr Pro Val Ile Glu Gly Gly Asp Val Lys
            820                 825                 830

Glu Pro Leu Arg Asp Arg Val Leu Gly Arg Val Thr Ala Glu Asp Val
        835                 840                 845

Leu Lys Pro Gly Thr Ala Asp Ile Leu Val Pro Arg Asn Thr Leu Leu
    850                 855                 860

His Glu Gln Trp Cys Asp Leu Leu Glu Glu Asn Ser Val Asp Ala Val
865                 870                 875                 880

Lys Val Arg Ser Val Ser Cys Asp Thr Asp Phe Gly Val Cys Ala
                885                 890                 895

His Cys Tyr Gly Arg Asp Leu Ala Arg Gly His Ile Ile Asn Lys Gly
            900                 905                 910

Glu Ala Ile Gly Val Ile Ala Ala Gln Ser Ile Gly Glu Pro Gly Thr
        915                 920                 925

Gln Leu Thr Met Arg Thr Phe His Ile Gly Gly Ala Ala Ser Arg Ala
    930                 935                 940

Ala Ala Glu Ser Ser Ile Gln Val Lys Asn Lys Gly Ser Ile Lys Leu
945                 950                 955                 960

Ser Asn Val Lys Ser Val Asn Ser Ser Gly Lys Leu Val Ile Thr
                965                 970                 975

Ser Arg Asn Thr Glu Leu Lys Leu Ile Asp Glu Phe Gly Arg Thr Lys
            980                 985                 990
```

```
Glu Ser Tyr Lys Val Pro Tyr Gly Ala Val Leu Ala Lys Gly Asp Gly
            995                 1000                1005

Glu Gln Val Ala Gly Gly Glu Thr Val Ala Asn Trp Asp Pro His
    1010            1015                1020

Thr Met Pro Val Ile Thr Glu Val Ser Gly Phe Val Arg Phe Thr
    1025            1030                1035

Asp Met Ile Asp Gly Gln Thr Ile Thr Arg Gln Thr Asp Glu Leu
    1040            1045                1050

Thr Gly Leu Ser Ser Leu Val Leu Asp Ser Ala Glu Arg Thr
    1055            1060                1065

Ala Gly Gly Lys Asp Leu Arg Pro Ala Leu Lys Ile Val Asp Ala
    1070            1075                1080

Gln Gly Asn Asp Val Leu Ile Pro Gly Thr Asp Met Pro Ala Gln
    1085            1090                1095

Tyr Phe Leu Pro Gly Lys Ala Ile Val Gln Leu Glu Asp Gly Val
    1100            1105                1110

Gln Ile Ser Ser Gly Asp Thr Leu Ala Arg Ile Pro Gln Glu Ser
    1115            1120                1125

Gly Gly Thr Lys Asp Ile Thr Gly Gly Leu Pro Arg Val Ala Asp
    1130            1135                1140

Leu Phe Glu Ala Arg Arg Pro Lys Glu Pro Ala Ile Leu Ala Glu
    1145            1150                1155

Ile Ser Gly Ile Val Ser Phe Gly Lys Glu Thr Lys Gly Lys Arg
    1160            1165                1170

Arg Leu Val Ile Thr Pro Val Asp Gly Ser Asp Pro Tyr Glu Glu
    1175            1180                1185

Met Ile Pro Lys Trp Arg Gln Leu Asn Val Phe Glu Gly Glu Arg
    1190            1195                1200

Val Glu Arg Gly Asp Val Ile Ser Asp Gly Pro Glu Ala Pro His
    1205            1210                1215

Asp Ile Leu Arg Leu Arg Gly Val His Ala Val Thr Arg Tyr Ile
    1220            1225                1230

Val Asn Glu Val Gln Asp Val Tyr Arg Leu Gln Gly Val Lys Ile
    1235            1240                1245

Asn Asp Lys His Ile Glu Val Ile Val Arg Gln Met Leu Arg Lys
    1250            1255                1260

Ala Thr Ile Val Asn Ala Gly Ser Ser Asp Phe Leu Glu Gly Glu
    1265            1270                1275

Gln Val Glu Tyr Ser Arg Val Lys Ile Ala Asn Arg Glu Leu Glu
    1280            1285                1290

Ala Asn Gly Lys Val Gly Ala Thr Tyr Ser Arg Asp Leu Leu Gly
    1295            1300                1305

Ile Thr Lys Ala Ser Leu Ala Thr Glu Ser Phe Ile Ser Ala Ala
    1310            1315                1320

Ser Phe Gln Glu Thr Thr Arg Val Leu Thr Glu Ala Ala Val Ala
    1325            1330                1335

Gly Lys Arg Asp Glu Leu Arg Gly Leu Lys Glu Asn Val Ile Val
    1340            1345                1350

Gly Arg Leu Ile Pro Ala Gly Thr Gly Tyr Ala Tyr His Gln Asp
    1355            1360                1365

Arg Met Arg Arg Arg Ala Ala Gly Glu Ala Pro Ala Ala Pro Gln
    1370            1375                1380

Val Thr Ala Glu Asp Ala Ser Ala Ser Leu Ala Glu Leu Leu Asn
```

-continued

```
             1385                1390                1395
Ala Gly  Leu Gly Gly Ser  Asp  Asn Glu
    1400                 1405

<210> SEQ ID NO 45
<211> LENGTH: 1407
<212> TYPE: PRT
<213> ORGANISM: Artificial Sequence
<220> FEATURE:
<223> OTHER INFORMATION: Synthetic construct modified RpoC

<400> SEQUENCE: 45

Met Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
                20                  25                  30

Trp Ser Phe Gly Glu Val Lys Lys Pro Glu Thr Ile Asn Tyr Cys Thr
            35                  40                  45

Phe Lys Pro Glu Arg Asp Gly Leu Phe Cys Ala Arg Ile Phe Gly Pro
    50                  55                  60

Val Lys Asp Tyr Glu Cys Leu Cys Gly Lys Tyr Lys Arg Leu Lys His
65              70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
                100                 105                 110

His Ile Trp Phe Leu Lys Ser Leu Pro Ser Arg Ile Gly Leu Leu Leu
            115                 120                 125

Asp Met Pro Leu Arg Asp Ile Glu Arg Val Leu Tyr Phe Glu Ser Tyr
    130                 135                 140

Val Val Ile Glu Gly Gly Met Thr Asn Leu Glu Arg Gln Gln Ile Leu
145             150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
                180                 185                 190

Asp Leu Glu Gln Glu Cys Glu Gln Leu Arg Glu Glu Leu Asn Glu Thr
            195                 200                 205

Asn Ser Glu Thr Lys Arg Lys Lys Leu Thr Lys Arg Ile Lys Leu Leu
    210                 215                 220

Glu Ala Phe Val Gln Ser Gly Asn Lys Pro Glu Trp Met Ile Leu Thr
225             230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
                260                 265                 270

Ile Asn Arg Asn Asn Arg Leu Lys Arg Leu Leu Asp Leu Ala Ala Pro
            275                 280                 285

Asp Ile Ile Val Arg Asn Glu Lys Arg Met Leu Gln Glu Ala Val Asp
    290                 295                 300

Ala Leu Leu Asp Asn Gly Arg Arg Gly Arg Ala Ile Thr Gly Ser Asn
305             310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
```

-continued

```
            340                 345                 350
Ser Val Ile Thr Val Gly Pro Tyr Leu Arg Leu His Gln Cys Gly Leu
            355                 360                 365
Pro Lys Lys Met Ala Leu Glu Leu Phe Lys Pro Phe Ile Tyr Gly Lys
            370                 375                 380
Leu Glu Leu Arg Gly Leu Ala Thr Thr Ile Lys Ala Ala Lys Lys Met
385                 390                 395                 400
Val Glu Arg Glu Glu Ala Val Val Trp Asp Ile Leu Asp Val Ile
                    405                 410                 415
Arg Glu His Pro Val Leu Leu Asn Arg Ala Pro Thr Leu His Arg Leu
                420                 425                 430
Gly Ile Gln Ala Phe Glu Pro Val Leu Ile Glu Gly Lys Ala Ile Gln
            435                 440                 445
Leu His Pro Leu Val Cys Ala Ala Tyr Asn Ala Asp Phe Asp Gly Asp
            450                 455                 460
Gln Met Ala Val His Val Pro Leu Thr Leu Glu Ala Gln Leu Glu Ala
465                 470                 475                 480
Arg Ala Leu Met Met Ser Thr Asn Asn Ile Leu Ser Pro Ala Asn Gly
                    485                 490                 495
Glu Pro Ile Ile Val Pro Ser Gln Asp Val Val Leu Gly Leu Tyr Tyr
            500                 505                 510
Met Thr Arg Asp Cys Val Asn Ala Lys Gly Glu Gly Met Val Leu Thr
            515                 520                 525
Gly Pro Lys Glu Ala Glu Arg Leu Tyr Arg Ser Gly Leu Ala Ser Leu
            530                 535                 540
His Ala Arg Val Lys Val Arg Ile Thr Glu Tyr Glu Lys Asp Ala Asn
545                 550                 555                 560
Gly Glu Leu Val Ala Lys Thr Ser Leu Lys Asp Thr Thr Val Gly Arg
                    565                 570                 575
Ala Ile Leu Trp Met Ile Val Pro Lys Gly Leu Pro Tyr Ser Ile Val
                580                 585                 590
Asn Gln Ala Leu Gly Lys Lys Ala Ile Ser Lys Met Leu Asn Thr Cys
            595                 600                 605
Tyr Arg Ile Leu Gly Leu Lys Pro Thr Val Ile Phe Ala Asp Gln Ile
            610                 615                 620
Met Tyr Thr Gly Phe Ala Tyr Ala Ala Arg Ser Gly Ala Ser Val Gly
625                 630                 635                 640
Ile Asp Asp Met Val Ile Pro Glu Lys Lys His Glu Ile Ile Ser Glu
                    645                 650                 655
Ala Glu Ala Glu Val Ala Glu Ile Gln Glu Gln Phe Gln Ser Gly Leu
                660                 665                 670
Val Thr Ala Gly Glu Arg Tyr Asn Lys Val Ile Asp Ile Trp Ala Ala
            675                 680                 685
Ala Asn Asp Arg Val Ser Lys Ala Met Met Asp Asn Leu Gln Thr Glu
            690                 695                 700
Thr Val Ile Asn Arg Asp Gly Gln Glu Glu Lys Gln Val Ser Phe Asn
705                 710                 715                 720
Ser Ile Tyr Met Met Ala Asp Ser Gly Ala Arg Gly Ser Ala Ala Gln
                    725                 730                 735
Ile Arg Gln Leu Ala Gly Met Arg Gly Leu Met Ala Lys Pro Asp Gly
                740                 745                 750
Ser Ile Ile Glu Thr Pro Ile Thr Ala Asn Phe Arg Glu Gly Leu Asn
            755                 760                 765
```

Val Leu Gln Tyr Phe Ile Ser Thr His Gly Ala Arg Lys Gly Leu Ala
    770             775             780

Asp Thr Ala Leu Lys Thr Ala Asn Ser Gly Tyr Leu Thr Arg Arg Leu
785             790             795             800

Val Asp Val Ala Gln Asp Leu Val Thr Glu Asp Cys Gly Thr
                805             810             815

His Glu Gly Ile Met Met Thr Pro Val Ile Glu Gly Gly Asp Val Lys
            820             825             830

Glu Pro Leu Arg Asp Arg Val Leu Gly Arg Val Thr Ala Glu Asp Val
        835             840             845

Leu Lys Pro Gly Thr Ala Asp Ile Leu Val Pro Arg Asn Thr Leu Leu
    850             855             860

His Glu Gln Trp Cys Asp Leu Leu Glu Glu Asn Ser Val Asp Ala Val
865             870             875             880

Lys Val Arg Ser Val Ser Cys Asp Thr Asp Phe Gly Val Cys Ala
                885             890             895

His Cys Tyr Gly Arg Asp Leu Ala Arg Gly His Ile Ile Asn Lys Gly
            900             905             910

Glu Ala Ile Gly Val Ile Ala Ala Gln Ser Ile Gly Glu Pro Gly Thr
    915             920             925

Gln Leu Thr Met Arg Thr Phe His Ile Gly Gly Ala Ala Ser Arg Ala
    930             935             940

Ala Ala Glu Ser Ser Ile Gln Val Lys Asn Lys Gly Ser Ile Lys Leu
945             950             955             960

Ser Asn Val Lys Ser Val Asn Ser Ser Gly Lys Leu Val Ile Thr
            965             970             975

Ser Arg Asn Thr Glu Leu Lys Leu Ile Asp Glu Phe Gly Arg Thr Lys
        980             985             990

Glu Ser Tyr Lys Val Pro Tyr Gly Ala Val Leu Ala Lys Gly Asp Gly
        995             1000            1005

Glu Gln Val Ala Gly Gly Glu Thr Val Ala Asn Trp Asp Pro His
    1010            1015            1020

Thr Met Pro Val Ile Thr Glu Val Ser Gly Phe Val Arg Phe Thr
    1025            1030            1035

Asp Met Ile Asp Gly Gln Thr Ile Thr Arg Gln Thr Asp Glu Leu
    1040            1045            1050

Thr Gly Leu Ser Ser Leu Val Val Leu Asp Ser Ala Glu Arg Thr
    1055            1060            1065

Ala Gly Gly Lys Asp Leu Arg Pro Ala Leu Lys Ile Val Asp Ala
    1070            1075            1080

Gln Gly Asn Asp Val Leu Ile Pro Gly Thr Asp Met Pro Ala Gln
    1085            1090            1095

Tyr Phe Leu Pro Gly Lys Ala Ile Val Gln Leu Glu Asp Gly Val
    1100            1105            1110

Gln Ile Ser Ser Gly Asp Thr Leu Ala Arg Ile Pro Gln Glu Ser
    1115            1120            1125

Gly Gly Thr Lys Asp Ile Thr Gly Gly Leu Pro Arg Val Ala Asp
    1130            1135            1140

Leu Phe Glu Ala Arg Arg Pro Lys Glu Pro Ala Ile Leu Ala Glu
    1145            1150            1155

Ile Ser Gly Ile Val Ser Phe Gly Lys Glu Thr Lys Gly Lys Arg
    1160            1165            1170

Arg Leu Val Ile Thr Pro Val Asp Gly Ser Asp Pro Tyr Glu Glu
    1175                1180                1185

Met Ile Pro Lys Trp Arg Gln Leu Asn Val Phe Glu Gly Glu Arg
    1190                1195                1200

Val Glu Arg Gly Asp Val Ile Ser Asp Gly Pro Glu Ala Pro His
    1205                1210                1215

Asp Ile Leu Arg Leu Arg Gly Val His Ala Val Thr Arg Tyr Ile
    1220                1225                1230

Val Asn Glu Val Gln Asp Val Tyr Arg Leu Gln Gly Val Lys Ile
    1235                1240                1245

Asn Asp Lys His Ile Glu Val Ile Val Arg Gln Met Leu Arg Lys
    1250                1255                1260

Ala Thr Ile Val Asn Ala Gly Ser Ser Asp Phe Leu Glu Gly Glu
    1265                1270                1275

Gln Val Glu Tyr Ser Arg Val Lys Ile Ala Asn Arg Glu Leu Glu
    1280                1285                1290

Ala Asn Gly Lys Val Gly Ala Thr Tyr Ser Arg Asp Leu Leu Gly
    1295                1300                1305

Ile Thr Lys Ala Ser Leu Ala Thr Glu Ser Phe Ile Ser Ala Ala
    1310                1315                1320

Ser Phe Gln Glu Thr Thr Arg Val Leu Thr Glu Ala Ala Val Ala
    1325                1330                1335

Gly Lys Arg Asp Glu Leu Arg Gly Leu Lys Glu Asn Val Ile Val
    1340                1345                1350

Gly Arg Leu Ile Pro Ala Gly Thr Gly Tyr Ala Tyr His Gln Asp
    1355                1360                1365

Arg Met Arg Arg Arg Ala Ala Gly Glu Ala Pro Ala Ala Pro Gln
    1370                1375                1380

Val Thr Ala Glu Asp Ala Ser Ala Ser Leu Ala Glu Leu Leu Asn
    1385                1390                1395

Ala Gly Leu Gly Gly Ser Asp Asn Glu
    1400                1405

<210> SEQ ID NO 46
<211> LENGTH: 9
<212> TYPE: PRT
<213> ORGANISM: Artificial Sequence
<220> FEATURE:
<223> OTHER INFORMATION: Synthetic construct modified RpoC N terminal
      domain

<400> SEQUENCE: 46

Lys Pro Glu Thr Ile Asn Tyr Cys Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic construct modified RpoC central
      domain

<400> SEQUENCE: 47

Asn Ala Asp Phe Asp Gly Asp
1               5

<210> SEQ ID NO 48
<211> LENGTH: 6

```
<212> TYPE: PRT
<213> ORGANISM: Artificial Sequence
<220> FEATURE:
<223> OTHER INFORMATION: Synthetic construct modified RpoC C-terminal
      domain

<400> SEQUENCE: 48

Ser Ala Ala Ser Phe Gln
1               5

<210> SEQ ID NO 49
<211> LENGTH: 25
<212> TYPE: PRT
<213> ORGANISM: Artificial Sequence
<220> FEATURE:
<223> OTHER INFORMATION: Synthetic construct modified RpoC N terminal
      domain extended

<400> SEQUENCE: 49

Trp Ser Phe Gly Glu Val Lys Lys Pro Glu Thr Ile Asn Tyr Cys Thr
1               5                   10                  15

Phe Lys Pro Glu Arg Asp Gly Leu Phe
            20                  25

<210> SEQ ID NO 50
<211> LENGTH: 23
<212> TYPE: PRT
<213> ORGANISM: Artificial Sequence
<220> FEATURE:
<223> OTHER INFORMATION: Synthetic construct modified RpoC central
      domain extended

<400> SEQUENCE: 50

His Pro Leu Val Cys Ala Ala Tyr Asn Ala Asp Phe Asp Gly Asp Gln
1               5                   10                  15

Met Ala Val His Val Pro Leu
            20

<210> SEQ ID NO 51
<211> LENGTH: 55
<212> TYPE: PRT
<213> ORGANISM: Artificial Sequence
<220> FEATURE:
<223> OTHER INFORMATION: Synthetic construct modified RpoC C-terminal
      domain extended

<400> SEQUENCE: 51

Gly Ile Thr Lys Ala Ser Leu Ala Thr Glu Ser Phe Ile Ser Ala Ala
1               5                   10                  15

Ser Phe Gln Glu Thr Thr Arg Val Leu Thr Glu Ala Ala Val Ala Gly
            20                  25                  30

Lys Arg Asp Glu Leu Arg Gly Leu Lys Glu Asn Val Ile Val Gly Arg
        35                  40                  45

Leu Ile Pro Ala Gly Thr Gly
    50                  55

<210> SEQ ID NO 52
<211> LENGTH: 1524
<212> TYPE: PRT
<213> ORGANISM: Thermus thermophilus

<400> SEQUENCE: 52

Met Lys Lys Glu Val Arg Lys Val Arg Ile Ala Leu Ala Ser Pro Glu
1               5                   10                  15
```

```
Lys Ile Arg Ser Trp Ser Tyr Gly Glu Val Lys Pro Glu Thr Ile
            20                  25                  30
Asn Tyr Arg Thr Leu Lys Pro Glu Arg Asp Gly Leu Phe Asp Glu Arg
                35                  40                  45
Ile Phe Gly Pro Ile Lys Asp Tyr Glu Cys Ala Cys Gly Lys Tyr Lys
50                  55                  60
Arg Gln Arg Phe Glu Gly Lys Val Cys Glu Arg Cys Gly Val Glu Val
65                  70                  75                  80
Thr Lys Ser Ile Val Arg Arg Tyr Arg Met Gly His Ile Glu Leu Ala
                85                  90                  95
Thr Pro Ala Ala His Ile Trp Phe Val Lys Asp Val Pro Ser Lys Ile
                100                 105                 110
Gly Thr Leu Leu Asp Leu Ser Ala Thr Glu Leu Glu Gln Val Leu Tyr
            115                 120                 125
Phe Ser Lys Tyr Ile Val Leu Asp Pro Lys Gly Ala Ile Leu Asn Gly
        130                 135                 140
Val Pro Val Glu Lys Arg Gln Leu Leu Thr Asp Glu Glu Tyr Arg Glu
145                 150                 155                 160
Leu Arg Tyr Gly Lys Gln Glu Thr Tyr Pro Leu Pro Pro Gly Val Asp
                165                 170                 175
Ala Leu Val Lys Asp Gly Glu Val Val Lys Gly Gln Glu Leu Ala
                180                 185                 190
Pro Gly Val Val Ser Arg Leu Asp Gly Val Ala Leu Tyr Arg Phe Pro
            195                 200                 205
Arg Arg Val Arg Val Glu Tyr Val Lys Lys Glu Arg Ala Gly Leu Arg
        210                 215                 220
Leu Pro Leu Ala Ala Trp Val Glu Lys Glu Ala Tyr Lys Pro Gly Glu
225                 230                 235                 240
Ile Leu Ala Glu Leu Pro Glu Pro Tyr Leu Phe Arg Ala Glu Glu Glu
                245                 250                 255
Gly Val Val Glu Leu Lys Glu Leu Glu Glu Gly Ala Phe Leu Val Leu
            260                 265                 270
Arg Arg Glu Asp Glu Pro Val Ala Thr Tyr Phe Leu Pro Val Gly Met
        275                 280                 285
Thr Pro Leu Val Val His Gly Glu Ile Val Glu Lys Gly Gln Pro Leu
290                 295                 300
Ala Glu Ala Lys Gly Leu Leu Arg Met Pro Arg Gln Val Arg Ala Ala
305                 310                 315                 320
Gln Val Glu Ala Glu Glu Gly Glu Thr Val Tyr Leu Thr Leu Phe
                325                 330                 335
Leu Glu Trp Thr Glu Pro Lys Asp Tyr Arg Val Gln Pro His Met Asn
                340                 345                 350
Val Val Pro Glu Gly Ala Arg Val Glu Ala Gly Asp Lys Ile Val
            355                 360                 365
Ala Ala Ile Asp Pro Glu Glu Val Ile Ala Glu Gly Val
        370                 375                 380
Val His Leu His Glu Pro Ala Ser Ile Leu Val Lys Ala Arg Val
385                 390                 395                 400
Tyr Pro Phe Glu Asp Asp Val Glu Val Ser Thr Gly Asp Arg Val Ala
                405                 410                 415
Pro Gly Asp Val Leu Ala Asp Gly Gly Lys Val Lys Ser Asp Val Tyr
            420                 425                 430
Gly Arg Val Glu Val Asp Leu Val Arg Asn Val Val Arg Val Val Glu
```

```
              435                 440                 445
Ser Tyr Asp Ile Asp Ala Arg Met Gly Ala Glu Ala Ile Gln Gln Leu
450                 455                 460

Leu Lys Glu Leu Asp Leu Glu Ala Leu Glu Lys Glu Leu Leu Glu Glu
465                 470                 475                 480

Met Lys His Pro Ser Arg Ala Arg Arg Ala Lys Ala Arg Lys Arg Leu
                485                 490                 495

Glu Val Val Arg Ala Phe Leu Asp Ser Gly Asn Arg Pro Glu Trp Met
            500                 505                 510

Ile Leu Glu Ala Val Pro Val Leu Pro Pro Asp Leu Arg Pro Met Val
        515                 520                 525

Gln Val Asp Gly Gly Arg Phe Ala Thr Ser Asp Leu Asn Asp Leu Tyr
    530                 535                 540

Arg Arg Leu Ile Asn Arg Asn Asn Arg Leu Lys Lys Leu Leu Ala Gln
545                 550                 555                 560

Gly Ala Pro Glu Ile Ile Ile Arg Asn Glu Lys Arg Met Leu Gln Glu
                565                 570                 575

Ala Val Asp Ala Leu Leu Asp Asn Gly Arg Arg Gly Ala Pro Val Thr
            580                 585                 590

Asn Pro Gly Ser Asp Arg Pro Leu Arg Ser Leu Thr Asp Ile Leu Ser
        595                 600                 605

Gly Lys Gln Gly Arg Phe Arg Gln Asn Leu Leu Gly Lys Arg Val Asp
    610                 615                 620

Tyr Ser Gly Arg Ser Val Ile Val Gly Pro Gln Leu Lys Leu His
625                 630                 635                 640

Gln Cys Gly Leu Pro Lys Arg Met Ala Leu Glu Leu Phe Lys Pro Phe
                645                 650                 655

Leu Leu Lys Lys Met Glu Glu Lys Gly Ile Ala Pro Asn Val Lys Ala
            660                 665                 670

Ala Arg Arg Met Leu Glu Arg Gln Arg Asp Ile Lys Asp Glu Val Trp
        675                 680                 685

Asp Ala Leu Glu Glu Val Ile His Gly Lys Val Val Leu Leu Asn Arg
    690                 695                 700

Ala Pro Thr Leu His Arg Leu Gly Ile Gln Ala Phe Gln Pro Val Leu
705                 710                 715                 720

Val Glu Gly Gln Ser Ile Gln Leu His Pro Leu Val Cys Glu Ala Phe
                725                 730                 735

Asn Ala Asp Phe Asp Gly Asp Gln Met Ala Val His Val Pro Leu Ser
            740                 745                 750

Ser Phe Ala Gln Ala Glu Ala Arg Ile Gln Met Leu Ser Ala His Asn
        755                 760                 765

Leu Leu Ser Pro Ala Ser Gly Glu Pro Leu Ala Lys Pro Ser Arg Asp
    770                 775                 780

Ile Ile Leu Gly Leu Tyr Tyr Ile Thr Gln Val Arg Lys Glu Lys Lys
785                 790                 795                 800

Gly Ala Gly Leu Glu Phe Ala Thr Pro Glu Glu Ala Leu Ala Ala His
                805                 810                 815

Glu Arg Gly Glu Val Ala Leu Asn Ala Pro Ile Lys Val Ala Gly Arg
            820                 825                 830

Glu Thr Ser Val Gly Arg Leu Lys Tyr Val Phe Ala Asn Pro Asp Glu
        835                 840                 845

Ala Leu Leu Ala Val Ala His Gly Ile Val Asp Leu Gln Asp Val Val
    850                 855                 860
```

-continued

```
Thr Val Arg Tyr Met Gly Lys Arg Leu Glu Thr Ser Pro Gly Arg Ile
865                 870                 875                 880

Leu Phe Ala Arg Ile Val Ala Glu Ala Val Glu Asp Glu Lys Val Ala
            885                 890                 895

Trp Glu Leu Ile Gln Leu Asp Val Pro Gln Lys Asn Ser Leu Lys
        900                 905                 910

Asp Leu Val Tyr Gln Ala Phe Leu Arg Leu Gly Met Glu Lys Thr Ala
            915                 920                 925

Arg Leu Leu Asp Ala Leu Lys Tyr Tyr Gly Phe Thr Phe Ser Thr Thr
        930                 935                 940

Ser Gly Ile Thr Ile Gly Ile Asp Asp Ala Val Ile Pro Glu Glu Lys
945                 950                 955                 960

Lys Gln Tyr Leu Glu Glu Ala Asp Arg Lys Leu Leu Gln Ile Glu Gln
            965                 970                 975

Ala Tyr Glu Met Gly Phe Leu Thr Asp Arg Glu Arg Tyr Asp Gln Ile
                980                 985                 990

Leu Gln Leu Trp Thr Glu Thr Thr Glu Lys Val Thr Gln Ala Val Phe
        995                 1000                1005

Lys Asn Phe Glu Glu Asn Tyr Pro Phe Asn Pro Leu Tyr Val Met
    1010                1015                1020

Ala Gln Ser Gly Ala Arg Gly Asn Pro Gln Gln Ile Arg Gln Leu
    1025                1030                1035

Cys Gly Leu Arg Gly Leu Met Gln Lys Pro Ser Gly Glu Thr Phe
    1040                1045                1050

Glu Val Pro Val Arg Ser Ser Phe Arg Glu Gly Leu Thr Val Leu
    1055                1060                1065

Glu Tyr Phe Ile Ser Ser His Gly Ala Arg Lys Gly Gly Ala Asp
    1070                1075                1080

Thr Ala Leu Arg Thr Ala Asp Ser Gly Tyr Leu Thr Arg Lys Leu
    1085                1090                1095

Val Asp Val Thr His Glu Ile Val Val Arg Glu Ala Asp Cys Gly
    1100                1105                1110

Thr Thr Asn Tyr Ile Ser Val Pro Leu Phe Gln Pro Asp Glu Val
    1115                1120                1125

Thr Arg Ser Leu Arg Leu Arg Lys Arg Ala Asp Ile Glu Ala Gly
    1130                1135                1140

Leu Tyr Gly Arg Val Leu Ala Arg Glu Val Glu Val Leu Gly Val
    1145                1150                1155

Arg Leu Glu Glu Gly Arg Tyr Leu Ser Met Asp Asp Val His Leu
    1160                1165                1170

Leu Ile Lys Ala Ala Glu Ala Gly Glu Ile Gln Glu Val Pro Val
    1175                1180                1185

Arg Ser Pro Leu Thr Cys Gln Thr Arg Tyr Gly Val Cys Gln Lys
    1190                1195                1200

Cys Tyr Gly Tyr Asp Leu Ser Met Ala Arg Pro Val Ser Ile Gly
    1205                1210                1215

Glu Ala Val Gly Ile Val Ala Ala Gln Ser Ile Gly Glu Pro Gly
    1220                1225                1230

Thr Gln Leu Thr Met Arg Thr Phe His Thr Gly Gly Val Ala Gly
    1235                1240                1245

Ala Ala Asp Ile Thr Gln Gly Leu Pro Arg Val Ile Glu Leu Phe
    1250                1255                1260
```

-continued

```
Glu Ala Arg Arg Pro Lys Ala Lys Ala Val Ile Ser Glu Ile Asp
    1265                1270                1275

Gly Val Val Arg Ile Glu Glu Thr Glu Lys Leu Ser Val Phe
    1280                1285                1290

Val Glu Ser Glu Gly Phe Ser Lys Glu Tyr Lys Leu Pro Lys Glu
    1295                1300                1305

Ala Arg Leu Leu Val Lys Asp Gly Asp Tyr Val Glu Ala Gly Gln
    1310                1315                1320

Pro Leu Thr Arg Gly Ala Ile Asp Pro His Gln Leu Leu Glu Ala
    1325                1330                1335

Lys Gly Pro Glu Ala Val Glu Arg Tyr Leu Val Glu Glu Ile Gln
    1340                1345                1350

Lys Val Tyr Arg Ala Gln Gly Val Lys Leu His Asp Lys His Ile
    1355                1360                1365

Glu Ile Val Val Arg Gln Met Met Lys Tyr Val Glu Val Thr Asp
    1370                1375                1380

Pro Gly Asp Ser Arg Leu Leu Glu Gly Gln Val Leu Glu Lys Trp
    1385                1390                1395

Asp Val Glu Ala Leu Asn Glu Arg Leu Ile Ala Glu Gly Lys Thr
    1400                1405                1410

Pro Val Ala Trp Lys Pro Leu Leu Met Gly Val Thr Lys Ser Ala
    1415                1420                1425

Leu Ser Thr Lys Ser Trp Leu Ser Ala Ala Ser Phe Gln Asn Thr
    1430                1435                1440

Thr His Val Leu Thr Glu Ala Ala Ile Ala Gly Lys Lys Asp Glu
    1445                1450                1455

Leu Ile Gly Leu Lys Glu Asn Val Ile Leu Gly Arg Leu Ile Pro
    1460                1465                1470

Ala Gly Thr Gly Ser Asp Phe Val Arg Phe Thr Gln Val Val Asp
    1475                1480                1485

Gln Lys Thr Leu Lys Ala Ile Glu Glu Ala Arg Lys Glu Ala Val
    1490                1495                1500

Glu Ala Lys Glu Arg Pro Ala Ala Arg Arg Gly Val Lys Arg Glu
    1505                1510                1515

Gln Pro Gly Lys Gln Ala
    1520

<210> SEQ ID NO 53
<211> LENGTH: 1391
<212> TYPE: PRT
<213> ORGANISM: Acetobacter pasteurianus

<400> SEQUENCE: 53

Met Asn Glu Leu Met Lys Ile Leu Gly Gln Thr Gly Gln Ala Met Thr
1               5                   10                  15

Phe Asp Gln Ile Lys Ile Gln Leu Ala Ser Pro Glu Gln Ile Arg Ser
            20                  25                  30

Trp Ser Tyr Gly Glu Ile Lys Lys Pro Glu Thr Ile Asn Tyr Arg Thr
        35                  40                  45

Phe Lys Pro Glu Arg Asp Gly Leu Phe Cys Ala Arg Ile Phe Gly Pro
    50                  55                  60

Ile Lys Asp Tyr Glu Cys Leu Cys Gly Lys Tyr Lys Arg Met Lys Phe
65                  70                  75                  80

Arg Gly Ile Ile Cys Glu Lys Cys Gly Val Glu Val Thr Leu Ala Lys
                85                  90                  95
```

```
Val Arg Arg Glu Arg Met Gly His Ile Gln Leu Ala Ser Pro Val Ala
                100                 105                 110

His Ile Trp Phe Leu Lys Ser Leu Pro Ser Arg Ile Gly Leu Met Val
            115                 120                 125

Asp Met Thr Leu Lys Asp Leu Glu Lys Val Leu Tyr Phe Glu Ser Tyr
        130                 135                 140

Leu Val Leu Glu Pro Gly Thr Ser Pro Leu Lys Gln Tyr Ser Leu Leu
145                 150                 155                 160

Thr Glu Glu Gln Tyr Leu Asp Ala Met Asp Glu Tyr Gly Asp Glu Gly
                165                 170                 175

Val Glu Val Gly Ile Gly Ala Glu Ala Ile Lys Lys Val Leu Glu Arg
            180                 185                 190

Ile Asp Cys Asp Ala Glu Lys Val Glu Leu Arg Gln Glu Leu Lys Glu
        195                 200                 205

Thr Thr Ser Glu Ala Lys Arg Lys Lys Leu Val Lys Arg Leu Lys Leu
210                 215                 220

Ile Glu Ala Phe Ala Glu Ser Gly Ser Arg Pro Glu Trp Met Ile Leu
225                 230                 235                 240

Asp Leu Val Pro Val Ile Pro Pro Asp Leu Arg Pro Leu Val Pro Leu
                245                 250                 255

Asp Gly Gly Arg Phe Ala Thr Ser Asp Leu Asn Asp Leu Tyr Arg Arg
            260                 265                 270

Val Ile Asn Arg Asn Asn Arg Leu Lys Arg Leu Met Glu Leu Arg Ala
        275                 280                 285

Pro Asp Ile Ile Val Arg Asn Glu Lys Arg Met Leu Gln Glu Ala Val
        290                 295                 300

Asp Ala Leu Phe Asp Asn Gly Arg Arg Gly Arg Ala Ile Thr Gly Ala
305                 310                 315                 320

Asn Lys Arg Pro Leu Lys Ser Leu Ser Asp Met Leu Lys Gly Lys Gln
                325                 330                 335

Gly Arg Phe Arg Gln Asn Leu Leu Gly Lys Arg Val Asp Tyr Ser Gly
            340                 345                 350

Arg Ser Val Ile Val Val Gly Pro Glu Leu Lys Leu His Gln Cys Gly
        355                 360                 365

Leu Pro Lys Lys Met Ala Leu Glu Leu Phe Lys Pro Phe Ile Tyr Ala
    370                 375                 380

Lys Leu Glu Lys Tyr Gly His Ala Thr Thr Ile Lys Ala Ala Lys Arg
385                 390                 395                 400

Met Val Glu Lys Glu Arg Pro Glu Val Trp Asp Ile Leu Glu Glu Val
                405                 410                 415

Ile Arg Glu His Pro Val Met Leu Asn Arg Ala Pro Thr Leu His Arg
            420                 425                 430

Leu Gly Ile Gln Ala Phe Glu Pro Val Leu Glu Gly Lys Ala Ile
        435                 440                 445

Gln Leu His Pro Leu Val Cys Thr Ala Phe Asn Ala Asp Phe Asp Gly
        450                 455                 460

Asp Gln Met Ala Val His Val Pro Leu Ser Leu Glu Ala Gln Leu Glu
465                 470                 475                 480

Ala Arg Val Leu Met Met Ser Thr Asn Asn Ile Leu Ser Pro Ala Asn
                485                 490                 495

Gly Lys Pro Ile Ile Val Pro Ser Gln Asp Ile Val Leu Gly Leu Tyr
            500                 505                 510
```

```
Tyr Leu Ser Leu Glu Thr Pro Glu Phe Lys Val Thr Pro Asp Arg Cys
            515                 520                 525

Glu Tyr Asp Glu Thr Thr Gly Ala Leu Thr Lys Glu Gly Ala Pro Ser
        530                 535                 540

Phe Ser Ser Ile Gly Glu Val Glu Tyr Ala Leu Ser Ala Gly Ala Leu
545                 550                 555                 560

Lys Leu His Asp Lys Ile Arg Ala Arg Phe Gln Lys Ile Gly Ala Asp
                565                 570                 575

Gly Lys Val Thr Tyr Glu Thr Ala Val Thr Thr Pro Gly Arg Val Leu
            580                 585                 590

Ile Ala Gln Ile Leu Pro Gln His Glu Ala Val Pro Phe Ser Leu Ile
        595                 600                 605

Asn Arg Gln Leu Thr Lys Lys Ala Val Ser Asp Val Ile Asp Thr Val
610                 615                 620

Tyr Arg His Cys Gly Gln Lys Glu Ala Val Ile Phe Cys Asp Arg Leu
625                 630                 635                 640

Met Ala Leu Gly Phe Arg His Ala Ala Lys Ala Gly Ile Ser Phe Gly
                645                 650                 655

Lys Asp Asp Met Ile Ile Pro Pro Glu Lys Lys Glu Leu Val Asp Arg
            660                 665                 670

Thr Ala Ala Glu Val Lys Glu Phe Glu Gln Gln Tyr Gln Asp Gly Leu
        675                 680                 685

Ile Thr Ala Gly Glu Arg Tyr Asn Lys Val Val Asp Ala Trp Ser Arg
690                 695                 700

Cys Thr Asp Glu Val Gln Ala Ala Met Thr Lys Glu Ile Ser Arg Gln
705                 710                 715                 720

Glu Val Gly Lys Gln Ile Asn Ser Val Trp Met Met Ser His Ser Gly
                725                 730                 735

Ala Arg Gly Ser Pro Ala Gln Met Lys Gln Leu Ala Gly Met Arg Gly
            740                 745                 750

Leu Met Ala Lys Pro Ser Gly Glu Ile Ile Glu Gln Pro Ile Ile Ala
        755                 760                 765

Asn Phe Lys Glu Gly Leu Ser Val Leu Asp Tyr Phe Thr Ser Thr His
770                 775                 780

Gly Ala Arg Lys Gly Leu Ala Asp Thr Ala Leu Lys Thr Ala Asn Ser
785                 790                 795                 800

Gly Tyr Leu Thr Arg Arg Leu Val Asp Val Ala Gln Asp Ser Ile Ile
                805                 810                 815

Ile Glu Glu Asp Cys Gly Ser Glu Arg Gly Leu Thr Val Arg Ala Val
            820                 825                 830

Met Asp Gly Gly Glu Val Val Ala Ser Leu Ser Glu Arg Ile Leu Gly
        835                 840                 845

Arg Thr Val Ala Ser Asp Val Val Pro Gly Thr Gly Glu Val Ile
850                 855                 860

Val Pro Arg Asn His Leu Ile Asp Glu Ala Asp Ala Glu Arg Ile Glu
865                 870                 875                 880

Lys Ser Gly Val Glu Thr Val His Ile Arg Ser Val Leu Thr Cys Asp
                885                 890                 895

Ser Arg Val Gly Val Cys Gly Arg Cys Tyr Gly Arg Asp Leu Ala Arg
            900                 905                 910

Gly Thr Pro Val Asn Ile Gly Glu Ala Val Gly Val Ile Ala Ala Gln
        915                 920                 925

Ser Ile Gly Glu Pro Gly Thr Gln Leu Thr Met Arg Thr Phe His Ile
```

-continued

```
                930             935             940
Gly Gly Ala Ala Gln Arg Gly Ala Glu Gln Ser Met Ile Glu Ala Ser
945                 950             955                 960

Arg Asp Gly His Val Val Ile Arg Asn Arg Asn Val Val His Asn Ser
                965             970             975

Gln Asn Val Pro Ile Val Met Ala Arg Asn Cys Glu Ile Leu Leu Ser
            980             985             990

Asp Asp Asn Gly Val Glu Lys Ala Arg Tyr Arg Val Pro Tyr Gly Ala
        995             1000            1005

Arg Leu Leu Thr Glu Glu Gly Ala Lys Val Ala Arg Gly Gln Lys
    1010            1015            1020

Leu Ala Glu Trp Asp Pro Tyr Thr Leu Pro Ile Ile Thr Glu Lys
    1025            1030            1035

Ala Gly Lys Val Glu Tyr Leu Asp Leu Ile Asp Ser Ile Thr Leu
    1040            1045            1050

Val Glu Arg Met Asp Glu Val Thr Gly Leu Thr Ser Lys Val Val
    1055            1060            1065

Val Asp Tyr Lys Gln Ala Gly Lys Gly Val Asp Leu Arg Pro Arg
    1070            1075            1080

Leu Gln Leu Lys Asp Ala Asn Gly Asp Val Val Lys Leu Asp Asn
    1085            1090            1095

Gly Ala Asp Ala Arg Tyr Phe Leu Ser Pro Glu Thr Leu Leu Ser
    1100            1105            1110

Val Glu Asn Gly Thr Glu Val Asn Ala Gly Asp Val Leu Ala Arg
    1115            1120            1125

Leu Pro Arg Glu Gly Ser Lys Thr Arg Asp Ile Thr Gly Gly Leu
    1130            1135            1140

Pro Arg Val Ala Glu Leu Phe Glu Ala Arg Arg Pro Lys Asp His
    1145            1150            1155

Ala Ile Ile Ala Glu Met Glu Gly Arg Val Glu Phe Gly Lys Asp
    1160            1165            1170

Tyr Lys Ser Lys Arg Arg Val Ile Val Lys Asn Asp Glu Thr Gly
    1175            1180            1185

Glu Glu Gln Glu Tyr Leu Ile Pro Lys Gly Lys His Ile Ser Val
    1190            1195            1200

Gln Glu Gly Asp Phe Val Glu Lys Gly Asp Pro Leu Val Asp Gly
    1205            1210            1215

Pro Arg Val Pro His Asp Ile Leu Lys Val Met Gly Val Glu Ala
    1220            1225            1230

Leu Ser Asp Tyr Leu Ile Asn Glu Ile Gln Asp Val Tyr Arg Leu
    1235            1240            1245

Gln Gly Val Lys Ile Asn Asp Lys His Ile Glu Val Ile Val Arg
    1250            1255            1260

Gln Met Leu Gln Lys Val Glu Ile Leu Glu Pro Gly Asp Thr Thr
    1265            1270            1275

Tyr Leu Ile Gly Glu Thr Val Asp Arg Ile Glu Phe Glu Ala Glu
    1280            1285            1290

Asn Ala Lys Cys Leu Lys Ala Gly Glu Arg Pro Ala Gln Gly Met
    1295            1300            1305

Pro Val Leu Gln Gly Ile Thr Lys Ala Ser Leu Gln Thr Gln Ser
    1310            1315            1320

Phe Ile Ser Ala Ala Ser Phe Gln Glu Thr Thr Arg Val Leu Thr
    1325            1330            1335
```

```
Glu Ala Ala Thr Ala Gly Lys Val Asp Lys Leu Met Gly Leu Lys
    1340            1345                1350

Glu Asn Val Ile Val Gly Arg Leu Ile Pro Ala Gly Thr Gly Ser
    1355            1360                1365

Val Met Lys Arg Leu Arg Ala Ile Ala Ala Glu Gln Asp Arg Gln
    1370            1375                1380

Arg Val Gly Arg Ser Ala Ala Glu
    1385            1390

<210> SEQ ID NO 54
<211> LENGTH: 1391
<212> TYPE: PRT
<213> ORGANISM: Neisseria gonorrhoeae

<400> SEQUENCE: 54

Met Asn Leu Leu Asn Leu Phe Asn Pro Leu Gln Thr Ala Gly Met Glu
1               5                   10                  15

Glu Glu Phe Asp Ala Ile Lys Ile Gly Ile Ala Ser Pro Glu Thr Ile
            20                  25                  30

Arg Ser Trp Ser Tyr Gly Glu Val Lys Lys Pro Glu Thr Ile Asn Tyr
        35                  40                  45

Arg Thr Phe Lys Pro Glu Arg Asp Gly Leu Phe Cys Ala Lys Ile Phe
    50                  55                  60

Gly Pro Val Lys Asp Tyr Glu Cys Leu Cys Gly Lys Tyr Lys Arg Leu
65                  70                  75                  80

Lys Phe Lys Gly Val Thr Cys Glu Lys Cys Gly Val Glu Val Thr Leu
                85                  90                  95

Ser Lys Val Arg Arg Glu Arg Met Gly His Ile Glu Leu Ala Ala Pro
            100                 105                 110

Val Ala His Ile Trp Phe Leu Lys Ser Leu Pro Ser Arg Leu Gly Met
        115                 120                 125

Val Leu Asn Met Thr Leu Arg Asp Ile Glu Arg Val Leu Tyr Phe Glu
    130                 135                 140

Ala Phe Val Val Thr Asp Pro Gly Met Thr Pro Leu Gln Arg Arg Gln
145                 150                 155                 160

Leu Leu Thr Glu Asp Asp Tyr Tyr Asn Lys Leu Asp Glu Tyr Gly Asp
                165                 170                 175

Asp Phe Asp Ala Lys Met Gly Ala Glu Gly Ile Arg Glu Leu Leu Arg
            180                 185                 190

Thr Leu Asp Val Ala Gly Glu Ile Glu Ile Leu Arg Gln Glu Leu Glu
        195                 200                 205

Ser Thr Gly Ser Asp Thr Lys Ile Lys Lys Ile Ala Lys Arg Leu Lys
    210                 215                 220

Val Leu Glu Ala Phe His Arg Ser Gly Met Lys Leu Glu Trp Met Ile
225                 230                 235                 240

Met Asp Val Leu Pro Val Leu Pro Pro Asp Leu Arg Pro Leu Val Pro
                245                 250                 255

Leu Asp Gly Gly Arg Phe Ala Thr Ser Asp Leu Asn Asp Leu Tyr Arg
            260                 265                 270

Arg Val Ile Asn Arg Asn Asn Arg Leu Lys Arg Leu Leu Glu Leu His
        275                 280                 285

Ala Pro Asp Ile Ile Val Arg Asn Glu Lys Arg Met Leu Gln Glu Ala
    290                 295                 300

Val Asp Ser Leu Leu Asp Asn Gly Arg Arg Gly Lys Ala Met Thr Gly
```

```
305                 310                 315                 320
Ala Asn Lys Arg Pro Leu Lys Ser Leu Ala Asp Met Ile Lys Gly Lys
                325                 330                 335
Gly Gly Arg Phe Arg Gln Asn Leu Leu Gly Lys Arg Val Asp Tyr Ser
                340                 345                 350
Gly Arg Ser Val Ile Thr Val Gly Pro Tyr Leu Arg Leu His Gln Cys
                355                 360                 365
Gly Leu Pro Lys Lys Met Ala Leu Glu Leu Phe Lys Pro Phe Ile Phe
                370                 375                 380
His Lys Leu Glu Lys Gln Gly Leu Ala Ser Thr Val Lys Ala Ala Lys
385                 390                 395                 400
Lys Leu Val Glu Gln Glu Val Pro Glu Val Trp Asp Ile Leu Glu Glu
                405                 410                 415
Val Ile Arg Glu His Pro Ile Met Leu Asn Arg Ala Pro Thr Leu His
                420                 425                 430
Arg Leu Gly Ile Gln Ala Phe Glu Pro Ile Leu Ile Glu Gly Lys Ala
                435                 440                 445
Ile Gln Leu His Pro Leu Val Cys Ala Ala Phe Asn Ala Asp Phe Asp
                450                 455                 460
Gly Asp Gln Met Ala Val His Val Pro Leu Ser Leu Glu Ala Gln Met
465                 470                 475                 480
Glu Ala Arg Thr Leu Met Leu Ala Ser Asn Asn Val Leu Ser Pro Ala
                485                 490                 495
Asn Gly Glu Pro Ile Ile Val Pro Ser Gln Asp Ile Val Leu Gly Leu
                500                 505                 510
Tyr Tyr Met Thr Arg Asp Arg Ile Asn Ala Lys Gly Glu Gly Ser Leu
                515                 520                 525
Phe Ala Asp Val Lys Glu Val His Arg Ala Tyr His Thr Lys Gln Val
                530                 535                 540
Glu Leu Gly Thr Lys Ile Thr Val Arg Leu Arg Glu Trp Val Lys Asn
545                 550                 555                 560
Glu Ala Gly Glu Phe Glu Pro Val Val Asn Arg Tyr Glu Thr Thr Val
                565                 570                 575
Gly Arg Ala Leu Leu Ser Glu Ile Leu Pro Lys Gly Leu Pro Phe Glu
                580                 585                 590
Tyr Val Asn Lys Ala Leu Lys Lys Lys Glu Ile Ser Lys Leu Ile Asn
                595                 600                 605
Ala Ser Phe Arg Leu Cys Gly Leu Arg Asp Thr Val Ile Phe Ala Asp
                610                 615                 620
His Leu Met Tyr Thr Gly Phe Gly Phe Ala Ala Lys Gly Gly Ile Ser
625                 630                 635                 640
Ile Ala Val Asp Asp Met Glu Ile Pro Lys Glu Lys Ala Ala Leu Leu
                645                 650                 655
Ala Glu Ala Asn Ala Glu Val Lys Glu Ile Glu Asp Gln Tyr Arg Gln
                660                 665                 670
Gly Leu Val Thr Asn Gly Glu Arg Tyr Asn Lys Val Val Asp Ile Trp
                675                 680                 685
Gly Arg Ala Gly Asp Lys Ile Ala Lys Ala Met Met Asp Asn Leu Ser
                690                 695                 700
Lys Gln Lys Val Ile Asp Arg Asp Gly Asn Glu Val Asp Gln Glu Ser
705                 710                 715                 720
Phe Asn Ser Ile Tyr Met Met Ala Asp Ser Gly Ala Arg Gly Ser Ala
                725                 730                 735
```

-continued

Ala Gln Ile Lys Gln Leu Ser Gly Met Arg Gly Leu Met Ala Lys Pro
            740                 745                 750

Asp Gly Ser Ile Ile Glu Thr Pro Ile Thr Ser Asn Phe Arg Glu Gly
            755                 760                 765

Leu Thr Val Leu Gln Tyr Phe Ile Ala Thr His Gly Ala Arg Lys Gly
    770                 775                 780

Leu Ala Asp Thr Ala Leu Lys Thr Ala Asn Ser Gly Tyr Leu Thr Arg
785                 790                 795                 800

Arg Leu Val Asp Val Thr Gln Asp Leu Val Val Glu Asp Asp Cys
                805                 810                 815

Gly Thr Ser Asp Gly Phe Val Met Lys Ala Val Val Gln Gly Gly Asp
            820                 825                 830

Val Ile Glu Ala Leu Arg Asp Arg Ile Leu Gly Arg Val Thr Ala Ser
            835                 840                 845

Asp Val Val Asp Pro Ser Ser Gly Glu Thr Leu Val Glu Ala Gly Thr
850                 855                 860

Leu Leu Thr Glu Lys Leu Val Asp Met Ile Asp Gln Ser Gly Val Asp
865                 870                 875                 880

Glu Val Lys Val Arg Thr Pro Ile Thr Cys Lys Thr Arg His Gly Leu
                885                 890                 895

Cys Ala His Cys Tyr Gly Arg Asp Leu Ala Arg Gly Lys Leu Val Asn
            900                 905                 910

Ala Gly Glu Ala Val Gly Val Ile Ala Ala Gln Ser Ile Gly Glu Pro
            915                 920                 925

Gly Thr Gln Leu Thr Met Arg Thr Phe His Ile Gly Gly Ala Ala Ser
            930                 935                 940

Arg Ala Ala Ala Ser Gln Val Glu Ala Lys Ser Asn Gly Thr Ala
945                 950                 955                 960

Arg Phe Ser Ser Gln Met Arg Tyr Val Ala Asn Asn Lys Gly Glu Leu
                965                 970                 975

Val Val Ile Gly Arg Ser Cys Glu Val Val Ile His Asp Asp Ile Gly
            980                 985                 990

Arg Glu Arg Glu Arg His Lys Val Pro Tyr Gly Ala Ile Leu Leu Val
            995                 1000                1005

Gln Asp Gly Met Ala Ile Lys Ala Gly Gln Thr Leu Ala Thr Trp
    1010                1015                1020

Asp Pro His Thr Arg Pro Met Ile Thr Glu His Ala Gly Met Val
    1025                1030                1035

Lys Phe Glu Asn Met Glu Glu Gly Val Thr Val Ala Lys Gln Thr
    1040                1045                1050

Asp Asp Val Thr Gly Leu Ser Thr Leu Val Val Ile Asp Gly Lys
    1055                1060                1065

Arg Arg Ser Ser Ser Ala Ser Lys Leu Leu Arg Pro Thr Val Lys
    1070                1075                1080

Leu Leu Asp Glu Asn Gly Val Glu Ile Cys Ile Pro Gly Thr Ser
    1085                1090                1095

Thr Pro Val Ser Met Ala Phe Pro Val Gly Ala Val Ile Thr Val
    1100                1105                1110

Arg Glu Gly Gln Glu Ile Gly Lys Gly Asp Val Leu Ala Arg Ile
    1115                1120                1125

Pro Gln Ala Ser Ser Lys Thr Arg Asp Ile Thr Gly Gly Leu Pro
    1130                1135                1140

```
Arg Val Ala Glu Leu Phe Glu Ala Arg Val Pro Lys Asp Ala Gly
    1145                1150                1155

Met Leu Ala Glu Ile Thr Gly Thr Val Ser Phe Gly Lys Glu Thr
    1160                1165                1170

Lys Gly Lys Gln Arg Leu Ile Ile Thr Asp Val Asp Gly Val Ala
    1175                1180                1185

Tyr Glu Thr Leu Ile Ser Lys Glu Lys Gln Ile Leu Val His Asp
    1190                1195                1200

Gly Gln Val Val Asn Arg Gly Glu Thr Ile Val Asp Gly Ala Val
    1205                1210                1215

Asp Pro His Asp Ile Leu Arg Leu Gln Gly Ile Glu Ala Leu Ala
    1220                1225                1230

Arg Tyr Ile Val Gln Glu Val Gln Glu Val Tyr Arg Leu Gln Gly
    1235                1240                1245

Val Lys Ile Ser Asp Lys His Ile Glu Val Ile Ile Arg Gln Met
    1250                1255                1260

Leu Arg Arg Val Asn Ile Ala Asp Ala Gly Glu Thr Gly Phe Ile
    1265                1270                1275

Thr Gly Glu Gln Val Glu Arg Gly Asp Val Met Ala Ala Asn Glu
    1280                1285                1290

Lys Ala Leu Glu Glu Gly Lys Glu Pro Ala Arg Tyr Glu Asn Ile
    1295                1300                1305

Leu Leu Gly Ile Thr Lys Ala Ser Leu Ser Thr Asp Ser Phe Ile
    1310                1315                1320

Ser Ala Ala Ser Phe Gln Glu Thr Thr Arg Val Leu Thr Glu Ala
    1325                1330                1335

Ala Ile Met Gly Lys Gln Asp Glu Leu Arg Gly Leu Lys Glu Asn
    1340                1345                1350

Val Ile Val Gly Arg Leu Ile Pro Ala Gly Thr Gly Leu Thr Tyr
    1355                1360                1365

His Arg Ser Arg His Gln Gln Trp Gln Gly Val Glu Gln Glu Thr
    1370                1375                1380

Ala Glu Thr Gln Val Thr Asp Glu
    1385                1390

<210> SEQ ID NO 55
<211> LENGTH: 1401
<212> TYPE: PRT
<213> ORGANISM: Legionella pneumophila

<400> SEQUENCE: 55

Met Ser Asp Leu Leu Gly Ile Leu Lys Gln Gln Gly Gln Ser Glu Glu
1               5                   10                  15

Phe Asp Ala Ile Lys Ile Ala Leu Ala Ser Pro Glu Leu Ile Arg Ser
                20                  25                  30

Trp Ser Tyr Gly Glu Val Lys Lys Pro Glu Thr Ile Asn Tyr Arg Thr
            35                  40                  45

Phe Lys Pro Glu Arg Asp Gly Leu Phe Cys Ala Lys Thr Phe Gly Pro
        50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Leu Ala Leu Ala Lys
                85                  90                  95

Val Arg Arg Glu Arg Met Gly His Ile Glu Leu Ala Ser Pro Val Ala
                100                 105                 110
```

```
His Ile Trp Phe Leu Lys Ser Leu Pro Ser Arg Ile Gly Leu Leu
            115                 120                 125

Asp Met Thr Leu Arg Asp Ile Glu Arg Val Leu Tyr Phe Glu Ala Phe
130                 135                 140

Val Val Val Asp Pro Gly Met Thr Glu Leu Glu Arg Gly Gln Leu Leu
145                 150                 155                 160

Asn Asp Glu Ala Tyr Leu Asp Ala Met Glu Gln Tyr Gly Asp Glu Phe
                165                 170                 175

Asp Ala Arg Met Gly Ala Glu Ala Ile Arg Asp Leu Leu Arg Gln Ile
            180                 185                 190

Asp Leu Glu Asp Glu Ile Arg Asn Leu Arg Glu Glu Leu Pro Thr Thr
        195                 200                 205

Asn Ser Glu Thr Lys Ile Lys Lys Ile Thr Lys Arg Leu Lys Leu Leu
    210                 215                 220

Glu Ala Phe Tyr Glu Ser Gly Asn Lys Pro Glu Trp Met Ile Met Asp
225                 230                 235                 240

Val Leu Pro Val Leu Pro Asp Leu Arg Pro Leu Val Pro Leu Asp
                245                 250                 255

Gly Gly Arg Phe Ala Thr Ser Asp Leu Asn Asp Leu Tyr Arg Arg Val
                260                 265                 270

Ile Asn Arg Asn Asn Arg Leu Lys Arg Leu Leu Asp Leu Asn Ala Pro
            275                 280                 285

Asp Ile Ile Val Arg Asn Glu Lys Arg Met Leu Gln Glu Ser Val Asp
        290                 295                 300

Ala Leu Leu Asp Asn Gly Arg Arg Gly Arg Ala Ile Thr Gly Thr Asn
305                 310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
                340                 345                 350

Ser Val Ile Val Val Gly Pro Thr Leu Lys Leu His Gln Cys Gly Leu
            355                 360                 365

Pro Lys Lys Met Ala Leu Glu Leu Phe Lys Pro Phe Ile Phe Ser Lys
        370                 375                 380

Leu Glu Phe Arg Gly Leu Ala Thr Thr Ile Lys Ala Ala Lys Lys Met
385                 390                 395                 400

Val Glu Arg Glu Glu Ser Val Val Trp Asp Ile Leu Asp Asp Val Ile
                405                 410                 415

Arg Glu His Pro Ile Leu Leu Asn Arg Ala Pro Thr Leu His Arg Leu
                420                 425                 430

Gly Ile Gln Ala Phe Glu Pro Val Leu Ile Glu Gly Lys Ala Ile Gln
            435                 440                 445

Leu His Pro Leu Val Cys Thr Ala Tyr Asn Ala Asp Phe Asp Gly Asp
    450                 455                 460

Gln Met Ala Val His Val Pro Leu Thr Leu Glu Ala Gln Leu Glu Ala
465                 470                 475                 480

Arg Ser Leu Met Met Ser Thr Asn Asn Ile Leu Ser Pro Ala Ser Gly
                485                 490                 495

Glu Pro Ile Ile Val Pro Ser Gln Asp Val Val Leu Gly Leu Tyr Tyr
            500                 505                 510

Leu Thr Arg Glu Lys Val Asn Ala Leu Gly Glu Gly Lys Ile Tyr Ser
        515                 520                 525
```

```
Ser Ala Gln Glu Ala Gln Asn Phe Tyr Glu Ala Gly His Leu Asp Ile
    530                 535                 540

His Ala Lys Ile Lys Ile Arg Met Pro Lys Glu Asp Gly Glu Thr Gly
545                 550                 555                 560

Tyr His Leu Val Glu Thr Thr Val Gly Arg Ala Ile Leu Ala Glu Ile
                565                 570                 575

Leu Pro Lys Gly Met Pro Phe Asp Tyr Ile Asn Arg Thr Met Thr Lys
            580                 585                 590

Lys Val Ile Ser Lys Val Ile Asp Ser Cys Tyr Arg Lys Phe Gly Leu
        595                 600                 605

Lys Glu Thr Val Ile Phe Ala Asp Gln Leu Met Tyr Thr Gly Phe Lys
    610                 615                 620

Tyr Ala Thr Arg Ser Gly Ala Ser Ile Gly Ile Glu Asp Met Glu Ile
625                 630                 635                 640

Pro Asp Asp Lys Ser Ser Ile Ile Glu His Ala Asp Asn Glu Val Arg
                645                 650                 655

Glu Ile Glu Ser Gln Phe Arg Ser Gly Leu Val Thr Asn Gly Glu Arg
            660                 665                 670

Tyr Asn Lys Val Ile Asp Ile Trp Ser Arg Thr Asn Glu Leu Val Ala
        675                 680                 685

Lys Ser Met Met Ser Lys Ile Ala Thr Glu Val Thr Asp Ala Lys
    690                 695                 700

Gly Asn Lys Val Arg Gln Glu Ser Phe Asn Pro Ile Phe Met Met Ala
705                 710                 715                 720

Asp Ser Gly Ala Arg Gly Ser Ala Ala Gln Ile Arg Gln Leu Ala Gly
                725                 730                 735

Met Arg Gly Leu Met Ala Ala Pro Asp Gly Ser Ile Ile Glu Thr Pro
            740                 745                 750

Ile Thr Ala Asn Phe Arg Glu Gly Leu Asn Val Phe Gln Tyr Phe Ile
        755                 760                 765

Ser Thr His Gly Ala Arg Lys Gly Leu Ala Asp Thr Ala Leu Lys Thr
    770                 775                 780

Ala Asn Ser Gly Tyr Leu Thr Arg Arg Leu Val Asp Val Ala Gln Asp
785                 790                 795                 800

Val Val Ile Thr Glu Asp Asp Cys Gly Thr Asp Thr Gly Ile Leu Met
                805                 810                 815

Gln Pro Leu Ile Glu Gly Gly Asp Ile Val Glu Pro Leu His Glu Arg
            820                 825                 830

Val Leu Gly Arg Val Ala Ser Asp Val Tyr Ile Pro Thr Gln Thr
    835                 840                 845

Glu Pro Val Val Lys Ala Gly Thr Leu Leu Asp Glu Glu Trp Val Glu
850                 855                 860

Lys Leu Glu Lys His Gly Val Asp Gln Val Met Val Arg Ser Pro Ile
865                 870                 875                 880

Thr Cys Gln Thr Arg Phe Gly Leu Cys Ala Lys Cys Tyr Gly Arg Asp
                885                 890                 895

Leu Ala Arg Gly His Leu Val Asn Thr Gly Glu Ala Val Gly Ile Ile
            900                 905                 910

Ala Ala Gln Ser Ile Gly Glu Pro Gly Thr Gln Leu Thr Met Arg Thr
        915                 920                 925

Phe His Ile Gly Gly Ala Ala Ser Arg Ala Thr Ala Ala Asn Asn Ile
    930                 935                 940

Gln Ile Lys Thr Lys Gly Val Ile Arg Leu His Asn Ile Lys Thr Val
```

-continued

Thr His Glu Asn Lys Asn Leu Val Ala Val Ser Arg Ser Gly Glu Val
945 950 955 960

Thr Ile Val Asp Glu Phe Gly Arg Glu Arg Glu Arg Tyr Lys Val Pro
965 970 975

Tyr Gly Ala Val Ile Ser Ala Gln Asp Asn Ser Pro Val Glu Ala Gly
980 985 990

Gln Val Ile Ala Thr Trp Asp Pro His Thr His Pro Val Ile Ser
995 1000 1005

Glu Val Ser Gly Arg Leu Lys Phe Val Asp Leu Ile Asp Gly Ile
1010 1015 1020

Thr Met Asn Arg Gln Thr Asp Glu Leu Thr Gly Leu Ser Asn Ile
1025 1030 1035

Val Ile Ile Asp Ala Lys Gln Arg Ser Ala Ala Gly Arg Asp Leu
1040 1045 1050

Arg Pro Met Val Lys Leu Val Thr Asp Glu Gly Asp Asp Ile Tyr
1055 1060 1065

Leu Ala Gly Thr Asn Val Pro Ala Gln Tyr Tyr Leu Pro Val Asp
1070 1075 1080

Ala Ile Val Asn Phe Glu Asp Gly Ser Leu Val Gly Ile Gly Asp
1085 1090 1095

Val Ile Ala Arg Ile Pro Gln Glu Arg Ser Lys Thr Arg Asp Ile
1100 1105 1110

Thr Gly Gly Leu Pro Arg Val Ala Asp Leu Phe Glu Ala Arg Lys
1115 1120 1125

Pro Lys Asp Ser Ala Val Met Ala Glu Val Ser Gly Leu Val Asn
1130 1135 1140

Phe Gly Lys Glu Thr Lys Gly Lys Arg Arg Leu Ile Ile Asn Val
1145 1150 1155

Ser Glu Asp Gln Cys His Glu Glu Leu Ile Pro Lys Trp Arg His
1160 1165 1170

Ile Ser Val Phe Glu Gly Glu His Val Glu Arg Gly Glu Ile Ile
1175 1180 1185

Ala Glu Gly Ala Leu Asn Pro His Asp Ile Leu Arg Leu Leu Gly
1190 1195 1200

Val Gly Ala Leu Ala Asn Tyr Ile Val Asn Glu Val Gln Asp Val
1205 1210 1215

Tyr Arg Leu Gln Gly Val Lys Ile Asn Asp Lys His Ile Glu Val
1220 1225 1230

Ile Val Arg Gln Met Leu Arg Lys Arg Val Ile Thr Phe Ala Gly
1235 1240 1245

Asp Ser Lys Phe Leu Val Gly Glu Gln Val Glu Glu Ser Ala Met
1250 1255 1260

Leu Gln Glu Asn Asp Lys Leu Leu Ala Glu Gly Lys Gln Ile Ala
1265 1270 1275

Arg Gly Thr Pro Ile Leu Leu Gly Ile Thr Lys Ala Ser Leu Ala
1280 1285 1290

Thr Glu Ser Phe Ile Ser Ala Ala Ser Phe Gln Glu Thr Thr Arg
1295 1300 1305

Val Leu Thr Glu Ala Ala Val Ser Gly Lys Val Asp Glu Leu Arg
1310 1315 1320

Gly Leu Lys Glu Asn Val Met Val Gly Arg Leu Ile Pro Ala Gly
1325 1330 1335

Thr Gly Tyr Thr Tyr His Gln Ser Arg Lys Ala Lys Arg Ala Arg
    1355                1360                1365

Ala Ala Ala Gly Gly Asp Ser Ser Ala Thr His Thr Val Thr Ala
    1370                1375                1380

Ser Asp Val Glu His Ala Leu Ser Glu Ala Leu Asn Ala Asp Asn
    1385                1390                1395

His Glu His
    1400

<210> SEQ ID NO 56
<211> LENGTH: 1399
<212> TYPE: PRT
<213> ORGANISM: Pseudomonas aeruginosa

<400> SEQUENCE: 56

Met Lys Asp Leu Leu Asn Leu Lys Asn Gln Gly Gln Ile Glu Glu
1               5                   10                  15

Phe Asp Ala Ile Arg Ile Gly Leu Ala Ser Pro Glu Met Ile Arg Ser
        20                  25                  30

Trp Ser Phe Gly Glu Val Lys Lys Pro Glu Thr Ile Asn Tyr Arg Thr
        35                  40                  45

Phe Lys Pro Glu Arg Asp Gly Leu Phe Cys Ala Lys Ile Phe Gly Pro
    50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Ala Leu Ala Lys
                85                  90                  95

Val Arg Arg Glu Arg Met Gly His Ile Glu Leu Ala Ser Pro Val Ala
            100                 105                 110

His Ile Trp Phe Leu Lys Ser Leu Pro Ser Arg Ile Gly Leu Leu Leu
        115                 120                 125

Asp Met Thr Leu Arg Asp Ile Glu Arg Val Leu Tyr Phe Glu Ser Tyr
    130                 135                 140

Val Val Ile Asp Pro Gly Met Thr Thr Leu Glu Lys Gly Gln Leu Leu
145                 150                 155                 160

Asn Asp Glu Gln Tyr Phe Glu Ala Leu Glu Glu Phe Gly Asp Asp Phe
                165                 170                 175

Asp Ala Arg Met Gly Ala Glu Ala Val His Glu Leu Leu Asn Ala Ile
            180                 185                 190

Asp Leu Glu His Glu Ile Gly Arg Leu Arg Glu Ile Pro Gln Thr
        195                 200                 205

Asn Ser Glu Thr Lys Ile Lys Lys Leu Ser Lys Arg Leu Lys Leu Met
    210                 215                 220

Glu Ala Phe Gln Gly Ser Gly Asn Lys Pro Glu Trp Met Val Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Asp Leu Ala Ala Pro
        275                 280                 285

Asp Ile Ile Val Arg Asn Glu Lys Arg Met Leu Gln Glu Ala Val Asp
    290                 295                 300

Ala Leu Leu Asp Asn Gly Arg Arg Gly Arg Ala Ile Thr Gly Ser Asn

-continued

```
            305                 310                 315                 320
        Lys Arg Pro Leu Lys Ser Leu Ala Asp Met Ile Lys Gly Lys Gln Gly
                        325                 330                 335
        Arg Phe Arg Gln Asn Leu Leu Gly Lys Arg Val Asp Tyr Ser Gly Arg
                        340                 345                 350
        Ser Val Ile Thr Val Gly Pro Thr Leu Arg Leu His Gln Cys Gly Leu
                        355                 360                 365
        Pro Lys Lys Met Ala Leu Glu Leu Phe Lys Pro Phe Ile Phe Gly Lys
                        370                 375                 380
        Leu Glu Gly Arg Gly Met Ala Thr Thr Ile Lys Ala Ala Lys Lys Met
        385                 390                 395                 400
        Val Glu Arg Glu Leu Pro Glu Val Trp Asp Val Leu Ala Glu Val Ile
                        405                 410                 415
        Arg Glu His Pro Val Leu Leu Asn Arg Ala Pro Thr Leu His Arg Leu
                        420                 425                 430
        Gly Ile Gln Ala Phe Glu Pro Val Leu Ile Glu Gly Lys Ala Ile Gln
                        435                 440                 445
        Leu His Pro Leu Val Cys Ala Ala Tyr Asn Ala Asp Phe Asp Gly Asp
                        450                 455                 460
        Gln Met Ala Val His Val Pro Leu Thr Leu Glu Ala Gln Leu Glu Ala
        465                 470                 475                 480
        Arg Ala Leu Met Met Ser Thr Asn Asn Ile Leu Ser Pro Ala Asn Gly
                        485                 490                 495
        Glu Pro Ile Ile Val Pro Ser Gln Asp Val Val Met Gly Leu Tyr Tyr
                        500                 505                 510
        Met Thr Arg Glu Ala Ile Asn Ala Lys Gly Glu Gly Met Ala Phe Ala
                        515                 520                 525
        Asp Leu Gln Glu Val Asp Arg Ala Tyr Arg Ser Gly Gln Ala Ser Leu
                        530                 535                 540
        His Ala Arg Val Lys Val Arg Ile Asn Glu Lys Ile Lys Gly Glu Asp
        545                 550                 555                 560
        Gly Gln Leu Thr Ala Asn Thr Arg Ile Val Asp Thr Thr Val Gly Arg
                        565                 570                 575
        Ala Leu Leu Phe Gln Val Val Pro Ala Gly Leu Pro Phe Asp Val Val
                        580                 585                 590
        Asn Gln Ser Met Lys Lys Ala Ile Ser Lys Leu Ile Asn His Cys
                        595                 600                 605
        Tyr Arg Val Val Gly Leu Lys Asp Thr Val Ile Phe Ala Asp Gln Leu
                        610                 615                 620
        Met Tyr Thr Gly Phe Ala Tyr Ser Thr Ile Ser Gly Val Ser Ile Gly
        625                 630                 635                 640
        Val Asn Asp Phe Val Ile Pro Asp Glu Lys Ala Arg Ile Ile Asn Ala
                        645                 650                 655
        Ala Thr Asp Glu Val Lys Glu Ile Glu Ser Gln Tyr Ala Ser Gly Leu
                        660                 665                 670
        Val Thr Gln Gly Glu Lys Tyr Asn Lys Val Ile Asp Leu Trp Ser Lys
                        675                 680                 685
        Ala Asn Asp Glu Val Ser Lys Ala Met Met Ala Asn Leu Ser Lys Glu
                        690                 695                 700
        Lys Val Val Asp Arg Glu Gly Lys Glu Val Asp Gln Glu Ser Phe Asn
        705                 710                 715                 720
        Ser Met Tyr Met Met Ala Asp Ser Gly Ala Arg Gly Ser Ala Ala Gln
                        725                 730                 735
```

```
Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
            755                 760                 765

Val Leu Gln Tyr Phe Ile Ser Thr His Gly Ala Arg Lys Gly Leu Ala
            770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Ile Asp Cys Gly Thr
                805                 810                 815

Glu His Gly Leu Leu Met Ser Pro His Ile Glu Gly Gly Asp Val Val
            820                 825                 830

Glu Pro Leu Gly Glu Arg Val Leu Gly Arg Val Ile Ala Arg Asp Val
            835                 840                 845

Phe Lys Pro Gly Ser Asp Glu Val Ile Val Pro Ala Gly Thr Leu Ile
            850                 855                 860

Asp Glu Lys Trp Val Asp Phe Leu Glu Val Met Ser Val Asp Glu Val
865                 870                 875                 880

Val Val Arg Ser Pro Ile Thr Cys Glu Thr Arg His Gly Ile Cys Ala
                885                 890                 895

Met Cys Tyr Gly Arg Asp Leu Ala Arg Gly His Arg Val Asn Ile Gly
            900                 905                 910

Glu Ala Val Gly Val Ile Ala Ala Gln Ser Ile Gly Glu Pro Gly Thr
            915                 920                 925

Gln Leu Thr Met Arg Thr Phe His Ile Gly Gly Ala Ala Ser Arg Thr
            930                 935                 940

Ser Ala Ala Asp Asn Val Gln Val Lys Asn Gly Gly Thr Ile Arg Leu
945                 950                 955                 960

His Asn Leu Lys His Val Val Arg Ala Asp Gly Ala Leu Val Ala Val
                965                 970                 975

Ser Arg Ser Gly Glu Leu Ala Val Ala Asp Phe Gly Arg Glu Arg
            980                 985                 990

Glu Arg Tyr Lys Leu Pro Tyr Gly Ala Val Ile Ser Val Lys Glu Gly
            995                 1000                1005

Asp Lys Val Asp Pro Gly Ala Ile Val Ala Lys Trp Asp Pro His
    1010                1015                1020

Thr His Pro Ile Val Thr Glu Val Asp Gly Thr Val Ala Phe Val
    1025                1030                1035

Gly Met Glu Glu Gly Ile Thr Val Lys Arg Gln Thr Asp Glu Leu
    1040                1045                1050

Thr Gly Leu Thr Asn Ile Glu Val Met Asp Pro Lys Asp Arg Pro
    1055                1060                1065

Ala Ala Gly Lys Asp Ile Arg Pro Ala Val Lys Leu Ile Asp Ala
    1070                1075                1080

Ala Gly Lys Asp Leu Leu Leu Pro Gly Thr Asp Val Pro Ala Gln
    1085                1090                1095

Tyr Phe Leu Pro Ala Asn Ala Leu Val Asn Leu Thr Asp Gly Ala
    1100                1105                1110

Lys Val Ser Ile Gly Asp Val Val Ala Arg Ile Pro Gln Glu Thr
    1115                1120                1125

Ser Lys Thr Arg Asp Ile Thr Gly Gly Leu Pro Arg Val Ala Asp
    1130                1135                1140
```

-continued

Leu Phe Glu Ala Arg Arg Pro Lys Glu Pro Ser Ile Leu Ala Glu
    1145                1150            1155

Ile Ser Gly Thr Ile Ser Phe Gly Lys Glu Thr Lys Gly Lys Arg
    1160                1165            1170

Arg Leu Val Ile Thr Pro Asn Asp Gly Ser Asp Pro Tyr Glu Glu
    1175                1180            1185

Leu Ile Pro Lys Trp Arg His Leu Asn Val Phe Glu Gly Glu Gln
    1190                1195            1200

Val Asn Arg Gly Glu Val Ile Ser Asp Gly Pro Ser Asn Pro His
    1205                1210            1215

Asp Ile Leu Arg Leu Leu Gly Val Ser Ser Leu Ala Lys Tyr Ile
    1220                1225            1230

Val Asn Glu Ile Gln Asp Val Tyr Arg Leu Gln Gly Val Lys Ile
    1235                1240            1245

Asn Asp Lys His Ile Glu Thr Ile Leu Arg Gln Met Leu Arg Lys
    1250                1255            1260

Val Glu Val Ser Glu Ser Gly Asp Ser Ser Phe Ile Lys Gly Asp
    1265                1270            1275

Gln Val Glu Leu Thr Gln Val Leu Glu Glu Asn Glu Gln Leu Gly
    1280                1285            1290

Thr Glu Asp Lys Phe Pro Ala Lys Tyr Glu Arg Val Leu Leu Gly
    1295                1300            1305

Ile Thr Lys Ala Ser Leu Ser Thr Glu Ser Phe Ile Ser Ala Ala
    1310                1315            1320

Ser Phe Gln Glu Thr Thr Arg Val Leu Thr Glu Ala Ala Val Thr
    1325                1330            1335

Gly Lys Arg Asp Phe Leu Arg Gly Leu Lys Glu Asn Val Val Val
    1340                1345            1350

Gly Arg Leu Ile Pro Ala Gly Thr Gly Leu Ala Tyr His Ser Glu
    1355                1360            1365

Arg Lys Arg Gln Arg Asp Leu Gly Lys Pro Gln Arg Val Ser Ala
    1370                1375            1380

Ser Glu Ala Glu Ala Ala Leu Thr Glu Ala Leu Asn Ser Ser Gly
    1385                1390            1395

Asn

<210> SEQ ID NO 57
<211> LENGTH: 1401
<212> TYPE: PRT
<213> ORGANISM: Vibrio cholerae

<400> SEQUENCE: 57

Met Lys Asp Leu Leu Asn Phe Leu Lys Ala Gln His Lys Thr Glu Glu
1               5                   10                  15

Phe Asp Ala Ile Lys Ile Gly Leu Ala Ser Pro Asp Met Ile Arg Ser
                20                  25                  30

Trp Ser Phe Gly Glu Val Lys Lys Pro Glu Thr Ile Asn Tyr Arg Thr
        35                  40                  45

Phe Lys Pro Glu Arg Asp Gly Leu Phe Cys Ala Arg Ile Phe Gly Pro
    50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

```
Val Arg Arg Asp Arg Met Gly His Ile Glu Leu Ala Ser Pro Val Ala
            100                 105                 110

His Ile Trp Phe Leu Lys Ser Leu Pro Ser Arg Ile Gly Leu Leu Met
        115                 120                 125

Asp Met Pro Leu Arg Asp Ile Glu Arg Val Leu Tyr Phe Glu Met Tyr
    130                 135                 140

Val Val Thr Glu Pro Gly Met Thr Asp Leu Glu Arg Gly Gln Met Leu
145                 150                 155                 160

Thr Glu Glu Tyr Leu Asp Arg Leu Glu Trp Gly Asp Glu Phe
                165                 170                 175

Thr Ala Lys Met Gly Ala Glu Ala Ile Lys Asp Leu Leu Ala Ser Met
            180                 185                 190

Asp Leu Pro Ala Glu Ala Glu Gln Met Arg Glu Glu Leu Asp Thr Thr
        195                 200                 205

Asn Ser Glu Thr Lys Arg Lys Lys Leu Thr Lys Arg Leu Lys Leu Val
    210                 215                 220

Glu Ala Phe Val Ala Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Glu Leu Ala Ala Pro
        275                 280                 285

Asp Ile Ile Val Arg Asn Glu Lys Arg Met Leu Gln Glu Ser Val Asp
    290                 295                 300

Ala Leu Leu Asp Asn Gly Arg Arg Gly Arg Ala Ile Thr Gly Ser Asn
305                 310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
            340                 345                 350

Ser Val Ile Thr Val Gly Pro Tyr Leu Arg Leu His Gln Cys Gly Leu
        355                 360                 365

Pro Lys Lys Met Ala Leu Glu Leu Phe Lys Pro Phe Ile Tyr Ser Lys
    370                 375                 380

Leu Glu Thr Arg Gly Leu Ala Thr Thr Ile Lys Ala Ala Lys Lys Met
385                 390                 395                 400

Val Glu Arg Glu Glu Ala Val Val Trp Asp Ile Leu Asp Glu Val Ile
                405                 410                 415

Arg Glu His Pro Val Leu Leu Asn Arg Ala Pro Thr Leu His Arg Leu
            420                 425                 430

Gly Ile Gln Ala Phe Glu Pro Val Leu Ile Glu Gly Lys Ala Ile Gln
        435                 440                 445

Leu His Pro Leu Val Cys Ala Ala Tyr Asn Ala Asp Phe Asp Gly Asp
    450                 455                 460

Gln Met Ala Val His Val Pro Leu Thr Leu Glu Ala Gln Leu Glu Ala
465                 470                 475                 480

Arg Thr Leu Met Met Ser Thr Asn Asn Ile Leu Ser Pro Ala Ser Gly
                485                 490                 495

Asp Pro Ile Ile Val Pro Ser Gln Asp Val Val Leu Gly Leu Tyr Tyr
            500                 505                 510

Met Thr Arg Glu Lys Ile Asn Ala Lys Gly Glu Gly Met Tyr Leu Thr
```

-continued

```
            515                 520                 525
Gly Pro Ala Glu Ala Glu Lys Ala Tyr Arg Thr Lys Thr Ala Glu Leu
        530                 535                 540

His Ala Arg Val Lys Val Arg Ile Thr Glu Thr Ile Lys His Glu Asn
545                 550                 555                 560

Gly Lys Leu Thr Thr Glu Thr Lys Met Ile Asp Thr Val Gly Arg
                565                 570                 575

Ala Met Leu Trp Gln Ile Val Pro Lys Gly Leu Pro Tyr Ser Leu Val
                580                 585                 590

Asn Gln Lys Leu Gly Lys Lys Gln Ile Ser Asn Leu Leu Asn Glu Ala
                595                 600                 605

Tyr Arg Lys Leu Gly Leu Lys Asp Thr Val Ile Phe Ala Asp Gln Ile
        610                 615                 620

Met Tyr Thr Gly Phe Ala Tyr Ala Ala Leu Ser Gly Val Ser Val Gly
625                 630                 635                 640

Ile Asp Asp Met Val Val Pro Ala Ala Lys Tyr Thr Glu Ile Ala Glu
                645                 650                 655

Ala Glu Glu Glu Val Arg Glu Ile Gln Glu Gln Phe Gln Ser Gly Leu
                660                 665                 670

Val Thr Ala Gly Glu Arg Tyr Asn Lys Val Ile Asp Ile Trp Ala Ser
        675                 680                 685

Thr Asn Asp Arg Val Ala Lys Ala Met Met Glu Asn Leu Ser Ser Glu
690                 695                 700

Gln Val Ile Asn Arg Gln Gly Glu Gln Glu Lys Gln Glu Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Arg Pro Asp Gly
                740                 745                 750

Ser Ile Ile Glu Thr Pro Ile Thr Ala Asn Phe Lys Glu Gly Leu Asn
        755                 760                 765

Val Leu Gln Tyr Phe Ile Ser Thr His Gly Ala Arg Lys Gly Leu Ala
        770                 775                 780

Asp Thr Ala Leu Lys Thr Ala Asn Ser Gly Tyr Leu Thr Arg Arg Leu
785                 790                 795                 800

Val Asp Val Ala Gln Asp Val Val Thr Glu His Asp Cys Gly Thr
                805                 810                 815

Leu Glu Gly Val Val Met Thr Pro His Ile Glu Gly Gly Asp Val Lys
                820                 825                 830

Val Ala Leu Thr Glu Leu Ala Leu Gly Arg Val Val Ser Glu Asp Ile
        835                 840                 845

Leu Lys Pro Gly Thr Asp Glu Val Leu Ile Pro Arg Asn Thr Leu Leu
        850                 855                 860

Asp Glu Lys Trp Cys Lys Val Ile Asn Asp Asn Ser Val Asp Gln Ile
865                 870                 875                 880

Lys Val Arg Ser Val Val Thr Cys Asp Ser Asp Phe Gly Cys Cys Ala
                885                 890                 895

Gln Cys Tyr Gly Arg Asp Leu Ala Arg Gly His Leu Val Asn Gln Gly
                900                 905                 910

Glu Ala Val Gly Val Ile Ala Ala Gln Ser Ile Gly Glu Pro Gly Thr
        915                 920                 925

Gln Leu Thr Met Arg Thr Phe His Ile Gly Gly Ala Ala Ser Thr Ala
        930                 935                 940
```

```
Ala Ala Glu Asn Ser Ile Gln Ala Lys Asn Asn Gly Ser Val Lys Leu
945                 950                 955                 960

His Asn Ala Lys Phe Val Thr Asn Lys Asp Gly Lys Leu Val Ile Thr
                965                 970                 975

Ser Arg Ala Ser Glu Leu Thr Ile Ile Asp Glu Phe Gly Arg Thr Lys
            980                 985                 990

Glu Lys His Lys Leu Pro Tyr Gly Ser Met Leu Ser Lys Ala Asp Gly
        995                 1000                1005

Asp Ala Val Ala Ala Gly Glu Thr Val Ala Asn Trp Glu Ala His
    1010                1015                1020

Thr Met Pro Ile Ile Thr Glu Val Ala Gly Arg Val Gln Phe Val
    1025                1030                1035

Asp Met Ile Asp Gly Val Thr Val Ser Arg Gln Thr Asp Asp Leu
    1040                1045                1050

Thr Gly Leu Ser Ser Ser Glu Val Thr Glu Ala Ala Ala Arg Pro
    1055                1060                1065

Ala Ala Gly Lys Asp Met Arg Pro Ala Ile Lys Leu Val Asp Ala
    1070                1075                1080

Asn Gly Lys Asp Val Leu Ile Pro Gly Thr Asp Met Pro Ala Gln
    1085                1090                1095

Tyr Phe Leu Pro Gly Lys Ala Ile Val Asn Leu Asp Asp Gly Ala
    1100                1105                1110

Glu Val Asn Val Gly Asp Thr Leu Ala Arg Ile Pro Gln Lys Ser
    1115                1120                1125

Gly Gly Asn Lys Asp Ile Thr Gly Gly Leu Pro Arg Val Ala Asp
    1130                1135                1140

Leu Phe Glu Ala Arg Lys Pro Lys Glu Pro Ala Ile Leu Ala Glu
    1145                1150                1155

His Ser Gly Thr Val Ser Phe Gly Lys Glu Thr Lys Gly Lys Arg
    1160                1165                1170

Arg Leu Ile Ile Thr Arg Asp Ser Gly Asp Thr Tyr Glu Glu Met
    1175                1180                1185

Ile Pro Lys His Arg Gln Leu Asn Val Phe Glu Gly Glu Arg Ile
    1190                1195                1200

Glu Arg Gly Asp Val Ile Ala Asp Gly Pro Glu Ser Pro His Asp
    1205                1210                1215

Ile Leu Arg Leu Arg Gly Ile His Ala Val Thr Thr Tyr Ile Ala
    1220                1225                1230

Asn Glu Val Gln Glu Val Tyr Arg Leu Gln Gly Val Lys Ile Asn
    1235                1240                1245

Asp Lys His Ile Glu Thr Ile Val Arg Gln Met Leu Arg Lys Cys
    1250                1255                1260

Thr Ile Thr Phe Ala Gly Asp Ser Glu Phe Leu Pro Gly Glu Thr
    1265                1270                1275

Val Glu Tyr Ser Gln Val Lys Ile Ala Asn Arg Lys Leu Val Glu
    1280                1285                1290

Glu Gly Lys Glu Pro Ala Arg Phe Glu Arg Glu Leu Leu Gly Ile
    1295                1300                1305

Thr Lys Ala Ser Leu Ala Thr Glu Ser Phe Ile Ser Ala Ala Ser
    1310                1315                1320

Phe Gln Glu Thr Thr Arg Val Leu Thr Glu Ala Ala Val Ser Gly
    1325                1330                1335
```

<210> SEQ ID NO 58
<211> LENGTH: 1407
<212> TYPE: PRT
<213> ORGANISM: Salmonella enterica

<400> SEQUENCE: 58

```
Lys Arg Asp Asp Leu Arg Gly Leu Lys Glu Asn Val Ile Val Gly
    1340                1345                1350

Arg Leu Ile Pro Ala Gly Thr Gly Phe Ala Tyr His Gln Asp Arg
    1355                1360                1365

Gln Ala Lys Arg Ala Gln Glu Gln Gln Gly Pro Ser Ala Glu Gln
    1370                1375                1380

Ala Thr Asp Asn Leu Ala Ala Leu Leu Asn Ala Gly Phe Ser Ser
    1385                1390                1395

Asp Asp Glu
    1400

Met Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
                20                  25                  30

Trp Ser Phe Gly Glu Val Lys Lys Pro Glu Thr Ile Asn Tyr Arg Thr
            35                  40                  45

Phe Lys Pro Glu Arg Asp Gly Leu Phe Cys Ala Arg Ile Phe Gly Pro
        50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
            100                 105                 110

His Ile Trp Phe Leu Lys Ser Leu Pro Ser Arg Ile Gly Leu Leu Leu
        115                 120                 125

Asp Met Pro Leu Arg Asp Ile Glu Arg Val Leu Tyr Phe Glu Ser Tyr
    130                 135                 140

Val Val Ile Glu Gly Gly Met Thr Asn Leu Glu Arg Gln Gln Ile Leu
145                 150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
            180                 185                 190

Asp Leu Glu Gln Glu Cys Glu Thr Leu Arg Glu Glu Leu Asn Glu Thr
        195                 200                 205

Asn Ser Glu Thr Lys Arg Lys Lys Leu Thr Lys Arg Ile Lys Leu Leu
    210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Asp Leu Ala Ala Pro
        275                 280                 285

Asp Ile Ile Val Arg Asn Glu Lys Arg Met Leu Gln Glu Ala Val Asp
    290                 295                 300
```

```
Ala Leu Leu Asp Asn Gly Arg Gly Arg Ala Ile Thr Gly Ser Asn
305                 310                 315                 320

Lys Arg Pro Leu Lys Ser Leu Ala Asp Met Ile Lys Gly Lys Gln Gly
            325                 330                 335

Arg Phe Arg Gln Asn Leu Leu Gly Lys Arg Val Asp Tyr Ser Gly Arg
            340                 345                 350

Ser Val Ile Thr Val Gly Pro Tyr Leu Arg Leu His Gln Cys Gly Leu
            355                 360                 365

Pro Lys Lys Met Ala Leu Glu Leu Phe Lys Pro Phe Ile Tyr Gly Lys
370                 375                 380

Leu Glu Leu Arg Gly Leu Ala Thr Thr Ile Lys Ala Ala Lys Lys Met
385                 390                 395                 400

Val Glu Arg Glu Glu Ala Val Val Trp Asp Ile Leu Asp Val Ile
                405                 410                 415

Arg Glu His Pro Val Leu Leu Asn Arg Ala Pro Thr Leu His Arg Leu
            420                 425                 430

Gly Ile Gln Ala Phe Glu Pro Val Leu Ile Glu Gly Lys Ala Ile Gln
        435                 440                 445

Leu His Pro Leu Val Cys Ala Ala Tyr Asn Ala Asp Phe Asp Gly Asp
    450                 455                 460

Gln Met Ala Val His Val Pro Leu Thr Leu Glu Ala Gln Leu Glu Ala
465                 470                 475                 480

Arg Ala Leu Met Met Ser Thr Asn Asn Ile Leu Ser Pro Ala Asn Gly
                485                 490                 495

Glu Pro Ile Ile Val Pro Ser Gln Asp Val Val Leu Gly Leu Tyr Tyr
            500                 505                 510

Met Thr Arg Asp Cys Val Asn Ala Lys Gly Glu Gly Met Val Leu Thr
            515                 520                 525

Gly Pro Lys Glu Ala Glu Arg Ile Tyr Arg Ala Gly Leu Ala Ser Leu
530                 535                 540

His Ala Arg Val Lys Val Arg Ile Thr Glu Tyr Glu Lys Asp Glu Asn
545                 550                 555                 560

Gly Glu Phe Val Ala His Thr Ser Leu Lys Asp Thr Thr Val Gly Arg
                565                 570                 575

Ala Ile Leu Trp Met Ile Val Pro Lys Gly Leu Pro Phe Ser Ile Val
            580                 585                 590

Asn Gln Ala Leu Gly Lys Lys Ala Ile Ser Lys Met Leu Asn Thr Cys
        595                 600                 605

Tyr Arg Ile Leu Gly Leu Lys Pro Thr Val Ile Phe Ala Asp Gln Thr
    610                 615                 620

Met Tyr Thr Gly Phe Ala Tyr Ala Ala Arg Ser Gly Ala Ser Val Gly
625                 630                 635                 640

Ile Asp Asp Met Val Ile Pro Glu Lys Lys His Glu Ile Ile Ser Glu
                645                 650                 655

Ala Glu Ala Glu Val Ala Glu Ile Gln Glu Gln Phe Gln Ser Gly Leu
            660                 665                 670

Val Thr Ala Gly Glu Arg Tyr Asn Lys Val Ile Asp Ile Trp Ala Ala
            675                 680                 685

Ala Asn Asp Arg Val Ser Lys Ala Met Met Asp Asn Leu Gln Thr Glu
        690                 695                 700

Thr Val Ile Asn Arg Asp Gly Gln Glu Glu Gln Gln Val Ser Phe Asn
705                 710                 715                 720
```

```
Ser Ile Tyr Met Met Ala Asp Ser Gly Ala Arg Gly Ser Ala Ala Gln
            725                 730                 735

Ile Arg Gln Leu Ala Gly Met Arg Gly Leu Met Ala Lys Pro Asp Gly
            740                 745                 750

Ser Ile Ile Glu Thr Pro Ile Thr Ala Asn Phe Arg Glu Gly Leu Asn
            755                 760                 765

Val Leu Gln Tyr Phe Ile Ser Thr His Gly Ala Arg Lys Gly Leu Ala
            770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Cys Gly Thr
                    805                 810                 815

His Glu Gly Ile Leu Met Thr Pro Val Ile Glu Gly Gly Asp Val Lys
            820                 825                 830

Glu Pro Leu Arg Asp Arg Val Leu Gly Arg Val Thr Ala Glu Asp Val
            835                 840                 845

Leu Lys Pro Gly Thr Ala Asp Ile Leu Val Pro Arg Asn Thr Leu Leu
            850                 855                 860

His Glu Gln Trp Cys Asp Leu Leu Glu Ala Asn Ser Val Asp Ala Val
865                 870                 875                 880

Lys Val Arg Ser Val Val Ser Cys Asp Thr Asp Phe Gly Val Cys Ala
                    885                 890                 895

His Cys Tyr Gly Arg Asp Leu Ala Arg Gly His Ile Ile Asn Lys Gly
            900                 905                 910

Glu Ala Ile Gly Val Ile Ala Ala Gln Ser Ile Gly Glu Pro Gly Thr
            915                 920                 925

Gln Leu Thr Met Arg Thr Phe His Ile Gly Gly Ala Ala Ser Arg Ala
            930                 935                 940

Ala Ala Glu Ser Ser Ile Gln Val Lys Asn Lys Gly Ser Ile Lys Leu
945                 950                 955                 960

Ser Asn Val Lys Ser Val Val Asn Ser Ser Gly Lys Leu Val Ile Thr
                    965                 970                 975

Ser Arg Asn Thr Glu Leu Lys Leu Ile Asp Glu Phe Gly Arg Thr Lys
            980                 985                 990

Glu Ser Tyr Lys Val Pro Tyr Gly Ala Val Met Ala Lys Gly Asp Gly
            995                 1000                1005

Glu Gln Val Ala Gly Gly Glu Thr Val Ala Asn Trp Asp Pro His
        1010                1015                1020

Thr Met Pro Val Ile Thr Glu Val Ser Gly Phe Ile Arg Phe Thr
    1025                1030                1035

Asp Met Ile Asp Gly Gln Thr Ile Thr Arg Gln Thr Asp Glu Leu
    1040                1045                1050

Thr Gly Leu Ser Ser Leu Val Val Leu Asp Ser Ala Glu Arg Thr
    1055                1060                1065

Thr Gly Gly Lys Asp Leu Arg Pro Ala Leu Lys Ile Val Asp Ala
    1070                1075                1080

Gln Gly Asn Asp Val Leu Ile Pro Gly Thr Asp Met Pro Ala Gln
    1085                1090                1095

Tyr Phe Leu Pro Gly Lys Ala Ile Val Gln Leu Glu Asp Gly Val
    1100                1105                1110

Gln Ile Ser Ser Gly Asp Thr Leu Ala Arg Ile Pro Gln Glu Ser
    1115                1120                1125

Gly Gly Thr Lys Asp Ile Thr Gly Gly Leu Pro Arg Val Ala Asp
```

```
                    1130                1135               1140
Leu Phe Glu Ala Arg Arg Pro Lys Glu Pro Ala Ile Leu Ala Glu
        1145                1150               1155

Ile Ala Gly Ile Val Ser Phe Gly Lys Glu Thr Lys Gly Lys Arg
        1160                1165               1170

Arg Leu Val Ile Thr Pro Val Asp Gly Ser Asp Pro Tyr Glu Glu
        1175                1180               1185

Met Ile Pro Lys Trp Arg Gln Leu Asn Val Phe Glu Gly Glu Arg
        1190                1195               1200

Val Glu Arg Gly Asp Val Ile Ser Asp Gly Pro Glu Ala Pro His
        1205                1210               1215

Asp Ile Leu Arg Leu Arg Gly Val His Ala Val Thr Arg Tyr Ile
        1220                1225               1230

Val Asn Glu Val Gln Asp Val Tyr Arg Leu Gln Gly Val Lys Ile
        1235                1240               1245

Asn Asp Lys His Ile Glu Val Ile Val Arg Gln Met Leu Arg Lys
        1250                1255               1260

Ala Thr Ile Glu Ser Ala Gly Ser Ser Asp Phe Leu Glu Gly Glu
        1265                1270               1275

Gln Val Glu Tyr Ser Arg Val Lys Ile Ala Asn Arg Glu Leu Glu
        1280                1285               1290

Ala Asn Gly Lys Val Gly Ala Thr Phe Ser Arg Asp Leu Leu Gly
        1295                1300               1305

Ile Thr Lys Ala Ser Leu Ala Thr Glu Ser Phe Ile Ser Ala Ala
        1310                1315               1320

Ser Phe Gln Glu Thr Thr Arg Val Leu Thr Glu Ala Ala Val Ala
        1325                1330               1335

Gly Lys Arg Asp Glu Leu Arg Gly Leu Lys Glu Asn Val Ile Val
        1340                1345               1350

Gly Arg Leu Ile Pro Ala Gly Thr Gly Tyr Ala Tyr His Gln Asp
        1355                1360               1365

Arg Met Arg Arg Arg Ala Ala Gly Glu Gln Pro Ala Thr Pro Gln
        1370                1375               1380

Val Thr Ala Glu Asp Ala Ser Ala Ser Leu Ala Glu Leu Leu Asn
        1385                1390               1395

Ala Gly Leu Gly Gly Ser Asp Asn Glu
        1400                1405

<210> SEQ ID NO 59
<211> LENGTH: 1300
<212> TYPE: PRT
<213> ORGANISM: Actinomyces odontolyticus

<400> SEQUENCE: 59

Met Leu Asp Ala Lys Thr Phe Asp Ser Leu Lys Ile Thr Leu Ala Thr
1               5                   10                  15

Gly Asp Asp Ile Ala Glu Trp Ser His Gly Glu Val Lys Lys Pro Glu
            20                  25                  30

Thr Ile Asn Tyr Arg Thr Leu Lys Pro Glu Arg Asp Gly Leu Phe Gly
        35                  40                  45

Glu Gln Ile Phe Gly Pro Thr Arg Asp Trp Glu Cys Ala Cys Gly Lys
    50                  55                  60

Tyr Lys Arg Val Arg Tyr Lys Gly Ile Val Cys Glu Lys Cys Gly Val
65                  70                  75                  80
```

```
Glu Val Thr Arg Ser Arg Val Arg Arg Glu Arg Met Gly His Ile Asp
             85                  90                  95
Leu Ala Ala Pro Val Thr His Ile Trp Tyr Phe Lys Gly Val Pro Ser
            100                 105                 110
Arg Leu Gly Tyr Val Leu Asn Leu Ala Pro Lys Asp Leu Glu Lys Val
            115                 120                 125
Ile Tyr Phe Ala Ala Tyr Met Ile Thr Glu Val Asp Glu Lys Gly Arg
            130                 135                 140
His Glu Asp Leu Ala Glu Leu Arg Ala Glu Leu Glu Val Gln Lys Lys
145                 150                 155                 160
Gln Met Glu Asn Asn Arg Asp Ala Thr Ile Asn Asp Phe Ala Glu Gln
                165                 170                 175
Leu Glu Ser Asp Met Ala Ala Leu Glu Lys Asp Gly Ala Ser Gln Ala
            180                 185                 190
Glu Arg Glu Arg Ala Arg Lys Gln Gly Glu Arg Glu Met Ala Lys Ile
            195                 200                 205
Arg Arg Arg Phe Asp Gly Asp Ile Glu Gly Leu Glu Ala Val Trp Glu
            210                 215                 220
Arg Phe Lys Asp Leu Lys Val Gly Asp Leu Glu Gly Asp Glu Arg Leu
225                 230                 235                 240
Tyr Arg Ala Met Val Ala Arg Tyr Gly Thr Tyr Phe Lys Gly Asp Met
            245                 250                 255
Gly Ala Ala Ala Ile Gln Lys Arg Leu Glu Thr Phe Asp Leu Glu Ala
            260                 265                 270
Glu Val Ala Ala Leu Arg Gln Thr Ile Gly Ser Asp Ser Gly Pro Arg
            275                 280                 285
Lys Ala Arg Ala Ile Lys Arg Leu Lys Val Ile Asn Ala Phe Val Ala
            290                 295                 300
Thr Gly Asn Ser Pro Ala Ser Met Val Leu Thr Lys Ile Pro Val Ile
305                 310                 315                 320
Pro Pro Asp Leu Arg Pro Met Val Gln Leu Asp Gly Gly Arg Phe Ala
            325                 330                 335
Thr Ser Asp Leu Asn Asp Leu Tyr Arg Arg Val Ile Asn Arg Asn Thr
            340                 345                 350
Arg Leu Lys Arg Leu Leu Glu Leu Gly Ala Pro Glu Ile Ile Val Asn
            355                 360                 365
Asn Glu Lys Arg Met Leu Gln Glu Ser Val Asp Ala Leu Phe Asp Asn
            370                 375                 380
Gly Arg Arg Gly Arg Pro Val Ala Gly Pro Gly Asn Arg Pro Leu Lys
385                 390                 395                 400
Ser Ile Ser Asp Met Leu Lys Gly Lys Gln Gly Arg Phe Arg Gln Asn
            405                 410                 415
Leu Leu Gly Lys Arg Val Asp Tyr Ser Gly Arg Ser Val Ile Val Val
            420                 425                 430
Gly Pro Gln Leu Gln Leu His Gln Cys Gly Leu Pro Lys Gln Met Ala
            435                 440                 445
Leu Glu Leu Phe Lys Pro Phe Val Met Lys Arg Leu Val Glu Lys Asn
            450                 455                 460
Tyr Ala Gln Asn Val Lys Ala Ala Lys Arg Lys Val Glu Arg Gln Arg
465                 470                 475                 480
Pro Glu Val Trp Asp Val Leu Asp Asp Val Ile Arg Glu His Pro Val
            485                 490                 495
Leu Leu Asn Arg Ala Pro Thr Leu His Arg Leu Gly Ile Gln Ala Phe
```

```
            500                 505                 510
Glu Pro Gln Leu Ile Glu Gly Lys Ala Ile Gln Leu His Pro Leu Ala
            515                 520                 525
Cys Gly Ala Phe Asn Ala Asp Phe Asp Gly Asp Gln Met Ala Val His
            530                 535                 540
Leu Pro Leu Gly Ala Glu Ala Gln Ala Glu Ala Arg Ile Leu Met Leu
545                 550                 555                 560
Ser Thr Asn Asn Ile Leu Lys Pro Ser Asp Gly Arg Pro Val Ala Met
                565                 570                 575
Pro Ser Gln Asp Met Ile Ile Gly Leu Phe His Leu Thr Ser Thr Pro
            580                 585                 590
Asp Pro Ser Val Pro Val Glu Lys Asp Glu Asp Gly Asn Pro Val Ile
            595                 600                 605
Pro Tyr Phe Ser Ser Gln Ala Glu Ala Gln Met Ala Tyr Asp Ala Gly
            610                 615                 620
Asn Leu His Leu Asn Ala Thr Ala Arg Ile Arg Phe Ala Asp Gly Thr
625                 630                 635                 640
Val Pro Pro Glu Gly Trp Glu Ala Pro Glu Gly Trp Glu Pro Gly Asp
                645                 650                 655
Glu Leu Ile Leu Glu Thr Ser Leu Gly Arg Ala Ile Phe Asn Glu Gln
            660                 665                 670
Leu Pro Thr Asp Tyr Pro Phe Ile Asn Glu Val Val Gly Lys Lys Gln
            675                 680                 685
Leu Gly Asn Ile Val Asn Thr Leu Thr Gln Arg Tyr Pro Asn Val Leu
            690                 695                 700
Val Ala Asp Cys Leu Asp Ala Leu Lys Ser Ala Gly Phe His Trp Ser
705                 710                 715                 720
Thr Trp Ser Gly Ile Thr Ile Ala Phe Ser Asp Ile Gln Ala Ser Pro
                725                 730                 735
Arg Lys Arg Glu Ile Leu Ala Arg Tyr Glu Ala Lys Ala Ala Glu Ile
            740                 745                 750
Val Glu Gln Phe Glu Thr Gly Ile Ile Leu Glu Glu Thr Arg Tyr Glu
            755                 760                 765
Glu Leu Val Lys Leu Trp Leu Gln Cys Thr Glu Glu Val Ala Asp Asp
            770                 775                 780
Met Arg Ala Asn Phe Asp Glu Arg Asn Thr Val Tyr Arg Met Val Asn
785                 790                 795                 800
Ser Gly Ala Arg Gly Asn Trp Ser Gln Val Gln Gln Ile Ala Gly Met
                805                 810                 815
Arg Gly Leu Val Ser Asp Pro Lys Gln Lys Leu Ile Glu Gln Pro Ile
            820                 825                 830
Lys Ala Asn Tyr Arg Glu Gly Leu Thr Val Leu Glu Tyr Phe Ile Ala
            835                 840                 845
Thr His Gly Ala Arg Lys Gly Leu Val Asp Thr Ala Leu Arg Thr Ala
            850                 855                 860
Glu Ser Gly Tyr Leu Thr Arg Arg Leu Val Asp Val Ser Gln Asp Val
865                 870                 875                 880
Ile Val Arg Glu Gly Asp Cys Gly Thr Arg Ala Gly Leu Lys Ile Asp
                885                 890                 895
Ile Ala His Lys Asn Glu Phe Gly Glu Trp Glu Ala Ser Glu Thr Ile
            900                 905                 910
Glu Thr Thr Ala Tyr Ala Arg Asn Leu Ala Arg Asp Ala Val Asn Glu
            915                 920                 925
```

```
Ala Gly Glu Val Val Met Pro Ala Gly Thr Asp Leu Gly Asp Asp Gln
            930                 935                 940

Leu Ala Glu Leu Val Ala Ala Gly Val Glu Gln Ile Val Cys Arg Ser
945                 950                 955                 960

Val Leu Thr Cys Glu Ser Gln Val Gly Thr Cys Ala Ala Cys Tyr Gly
                965                 970                 975

Arg Ser Leu Ala Thr Gly Lys Gln Val Asp Ile Gly Glu Ala Val Gly
            980                 985                 990

Ile Ile Ala Ala Gln Ser Ile Gly Glu Pro Gly Thr Gln Leu Thr Met
        995                 1000                1005

Arg Thr Phe His Thr Gly Gly Ala Ala Ser Ala Ala Asp Ile Thr
    1010                1015                1020

Gln Gly Leu Pro Arg Val Gln Glu Leu Phe Glu Ala Arg Ser Pro
    1025                1030                1035

Lys Val Glu Ala Lys Met Asn Glu Ala Ala Gly Arg Val His Ile
    1040                1045                1050

Asp Asp Glu Asp Pro Ser Ala Arg Lys Val Val Ile Thr Arg Asp
    1055                1060                1065

Asp Gly Lys Glu Asp Leu Val Ile Glu Val Ser Arg Arg Gln Lys
    1070                1075                1080

Leu Leu Val Ser Glu Gly Gln His Ile Glu Ala Gly Thr Pro Leu
    1085                1090                1095

Thr Glu Gly Gln Leu Asp Pro Lys Glu Ile Leu Arg Ile Met Gly
    1100                1105                1110

Arg Asn Val Ser Gln Lys Met Leu Val Asp Glu Val Gln Lys Val
    1115                1120                1125

Tyr Arg Asp Gln Gly Val Gly Ile His Ala Lys His Ile Glu Val
    1130                1135                1140

Ile Val Arg Gln Met Leu Arg Arg Val Thr Ile Leu Glu Pro Gly
    1145                1150                1155

Asp Thr Thr Phe Met Pro Gly Glu Leu Val Asp Arg Met Ala Tyr
    1160                1165                1170

Leu Thr Gln Asn Arg Arg Val Ala Ala Glu Gly Gly Gln Pro Ala
    1175                1180                1185

Ser Gly Arg Gln Met Leu Met Gly Ile Thr Lys Ala Ser Leu Ala
    1190                1195                1200

Thr Asp Ser Trp Leu Ser Ala Ala Ser Phe Gln Glu Thr Thr Lys
    1205                1210                1215

Val Leu Thr Glu Ala Ala Met Asn Gly Lys Ser Asp Ser Leu Val
    1220                1225                1230

Gly Leu Lys Glu Asn Val Ile Leu Gly Lys Leu Ile Pro Ala Gly
    1235                1240                1245

Thr Gly Leu Ser Arg Tyr Asn Asp Val Ile Val Glu Pro Thr Ala
    1250                1255                1260

Glu Ala Met Ala Asn Ser Asn Tyr Ser Glu Ala Asp Phe Gly Asp
    1265                1270                1275

Gly Ser Val Ser Glu Asp Phe Leu Asp Ala Leu Gly Ala Ile Asp
    1280                1285                1290

Phe Gly Met Asn Phe Arg Glu
    1295                1300

<210> SEQ ID NO 60
<211> LENGTH: 1299
```

```
<212> TYPE: PRT
<213> ORGANISM: Streptomyces coelicolor

<400> SEQUENCE: 60
```

| | | | | | | | | | | | | | | |
|---|---|---|---|---|---|---|---|---|---|---|---|---|---|---|
| Met | Leu | Asp | Val | Asn | Phe | Phe | Asp | Glu | Leu | Arg | Ile | Gly | Leu | Ala | Thr |
| 1 | | | | 5 | | | | | 10 | | | | | 15 | |
| Ala | Asp | Asp | Ile | Arg | Gln | Trp | Ser | His | Gly | Glu | Val | Lys | Lys | Pro | Glu |
| | | | 20 | | | | | 25 | | | | | 30 | | |
| Thr | Ile | Asn | Tyr | Arg | Thr | Leu | Lys | Pro | Glu | Lys | Asp | Gly | Leu | Phe | Cys |
| | | 35 | | | | | 40 | | | | | 45 | | | |
| Glu | Lys | Ile | Phe | Gly | Pro | Thr | Arg | Asp | Trp | Glu | Cys | Tyr | Cys | Gly | Lys |
| | 50 | | | | | 55 | | | | | 60 | | | | |
| Tyr | Lys | Arg | Val | Arg | Phe | Lys | Gly | Ile | Ile | Cys | Glu | Arg | Cys | Gly | Val |
| 65 | | | | | 70 | | | | | 75 | | | | | 80 |
| Glu | Val | Thr | Arg | Ala | Lys | Val | Arg | Glu | Arg | Met | Gly | His | Ile | Glu |
| | | | | 85 | | | | | 90 | | | | | 95 |
| Leu | Ala | Ala | Pro | Val | Thr | His | Ile | Trp | Tyr | Phe | Lys | Gly | Val | Pro | Ser |
| | | | 100 | | | | | 105 | | | | | 110 | | |
| Arg | Leu | Gly | Tyr | Leu | Leu | Asp | Leu | Ala | Pro | Lys | Asp | Leu | Glu | Lys | Val |
| | | 115 | | | | | 120 | | | | | 125 | | | |
| Ile | Tyr | Phe | Ala | Ala | Tyr | Met | Ile | Thr | Phe | Val | Asp | Glu | Glu | Arg | Arg |
| | 130 | | | | | 135 | | | | | 140 | | | | |
| Thr | Arg | Asp | Leu | Pro | Ser | Leu | Glu | Ala | His | Val | Ser | Val | Glu | Arg | Gln |
| 145 | | | | | 150 | | | | | 155 | | | | | 160 |
| Gln | Ile | Glu | Gln | Arg | Arg | Asp | Ser | Asp | Leu | Glu | Ala | Arg | Ala | Lys | Lys |
| | | | | 165 | | | | | 170 | | | | | 175 | |
| Leu | Glu | Thr | Asp | Leu | Ala | Glu | Leu | Glu | Ala | Glu | Gly | Ala | Lys | Ala | Asp |
| | | | 180 | | | | | 185 | | | | | 190 | | |
| Val | Arg | Arg | Lys | Val | Arg | Glu | Gly | Ala | Glu | Arg | Glu | Met | Lys | Gln | Leu |
| | | 195 | | | | | 200 | | | | | 205 | | | |
| Arg | Asp | Arg | Ala | Gln | Arg | Glu | Ile | Asp | Arg | Leu | Asp | Glu | Val | Trp | Asn |
| 210 | | | | | 215 | | | | | 220 | | | | | |
| Arg | Phe | Lys | Asn | Leu | Lys | Val | Gln | Asp | Leu | Glu | Gly | Asp | Glu | Leu | Leu |
| 225 | | | | | 230 | | | | | 235 | | | | | 240 |
| Tyr | Arg | Glu | Leu | Arg | Asp | Arg | Phe | Gly | Thr | Tyr | Phe | Asp | Gly | Ser | Met |
| | | | | 245 | | | | | 250 | | | | | 255 | |
| Gly | Ala | Ala | Ala | Leu | Gln | Lys | Arg | Leu | Glu | Ser | Phe | Asp | Leu | Asp | Glu |
| | | | 260 | | | | | 265 | | | | | 270 | | |
| Glu | Ala | Glu | Arg | Leu | Arg | Glu | Ile | Ile | Arg | Thr | Gly | Lys | Gly | Gln | Lys |
| | | 275 | | | | | 280 | | | | | 285 | | | |
| Lys | Thr | Arg | Ala | Leu | Lys | Arg | Leu | Lys | Val | Val | Ser | Ala | Phe | Leu | Gln |
| | 290 | | | | | 295 | | | | | 300 | | | | |
| Thr | Ser | Asn | Ser | Pro | Lys | Gly | Met | Val | Leu | Asp | Cys | Val | Pro | Val | Ile |
| 305 | | | | | 310 | | | | | 315 | | | | | 320 |
| Pro | Pro | Asp | Leu | Arg | Pro | Met | Val | Gln | Leu | Asp | Gly | Gly | Arg | Phe | Ala |
| | | | | 325 | | | | | 330 | | | | | 335 | |
| Thr | Ser | Asp | Leu | Asn | Asp | Leu | Tyr | Arg | Arg | Val | Ile | Asn | Arg | Asn | Asn |
| | | | 340 | | | | | 345 | | | | | 350 | | |
| Arg | Leu | Lys | Arg | Leu | Leu | Asp | Leu | Gly | Ala | Pro | Glu | Ile | Ile | Val | Asn |
| | | 355 | | | | | 360 | | | | | 365 | | | |
| Asn | Glu | Lys | Arg | Met | Leu | Gln | Glu | Ala | Val | Asp | Ala | Leu | Phe | Asp | Asn |
| | 370 | | | | | 375 | | | | | 380 | | | | |
| Gly | Arg | Arg | Gly | Arg | Pro | Val | Thr | Gly | Pro | Gly | Asn | Arg | Pro | Leu | Lys |
| 385 | | | | | 390 | | | | | 395 | | | | | 400 |

Ser Leu Ser Asp Met Leu Lys Gly Lys Gln Gly Arg Phe Arg Gln Asn
            405                 410                 415

Leu Leu Gly Lys Arg Val Asp Tyr Ser Ala Arg Ser Val Ile Val Val
        420                 425                 430

Gly Pro Gln Leu Lys Leu His Gln Cys Gly Leu Pro Lys Ala Met Ala
            435                 440                 445

Leu Glu Leu Phe Lys Pro Phe Val Met Lys Arg Leu Val Asp Leu Asn
    450                 455                 460

His Ala Gln Asn Ile Lys Ser Ala Lys Arg Met Val Glu Arg Gly Arg
465                 470                 475                 480

Thr Val Val Tyr Asp Val Leu Glu Glu Val Ile Ala Glu His Pro Val
                485                 490                 495

Leu Leu Asn Arg Ala Pro Thr Leu His Arg Leu Gly Ile Gln Ala Phe
            500                 505                 510

Glu Pro Gln Leu Val Glu Gly Lys Ala Ile Gln Ile His Pro Leu Val
        515                 520                 525

Cys Thr Ala Phe Asn Ala Asp Phe Asp Gly Asp Gln Met Ala Val His
    530                 535                 540

Leu Pro Leu Ser Ala Glu Ala Gln Ala Glu Ala Arg Ile Leu Met Leu
545                 550                 555                 560

Ser Ser Asn Asn Ile Leu Lys Pro Ala Asp Gly Arg Pro Val Thr Met
                565                 570                 575

Pro Thr Gln Asp Met Val Leu Gly Leu Phe Phe Leu Thr Thr Asp Ser
            580                 585                 590

Glu Gly Arg Ser Pro Lys Gly Gly Arg Ala Phe Gly Ser Ser Ala
        595                 600                 605

Glu Ala Ile Met Ala Phe Asp Ala Gly Asp Leu Thr Leu Gln Ala Lys
    610                 615                 620

Ile Asp Ile Arg Phe Pro Val Gly Thr Ile Pro Pro Arg Gly Phe Glu
625                 630                 635                 640

Pro Pro Ala Arg Glu Glu Gly Glu Pro Glu Trp Gln Gln Gly Asp Thr
                645                 650                 655

Phe Thr Leu Lys Thr Thr Leu Gly Arg Ala Leu Phe Asn Glu Leu Leu
            660                 665                 670

Pro Glu Asp Tyr Pro Phe Val Asp Tyr Glu Val Gly Lys Lys Gln Leu
        675                 680                 685

Ser Glu Ile Val Asn Asp Leu Ala Glu Arg Tyr Pro Lys Val Ile Val
    690                 695                 700

Ala Ala Thr Leu Asp Asn Leu Lys Ala Ala Gly Phe Phe Trp Ala Thr
705                 710                 715                 720

Arg Ser Gly Val Thr Val Ala Ile Ser Asp Ile Val Val Pro Asp Ala
                725                 730                 735

Lys Lys Glu Ile Val Lys Gly Tyr Glu Gly Gln Asp Glu Lys Val Gln
            740                 745                 750

Lys Gln Tyr Glu Arg Gly Leu Ile Thr Lys Glu Glu Arg Thr Gln Glu
        755                 760                 765

Leu Ile Ala Ile Trp Thr Lys Ala Thr Asn Glu Val Ala Glu Ala Met
    770                 775                 780

Asn Asp Asn Phe Pro Lys Thr Asn Pro Val Ser Met Met Val Asn Ser
785                 790                 795                 800

Gly Ala Arg Gly Asn Met Met Gln Met Arg Gln Ile Ala Gly Met Arg
                805                 810                 815

```
Gly Leu Val Ser Asn Ala Lys Asn Glu Thr Ile Pro Arg Pro Ile Lys
            820                 825                 830

Ala Ser Phe Arg Glu Gly Leu Ser Val Leu Glu Tyr Phe Ile Ser Thr
        835                 840                 845

His Gly Ala Arg Lys Gly Leu Ala Asp Thr Ala Leu Arg Thr Ala Asp
    850                 855                 860

Ser Gly Tyr Leu Thr Arg Arg Leu Val Asp Val Ser Gln Asp Val Ile
865                 870                 875                 880

Ile Arg Glu Glu Asp Cys Gly Thr Glu Arg Gly Leu Lys Leu Pro Ile
                885                 890                 895

Ala Thr Arg Asp Ala Asp Gly Thr Leu Arg Lys Ala Glu Asp Val Glu
            900                 905                 910

Thr Ser Val Tyr Ala Arg Met Leu Ala Glu Asp Val Ile Asp Gly
        915                 920                 925

Lys Val Ile Ala Pro Ala Asn Val Asp Leu Gly Asp Val Leu Ile Asp
    930                 935                 940

Ala Leu Val Ala His Gly Val Glu Glu Val Lys Thr Arg Ser Ile Leu
945                 950                 955                 960

Thr Cys Glu Ser Gln Val Gly Thr Cys Ala Met Cys Tyr Gly Arg Ser
                965                 970                 975

Leu Ala Thr Gly Lys Leu Val Asp Ile Gly Glu Ala Val Gly Ile Ile
            980                 985                 990

Ala Ala Gln Ser Ile Gly Glu Pro Gly Thr Gln Leu Thr Met Arg Thr
        995                 1000                1005

Phe His Thr Gly Gly Val Ala  Gly Asp Asp Ile Thr  Gln Gly Leu
    1010                1015                1020

Pro Arg Val Val Glu Leu Phe  Glu Ala Arg Thr Pro  Lys Gly Val
    1025                1030                1035

Ala Pro Ile Ser Glu Ala Ser  Gly Arg Val Arg Ile  Glu Glu Thr
    1040                1045                1050

Glu Lys Thr Lys Lys Ile Val  Val Thr Pro Asp Asp  Gly Ser Asp
    1055                1060                1065

Glu Thr Ala Phe Pro Ile Ser  Lys Arg Ala Arg Leu  Leu Val Gly
    1070                1075                1080

Glu Gly Asp His Val Glu Val  Gly Gln Lys Leu Thr  Val Gly Ala
    1085                1090                1095

Thr Asn Pro His Asp Val Leu  Arg Ile Leu Gly Gln  Arg Ala Val
    1100                1105                1110

Gln Val His Leu Val Gly Glu  Val Gln Lys Val Tyr  Asn Ser Gln
    1115                1120                1125

Gly Val Ser Ile His Asp Lys  His Ile Glu Ile Ile  Ile Arg Gln
    1130                1135                1140

Met Leu Arg Arg Val Thr Ile  Ile Glu Ser Gly Asp  Ala Glu Leu
    1145                1150                1155

Leu Pro Gly Glu Leu Val Glu  Arg Thr Lys Phe Glu  Thr Glu Asn
    1160                1165                1170

Arg Arg Val Val Gln Glu Gly  Gly His Pro Ala Ser  Gly Arg Pro
    1175                1180                1185

Gln Leu Met Gly Ile Thr Lys  Ala Ser Leu Ala Thr  Glu Ser Trp
    1190                1195                1200

Leu Ser Ala Ala Ser Phe Gln  Glu Thr Thr Arg Val  Leu Thr Asp
    1205                1210                1215

Ala Ala Ile Asn Ala Lys Ser  Asp Ser Leu Ile Gly  Leu Lys Glu
```

```
            1220                1225                1230

Asn Val Ile Ile Gly Lys Leu Ile Pro Ala Gly Thr Gly Leu Ser
        1235                1240                1245

Arg Tyr Arg Asn Ile Arg Val Glu Pro Thr Glu Ala Lys Ala
    1250                1255                1260

Ala Met Tyr Ser Ala Val Gly Tyr Asp Asp Ile Asp Tyr Ser Pro
        1265                1270                1275

Phe Gly Thr Gly Ser Gly Gln Ala Val Pro Leu Glu Asp Tyr Asp
        1280                1285                1290

Tyr Gly Pro Tyr Asn Gln
        1295

<210> SEQ ID NO 61
<211> LENGTH: 1336
<212> TYPE: PRT
<213> ORGANISM: Corynebacterium diphtheriae

<400> SEQUENCE: 61

Met Ile Asp Val Asn Phe Phe Asp Glu Leu Arg Ile Gly Leu Ala Thr
1               5                   10                  15

Ala Asp Asp Ile Arg Arg Trp Ser Lys Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Arg Asp Trp Glu Cys Ala Cys Gly Lys
    50                  55                  60

Tyr Lys Arg Val Arg Tyr Lys Gly Ile Ile Cys Glu Arg Cys Gly Val
65                  70                  75                  80

Glu Val Thr Lys Ser Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Glu Arg Ile
        115                 120                 125

Ile Tyr Phe Ala Ala Asn Ile Ile Thr Ser Val Asp Asp Glu Ala Arg
    130                 135                 140

His Ala Asp Gln Thr Thr Leu Glu Ala Glu Met Leu Leu Glu Lys Lys
145                 150                 155                 160

Asp Val Glu Ala Asp Met Gly Ser Glu Ile Ala Glu Arg Ala Ala Lys
                165                 170                 175

Leu Glu Glu Asp Leu Ala Glu Leu Ala Ala Gly Ala Lys Ala Asp
            180                 185                 190

Ala Arg Asn Lys Val Lys Lys Ala Ala Glu Lys Glu Met Gln His Ile
        195                 200                 205

Arg Glu Arg Ala Glu Arg Glu Ile Asp Arg Leu Glu Glu Ile Trp Gln
    210                 215                 220

Thr Phe Ile Lys Leu Ala Pro Lys Gln Met Ile Asp Glu Thr Ile
225                 230                 235                 240

Tyr Glu Glu Leu Val Asp Arg Tyr Glu Asp Tyr Phe Thr Gly Gly Met
                245                 250                 255

Gly Ala Glu Ala Ile Gln Thr Leu Ile Arg Asn Phe Asp Leu Asp Ser
            260                 265                 270

Glu Ala Glu Glu Leu Arg Glu Ile Ile Asn Asn Gly Lys Gly Gln Lys
        275                 280                 285
```

```
Lys Met Arg Ala Leu Lys Arg Leu Lys Val Val Ala Ala Phe Gln Arg
290                 295                 300

Ser Gly Asn Asp Pro Ala Gly Met Val Leu Asp Cys Ile Pro Val Ile
305                 310                 315                 320

Pro Pro Glu Leu Arg Pro Met Val Gln Leu Asp Gly Gly Arg Phe Ala
            325                 330                 335

Thr Ser Asp Leu Asn Asp Leu Tyr Arg Arg Val Ile Asn Arg Asn Asn
            340                 345                 350

Arg Leu Lys Arg Met Ile Glu Leu Gly Ala Pro Glu Ile Ile Val Asn
        355                 360                 365

Asn Glu Lys Arg Met Leu Gln Glu Ser Val Asp Ala Leu Phe Asp Asn
370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
            405                 410                 415

Leu Leu Gly Lys Arg Val Asp Tyr Ser Gly Arg Ser Val Ile Ile Val
            420                 425                 430

Gly Pro Gln Leu Lys Leu His Glu Cys Gly Leu Pro Lys Leu Met Ala
        435                 440                 445

Leu Glu Leu Phe Lys Pro Phe Val Met Lys Arg Leu Val Glu Asn Asp
450                 455                 460

Tyr Ala Gln Asn Ile Lys Ser Ala Lys Arg Met Val Glu Arg Gln Arg
465                 470                 475                 480

Pro Glu Val Trp Asp Val Leu Glu Glu Ala Ile Ser Glu His Pro Val
            485                 490                 495

Met Leu Asn Arg Ala Pro Thr Leu His Arg Leu Gly Ile Gln Ala Phe
            500                 505                 510

Glu Pro Lys Leu Val Glu Gly Lys Ala Ile Gln Leu His Pro Leu Ala
        515                 520                 525

Cys Glu Ala Phe Asn Ala Asp Phe Asp Gly Asp Gln Met Ala Val His
530                 535                 540

Leu Pro Leu Ser Ala Glu Ala Gln Ala Glu Ala Arg Ile Leu Met Leu
545                 550                 555                 560

Ala Ser Asn Asn Ile Leu Ser Pro Ala Ser Gly Lys Pro Leu Ala Met
            565                 570                 575

Pro Arg Leu Asp Met Val Thr Gly Leu Tyr Tyr Leu Thr Met Asp Lys
            580                 585                 590

Asn Glu Asn Glu Ile Gly Gly Gln Gly Ala Tyr Ala Ser Ala Thr Glu
        595                 600                 605

Glu Gly Pro Ala Gln Gly Val Tyr Ser Ser Tyr Ala Glu Ala Ile Met
610                 615                 620

Ala Arg Asp Arg Gly Val Leu Gly Leu Gln Ala Lys Ile Lys Val Arg
625                 630                 635                 640

Ile Ser His Leu Arg Pro Pro Val Asp Ile Glu Ala Glu Gln Phe Pro
            645                 650                 655

Glu Gly Trp Asn Lys Gly Asp Val Trp Leu Ala Asp Thr Thr Leu Gly
            660                 665                 670

Arg Ile Met Phe Asn Glu Leu Leu Pro Trp Asn Tyr Pro Tyr Leu Glu
        675                 680                 685

Gly Val Met Val Arg Lys Gly Gly Gly Thr Gly Lys Ile Met Leu Gly
690                 695                 700

Asp Val Ile Asn Asp Leu Ala Ala Thr Tyr Pro Met Ile Thr Val Ala
```

```
              705                 710                 715                 720
    Gln Thr Met Asp Lys Met Lys Asp Ala Gly Phe Tyr Trp Ala Thr Arg
                    725                 730                 735
    Ser Gly Val Thr Ile Thr Met Ser Asp Val Leu Val Leu Pro Asn Lys
                    740                 745                 750
    Glu Glu Ile Leu Asp Arg Tyr Glu Ala Glu Ala Arg Lys Ile Glu Arg
                    755                 760                 765
    Lys Tyr Trp Glu Gln Gly Ala Leu Thr Glu Arg Glu Arg Tyr Asp Arg
                    770                 775                 780
    Leu Val Glu Leu Trp Lys Asp Ala Thr Asp Glu Val Gly Asn Ala Val
    785                 790                 795                 800
    Glu Lys Leu Tyr Pro Asp Asn Pro Ile Pro Met Ile Val Lys Ser
                    805                 810                 815
    Gly Ala Ala Gly Asn Met Arg Gln Ile Trp Thr Leu Ala Gly Met Lys
                    820                 825                 830
    Gly Met Val Val Asn Ser Lys Gly Asp Tyr Ile Thr Arg Pro Ile Lys
                    835                 840                 845
    Thr Ser Phe Arg Glu Gly Leu Ser Val Leu Glu Tyr Phe Asn Asn Ser
                    850                 855                 860
    His Gly Ser Arg Lys Gly Leu Ala Asp Thr Ala Leu Arg Thr Ala Asp
    865                 870                 875                 880
    Ser Gly Tyr Leu Thr Arg Arg Leu Val Asp Val Ala Gln Asp Val Ile
                    885                 890                 895
    Val Arg Glu Asp Asp Cys Gly Thr Lys Gln Gly Ile Arg Val Pro Val
                    900                 905                 910
    Ala Val Glu Val Lys Asp Ala Glu Gly Asn Val Thr Gly Tyr Thr Gly
                    915                 920                 925
    His Ser Leu Ile Glu Thr Ser Val Ala Gly Arg Val Ala Ala Thr Ala
                    930                 935                 940
    Val Lys Asp Ala Glu Gly Asn Val Met Val Glu Pro Gly Glu Asn Leu
    945                 950                 955                 960
    Thr Asp Gln Leu Ile Asp Glu Leu Ile Ala Ala Gly Val Lys Glu Val
                    965                 970                 975
    Lys Val Arg Ser Val Leu Thr Cys Gln Thr Pro Thr Gly Val Cys Ala
                    980                 985                 990
    Lys Cys Tyr Gly Lys Ser Met Ala Thr Gly Lys Leu Val Asp Ile Gly
                    995                 1000                1005
    Glu Ala Val Gly Ile Val Ala Ala Gln Ser Ile Gly Glu Pro Gly
                    1010                1015                1020
    Thr Gln Leu Thr Met Arg Thr Phe His Gln Gly Gly Val Gly Gly
                    1025                1030                1035
    Asp Ile Thr Gly Gly Leu Pro Arg Val Gln Glu Leu Phe Glu Ala
                    1040                1045                1050
    Arg Val Pro Lys Asn Arg Ala Pro Ile Ala Ser Val Ala Gly Thr
                    1055                1060                1065
    Val His Leu Asp Asp Glu Gly Asn Phe Tyr Thr Leu Thr Ile Asn
                    1070                1075                1080
    Pro Asp Asp Gly Ser Asp Val Val Val Tyr Glu Lys Leu Ser Lys
                    1085                1090                1095
    Arg Gln Gly Leu Ala Thr Val Arg Val Pro Met Glu Ser Asn Pro
                    1100                1105                1110
    Gly Ala Met Ile Glu Arg Thr Leu Ala Glu Gly Asp His Val Glu
                    1115                1120                1125
```

```
Val Gly Asp Arg Leu Leu Arg Gly Pro Ala Asp Pro His Asp Val
        1130                1135                1140

Leu Glu Val Leu Gly Arg Arg Gly Val Glu Gln His Leu Val Asp
        1145                1150                1155

Glu Val Gln Asp Val Tyr Arg Ala Gln Gly Val Ala Ile His Asp
        1160                1165                1170

Lys His Ile Glu Ile Ile Ile Arg Gln Met Leu Arg Arg Gly Thr
        1175                1180                1185

Val Ile Glu Ser Gly Ser Thr Glu Phe Leu Pro Gly Thr Leu Val
        1190                1195                1200

Asp Leu Ser Glu Ala Lys Ala Ala Asn Ala Glu Ala Leu Ala Asn
        1205                1210                1215

Gly Gly Gln Pro Ala Glu Leu Arg Ser Glu Ile Met Gly Ile Thr
        1220                1225                1230

Lys Ala Ser Leu Ala Thr Glu Ser Trp Leu Ser Ala Ala Ser Phe
        1235                1240                1245

Gln Glu Thr Thr Arg Val Leu Thr Asp Ala Ala Ile Asn Lys Arg
        1250                1255                1260

Ser Asp Lys Leu Ile Gly Leu Lys Glu Asn Val Ile Ile Gly Lys
        1265                1270                1275

Leu Ile Pro Ala Gly Thr Gly Ile Ser Arg Tyr Arg Asn Ile Ser
        1280                1285                1290

Val Lys Pro Thr Glu Ala Ala Arg Asn Ala Ala Tyr Ser Ile Pro
        1295                1300                1305

Thr Tyr Gly Asp Ser Ile Tyr Gly Asp Asp Gly Tyr Gly Glu Phe
        1310                1315                1320

Thr Gly Ala Ser Val Pro Leu Asp Glu Ala Tyr Asp Leu
        1325                1330                1335

<210> SEQ ID NO 62
<211> LENGTH: 1316
<212> TYPE: PRT
<213> ORGANISM: Mycobacterium tuberculosis

<400> SEQUENCE: 62

Met Leu Asp Val Asn Phe Phe Asp Glu Leu Arg Ile Gly Leu Ala Thr
1               5                   10                  15

Ala Glu Asp Ile Arg Gln Trp Ser Tyr Gly Glu Val Lys Lys Pro Glu
                20                  25                  30

Thr Ile Asn Tyr Arg Thr Leu Lys Pro Glu Lys Asp Gly Leu Phe Cys
            35                  40                  45

Glu Lys Ile Phe Gly Pro Thr Arg Asp Trp Glu Cys Tyr Cys Gly Lys
        50                  55                  60

Tyr Lys Arg Val Arg Phe Lys Gly Ile Ile Cys Glu Arg Cys Gly Val
65                  70                  75                  80

Glu Val Thr Arg Ala Lys Val Arg Arg Glu Arg Met Gly His Ile Glu
                85                  90                  95

Leu Ala Ala Pro Val Thr His Ile Trp Tyr Phe Lys Gly Val Pro Ser
            100                 105                 110

Arg Leu Gly Tyr Leu Leu Asp Leu Ala Pro Lys Asp Leu Glu Lys Ile
        115                 120                 125

Ile Tyr Phe Ala Ala Tyr Val Ile Thr Ser Val Asp Glu Glu Met Arg
    130                 135                 140

His Asn Glu Leu Ser Thr Leu Glu Ala Glu Met Ala Val Glu Arg Lys
```

```
            145                 150                 155                 160
        Ala Val Glu Asp Gln Arg Asp Gly Glu Leu Glu Ala Arg Ala Gln Lys
                        165                 170                 175

Leu Glu Ala Asp Leu Ala Glu Leu Glu Ala Glu Gly Ala Lys Ala Asp
                        180                 185                 190

Ala Arg Arg Lys Val Arg Asp Gly Glu Arg Glu Met Arg Gln Ile
                    195                 200                 205

Arg Asp Arg Ala Gln Arg Glu Leu Asp Arg Leu Glu Asp Ile Trp Ser
                        210                 215                 220

Thr Phe Thr Lys Leu Ala Pro Lys Gln Leu Ile Val Asp Glu Asn Leu
        225                 230                 235                 240

Tyr Arg Glu Leu Val Asp Arg Tyr Gly Glu Tyr Phe Thr Gly Ala Met
                            245                 250                 255

Gly Ala Glu Ser Ile Gln Lys Leu Ile Glu Asn Phe Asp Ile Asp Ala
                        260                 265                 270

Glu Ala Glu Ser Leu Arg Asp Val Ile Arg Asn Gly Lys Gly Gln Lys
                        275                 280                 285

Lys Leu Arg Ala Leu Lys Arg Leu Lys Val Val Ala Ala Phe Gln Gln
                        290                 295                 300

Ser Gly Asn Ser Pro Met Gly Met Val Leu Asp Ala Val Pro Val Ile
        305                 310                 315                 320

Pro Pro Glu Leu Arg Pro Met Val Gln Leu Asp Gly Gly Arg Phe Ala
                        325                 330                 335

Thr Ser Asp Leu Asn Asp Leu Tyr Arg Arg Val Ile Asn Arg Asn Asn
                        340                 345                 350

Arg Leu Lys Arg Leu Ile Asp Leu Gly Ala Pro Glu Ile Ile Val Asn
                        355                 360                 365

Asn Glu Lys Arg Met Leu Gln Glu Ser Val Asp Ala Leu Phe Asp Asn
                        370                 375                 380

Gly Arg Arg Gly Arg Pro Val Thr Gly Pro Gly Asn Arg Pro Leu Lys
        385                 390                 395                 400

Ser Leu Ser Asp Leu Leu Lys Gly Lys Gln Gly Arg Phe Arg Gln Asn
                        405                 410                 415

Leu Leu Gly Lys Arg Val Asp Tyr Ser Gly Arg Ser Val Ile Val Val
                        420                 425                 430

Gly Pro Gln Leu Lys Leu His Gln Cys Gly Leu Pro Lys Leu Met Ala
                        435                 440                 445

Leu Glu Leu Phe Lys Pro Phe Val Met Lys Arg Leu Val Asp Leu Asn
                        450                 455                 460

His Ala Gln Asn Ile Lys Ser Ala Lys Arg Met Val Glu Arg Gln Arg
        465                 470                 475                 480

Pro Gln Val Trp Asp Val Leu Glu Glu Val Ile Ala Glu His Pro Val
                        485                 490                 495

Leu Leu Asn Arg Ala Pro Thr Leu His Arg Leu Gly Ile Gln Ala Phe
                        500                 505                 510

Glu Pro Met Leu Val Glu Gly Lys Ala Ile Gln Leu His Pro Leu Val
                        515                 520                 525

Cys Glu Ala Phe Asn Ala Asp Phe Asp Gly Asp Gln Met Ala Val His
                        530                 535                 540

Leu Pro Leu Ser Ala Glu Ala Gln Ala Glu Ala Arg Ile Leu Met Leu
        545                 550                 555                 560

Ser Ser Asn Asn Ile Leu Ser Pro Ala Ser Gly Arg Pro Leu Ala Met
                        565                 570                 575
```

```
Pro Arg Leu Asp Met Val Thr Gly Leu Tyr Leu Thr Thr Glu Val
            580                 585                 590

Pro Gly Asp Thr Gly Glu Tyr Gln Pro Ala Ser Gly Asp His Pro Glu
        595                 600                 605

Thr Gly Val Tyr Ser Ser Pro Ala Glu Ala Ile Met Ala Ala Asp Arg
    610                 615                 620

Gly Val Leu Ser Val Arg Ala Lys Ile Lys Val Arg Leu Thr Gln Leu
625                 630                 635                 640

Arg Pro Pro Val Glu Ile Glu Ala Glu Leu Phe Gly His Ser Gly Trp
                645                 650                 655

Gln Pro Gly Asp Ala Trp Met Ala Glu Thr Thr Leu Gly Arg Val Met
            660                 665                 670

Phe Asn Glu Leu Leu Pro Leu Gly Tyr Pro Phe Val Asn Lys Gln Met
        675                 680                 685

His Lys Lys Val Gln Ala Ala Ile Ile Asn Asp Leu Ala Glu Arg Tyr
    690                 695                 700

Pro Met Ile Val Val Ala Gln Thr Val Asp Lys Leu Lys Asp Ala Gly
705                 710                 715                 720

Phe Tyr Trp Ala Thr Arg Ser Gly Val Thr Val Ser Met Ala Asp Val
                725                 730                 735

Leu Val Pro Pro Arg Lys Lys Glu Ile Leu Asp His Tyr Glu Glu Arg
            740                 745                 750

Ala Asp Lys Val Glu Lys Gln Phe Gln Arg Gly Ala Leu Asn His Asp
        755                 760                 765

Glu Arg Asn Glu Ala Leu Val Glu Ile Trp Lys Glu Ala Thr Asp Glu
    770                 775                 780

Val Gly Gln Ala Leu Arg Glu His Tyr Pro Asp Asp Asn Pro Ile Ile
785                 790                 795                 800

Thr Ile Val Asp Ser Gly Ala Thr Gly Asn Phe Thr Gln Thr Arg Thr
                805                 810                 815

Leu Ala Gly Met Lys Gly Leu Val Thr Asn Pro Lys Gly Glu Phe Ile
            820                 825                 830

Pro Arg Pro Val Lys Ser Ser Phe Arg Glu Gly Leu Thr Val Leu Glu
        835                 840                 845

Tyr Phe Ile Asn Thr His Gly Ala Arg Lys Gly Leu Ala Asp Thr Ala
    850                 855                 860

Leu Arg Thr Ala Asp Ser Gly Tyr Leu Thr Arg Arg Leu Val Asp Val
865                 870                 875                 880

Ser Gln Asp Val Ile Val Arg Glu His Asp Cys Gln Thr Glu Arg Gly
                885                 890                 895

Ile Val Val Glu Leu Ala Glu Arg Ala Pro Asp Gly Thr Leu Ile Arg
            900                 905                 910

Asp Pro Tyr Ile Glu Thr Ser Ala Tyr Ala Arg Thr Leu Gly Thr Asp
        915                 920                 925

Ala Val Asp Glu Ala Gly Asn Val Ile Val Glu Arg Gly Gln Asp Leu
    930                 935                 940

Gly Asp Pro Glu Ile Asp Ala Leu Leu Ala Ala Gly Ile Thr Gln Val
945                 950                 955                 960

Lys Val Arg Ser Val Leu Thr Cys Ala Thr Ser Thr Gly Val Cys Ala
                965                 970                 975

Thr Cys Tyr Gly Arg Ser Met Ala Thr Gly Lys Leu Val Asp Ile Gly
            980                 985                 990
```

```
Glu Ala Val Gly Ile Val Ala Ala Gln Ser Ile Gly Glu Pro Gly Thr
            995                 1000                1005

Gln Leu Thr Met Arg Thr Phe His Gln Gly Gly Val Gly Glu Asp
        1010                1015                1020

Ile Thr Gly Gly Leu Pro Arg Val Gln Glu Leu Phe Glu Ala Arg
        1025                1030                1035

Val Pro Arg Gly Lys Ala Pro Ile Ala Asp Val Thr Gly Arg Val
        1040                1045                1050

Arg Leu Glu Asp Gly Glu Arg Phe Tyr Lys Ile Thr Ile Val Pro
        1055                1060                1065

Asp Asp Gly Gly Glu Glu Val Val Tyr Asp Lys Ile Ser Lys Arg
        1070                1075                1080

Gln Arg Leu Arg Val Phe Lys His Glu Asp Gly Ser Glu Arg Val
        1085                1090                1095

Leu Ser Asp Gly Asp His Val Glu Val Gly Gln Gln Leu Met Glu
        1100                1105                1110

Gly Ser Ala Asp Pro His Glu Val Leu Arg Val Gln Gly Pro Arg
        1115                1120                1125

Glu Val Gln Ile His Leu Val Arg Glu Val Gln Glu Val Tyr Arg
        1130                1135                1140

Ala Gln Gly Val Ser Ile His Asp Lys His Ile Glu Val Ile Val
        1145                1150                1155

Arg Gln Met Leu Arg Arg Val Thr Ile Ile Asp Ser Gly Ser Thr
        1160                1165                1170

Glu Phe Leu Pro Gly Ser Leu Ile Asp Arg Ala Glu Phe Glu Ala
        1175                1180                1185

Glu Asn Arg Arg Val Val Ala Glu Gly Gly Glu Pro Ala Ala Gly
        1190                1195                1200

Arg Pro Val Leu Met Gly Ile Thr Lys Ala Ser Leu Ala Thr Asp
        1205                1210                1215

Ser Trp Leu Ser Ala Ala Ser Phe Gln Glu Thr Thr Arg Val Leu
        1220                1225                1230

Thr Asp Ala Ala Ile Asn Cys Arg Ser Asp Lys Leu Asn Gly Leu
        1235                1240                1245

Lys Glu Asn Val Ile Ile Gly Lys Leu Ile Pro Ala Gly Thr Gly
        1250                1255                1260

Ile Asn Arg Tyr Arg Asn Ile Ala Val Gln Pro Thr Glu Glu Ala
        1265                1270                1275

Arg Ala Ala Ala Tyr Thr Ile Pro Ser Tyr Glu Asp Gln Tyr Tyr
        1280                1285                1290

Ser Pro Asp Phe Gly Ala Ala Thr Gly Ala Ala Val Pro Leu Asp
        1295                1300                1305

Asp Tyr Gly Tyr Ser Asp Tyr Arg
        1310                1315

<210> SEQ ID NO 63
<211> LENGTH: 1319
<212> TYPE: PRT
<213> ORGANISM: Rhodococcus equi

<400> SEQUENCE: 63

Met Leu Asp Val Asn Phe Phe Asp Glu Leu Arg Ile Gly Leu Ala Thr
1               5                   10                  15

Ala Glu Asp Ile Arg Asn Trp Ser Tyr Gly Glu Val Lys Lys Pro Glu
            20                  25                  30
```

```
Thr Ile Asn Tyr Arg Thr Leu Lys Pro Glu Lys Asp Gly Leu Phe Cys
         35                  40                  45

Glu Lys Ile Phe Gly Pro Thr Arg Asp Trp Glu Cys Tyr Cys Gly Lys
 50                  55                  60

Tyr Lys Arg Val Arg Phe Lys Gly Ile Ile Cys Glu Arg Cys Gly Val
 65                  70                  75                  80

Glu Val Thr Arg Ala Lys Val Arg Arg Glu Arg Met Gly His Ile Glu
                 85                  90                  95

Leu Ala Ala Pro Val Thr His Ile Trp Tyr Phe Lys Gly Val Pro Ser
             100                 105                 110

Arg Leu Gly Tyr Leu Leu Asp Leu Ala Pro Lys Asp Leu Glu Lys Ile
         115                 120                 125

Ile Tyr Phe Ala Ala Tyr Val Ile Val Gly Val Asp Glu Glu Leu Arg
         130                 135                 140

His Asn Glu Leu Ser Thr Leu Glu Ala Glu Met Glu Val Glu Lys Lys
145                 150                 155                 160

Thr Val Ala Asp Gln Arg Asp Ala Asp Leu Glu Ala Arg Ala Gln Lys
                 165                 170                 175

Leu Glu Ala Asp Ile Ala Glu Leu Glu Ala Glu Gly Ala Lys Ser Asp
             180                 185                 190

Val Arg Arg Lys Val Lys Asp Gly Gly Glu Arg Glu Met Arg Gln Leu
         195                 200                 205

Arg Asp Arg Ala Gln Arg Glu Leu Asp Arg Leu Asp Glu Ile Trp Thr
         210                 215                 220

Thr Phe Thr Lys Leu Ser Val Lys Gln Leu Ile Val Asp Glu Ser Leu
225                 230                 235                 240

Tyr Arg Glu Leu Val Asp Arg Tyr Gly Glu Tyr Phe Thr Gly Ala Met
                 245                 250                 255

Gly Ala Glu Ser Ile Gln Lys Leu Met Glu Asn Phe Asp Ile Glu Ala
             260                 265                 270

Glu Ala Glu Ser Leu Arg Glu Thr Ile Arg Ser Gly Lys Gly Gln Lys
         275                 280                 285

Lys Leu Arg Ala Leu Lys Arg Leu Lys Val Val Ala Ala Phe Gln Gln
         290                 295                 300

Ser Gly Asn Ser Pro Met Gly Met Val Leu Asp Ala Val Pro Val Ile
305                 310                 315                 320

Pro Pro Glu Leu Arg Pro Met Val Gln Leu Asp Gly Gly Arg Phe Ala
                 325                 330                 335

Thr Ser Asp Leu Asn Asp Leu Tyr Arg Arg Val Ile Asn Arg Asn Asn
             340                 345                 350

Arg Leu Lys Arg Leu Ile Asp Leu Gly Ala Pro Glu Ile Ile Val Asn
         355                 360                 365

Asn Glu Lys Arg Met Leu Gln Glu Ser Val Asp Ala Leu Phe Asp Asn
         370                 375                 380

Gly Arg Arg Gly Arg Pro Val Thr Gly Pro Gly Asn Arg Pro Leu Lys
385                 390                 395                 400

Ser Leu Ser Asp Leu Leu Lys Gly Lys Gln Gly Arg Phe Arg Gln Asn
                 405                 410                 415

Leu Leu Gly Lys Arg Val Asp Tyr Ser Gly Arg Ser Val Ile Val Val
             420                 425                 430

Gly Pro Gln Leu Lys Leu His Gln Cys Gly Leu Pro Lys Leu Met Ala
         435                 440                 445
```

```
Leu Glu Leu Phe Lys Pro Phe Val Met Lys Arg Leu Val Asp Leu Asn
            450                 455                 460
His Ala Gln Asn Ile Lys Ser Ala Lys Arg Met Val Glu Arg Gln Arg
465                 470                 475                 480
Pro Gln Val Trp Asp Val Leu Glu Glu Val Ile Asn Glu His Pro Val
                    485                 490                 495
Leu Leu Asn Arg Ala Pro Thr Leu His Arg Leu Gly Ile Gln Ala Phe
            500                 505                 510
Glu Pro Gln Leu Val Glu Gly Lys Ala Ile Gln Leu His Pro Leu Val
            515                 520                 525
Cys Glu Ala Phe Asn Ala Asp Phe Asp Gly Asp Gln Met Ala Val His
530                 535                 540
Leu Pro Leu Ser Ala Glu Ala Gln Ala Glu Ala Arg Ile Leu Met Leu
545                 550                 555                 560
Ser Ser Asn Asn Ile Leu Ser Pro Ala Ser Gly Arg Pro Leu Ala Met
                565                 570                 575
Pro Arg Leu Asp Met Val Thr Gly Leu Phe His Leu Thr Arg Glu Val
            580                 585                 590
Glu Gly Ala Ile Gly Ala Tyr Gln Pro Ala Ala Asp Gly Gln Pro Glu
            595                 600                 605
Gln Gly Val Tyr Ser Ser Pro Ala Glu Ala Gln Met Ala Val Asp Arg
            610                 615                 620
Gly Val Leu Ser Val Gln Ala Lys Ile Lys Val Arg Leu Thr His Gln
625                 630                 635                 640
Arg Pro Pro Arg Glu Ile Glu Ala Glu Leu Phe Pro Glu Gly Trp Asn
                    645                 650                 655
Phe Gly Asp Gly Trp Met Val Glu Thr Thr Leu Gly Arg Val Met Phe
                660                 665                 670
Asn Asp Leu Leu Pro Ala Asp Tyr Pro Phe Ile Asn Glu Gln Met Pro
            675                 680                 685
Lys Lys Arg Gln Ala Thr Ile Ile Asn Asp Leu Ala Glu Arg Tyr Pro
            690                 695                 700
Met Ile Val Val Ala Gln Thr Val Asp Lys Met Lys Asp Thr Gly Phe
705                 710                 715                 720
Tyr Trp Ala Thr Arg Ser Gly Val Thr Val Ser Ile Ser Asp Val Leu
                    725                 730                 735
Val Pro Pro Glu Lys Ala Gln Ile Met Glu Gln Phe Glu Ala Gln Ala
                740                 745                 750
Asp Gln Ile Glu Lys Lys Tyr Gln Arg Gly Ala Leu Asn His Thr Glu
            755                 760                 765
Arg Asn Ser Ala Leu Val Lys Ile Trp Ser Glu Ala Thr Asp Glu Val
770                 775                 780
Gly Lys Ala Met Glu Ala His Phe Pro Asp Asp Asn Pro Ile Pro Met
785                 790                 795                 800
Ile Val Lys Ser Gly Ala Gly Asn Met Thr Gln Val Arg Ser Leu
                    805                 810                 815
Ala Gly Met Lys Gly Leu Val Thr Asn Pro Lys Gly Glu Phe Ile Pro
                820                 825                 830
Arg Pro Ile Lys Ser Ser Phe Lys Glu Gly Leu Thr Val Leu Glu Tyr
            835                 840                 845
Phe Ile Asn Thr His Gly Ala Arg Lys Gly Leu Ala Asp Thr Ala Leu
            850                 855                 860
Arg Thr Ala Asp Ser Gly Tyr Leu Thr Arg Arg Leu Val Asp Val Ser
```

```
            865                 870                 875                 880
       Gln Asp Val Ile Val Arg Glu Val Asp Cys Gly Thr Glu Arg Gly Ile
                       885                 890                 895

Leu Thr Thr Ile Ala Glu Lys Ala Ala Asp Gly Thr Met Ile Arg Asp
                       900                 905                 910

Ala His Val Glu Thr Ser Thr Tyr Ala Arg Thr Leu Ala Ala Asp Ala
                       915                 920                 925

Ile Asp Glu Asn Gly Asn Val Val Val Glu Arg Gly His Asp Leu Gly
                       930                 935                 940

Asp Pro Ala Ile Asp Ala Leu Leu Ala Ala Gly Ile Thr Gln Val Lys
       945                 950                 955                 960

Val Arg Ser Val Leu Thr Cys Thr Thr Ala Thr Gly Val Cys Ala Thr
                       965                 970                 975

Cys Tyr Gly Arg Ser Met Ala Thr Gly Lys Leu Val Asp Ile Gly Glu
                       980                 985                 990

Ala Val Gly Ile Val Ala Ala Gln Ser Ile Gly Glu Pro Gly Thr Gln
                       995                 1000                1005

Leu Thr Met Arg Thr Phe His Gln Gly Gly Ala Ala  Gly Ala Ala
                       1010                1015                1020

Asp Ile Thr Gly Gly Leu Pro Arg Val Gln Glu Leu  Phe Glu Ala
                       1025                1030                1035

Arg Val Pro Lys Gly Lys Ala Pro Ile Thr Glu Val  Ser Gly Arg
                       1040                1045                1050

Val Gln Leu Asp Asp Asp Arg Phe Tyr Lys Ile  Thr Val Val
                       1055                1060                1065

Pro Asp Asp Gly Gly Glu Glu Val Val Tyr Asp Lys  Leu Ser Lys
                       1070                1075                1080

Arg Gln Arg Leu Arg Val Phe Lys His Asp Asp Gly  Ser Glu Arg
                       1085                1090                1095

Leu Leu Ser Asp Gly Asp His Val Asp Val Gly Gln  Gln Leu Leu
                       1100                1105                1110

Glu Gly Ala Ala Asp Pro His Asp Val Leu Arg Val  Met Gly Pro
                       1115                1120                1125

Arg Gln Val Gln Ile His Leu Val Asn Glu Val Gln  Glu Val Tyr
                       1130                1135                1140

Arg Ser Gln Gly Val Ser Ile His Asp Lys His Ile  Glu Val Ile
                       1145                1150                1155

Val Arg Gln Met Leu Arg Arg Val Thr Ile Ile Asp  Ser Gly Ser
                       1160                1165                1170

Thr Glu Phe Leu Pro Gly Ser Leu Val Glu Arg Ala  Glu Phe Glu
                       1175                1180                1185

Ala Ser Asn Arg Arg Val Val Ala Glu Gly Gly Glu  Pro Ala Ala
                       1190                1195                1200

Gly Arg Pro Val Leu Met Gly Ile Thr Lys Ala Ser  Leu Ala Thr
                       1205                1210                1215

Asp Ser Trp Leu Ser Ala Ala Ser Phe Gln Glu Thr  Thr Arg Val
                       1220                1225                1230

Leu Thr Asp Ala Ala Ile Asn Cys Arg Ser Asp Lys  Leu Ile Gly
                       1235                1240                1245

Leu Lys Glu Asn Val Ile Ile Gly Lys Leu Ile Pro  Ala Gly Thr
                       1250                1255                1260

Gly Ile Asn Arg Tyr Arg Asn Ile Gln Val Gln Pro  Thr Glu Glu
                       1265                1270                1275
```

Ala Arg Ala Ala Ala Tyr Ala Val Pro Ser Tyr Asp Asp Gln Tyr
    1280                1285                1290

Tyr Ser Pro Glu Gly Phe Gly Thr Gly Thr Gly Ala Ala Val Pro
    1295                1300                1305

Leu Asp Asp Tyr Gly Phe Gly Ser Asp Tyr Arg
    1310                1315

<210> SEQ ID NO 64
<211> LENGTH: 1396
<212> TYPE: PRT
<213> ORGANISM: Chlamydia trachomatis

<400> SEQUENCE: 64

Met Phe Arg Glu Gly Ser Arg Asp Asp Ala Ala Leu Val Lys Glu Gly
1               5                   10                  15

Leu Phe Asp Lys Leu Glu Ile Gly Ile Ala Ser Asp Val Thr Ile Arg
                20                  25                  30

Asp Lys Trp Ser Cys Gly Glu Ile Lys Lys Pro Glu Thr Ile Asn Tyr
            35                  40                  45

Arg Thr Phe Lys Pro Glu Lys Gly Gly Leu Phe Cys Glu Lys Ile Phe
        50                  55                  60

Gly Pro Thr Lys Asp Trp Glu Cys Tyr Cys Gly Lys Tyr Lys Lys Ile
65                  70                  75                  80

Lys His Lys Gly Ile Val Cys Asp Arg Cys Gly Val Glu Val Thr Leu
                85                  90                  95

Ser Lys Val Arg Arg Glu Arg Met Ala His Ile Glu Leu Ala Val Pro
            100                 105                 110

Ile Val His Ile Trp Phe Phe Lys Thr Thr Pro Ser Arg Ile Gly Asn
        115                 120                 125

Val Leu Gly Met Thr Ala Ser Asp Leu Glu Arg Val Ile Tyr Tyr Glu
    130                 135                 140

Glu Tyr Val Val Ile Asp Pro Gly Asn Thr Asp Leu Val Lys Lys Gln
145                 150                 155                 160

Leu Leu Asn Asp Ala Lys Tyr Arg Glu Val Val Glu Lys Trp Gly Lys
                165                 170                 175

Asp Ala Phe Val Ala Lys Met Gly Gly Glu Ala Val Tyr Asp Leu Leu
            180                 185                 190

Lys Ser Glu Asp Leu Glu Ser Leu Gly Glu Leu Lys Glu Arg Leu
        195                 200                 205

Arg Lys Thr Lys Ser Gln Gln Ala Arg Met Lys Leu Ala Lys Arg Leu
    210                 215                 220

Lys Ile Val Glu Gly Phe Val Ser Ser Asn Arg Pro Glu Trp Met
225                 230                 235                 240

Val Leu Lys Asn Ile Pro Val Val Pro Pro Asp Leu Arg Pro Leu Val
                245                 250                 255

Pro Leu Asp Gly Gly Arg Phe Ala Thr Ser Asp Leu Asn Asp Leu Tyr
            260                 265                 270

Arg Arg Val Ile Asn Arg Asn Asn Arg Leu Lys Ala Ile Leu Arg Leu
        275                 280                 285

Lys Thr Pro Glu Val Ile Val Arg Asn Glu Lys Arg Met Leu Gln Glu
    290                 295                 300

Ala Val Asp Ala Leu Phe Asp Asn Gly Arg His Gly His Pro Val Met
305                 310                 315                 320

Gly Ala Gly Asn Arg Pro Leu Lys Ser Leu Ser Glu Met Leu Lys Gly

```
            325                 330                 335
Lys Asn Gly Arg Phe Arg Gln Asn Leu Leu Gly Lys Arg Val Asp Tyr
            340                 345                 350

Ser Gly Arg Ser Val Ile Ile Val Gly Pro Glu Leu Lys Phe Asn Gln
            355                 360                 365

Cys Gly Leu Pro Lys Glu Met Ala Leu Glu Leu Phe Glu Pro Phe Ile
            370                 375                 380

Ile Lys Arg Leu Lys Asp Gln Gly Ser Val Tyr Thr Ile Arg Ser Ala
385                 390                 395                 400

Lys Lys Met Ile Gln Arg Gly Ala Pro Glu Val Trp Asp Val Leu Glu
            405                 410                 415

Glu Ile Ile Lys Gly His Pro Val Leu Leu Asn Arg Ala Pro Thr Leu
            420                 425                 430

His Arg Leu Gly Ile Gln Ala Phe Glu Pro Val Leu Ile Glu Gly Lys
            435                 440                 445

Ala Ile Arg Val His Pro Leu Val Cys Ala Ala Phe Asn Ala Asp Phe
            450                 455                 460

Asp Gly Asp Gln Met Ala Val His Val Pro Leu Ser Ile Glu Ala Gln
465                 470                 475                 480

Leu Glu Ala Lys Val Leu Met Met Ala Pro Asp Asn Ile Phe Leu Pro
            485                 490                 495

Ser Ser Gly Lys Pro Val Ala Thr Pro Ser Lys Asp Met Thr Leu Gly
            500                 505                 510

Ile Tyr Tyr Leu Met Ala Asp Pro Thr Tyr Phe Pro Glu Glu His Gly
            515                 520                 525

Gly Lys Thr Lys Ala Phe Lys Asp Glu Val Glu Val Leu Arg Ala Leu
            530                 535                 540

Asn Ala Gly Gly Phe Ile Leu Lys Asp Glu Ile Cys Gly Ser Arg Arg
545                 550                 555                 560

Asp Glu Thr Gly Arg Gly Ile His Ile His Glu Lys Ile Lys Val Arg
            565                 570                 575

Ile Asp Gly Gln Ile Ile Glu Thr Thr Pro Gly Arg Val Phe Phe Asn
            580                 585                 590

Thr Ile Val Pro Lys Glu Leu Gly Phe Gln Asn Tyr Ser Met Pro Ser
            595                 600                 605

Lys Arg Ile Ser Glu Leu Ile Leu Gln Cys Tyr Lys Lys Val Gly Leu
            610                 615                 620

Glu Ala Thr Val Arg Phe Leu Asp Asp Leu Lys Glu Leu Gly Phe Val
625                 630                 635                 640

Gln Ser Thr Lys Ala Ala Ile Ser Met Gly Leu Lys Asp Val Lys Ile
            645                 650                 655

Pro Glu Ile Lys Lys Glu Ile Leu Lys Asp Ala Tyr Asp Lys Val Ala
            660                 665                 670

Val Val Lys Lys Gln Tyr Glu Asp Gly Ile Ile Thr Asp Gly Glu Arg
            675                 680                 685

His Ser Lys Thr Ile Ser Ile Trp Thr Glu Val Ser Asp Leu Leu Ser
            690                 695                 700

Asn Ala Leu Tyr Ser Glu Ile Lys Lys Gln Thr Asn Ser Lys His Asn
705                 710                 715                 720

Pro Leu Phe Leu Met Ile Asp Ser Gly Ala Arg Gly Asn Lys Ser Gln
            725                 730                 735

Leu Lys Gln Leu Gly Ala Leu Arg Gly Leu Met Ala Lys Pro Asn Gly
            740                 745                 750
```

-continued

```
Ala Ile Ile Glu Ser Pro Ile Thr Ser Asn Phe Arg Glu Gly Leu Thr
            755                 760                 765

Val Leu Glu Tyr Ser Ile Ser Ser His Gly Ala Arg Lys Gly Leu Ala
770             775                 780

Asp Thr Ala Leu Lys Thr Ala Asp Ser Gly Tyr Leu Thr Arg Arg Leu
785                 790                 795                 800

Val Asp Val Ala Gln Asp Val Ile Ile Thr Glu Arg Asp Cys Gly Thr
                805                 810                 815

Leu Asn His Ile Glu Val Ser Thr Ile Arg Gln Gly Ser Glu Glu Leu
                820                 825                 830

Leu Pro Leu Lys Asp Arg Val Tyr Gly Arg Thr Val Ser Glu Asn Ile
                835                 840                 845

Tyr Gln Pro Gly Asp Lys Ser Asn Val Leu Ala Tyr Ala Gly Asp Val
850                 855                 860

Leu Thr Ser Ala Gln Ala Glu Ala Ile Asp Asp Ala Gly Ile Glu Ser
865                 870                 875                 880

Val Lys Ile Arg Ser Thr Leu Thr Cys Glu Ser Arg Arg Gly Val Cys
                885                 890                 895

Ala Lys Cys Tyr Gly Leu Asn Leu Ala Asn Gly Arg Leu Ile Gly Leu
                900                 905                 910

Gly Glu Ala Val Gly Ile Ile Ala Ala Gln Ser Ile Gly Glu Pro Gly
                915                 920                 925

Thr Gln Leu Thr Met Arg Thr Phe His Leu Gly Gly Ile Ala Ala Thr
                930                 935                 940

Ser Ser Thr Pro Glu Ile Val Ala Glu Cys Asp Gly Ile Leu Val Tyr
945                 950                 955                 960

Leu Asp Leu Arg Val Val Val Asp Gln Glu Gly Asn Asn Leu Val Leu
                965                 970                 975

Asn Lys Met Gly Ala Leu His Leu Val Gln Asp Glu Gly Arg Ser Leu
                980                 985                 990

Ser Glu Tyr Lys Lys Leu Leu Ser Thr Lys Ser Ile Glu Ser Leu Ala
                995                 1000                1005

Thr Phe Pro Val Glu Leu Gly Ala Lys Ile Leu Val Asn Asp Gly
        1010                1015                1020

Ala Ala Val Ala Ala Gly Gln Arg Ile Ala Glu Val Glu Leu His
        1025                1030                1035

Asn Ile Pro Ile Ile Cys Asp Lys Pro Gly Phe Val His Tyr Glu
        1040                1045                1050

Asp Leu Val Glu Gly Val Ser Thr Glu Lys Val Thr Asn Lys Asn
        1055                1060                1065

Thr Gly Leu Val Glu Leu Ile Val Lys Gln His Arg Gly Glu Leu
        1070                1075                1080

His Pro Gln Ile Ala Ile Tyr Ala Asp Ala Asn Met Lys Glu Leu
        1085                1090                1095

Val Gly Thr Tyr Ala Ile Pro Ser Gly Ala Ile Ile Ser Val Glu
        1100                1105                1110

Glu Gly Gln Arg Ile Ala Pro Gly Met Leu Leu Ala Arg Leu Pro
        1115                1120                1125

Arg Gly Ala Ile Lys Thr Lys Asp Ile Thr Gly Gly Leu Pro Arg
        1130                1135                1140

Val Ala Glu Leu Val Glu Ala Arg Lys Pro Glu Asp Ala Ala Asp
        1145                1150                1155
```

-continued

```
Ile Ala Lys Ile Asp Gly Val Val Asp Phe Lys Gly Ile Gln Lys
    1160                1165                1170

Asn Lys Arg Ile Leu Val Val Arg Asp Glu Ile Thr Gly Met Glu
    1175                1180                1185

Glu Glu His Leu Ile Ser Leu Thr Lys His Leu Ile Val Gln Arg
    1190                1195                1200

Gly Asp Ser Val Ile Lys Gly Gln Gln Leu Thr Asp Gly Leu Val
    1205                1210                1215

Val Pro His Glu Ile Leu Glu Ile Cys Gly Val Arg Glu Leu Gln
    1220                1225                1230

Lys Tyr Leu Val Asn Glu Val Gln Glu Val Tyr Arg Leu Gln Gly
    1235                1240                1245

Val Asp Ile Asn Asp Lys His Val Glu Ile Ile Val Arg Gln Met
    1250                1255                1260

Leu Gln Lys Val Arg Ile Thr Asp Pro Gly Asp Thr Thr Leu Leu
    1265                1270                1275

Phe Gly Glu Asp Val Asp Lys Lys Glu Phe Tyr Glu Glu Asn Arg
    1280                1285                1290

Arg Thr Glu Glu Asp Gly Gly Lys Pro Ala Gln Ala Val Pro Val
    1295                1300                1305

Leu Leu Gly Ile Thr Lys Ala Ser Leu Gly Thr Glu Ser Phe Ile
    1310                1315                1320

Ser Ala Ala Ser Phe Gln Asp Thr Thr Arg Val Leu Thr Asp Ala
    1325                1330                1335

Ala Cys Ser Ser Lys Thr Asp Tyr Leu Leu Gly Phe Lys Glu Asn
    1340                1345                1350

Val Ile Met Gly His Met Ile Pro Gly Gly Thr Gly Phe Asp Thr
    1355                1360                1365

His Lys Arg Ile Lys Gln His Leu Glu Lys Glu Gln Glu Asp Leu
    1370                1375                1380

Val Phe Asp Phe Asp Ser Glu Phe Glu Ser Val Ala Gly
    1385                1390                1395

<210> SEQ ID NO 65
<211> LENGTH: 1178
<212> TYPE: PRT
<213> ORGANISM: Clostridium botulinum

<400> SEQUENCE: 65

Met Phe Glu Leu Asn Asn Phe Asp Ala Leu Gln Ile Gly Leu Ala Ser
1               5                   10                  15

Pro Glu Lys Ile Arg Glu Trp Ser Arg Gly Glu Val Lys Lys Pro Glu
                20                  25                  30

Thr Ile Asn Tyr Arg Thr Leu Lys Pro Glu Arg Asp Gly Leu Phe Cys
            35                  40                  45

Glu Arg Ile Phe Gly Pro Met Lys Asp Trp Glu Cys His Cys Gly Lys
        50                  55                  60

Tyr Lys Arg Ile Arg Tyr Lys Gly Ile Val Cys Asp Arg Cys Gly Val
65                  70                  75                  80

Glu Val Thr Lys Ala Lys Val Arg Arg Glu Arg Met Gly His Ile Glu
                85                  90                  95

Leu Ala Ala Pro Val Ser His Ile Trp Tyr Phe Lys Gly Ile Pro Ser
            100                 105                 110

Arg Met Gly Leu Ile Leu Asp Met Ser Pro Arg Ala Leu Glu Lys Val
        115                 120                 125
```

```
Leu Tyr Phe Ala Ser Tyr Val Leu Asp Pro Lys Glu Thr Pro Leu
    130                 135                 140

Leu Lys Lys Gln Leu Leu Asn Glu Lys Glu Tyr Arg Glu Ser Ile Asp
145                 150                 155                 160

Lys Tyr Gly Asp Asp Ser Phe Val Ala Ala Met Gly Ala Glu Ala Val
                165                 170                 175

Lys Thr Leu Leu Asp Glu Ile Asp Leu Glu Gln Ser Ser Ile Glu Leu
            180                 185                 190

Lys Glu Glu Leu Lys Thr Ser Thr Gly Gln Lys Lys Ile Arg Ile Ile
                195                 200                 205

Arg Arg Leu Glu Val Val Glu Ser Phe Arg Lys Ser Gly Asn Arg Pro
210                 215                 220

Asp Trp Met Val Ile Asp Val Ile Pro Val Ile Pro Pro Asp Leu Arg
225                 230                 235                 240

Pro Met Val Gln Leu Asp Gly Gly Arg Phe Ala Thr Ser Asp Leu Asn
                245                 250                 255

Asp Leu Tyr Arg Arg Val Ile Asn Arg Asn Asn Arg Leu Lys Lys Leu
            260                 265                 270

Leu Asp Leu Gly Ala Pro Asp Ile Ile Val Arg Asn Glu Lys Arg Met
        275                 280                 285

Leu Gln Glu Ala Val Asp Ala Leu Ile Asp Asn Gly Arg Arg Gly Arg
    290                 295                 300

Pro Val Thr Gly Pro Gly Asn Arg Pro Leu Lys Ser Leu Ser Asp Met
305                 310                 315                 320

Leu Lys Gly Lys Gln Gly Arg Phe Arg Gln Asn Leu Leu Gly Lys Arg
                325                 330                 335

Val Asp Tyr Ser Gly Arg Ser Val Ile Val Val Gly Pro Glu Leu Lys
            340                 345                 350

Met Tyr Gln Cys Gly Leu Pro Lys Glu Met Ala Leu Glu Leu Phe Lys
                355                 360                 365

Pro Phe Val Met Lys Lys Leu Val Gln Asn Gly Leu Ala His Asn Ile
370                 375                 380

Lys Ser Ala Lys Arg Met Val Glu Arg Val Gln Pro Gln Val Trp Asp
385                 390                 395                 400

Val Leu Glu Glu Val Ile Ser Asp His Pro Val Leu Leu Asn Arg Ala
                405                 410                 415

Pro Thr Leu His Arg Leu Gly Ile Gln Ala Phe Gln Pro Val Leu Val
            420                 425                 430

Glu Gly Arg Ala Ile Lys Leu His Pro Leu Val Cys Thr Ala Tyr Asn
        435                 440                 445

Ala Asp Phe Asp Gly Asp Gln Met Ala Val His Val Pro Leu Ser Val
    450                 455                 460

Glu Ala Gln Ala Glu Ala Arg Phe Leu Met Leu Ala Ala His Asn Ile
465                 470                 475                 480

Leu Lys Pro Ser Asp Gly Lys Pro Val Ser Val Pro Thr Gln Asp Met
                485                 490                 495

Val Leu Gly Ser Tyr Tyr Leu Thr Met Asp Lys Asp Gly Val Lys Gly
            500                 505                 510

Glu Gly Lys Val Phe Ser Cys Pro Glu Glu Val Leu Met Ala Tyr Gln
        515                 520                 525

Cys Lys Ala Val Asp Ile His Ala Lys Ile Lys Val Arg Leu Lys Lys
    530                 535                 540
```

Val Ile Asp Gly Glu Thr Ile Glu Gly Ile Ile Glu Thr Thr Pro Gly
545                 550                 555                 560

Lys Ile Ile Phe Asn Glu Ser Ile Pro Gln Asp Leu Gly Tyr Ile Asp
            565                 570                 575

Arg Thr Val Pro Glu Asn Lys Leu Lys Leu Glu Val Asp Phe Leu Val
        580                 585                 590

Ser Lys Lys Thr Leu Gly Gly Ile Ile Asn Arg Cys Tyr Met Lys His
    595                 600                 605

Gly Ala Thr Lys Thr Ser Ile Met Leu Asp Lys Ile Lys Ala Lys Gly
610                 615                 620

Tyr His Tyr Ser Thr Ile Gly Ala Ile Thr Ile Ser Thr Ser Asp Met
625                 630                 635                 640

Val Val Pro Glu Ala Lys Arg Glu Leu Leu Gln Asn Thr Glu Lys Gln
            645                 650                 655

Val Glu Lys Ile Gln Lys Met Tyr Arg Arg Gly Phe Ile Ser Glu Glu
        660                 665                 670

Glu Arg Tyr Glu Lys Val Ile Asp Leu Trp Thr Lys Thr Thr Glu Asp
    675                 680                 685

Val Ala Asn Ala Leu Met Ala Ser Leu Asp Ser Phe Asn Pro Ile Tyr
690                 695                 700

Met Met Ala Asp Ser Gly Ala Arg Gly Ser Lys Ser Gln Ile Lys Gln
705                 710                 715                 720

Leu Ala Gly Met Arg Gly Leu Met Ala Asn Pro Ser Gly Lys Ile Ile
            725                 730                 735

Glu Leu Pro Ile Lys Ala Ser Phe Arg Glu Gly Leu Asp Val Leu Glu
        740                 745                 750

Tyr Phe Ile Ser Thr His Gly Ala Arg Lys Gly Asn Ala Asp Thr Ala
    755                 760                 765

Leu Lys Thr Ala Asp Ser Gly Tyr Leu Thr Arg Arg Leu Val Asp Val
770                 775                 780

Ser Gln Asp Val Ile Val Arg Gln Glu Asp Cys Gly Thr Glu Glu Gly
785                 790                 795                 800

Tyr Glu Val Ser Glu Ile Lys Glu Gly Asn Glu Val Ile Glu Pro Leu
            805                 810                 815

Val Glu Arg Leu Ser Gly Arg Tyr Pro Ser Glu Asp Ile Ile Asn Pro
        820                 825                 830

Thr Thr Gly Glu Val Ile Val Lys Arg Asn Thr Tyr Met Asn Glu Asp
    835                 840                 845

Ile Ala Lys Lys Val Ser Asp Ala Gly Ile Lys Lys Val Lys Ile Arg
850                 855                 860

Ser Val Phe Thr Cys Lys Ser Lys His Gly Val Cys Ala Arg Cys Tyr
865                 870                 875                 880

Gly Met Asn Met Ala Thr Ser Gln Lys Ile His Ile Gly Glu Ala Val
            885                 890                 895

Gly Ile Val Ala Ala Gln Ser Ile Gly Glu Pro Gly Thr Gln Leu Thr
        900                 905                 910

Met Arg Thr Phe His Thr Gly Gly Val Ala Gly Ala Asp Ile Thr Gln
    915                 920                 925

Gly Leu Pro Arg Val Glu Glu Leu Phe Glu Ala Arg Lys Pro Lys Gly
930                 935                 940

Leu Ala Ile Val Ser Glu Val Ser Gly Thr Val Lys Met Glu Glu Thr
945                 950                 955                 960

Lys Lys Lys Arg Thr Ile Ile Val Val Thr Asp Asp Gly Glu Glu Val

```
                965                 970                 975
Ser Tyr Asp Ile Pro Phe Gly Ser Arg Ile Lys Val Lys Asn Gly Asp
            980                 985                 990

Ile Ile Ser Ala Gly Asp Glu Ile  Thr Glu Gly Ser Ile  Asn Pro His
            995                 1000                1005

Asp Ile Leu Arg Ile Lys Gly  Val Asp Gly Val Lys  Asn Tyr Leu
            1010                1015                1020

Leu Ser Glu Val Gln Lys Val  Tyr Arg Leu Gln Gly  Val Asp Ile
            1025                1030                1035

Asn Asp Lys His Leu Glu Val  Val Ile Arg Gln Met  Thr Arg Lys
            1040                1045                1050

Ile Lys Ile Glu Asp Ser Gly  Asp Thr Glu Leu Leu  Pro Gly Thr
            1055                1060                1065

Met Ile Asp Val Phe Asp Phe  Glu Glu Ala Asn Arg  Glu Ile Leu
            1070                1075                1080

Glu Lys Gly Gly Glu Pro Ala  Val Gly Arg Ile Ala  Leu Leu Gly
            1085                1090                1095

Ile Thr Lys Ala Ala Leu Ala  Thr Asp Ser Phe Leu  Ser Ala Ala
            1100                1105                1110

Ser Phe Gln Glu Thr Thr Arg  Val Leu Thr Asp Ala  Ala Ile Lys
            1115                1120                1125

Gly Lys Ile Asp Pro Leu Leu  Gly Leu Lys Glu Asn  Val Ile Ile
            1130                1135                1140

Gly Lys Leu Ile Pro Ala Gly  Thr Gly Met Thr Arg  Tyr Arg Ser
            1145                1150                1155

Ile Gln Ile Asn Thr Asp Asp  Glu Asn Ile Glu Glu  Asp Ser Met
            1160                1165                1170

Asp Ser Ile Glu Val
        1175

<210> SEQ ID NO 66
<211> LENGTH: 1199
<212> TYPE: PRT
<213> ORGANISM: Bacillus subtilis

<400> SEQUENCE: 66

Met Leu Asp Val Asn Asn Phe Glu Tyr Met Asn Ile Gly Leu Ala Ser
1               5                   10                  15

Pro Asp Lys Ile Arg Ser Trp Ser Phe Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Lys Asp Trp Glu Cys His Cys Gly Lys
    50                  55                  60

Tyr Lys Arg Val Arg Tyr Lys Gly Val Val Cys Asp Arg Cys Gly Val
65                  70                  75                  80

Glu Val Thr Arg Ala Lys Val Arg Arg Glu Arg Met Gly His Ile Glu
                85                  90                  95

Leu Ala Ala Pro Val Ser His Ile Trp Tyr Phe Lys Gly Ile Pro Ser
            100                 105                 110

Arg Met Gly Leu Val Leu Asp Met Ser Pro Arg Ala Leu Glu Glu Val
        115                 120                 125

Ile Tyr Phe Ala Ser Tyr Val Val Thr Asp Pro Ala Asn Thr Pro Leu
    130                 135                 140
```

-continued

| | | | | | | | | | | | |
|---|---|---|---|---|---|---|---|---|---|---|---|
|Glu|Lys|Lys|Gln|Leu|Leu|Ser|Glu|Lys|Glu|Tyr|Arg|Ala|Tyr|Leu|Asp|
|145| | | | |150| | | | |155| | | | |160|

Lys Tyr Gly Asn Lys Phe Gln Ala Ser Met Gly Ala Glu Ala Ile His
                165                 170                 175

Lys Leu Leu Gln Asp Ile Asp Leu Val Lys Glu Val Asp Met Leu Lys
            180                 185                 190

Glu Glu Leu Lys Thr Ser Gln Gly Gln Arg Thr Arg Ala Ile Lys
        195                 200                 205

Arg Leu Glu Val Leu Glu Ala Phe Arg Asn Ser Gly Asn Lys Pro Ser
    210                 215                 220

Trp Met Ile Leu Asp Val Leu Pro Val Ile Pro Pro Glu Leu Arg Pro
225                 230                 235                 240

Met Val Gln Leu Asp Gly Gly Arg Phe Ala Thr Ser Asp Leu Asn Asp
                245                 250                 255

Leu Tyr Arg Arg Val Ile Asn Arg Asn Asn Arg Leu Lys Arg Leu Leu
            260                 265                 270

Asp Leu Gly Ala Pro Ser Ile Ile Val Gln Asn Glu Lys Arg Met Leu
        275                 280                 285

Gln Glu Ala Val Asp Ala Leu Ile Asp Asn Gly Arg Arg Gly Arg Pro
    290                 295                 300

Val Thr Gly Pro Gly Asn Arg Pro Leu Lys Ser Leu Ser His Met Leu
305                 310                 315                 320

Lys Gly Lys Gln Gly Arg Phe Arg Gln Asn Leu Leu Gly Lys Arg Val
                325                 330                 335

Asp Tyr Ser Gly Arg Ser Val Ile Val Val Gly Pro His Leu Lys Met
            340                 345                 350

Tyr Gln Cys Gly Leu Pro Lys Glu Met Ala Leu Glu Leu Phe Lys Pro
        355                 360                 365

Phe Val Met Lys Glu Leu Val Glu Lys Gly Leu Ala His Asn Ile Lys
    370                 375                 380

Ser Ala Lys Arg Lys Ile Glu Arg Val Gln Pro Glu Val Trp Asp Val
385                 390                 395                 400

Leu Glu Ser Val Ile Lys Glu His Pro Val Leu Leu Asn Arg Ala Pro
                405                 410                 415

Thr Leu His Arg Leu Gly Ile Gln Ala Phe Glu Pro Thr Leu Val Glu
            420                 425                 430

Gly Arg Ala Ile Arg Leu His Pro Leu Val Cys Thr Ala Tyr Asn Ala
        435                 440                 445

Asp Phe Asp Gly Asp Gln Met Ala Val His Val Pro Leu Ser Ala Glu
    450                 455                 460

Ala Gln Ala Glu Ala Arg Ile Leu Met Leu Ala Ala Gln Asn Ile Leu
465                 470                 475                 480

Asn Pro Lys Asp Gly Lys Pro Val Val Thr Pro Ser Gln Asp Met Val
                485                 490                 495

Leu Gly Asn Tyr Tyr Leu Thr Leu Glu Arg Ala Gly Ala Val Gly Glu
            500                 505                 510

Gly Met Val Phe Lys Asn Thr Asp Glu Ala Leu Leu Ala Tyr Gln Asn
        515                 520                 525

Gly Tyr Val His Leu His Thr Arg Val Ala Val Ala Ala Asn Ser Leu
    530                 535                 540

Lys Asn Val Thr Phe Thr Glu Glu Gln Arg Ser Lys Leu Leu Ile Thr
545                 550                 555                 560

Thr Val Gly Lys Leu Val Phe Asn Glu Ile Leu Pro Glu Ser Phe Pro

-continued

```
                565                 570                 575
Tyr Met Asn Glu Pro Thr Lys Ser Asn Ile Glu Glu Lys Thr Pro Asp
            580                 585                 590
Arg Phe Phe Leu Glu Lys Gly Ala Asp Val Lys Ala Val Ile Ala Gln
            595                 600                 605
Gln Pro Ile Asn Ala Pro Phe Lys Lys Gly Ile Leu Gly Lys Ile Ile
    610                 615                 620
Ala Glu Ile Phe Lys Arg Phe His Ile Thr Glu Thr Ser Lys Met Leu
625                 630                 635                 640
Asp Arg Met Lys Asn Leu Gly Phe Lys Tyr Ser Thr Lys Ala Gly Ile
                645                 650                 655
Thr Val Gly Val Ser Asp Ile Val Val Leu Asp Asp Lys Gln Glu Ile
            660                 665                 670
Leu Glu Glu Ala Gln Ser Lys Val Asp Asn Val Met Lys Gln Phe Arg
            675                 680                 685
Arg Gly Leu Ile Thr Glu Glu Arg Tyr Glu Arg Val Ile Ser Ile
            690                 695                 700
Trp Ser Ala Ala Lys Asp Val Ile Gln Gly Lys Leu Met Lys Ser Leu
705                 710                 715                 720
Asp Glu Leu Asn Pro Ile Tyr Met Met Ser Asp Ser Gly Ala Arg Gly
                725                 730                 735
Asn Ala Ser Asn Phe Thr Gln Leu Ala Gly Met Arg Gly Leu Met Ala
            740                 745                 750
Asn Pro Ala Gly Arg Ile Ile Glu Leu Pro Ile Lys Ser Ser Phe Arg
            755                 760                 765
Glu Gly Leu Thr Val Leu Glu Tyr Phe Ile Ser Thr His Gly Ala Arg
            770                 775                 780
Lys Gly Leu Ala Asp Thr Ala Leu Lys Thr Ala Asp Ser Gly Tyr Leu
785                 790                 795                 800
Thr Arg Arg Leu Val Asp Val Ala Gln Asp Val Ile Ile Arg Glu Thr
                805                 810                 815
Asp Cys Gly Thr Asp Arg Gly Ile Leu Ala Lys Pro Leu Lys Glu Gly
            820                 825                 830
Thr Glu Thr Ile Glu Arg Leu Glu Glu Arg Leu Ile Gly Arg Phe Ala
            835                 840                 845
Arg Lys Gln Val Lys His Pro Glu Thr Gly Glu Val Leu Val Asn Glu
            850                 855                 860
Asn Glu Leu Ile Asp Glu Asp Lys Ala Leu Glu Ile Val Glu Ala Gly
865                 870                 875                 880
Ile Glu Glu Val Trp Ile Arg Ser Ala Phe Thr Cys Asn Thr Pro His
                885                 890                 895
Gly Val Cys Lys Arg Cys Tyr Gly Arg Asn Leu Ala Thr Gly Ser Asp
            900                 905                 910
Val Glu Val Gly Glu Ala Val Gly Ile Ile Ala Ala Gln Ser Ile Gly
            915                 920                 925
Glu Pro Gly Thr Gln Leu Thr Met Arg Thr Phe His Thr Gly Gly Val
            930                 935                 940
Ala Gly Asp Asp Ile Thr Gln Gly Leu Pro Arg Ile Gln Glu Leu Phe
945                 950                 955                 960
Glu Ala Arg Asn Pro Lys Gly Gln Ala Thr Ile Thr Glu Ile Asp Gly
                965                 970                 975
Thr Val Val Glu Ile Asn Glu Val Arg Asp Lys Gln Gln Glu Ile Val
            980                 985                 990
```

```
Val Gln Gly Ala Val Glu Thr Arg Ser Tyr Thr Ala Pro Tyr Asn Ser
            995                 1000                1005

Arg Leu Lys Val Ala Glu Gly Asp Lys Ile Thr Arg Gly Gln Val
    1010                1015                1020

Leu Thr Glu Gly Ser Ile Asp Pro Lys Glu Leu Leu Lys Val Thr
    1025                1030                1035

Asp Leu Thr Thr Val Gln Glu Tyr Leu Leu His Glu Val Gln Lys
    1040                1045                1050

Val Tyr Arg Met Gln Gly Val Glu Ile Gly Asp Lys His Val Glu
    1055                1060                1065

Val Met Val Arg Gln Met Leu Arg Lys Val Arg Val Ile Asp Ala
    1070                1075                1080

Gly Asp Thr Asp Val Leu Pro Gly Thr Leu Leu Asp Ile His Gln
    1085                1090                1095

Phe Thr Glu Ala Asn Lys Lys Val Leu Leu Glu Gly Asn Arg Pro
    1100                1105                1110

Ala Thr Gly Arg Pro Val Leu Leu Gly Ile Thr Lys Ala Ser Leu
    1115                1120                1125

Glu Thr Asp Ser Phe Leu Ser Ala Ala Ser Phe Gln Glu Thr Thr
    1130                1135                1140

Arg Val Leu Thr Asp Ala Ala Ile Lys Gly Lys Arg Asp Glu Leu
    1145                1150                1155

Leu Gly Leu Lys Glu Asn Val Ile Ile Gly Lys Leu Val Pro Ala
    1160                1165                1170

Gly Thr Gly Met Met Lys Tyr Arg Lys Val Lys Pro Val Ser Asn
    1175                1180                1185

Val Gln Pro Thr Asp Asp Met Val Pro Val Glu
    1190                1195

<210> SEQ ID NO 67
<211> LENGTH: 1225
<212> TYPE: PRT
<213> ORGANISM: Streptococcus pneumoniae

<400> SEQUENCE: 67

Met Val Asp Val Asn Arg Phe Lys Ser Met Gln Ile Thr Leu Ala Ser
1               5                   10                  15

Pro Ser Lys Val Arg Ser Trp Ser Tyr Gly Glu Val Lys Lys Pro Glu
            20                  25                  30

Thr Ile Asn Tyr Arg Thr Leu Lys Pro Glu Arg Glu Gly Leu Phe Asp
        35                  40                  45

Glu Val Ile Phe Gly Pro Thr Lys Asp Trp Glu Cys Ala Cys Gly Lys
    50                  55                  60

Tyr Lys Arg Ile Arg Tyr Arg Gly Ile Val Cys Asp Arg Cys Gly Val
65                  70                  75                  80

Glu Val Thr Arg Thr Lys Val Arg Arg Glu Arg Met Gly His Ile Glu
                85                  90                  95

Leu Lys Ala Pro Val Ser His Ile Trp Tyr Phe Lys Gly Ile Pro Ser
            100                 105                 110

Arg Met Gly Leu Thr Leu Asp Met Ser Pro Arg Ala Leu Glu Glu Val
        115                 120                 125

Ile Tyr Phe Ala Ala Tyr Val Val Ile Asp Pro Lys Asp Thr Pro Leu
    130                 135                 140

Glu His Lys Ser Ile Met Thr Glu Arg Glu Tyr Arg Glu Arg Leu Arg
```

```
                145                 150                 155                 160
        Glu Tyr Gly Tyr Gly Ser Phe Val Ala Lys Met Gly Glu Ala Ile
                        165                 170                 175

Gln Asp Leu Leu Lys Gln Val Asp Leu Glu Lys Glu Ile Ala Glu Leu
                        180                 185                 190

Lys Glu Glu Leu Lys Thr Ala Thr Gly Gln Lys Arg Val Lys Ala Ile
                        195                 200                 205

Arg Arg Leu Asp Val Leu Asp Ala Phe Tyr Lys Ser Gly Asn Lys Pro
                210                 215                 220

Glu Trp Met Ile Leu Asn Ile Leu Pro Val Ile Pro Pro Asp Leu Arg
        225                 230                 235                 240

Pro Met Leu Gln Leu Asp Gly Gly Arg Phe Ala Ser Ser Asp Leu Asn
                        245                 250                 255

Asp Leu Tyr Arg Arg Val Ile Asn Arg Asn Asn Arg Leu Ala Arg Leu
                        260                 265                 270

Leu Glu Leu Asn Ala Pro Gly Ile Ile Val Gln Asn Glu Lys Arg Met
                        275                 280                 285

Leu Gln Glu Ala Val Asp Ala Leu Ile Asp Asn Gly Arg Arg Gly Arg
                        290                 295                 300

Pro Ile Thr Gly Pro Gly Ser Arg Pro Leu Lys Ser Leu Ser His Met
        305                 310                 315                 320

Leu Lys Gly Lys Gln Gly Arg Phe Arg Gln Asn Leu Leu Gly Lys Arg
                        325                 330                 335

Val Asp Phe Ser Gly Arg Ser Val Ile Ala Val Gly Pro Thr Leu Lys
                        340                 345                 350

Met Tyr Gln Cys Gly Val Pro Arg Glu Met Ala Ile Glu Leu Phe Lys
                        355                 360                 365

Pro Phe Val Met Arg Glu Ile Val Ala Arg Asp Ile Val Gln Asn Val
                        370                 375                 380

Lys Ala Ala Lys Arg Leu Val Glu Arg Gly Asp Glu Arg Ile Trp Asp
        385                 390                 395                 400

Ile Leu Glu Glu Val Ile Lys Glu His Pro Val Leu Leu Asn Arg Ala
                        405                 410                 415

Pro Thr Leu His Arg Leu Gly Ile Gln Ala Phe Glu Pro Val Leu Ile
                        420                 425                 430

Asp Gly Lys Ala Leu Arg Leu His Pro Leu Val Cys Glu Ala Tyr Asn
                        435                 440                 445

Ala Asp Phe Asp Gly Asp Gln Met Ala Ile His Val Pro Leu Ser Glu
                450                 455                 460

Glu Ala Gln Ala Glu Ala Arg Ile Leu Met Leu Ala Ala Glu His Ile
        465                 470                 475                 480

Leu Asn Pro Lys Asp Gly Lys Pro Val Val Thr Pro Ser Gln Asp Met
                        485                 490                 495

Val Leu Gly Asn Tyr Tyr Leu Thr Met Glu Glu Ala Gly Arg Glu Gly
                        500                 505                 510

Glu Gly Met Val Phe Lys Asp Arg Asp Glu Ala Val Met Ala Tyr Arg
                        515                 520                 525

Asn Gly Tyr Val His Leu His Ser Arg Val Gly Ile Ala Thr Asp Ser
                        530                 535                 540

Leu Asn Lys Pro Trp Thr Glu Glu Gln Arg His Lys Val Leu Leu Thr
        545                 550                 555                 560

Thr Val Gly Lys Ile Leu Phe Asn Asp Ile Met Pro Glu Gly Leu Pro
                        565                 570                 575
```

```
Tyr Leu Gln Glu Pro Asn Asn Ala Asn Leu Thr Glu Gly Val Pro Ala
            580                 585                 590

Lys Tyr Phe Leu Pro Leu Gly Gly Asp Ile Lys Glu Ala Ile Ser Asn
        595                 600                 605

Leu Glu Leu Asn Pro Pro Phe Lys Lys Asn Leu Gly Asn Ile Ile
610                 615                 620

Ala Glu Ile Phe Lys Arg Phe Arg Thr Thr Glu Thr Ser Ala Leu Leu
625                 630                 635                 640

Asp Arg Met Lys Asn Leu Gly Tyr His His Ser Thr Leu Ala Gly Leu
                645                 650                 655

Thr Val Gly Ile Ala Asp Ile Pro Val Val Asp Lys Ala Glu Ile
            660                 665                 670

Ile Glu Glu Ser His Lys Arg Val Glu Gln Ile Thr Lys Gln Phe Arg
        675                 680                 685

Arg Gly Met Ile Thr Asp Asp Glu Arg Tyr Asn Ala Val Thr Ala Glu
    690                 695                 700

Trp Arg Ala Ala Arg Glu Lys Leu Glu Lys Arg Leu Ile Ala Asn Gln
705                 710                 715                 720

Asp Pro Lys Asn Pro Ile Val Met Met Asp Ser Gly Ala Arg Gly
                725                 730                 735

Asn Ile Ser Asn Phe Ser Gln Leu Ala Gly Met Arg Gly Leu Met Ala
                740                 745                 750

Ala Pro Asn Gly Arg Ile Met Glu Leu Pro Ile Leu Ser Asn Phe Arg
            755                 760                 765

Glu Gly Leu Ser Val Leu Glu Met Phe Phe Ser Thr His Gly Ala Arg
        770                 775                 780

Lys Gly Met Thr Asp Thr Ala Leu Lys Thr Ala Asp Ser Gly Tyr Leu
785                 790                 795                 800

Thr Arg Arg Leu Val Asp Val Ala Gln Asp Val Ile Ile Arg Glu Asp
                805                 810                 815

Asp Cys Gly Thr Asp Arg Gly Leu Leu Ile Arg Ser Ile Ala Glu Gly
            820                 825                 830

Lys Glu Met Ile Glu Ser Leu Glu Glu Arg Leu Asn Gly Arg Tyr Thr
        835                 840                 845

Lys Lys Thr Val Lys His Pro Glu Thr Gly Ala Val Ile Ile Gly Pro
    850                 855                 860

Asn Glu Leu Ile Thr Glu Asp Lys Ala Arg Glu Ile Val Asn Ala Gly
865                 870                 875                 880

Val Glu Glu Val Thr Ile Arg Ser Val Phe Thr Cys Asn Thr Arg His
                885                 890                 895

Gly Val Cys Arg His Cys Tyr Gly Ile Asn Leu Ala Thr Gly Asp Ala
            900                 905                 910

Val Glu Val Gly Glu Ala Val Gly Thr Ile Ala Ala Gln Ser Ile Gly
        915                 920                 925

Glu Pro Gly Thr Gln Leu Thr Met Arg Thr Phe His Thr Gly Gly Val
    930                 935                 940

Ala Ser Asn Thr Asp Ile Thr Gln Gly Leu Pro Arg Val Gln Glu Ile
945                 950                 955                 960

Phe Glu Ala Arg Asn Pro Lys Gly Glu Ala Val Ile Thr Glu Val Lys
                965                 970                 975

Gly Gln Val Thr Ala Ile Glu Glu Asp Ala Ser Thr Arg Thr Lys Lys
            980                 985                 990
```

-continued

```
Val Phe Val Lys Gly Glu Thr Gly Glu Gly Glu Tyr Val Val Pro Phe
        995                 1000                1005

Thr Ala Arg Met Arg Val Glu Val Gly Gly Gln Val Ala Arg Gly
        1010                1015                1020

Ala Ala Leu Thr Glu Gly Ser Ile Gln Pro Lys Arg Leu Leu Ala
        1025                1030                1035

Val Arg Asp Val Leu Ser Val Glu Thr Tyr Leu Leu Gly Glu Val
        1040                1045                1050

Gln Lys Val Tyr Arg Ser Gln Gly Val Glu Ile Gly Asp Lys His
        1055                1060                1065

Ile Glu Val Met Val Arg Gln Met Ile Arg Lys Val Arg Val Met
        1070                1075                1080

Asp Pro Gly Asp Thr Asp Leu Leu Met Gly Thr Leu Met Asp Ile
        1085                1090                1095

Asn Asp Phe Thr Asp Ala Asn Lys Asp Val Leu Ile Ala Gly Gly
        1100                1105                1110

Val Pro Ala Thr Gly Arg Pro Val Leu Met Gly Ile Thr Lys Ala
        1115                1120                1125

Ser Leu Glu Thr Asn Ser Phe Leu Ser Ala Ala Ser Phe Gln Glu
        1130                1135                1140

Thr Thr Arg Val Leu Thr Asp Ala Ala Ile Arg Gly Lys Lys Asp
        1145                1150                1155

His Leu Leu Gly Leu Lys Glu Asn Val Ile Ile Gly Lys Ile Ile
        1160                1165                1170

Pro Ala Gly Thr Gly Met Ala Arg Tyr Arg Asn Leu Glu Pro His
        1175                1180                1185

Ala Val Asn Glu Glu Glu Tyr Leu Asn Pro Pro Val Glu Glu Glu
        1190                1195                1200

Gly Asn Glu Glu Thr Thr Glu Val Val Asp Thr Ala Val Glu
        1205                1210                1215

Thr Val Glu Glu Thr Val Glu
        1220                1225

<210> SEQ ID NO 68
<211> LENGTH: 1217
<212> TYPE: PRT
<213> ORGANISM: Enterococcus faecalis

<400> SEQUENCE: 68

Met Ile Asp Val Asn Lys Phe Glu Ser Met Gln Ile Gly Leu Ala Ser
1               5                   10                  15

Pro Glu Lys Ile Arg Ser Trp Ser Tyr Gly Glu Val Lys Lys Pro Glu
                20                  25                  30

Thr Ile Asn Tyr Arg Thr Leu Lys Pro Glu Arg Glu Gly Leu Phe Cys
            35                  40                  45

Glu Arg Ile Phe Gly Pro Thr Lys Asp Trp Glu Cys Ala Cys Gly Lys
        50                  55                  60

Tyr Lys Arg Ile Arg Tyr Lys Gly Ile Val Cys Asp Arg Cys Gly Val
65                  70                  75                  80

Glu Val Thr Arg Ser Lys Val Arg Arg Glu Arg Met Gly His Ile Glu
                85                  90                  95

Leu Ala Ala Pro Val Ser His Ile Trp Tyr Phe Lys Gly Ile Pro Ser
            100                 105                 110

Arg Met Gly Leu Val Leu Asp Met Ser Pro Arg Ala Leu Glu Glu Val
        115                 120                 125
```

```
Ile Tyr Phe Ala Ser Tyr Val Ile Glu Pro Gly Asp Thr Thr Leu
    130                 135             140
Glu Lys Lys Gln Leu Leu Thr Glu Arg Glu Tyr Arg Glu Lys Arg Glu
145                 150                 155                 160
Gln Tyr Gly Gln Ala Phe Lys Ala Ala Met Gly Ala Glu Ala Val Lys
                165                 170                 175
Gln Leu Leu Asp Asn Val Asp Leu Asp Gly Glu Val Ala Gln Leu Lys
                180                 185                 190
Glu Glu Leu Lys Thr Ala Ser Gly Gln Lys Arg Thr Arg Ala Ile Arg
            195                 200                 205
Arg Leu Asp Ile Leu Glu Ala Phe Arg Ala Ser Gly Asn Gln Pro Ser
    210                 215                 220
Trp Met Val Met Asp Val Ile Pro Val Ile Pro Pro Asp Leu Arg Pro
225                 230                 235                 240
Met Val Gln Leu Glu Gly Gly Arg Phe Ala Thr Ser Asp Leu Asn Asp
                245                 250                 255
Leu Tyr Arg Arg Val Ile Asn Arg Asn Asn Arg Leu Lys Arg Leu Leu
                260                 265                 270
Asp Leu Asn Ala Pro Ser Ile Ile Val Gln Asn Glu Lys Arg Met Leu
            275                 280                 285
Gln Glu Ala Val Asp Ala Leu Ile Asp Asn Gly Arg Arg Gly Arg Pro
    290                 295                 300
Val Thr Gly Pro Gly Asn Arg Pro Leu Lys Ser Leu Ser His Met Leu
305                 310                 315                 320
Lys Gly Lys Gln Gly Arg Phe Arg Gln Asn Leu Leu Gly Lys Arg Val
                325                 330                 335
Asp Tyr Ser Gly Arg Ser Val Ile Val Val Gly Pro Phe Leu Lys Met
                340                 345                 350
Tyr Gln Cys Gly Leu Pro Lys Glu Met Ala Ile Glu Leu Phe Lys Pro
            355                 360                 365
Phe Val Met Arg Glu Leu Val Gln Arg Glu Ile Ala Thr Asn Ile Lys
    370                 375                 380
Asn Ala Lys Arg Lys Ile Glu Arg Gly Glu Asp Glu Val Trp Asp Ile
385                 390                 395                 400
Leu Glu Glu Val Ile Gln Glu His Pro Val Leu Leu Asn Arg Ala Pro
                405                 410                 415
Thr Leu His Arg Leu Gly Ile Gln Ala Phe Glu Pro Val Leu Val Glu
                420                 425                 430
Gly Arg Ala Ile Arg Leu His Pro Leu Val Cys Glu Ala Tyr Asn Ala
            435                 440                 445
Asp Phe Asp Gly Asp Gln Met Ala Val His Val Pro Leu Asn Glu Glu
    450                 455                 460
Ala Gln Ala Glu Ala Arg Met Leu Met Leu Ala Ala Gln Asn Ile Leu
465                 470                 475                 480
Asn Pro Lys Asp Gly Lys Pro Val Val Thr Pro Ser Gln Asp Met Val
                485                 490                 495
Leu Gly Asn Tyr Tyr Leu Thr Met Glu Glu Glu Gly Arg Glu Gly Glu
                500                 505                 510
Gly Met Ile Phe Arg Asp Met Asn Glu Ala Val Leu Ala Trp Gln Asn
            515                 520                 525
Gly Tyr Val His Leu His Ser Arg Ile Gly Val Gln Thr Thr Leu Leu
    530                 535                 540
```

```
Gly Asp Lys Pro Phe Thr Asp Trp Gln Lys Glu Arg Ile Leu Ile Thr
545                 550                 555                 560

Thr Val Gly Lys Ile Ile Phe Asn Glu Ile Met Pro Val Glu Phe Pro
                565                 570                 575

Tyr Leu Asn Glu Pro Thr Asp Tyr Asn Leu Thr Val Gln Thr Pro Asp
            580                 585                 590

Lys Tyr Phe Val Glu Ala Gly Thr Asp Ile Pro Ala His Ile Lys Glu
        595                 600                 605

Gln Glu Leu Val Leu Pro Phe Lys Lys Asn Leu Gly Asn Ile Ile
    610                 615                 620

Ala Glu Val Phe Lys Arg Phe His Ile Thr Glu Thr Ser Lys Met Leu
625                 630                 635                 640

Asp Arg Met Lys Asp Leu Gly Tyr Lys His Ser Thr Tyr Ala Gly Met
                645                 650                 655

Thr Val Gly Ile Ala Asp Ile Met Val Leu His Glu Lys Gln Ala Ile
                660                 665                 670

Ile Asp Ala Ala His Lys Gln Val Glu Thr Ile Thr Lys Gln Phe Arg
            675                 680                 685

Arg Gly Leu Ile Thr Asp Asp Glu Arg Tyr Glu Arg Val Ile Gly Val
        690                 695                 700

Trp Asn Gly Ala Lys Asp Glu Ile Gln Gln Lys Leu Ile Glu Ser Met
705                 710                 715                 720

Glu Ala Arg Asn Pro Ile Phe Met Met Ser Asp Ser Gly Ala Arg Gly
                725                 730                 735

Asn Ile Ser Asn Phe Thr Gln Leu Ala Gly Met Arg Gly Leu Met Ala
            740                 745                 750

Ala Pro Asn Gly Arg Ile Met Glu Leu Pro Ile Ile Ser Asn Phe Arg
        755                 760                 765

Glu Gly Leu Ser Val Leu Glu Met Phe Ile Ser Thr His Gly Ala Arg
    770                 775                 780

Lys Gly Met Thr Asp Thr Ala Leu Lys Thr Ala Asp Ser Gly Tyr Leu
785                 790                 795                 800

Thr Arg Arg Leu Val Asp Val Ala Gln Asp Val Ile Ile Arg Glu Asp
                805                 810                 815

Asp Cys Gly Thr Asp Arg Gly Leu Glu Ile Glu Ala Ile Arg Glu Gly
            820                 825                 830

Asn Glu Ile Ile Glu Pro Leu Asp Glu Arg Leu Leu Gly Arg Tyr Thr
        835                 840                 845

Arg Lys Ser Val Val His Pro Glu Thr Gly Ala Ile Ile Ile Gly Ala
850                 855                 860

Asp Gln Leu Ile Thr Glu Asp Leu Ala Arg Glu Ile Val Asp Ala Gly
865                 870                 875                 880

Ile Glu Lys Val Thr Ile Arg Ser Val Phe Thr Cys Asn Thr Lys His
                885                 890                 895

Gly Val Cys Lys His Cys Tyr Gly Arg Asn Leu Ala Thr Gly Ser Asp
            900                 905                 910

Val Glu Val Gly Glu Ala Val Gly Thr Ile Ala Ala Gln Ser Ile Gly
        915                 920                 925

Glu Pro Gly Thr Gln Leu Thr Met Arg Thr Phe His Thr Gly Gly Val
    930                 935                 940

Ala Gly Asp Asp Ile Thr Gln Gly Leu Pro Arg Ile Gln Glu Ile Phe
945                 950                 955                 960

Glu Ala Arg Asn Pro Lys Gly Gln Ala Val Ile Thr Glu Val Thr Gly
```

```
                    965                 970                 975
Glu Val Ile Asp Ile Ser Glu Asp Pro Ala Thr Arg Gln Lys Glu Val
                980                 985                 990

Thr Ile Lys Gly Lys Thr Asp Thr Arg Thr Tyr Thr Val Pro Tyr Thr
            995                1000                1005

Ala Arg Met Lys Val Ala Glu Gly Asp Ile Ile His Arg Gly Ala
       1010                1015                1020

Pro Leu Thr Glu Gly Ser Ile Asp Pro Lys Gln Leu Leu Gln Val
       1025                1030                1035

Arg Asp Val Leu Ser Val Glu Asn Tyr Leu Leu Arg Glu Val Gln
       1040                1045                1050

Arg Val Tyr Arg Met Gln Gly Val Glu Ile Gly Asp Lys His Ile
       1055                1060                1065

Glu Val Met Val Arg Gln Met Leu Arg Lys Ile Arg Val Met Asp
       1070                1075                1080

Pro Gly Asp Thr Glu Ile Leu Pro Gly Thr Leu Met Asp Ile Ala
       1085                1090                1095

Glu Phe Lys Asp Arg Asn Tyr Asp Thr Leu Val Ala Gly Gly Val
       1100                1105                1110

Pro Ala Thr Ser Arg Pro Val Leu Leu Gly Ile Thr Lys Ala Ser
       1115                1120                1125

Leu Glu Thr Asn Ser Phe Leu Ser Ala Ala Ser Phe Gln Glu Thr
       1130                1135                1140

Thr Arg Val Leu Thr Asp Ala Ala Ile Arg Gly Lys Lys Asp Pro
       1145                1150                1155

Leu Leu Gly Leu Lys Glu Asn Val Ile Ile Gly Lys Ile Ile Pro
       1160                1165                1170

Ala Gly Thr Gly Met Ala Arg Tyr Arg Asn Met Glu Pro Lys Glu
       1175                1180                1185

Val Gly Val Ala Ser Glu Asn Val Tyr Ser Ile Ser Asp Ile Glu
       1190                1195                1200

Ala Gln Met Ala Ala Glu Asp Ala Met Lys Asn Ile Asn Lys
       1205                1210                1215

<210> SEQ ID NO 69
<211> LENGTH: 1215
<212> TYPE: PRT
<213> ORGANISM: Lactobacillus brevis

<400> SEQUENCE: 69

Met Val Asp Val Asn Lys Phe Glu Ser Met Gln Ile Gly Leu Ala Ser
1               5                   10                  15

Pro Asp Lys Ile Arg Ser Trp Ser Tyr Gly Glu Val Lys Pro Glu
            20                  25                  30

Thr Ile Asn Tyr Arg Thr Leu Lys Pro Glu Lys Asp Gly Leu Phe Asp
        35                  40                  45

Glu Arg Ile Phe Gly Pro Thr Lys Asp Trp Glu Cys Ala Cys Gly Lys
    50                  55                  60

Tyr Lys Arg Ile Arg Tyr Lys Gly Val Val Cys Asp Arg Cys Gly Val
65                  70                  75                  80

Glu Val Thr Arg Ser Lys Val Arg Arg Glu Arg Met Gly His Ile Glu
                85                  90                  95

Leu Ala Ala Pro Val Thr His Ile Trp Tyr Phe Lys Gly Ile Pro Ser
            100                 105                 110
```

-continued

Arg Met Gly Leu Val Leu Asp Met Ser Pro Arg Ala Leu Glu Glu Ile
         115                 120                 125

Ile Tyr Phe Ala Ser Tyr Val Val Leu Asp Pro Gly Asn Thr Pro Leu
130                 135                 140

Glu Lys Lys Gln Leu Leu Ser Glu Arg Asp Tyr Arg Asp Lys Leu Leu
145                 150                 155                 160

Glu Tyr Gly Ser Asp Ala Phe Lys Ala Glu Met Gly Ala Glu Ala Ile
                165                 170                 175

Lys Lys Leu Leu Met Ser Val Asp Leu Asp Lys Glu Val Thr Glu Leu
            180                 185                 190

Lys Glu Glu Leu Lys Glu Ala Thr Gly Gln Lys Arg Thr Arg Ala Val
            195                 200                 205

Arg Arg Leu Asp Ile Leu Glu Ala Phe Val Met Ser Gly Asn Arg Pro
210                 215                 220

Glu Trp Met Val Met Asp Ala Ile Pro Val Ile Pro Pro Asp Leu Arg
225                 230                 235                 240

Pro Met Val Gln Leu Glu Gly Gly Arg Phe Ala Thr Ser Asp Leu Asn
                245                 250                 255

Asp Leu Tyr Arg Arg Val Ile Asn Arg Asn Ser Arg Leu Lys Arg Leu
                260                 265                 270

Leu Asp Leu Asn Ala Pro Gly Ile Ile Val Gln Asn Glu Lys Arg Met
            275                 280                 285

Leu Gln Glu Ala Val Asp Ala Leu Ile Asp Asn Gly Arg Arg Gly Arg
        290                 295                 300

Pro Val Ala Gly Pro Gly Asn Arg Pro Leu Lys Ser Leu Ser His Met
305                 310                 315                 320

Leu Lys Gly Lys Gln Gly Arg Phe Arg Gln Asn Leu Leu Gly Lys Arg
                325                 330                 335

Val Asp Tyr Ser Gly Arg Ser Val Ile Asp Val Gly Pro Ser Leu Lys
                340                 345                 350

Phe Asn Gln Met Gly Leu Pro Val Pro Met Ala Leu Glu Leu Phe Arg
            355                 360                 365

Pro Phe Ile Met Lys Glu Leu Val Ala Arg Gly Leu Ala Ser Asn Ile
370                 375                 380

Lys Asn Ala Lys Arg Gln Ile Asp Arg Glu Asp Asp Val Phe Asn
385                 390                 395                 400

Val Leu Glu Asp Val Ile Lys Glu His Pro Val Leu Leu Asn Arg Ala
                405                 410                 415

Pro Thr Leu His Arg Leu Gly Ile Gln Ala Phe Glu Pro Val Leu Val
                420                 425                 430

Ser Gly Lys Ala Met Arg Leu His Pro Leu Ala Cys Glu Ala Tyr Asn
            435                 440                 445

Ala Asp Phe Asp Gly Asp Gln Met Ala Ile His Val Pro Leu Ser Asp
        450                 455                 460

Glu Ala Gln Ala Glu Ala Arg Leu Leu Met Leu Ala Ala His His Ile
465                 470                 475                 480

Leu Ala Pro Ala Ser Gly Lys Pro Val Val Ala Pro Ser Gln Asp Met
                485                 490                 495

Val Ile Gly Asn Tyr Tyr Leu Thr Met Glu Ala Asn Arg Glu Gly
                500                 505                 510

Glu Gly Met Ile Phe Thr Asp Leu Asp Glu Ala Thr Leu Ala Tyr Arg
            515                 520                 525

Asn Gly Ile Val His Trp His Thr Arg Val Gly Val Gln Val Thr Ser

```
            530                 535                 540
Met Pro Asp Lys Pro Phe Thr Asp Glu Gln Arg Ser Lys Ile Met Val
545                 550                 555                 560

Thr Thr Val Gly Lys Leu Ile Phe Asn Asn Ile Leu Pro Lys Ser Phe
                565                 570                 575

Pro Tyr Leu Asn Glu Pro Thr Ser Thr Asn Leu Asn Gly Tyr Val Pro
                580                 585                 590

Asp Lys Tyr Phe Leu Glu Pro Gly Glu Asp Ile His Asp Tyr Leu Gln
                595                 600                 605

Asn Ala Glu Ile Ile Pro Pro Phe Lys Lys Gly Phe Leu Ser Asp Ile
                610                 615                 620

Ile Ala Ala Val Tyr Gln Gln Tyr Lys Val Thr Ala Thr Ser Glu Leu
625                 630                 635                 640

Leu Asp Arg Ile Lys Asp Leu Gly Tyr Asn Glu Ser Thr Lys Ser Gly
                645                 650                 655

Leu Thr Val Gly Met Val Asp Val Thr Asp Leu Lys Glu Lys Pro Glu
                660                 665                 670

Ile Ile Ala Ala Ala His Lys Gln Val Ser Thr Val Thr Lys Gln Phe
675                 680                 685

Arg Arg Gly Leu Ile Thr Asp His Glu Arg Tyr Glu Arg Val Ile Gly
                690                 695                 700

Ile Trp Asn Asp Ala Lys Asp Glu Ile Gln Asn Ala Leu Ile His Ser
705                 710                 715                 720

Phe Asp Gln Gln Asn Pro Ile Phe Met Met Ser Asp Ser Gly Ala Arg
                725                 730                 735

Gly Asn Ile Ser Asn Phe Thr Gln Leu Ala Gly Met Arg Gly Leu Met
                740                 745                 750

Ala Ala Pro Ser Gly Asp Ile Met Glu Leu Pro Ile Thr Ser Asn Phe
                755                 760                 765

Arg Glu Gly Leu Thr Val Met Glu Met Phe Ile Ser Thr His Gly Ala
                770                 775                 780

Arg Lys Gly Met Thr Asp Thr Ala Leu Lys Thr Ala Asn Ser Gly Tyr
785                 790                 795                 800

Leu Thr Arg Arg Leu Val Asp Val Ala Gln Asp Val Ile Ile Arg Glu
                805                 810                 815

Lys Asp Cys Gly Thr Asp Arg Gly Leu Lys Ile Arg Ala Ile Thr Asp
                820                 825                 830

Gly Asn Glu Met Ile Glu Pro Leu Tyr Asp Arg Ile Leu Gly Arg Tyr
                835                 840                 845

Thr Gln Lys Thr Val Tyr Asp Pro Gln Thr Gly Asp Val Ile Val Pro
850                 855                 860

Lys Asn Gln Met Ile Val Glu Asp Thr Ala Gln Ile Val Asp Ala
865                 870                 875                 880

Gly Val Glu Glu Val Thr Ile Arg Ser Ala Phe Thr Cys Asn Thr Glu
                885                 890                 895

His Gly Val Cys Glu His Cys Tyr Gly Arg Asn Met Ala Thr Gly Asp
                900                 905                 910

Glu Val Glu Val Gly Glu Ala Val Gly Thr Val Ala Ala Gln Ser Ile
                915                 920                 925

Gly Glu Pro Gly Thr Gln Leu Thr Met Arg Asn Phe His Thr Gly Gly
                930                 935                 940

Val Ala Gly Asn Glu Asp Ile Thr Gln Gly Leu Pro Arg Val Gln Glu
945                 950                 955                 960
```

```
Leu Phe Glu Ser Arg Asn Pro Lys Gly Lys Ala Glu Ile Thr Glu Val
                965                 970                 975

Thr Gly Thr Val Glu Ser Ile Glu Glu Asn Pro Ala Glu Arg Thr Lys
                980                 985                 990

Glu Ile Thr Ile Lys Gly Glu Ala  Asp Thr Arg Ser Tyr  Thr Leu Pro
        995                 1000                1005

Ile Thr Ala Arg Met Arg Val  Ser Glu Gly Asp Phe  Ile His Arg
        1010                1015                1020

Gly Gly Ala Leu Asn Tyr Gly  Ser Val Asp Pro Lys  Glu Leu Leu
        1025                1030                1035

Arg Val Arg Asp Val Leu Ser  Thr Glu Thr Tyr Ile  Leu Gly Glu
        1040                1045                1050

Val Gln Arg Val Tyr Arg Met  Gln Gly Val Ala Ile  Ser Asp Lys
        1055                1060                1065

His Val Glu Ile Met Val Arg  Gln Met Leu Arg Lys  Val Arg Ile
        1070                1075                1080

Met Asp Pro Gly Asp Thr Asp  Val Leu Pro Gly Thr  Leu Met Asp
        1085                1090                1095

Ile Gln Asp Phe Arg Arg Ala  Asn Tyr Gln Thr Leu  Ile Asp Gly
        1100                1105                1110

Gly Ile Ala Ala Thr Ala Arg  Pro Val Ile Leu Gly  Ile Thr Lys
        1115                1120                1125

Ala Ala Leu Glu Thr Asn Ser  Phe Leu Ser Ala Ala  Ser Phe Gln
        1130                1135                1140

Glu Thr Thr Arg Val Leu Thr  Asp Ala Ala Ile Arg  Gly Lys Asn
        1145                1150                1155

Asp Pro Leu Val Gly Leu Lys  Glu Asn Val Ile Ile  Gly Lys Ile
        1160                1165                1170

Ile Pro Ala Gly Thr Gly Met  Pro Asp Tyr Arg Gln  Ile Lys Pro
        1175                1180                1185

Lys Glu Val Gly Gly Thr Ser  Thr Glu Gly Val Tyr  Ser Ile Ser
        1190                1195                1200

Asp Leu Glu Lys Gln Met Gln  Glu Asp Ser Gln Ala
        1205                1210                1215
```

NUCLEIC ACID MOLECULES COMPRISING A VARIANT INC CODING STRAND

CROSS-REFERENCE TO RELATED APPLICATIONS

This application claims the benefit of U.S. Provisional Application No. 62/715,571, filed Aug. 7, 2018, which is hereby incorporated by reference.

FIELD OF THE INVENTION

The invention relates to nucleic acid molecules comprising a variant inc coding strand, wherein the variant inc coding strand encodes a variant inc RNA, and the variant inc RNA is a regulator of plasmid copy number.

BACKGROUND OF THE INVENTION

Plasmids play an important role in biotechnology, providing a means for introducing, modifying, and removing target genes from microorganisms, and for producing corresponding proteins encoded by the target genes. Plasmids are nucleic acid molecules that occur naturally in a diverse range of microorganisms of the domains Bacteria, Archaea, and Eukaryota, that are physically separate from chromosomes of the microorganisms in which they occur, and that replicate independently of the chromosomes. Plasmids are typically double-stranded circular DNA molecules, but can also be linear DNA molecules and/or RNA molecules. Plasmids occur in a range of sizes, from about 1 kb to more than 2 Mb. For example, according to a recent review article of Shintani et al., Frontiers in Microbiology 6:242 (2015), wide variations of size were observed among 4602 plasmids found in the GenBank database, with the plasmids ranging in size from 744 bp to 2.58 Mb, and having an average size of 80 kb. Plasmids also occur in a range of copies per cell. For example, plasmids are generally characterized as low copy, e.g. 1-20 copies per cell, medium copy, e.g. 20-100 copies per cell, or high copy, e.g. 500-700 copies or more per cell. Plasmids can be modified to include target genes.

A challenge associated with using plasmids in biotechnology is that biotechnological applications generally require stable incorporation of target genes in microorganisms and careful control of yield of the target genes and their corresponding protein products during cultivation, but efforts to accomplish one can work against accomplishing the other. During cultivation of a microorganism including a plasmid with a target gene, it is generally advantageous to have the plasmid segregate stably as cells of the microorganism grow and divide, so that a high percentage of cells of the microorganism will include the target gene throughout the cultivation. It also is generally advantageous to have the target gene remain structurally stable, maintaining a constant nucleotide sequence, to ensure production of only intended products. It also is generally advantageous to express a target gene at a level that is sufficiently high to achieve a desired result, e.g. production of a corresponding protein product in sufficient quantities and in an active form. Unfortunately, techniques for replicating plasmids and expressing target genes from the plasmids, particularly at high levels, exert metabolic burdens on cells. This can lead to plasmids being lost from cells and/or mutations changing expression levels or identity of target genes. This also can lead to aggregation and inactivity of corresponding protein products. Thus, balancing stable incorporation and control of yield during use of plasmids in biotechnical applications is generally an empirical process, involving trial and error.

Plasmid copy number is an important consideration regarding both stable incorporation and control of yield. The copy number of a plasmid is generally determined by three factors, the origin of replication of the plasmid, the size of the plasmid, including target genes included therein, and cultivation conditions. Regarding origins of replication, plasmids can be classified in incompatibility groups based on features of their replication, particularly their origins of replication. Specifically, a plasmid generally includes a replicon, corresponding to a region of the plasmid that replicates from a single origin of replication. A plasmid also generally includes genes that encode proteins that recognize the origin of replication of the plasmid and initiate replication there. Interactions between the proteins of the plasmid and the origin of replication determine specificity of replication and copy number of the replicon, and thus of the plasmid. Plasmids that have identical origins of replication are classified within the same incompatibility group, based on the plasmids being incompatible with each other regarding segregational stability. Plasmids that have different origins of replication may be classified within different incompatibility groups, if the plasmids are compatible with each other. Regarding size of the plasmid, increasing size generally leads to an increasing metabolic burden associated with replication of the plasmid and expression of target genes from the plasmid, and thus to a decrease in copy number of the plasmid. Regarding cultivation conditions, these also affect metabolic burden, and depending on specific conditions, can result in an increase or decrease in copy number.

Of the three factors, the origin of replication is generally the primary consideration in choosing a plasmid for a particular application, because the origin of replication establishes a base line for copy number. Unfortunately, no general approaches exist for predictably changing the base line for copy number of a plasmid by modifying the origin of replication of the plasmid. Determining whether and to what extent a particular origin of replication could be modified to change copy number also would be an empirical process.

RepFIC is an exemplary replicon. As described by Saadi et al., Journal of Bacteriology 169:1836-1846 (1987), RepFIC is a replicon of IncFI plasmids. RepFIC is present in complete form in plasmid P307. RepFIC also is present in truncated form in plasmid F. RepFIC encodes an RNA, termed inc RNA. The inc RNA of RepFIC determines incompatibility of the RepFIC replicon based on its sequence and structure.

The RNA sequence of inc RNA has been inferred from the DNA sequence of the RepFIC replicon. The inferred sequence of inc RNA of RepFIC varies depending on the source of the RepFIC replicon. The inferred sequence also varies depending on the 5' end and the 3' end predicted for the inc RNA.

For example, the inc RNA of RepFIC of plasmid P307 is encoded by a DNA coding strand corresponding to the reverse complement of nucleotides 575 to 665 of a portion of the RepFIC replicon, as disclosed by Saadi et al. This coding strand corresponds to a sequence of 91 nucleotides as provided within SEQ ID NO: 23, specifically nucleotides 8-98 of SEQ ID NO: 23. Also according to Saadi et al., the inc RNA of RepFIC of plasmid F is encoded by a DNA coding strand that differs from that of the inc RNA of RepFIC of plasmid P307 by substitutions of two bases. This coding strand corresponds to a sequence of 91 nucleotides as provided within SEQ ID NO: 21, specifically nucleotides 8-98 of SEQ ID NO: 21. Also for example, according to GenBank, the inc RNA of RepFIC of *Escherichia coli* strain K-12 is encoded by a DNA coding strand corresponding to the reverse complement of GenBank Accession AP001918.1, location 3747 to 3839. This coding strand corresponds to a sequence of 93 nucleotides as provided within SEQ ID NO: 21, specifically nucleotides 1-93 of SEQ ID NO: 21. Also according to GenBank, a non-coding RNA sequence of *E. coli* strain to1C, termed copA, which corresponds to inc RNA, is encoded by a DNA coding strand corresponding to GenBank Accession CP018801.1, location U.S. Pat. Nos. 3,463,977 to 3,464,067. This coding strand corresponds to a sequence of 91 nucleotides as provided in SEQ ID NO: 21, specifically nucleotides 8-98 of SEQ ID NO: 21. Also according to GenBank, a sequence of *E. coli* strain NCM3722 F-like plasmid, which apparently corresponds to inc RNA, is encoded by a DNA coding strand corresponding to the reverse complement of GenBank Accession CP011496.1, location 37765 to 37862. This coding strand corresponds to a sequence of 98 nucleotides as provided in SEQ ID NO: 19.

The inc RNA of RepFIC is predicted to have a stem-loop structure. According to Saadi et al., this structure is believed to be critical for function of the inc RNA.

According to Saadi et al., the inc RNA of RepFIC differs from inc RNA of another replicon, RepFIIA, by nine base pairs. Based on this difference, the RepFIC replicon and the RepFIIA replicons are compatible. In contrast, as noted, also according to Saadi et al., the inc RNA sequence of plasmid F differs from the inc RNA sequence of plasmid P307 by two bases. According to Saadi et al., this difference has no demonstrable effect on incompatibility, meaning that a plasmid expressing the inc RNA sequence of plasmid F would be incompatible with a plasmid expressing the inc RNA sequence of plasmid P307.

Saadi is silent regarding copy number of plasmids including the RepFIC replicon. Saadi also is silent regarding use of such plasmids for biotechnological applications.

Use of mutant RNA polymerases is another potential approach to alter the copy number of a plasmid. RNA polymerase plays a role in transcription. RNA polymerase also plays a role in replication of chromosomes and plasmids. RNA polymerase sequences have been determined in many bacteria, providing a basis for identifying conserved regions within RNA polymerases. For example, Lee et al., Antimicrobial Agents and Chemotherapy 57:56-65 (2013), provides an alignment of a C-terminal domain of RNA polymerase β' subunits from 21 strains. Structures of bacterial RNA polymerases also have been determined. For example, Mukhopadhyay et al., Cell 135:295-307 (2008), reports that structures reveal that RNA polymerases have dimensions of ~150 angstroms×~100 angstroms×~100 angstroms and a shape reminiscent of a crab claw. The RNA polymerase β' subunit makes up a pincer, termed a "clamp," and part of an active center cleft.

Two mutations in the rpoC gene of *E. coli*, which encodes the RNA polymerase β' subunit, have been reported to cause a decrease in copy number of ColE1-type plasmids. Specifically, Ederth et al., Molecular Genetics and Genomics 267:587-592 (2002), identified a single amino acid substitution (G1161R) and a 41-amino acid deletion. Both are located near the 3'-terminal region of the rpoC gene. The two mutations cause over 10-fold and 20-fold reductions in copy numbers of ColE1 plasmids, respectively (presumably corresponding to decreases of over 90% and 95%, respectively). Ederth et al. proposed that altered expression from promoters for RNA II and RNA I, which encode a preprimer for DNA polymerase I and an antisense inhibitor of the preprimer, may cause the decrease.

A mutation in rpoC also has been reported to cause an increase in copy number of plasmid pBR322. Specifically, Petersen et al., Journal of Bacteriology 173:5200-5206 (1991), identified a single amino acid substitution (G1033D), which also is located near the 3'-terminal region of the rpoC gene, that causes an increase in copy number of pBR322 at a semi-permissive growth temperature of 39° C. Petersen notes that mutation also causes an increase in chromosomal copy number.

Unfortunately, no general approaches exist for predictably modifying RNA polymerase β' subunit to obtain further mutants that change copy number of a plasmid. Determining whether and to what extent a particular mutation may alter copy number of a plasmid also would be an empirical process. Also, no general approaches exist for predictably modifying RNA polymerase β' subunit to obtain such mutants that would not cause a corresponding change in chromosomal copy number.

As noted above, plasmid copy number tends to be an important consideration regarding balancing stable incorporation and control of yield during use of plasmids in biotechnical applications, but no general approaches exist for predictably changing the base line for copy number of a plasmid by modifying the origin of replication of the plasmid. Accordingly, a need exists for origins of replication that are modified to change the base line for copy number of plasmids including the modified origins of replication. A need also exists for further mutants of RNA polymerase β' subunit that are modified to change copy number of plasmids, ideally without causing a corresponding change in chromosomal copy number.

BRIEF SUMMARY OF THE INVENTION

In accordance with one aspect of the present disclosure, a nucleic acid molecule comprising a variant inc coding strand that comprises SEQ ID NO: 15 is disclosed. The variant inc coding strand encodes a variant inc RNA. The variant inc RNA is a regulator of plasmid copy number.

In some examples, expression of the variant inc RNA increases copy number of a vector relative to expression of wild-type inc RNA encoded by an inc sequence comprising SEQ ID NO: 19.

Also in some examples, the variant inc coding strand comprises a nucleotide sequence that is at least 90% identical to SEQ ID NO: 17.

Also in some examples, the variant inc coding strand comprises SEQ ID NO: 17.

In accordance with another aspect of the present disclosure, a replicon comprising the nucleic acid molecule, a promoter, and an origin of replication is disclosed. The promoter is operably linked to the variant inc coding strand. The variant inc RNA regulates copy number of the replicon.

In accordance with another aspect of the present disclosure, a vector comprising the replicon is disclosed.

In accordance with another aspect of the present disclosure, a recombinant microorganism comprising the replicon is disclosed.

In accordance with another aspect of the present disclosure, a recombinant microorganism comprising the vector is disclosed.

In accordance with another aspect of the present disclosure, a method for regulating copy number of the vector in a recombinant microorganism is disclosed. The method comprises the steps of: (1) introducing the vector into a precursor microorganism, thereby obtaining the recombinant microorganism, and (2) cultivating the recombinant microorganism in a culture medium under conditions sufficient for replication of the vector, thereby regulating copy number of the vector.

In accordance with another aspect of the present disclosure, a method for making a target product by use of the vector in a recombinant microorganism is disclosed. The vector further comprises a target gene for making the target product. The method comprises the steps of: (1) introducing the vector into a precursor microorganism, thereby obtaining the recombinant microorganism, (2) cultivating the recombinant microorganism in a culture medium under conditions under which the recombinant microorganism expresses the target gene, thereby making the target product, and (3) recovering the target product from the recombinant microorganism and/or the culture medium.

In accordance with another aspect of the present disclosure, a recombinant microorganism comprising the vector and another nucleic acid molecule is disclosed. The other nucleic acid molecule comprises a variant rpoC RNA-polymerase β' subunit protein coding sequence (also termed "variant rpoC coding sequence"). The variant rpoC coding sequence encodes a variant RpoC RNA-polymerase β' subunit protein (also termed "variant RpoC"). The variant RpoC comprises an R47C substitution, with numbering of the R47C substitution defined based on wild-type RpoC RNA-polymerase β' subunit protein (also termed "wild-type RpoC"; SEQ ID NO: 44) of *Escherichia coli*.

In accordance with another aspect of the present disclosure, a method for regulating copy number of the vector in a recombinant microorganism is disclosed. The method comprises the steps of: (1) introducing the vector into a precursor microorganism, thereby obtaining the recombinant microorganism, and (2) cultivating the recombinant microorganism in a culture medium under conditions sufficient for replication of the vector, thereby regulating copy number of the vector. The recombinant microorganism comprises the other nucleic acid molecule comprising the variant rpoC coding sequence. The variant rpoC coding sequence encodes a variant RpoC. The variant RpoC comprises an R47C substitution, with numbering of the R47C substitution defined based on wild-type RpoC of *Escherichia coli*.

In accordance with another aspect of the present disclosure, a method for making a target product by use of the vector in a recombinant microorganism is disclosed. The vector further comprises a target gene for making the target product. The method comprises the steps of: (1) introducing the vector into a precursor microorganism, thereby obtaining the recombinant microorganism, (2) cultivating the recombinant microorganism in a culture medium under conditions under which the recombinant microorganism expresses the target gene, thereby making the target product, and (3) recovering the target product from the recombinant microorganism and/or the culture medium. The recombinant microorganism comprises another nucleic acid molecule comprising a variant rpoC coding sequence. The variant rpoC coding sequence encodes a variant RpoC. The variant RpoC comprises an R47C substitution, with numbering of the R47C substitution defined based on wild-type RpoC of *Escherichia coli*.

BRIEF DESCRIPTION OF THE DRAWINGS

FIG. 1 shows a multiple sequence alignment of DNA sequences of coding strands for the following:

(1) inc RNA of RepFIC of plasmid P307, encoded by a DNA coding strand corresponding to the reverse complement of nucleotides 575 to 665 of a portion of the RepFIC replicon, as disclosed by Saadi et al. (SEQ ID NO: 23, nucleotides 8-98);

(2) inc RNA of RepFIC of plasmid F, encoded by a DNA coding strand that differs from that of the inc RNA of RepFIC of plasmid P307 by substitutions of two bases, as disclosed by Saadi et al. (SEQ ID NO: 21, nucleotides 8-98);

(3) non-coding RNA sequence of *E. coli* strain to1C, termed copA, which corresponds to inc RNA, encoded by a DNA coding strand corresponding to GenBank Accession CP018801.1, location 3,463,977 to 3,464,067 (SEQ ID NO: 21, nucleotides 8-98);

(4) inc RNA of RepFIC of *E. coli* strain K-12, encoded by a DNA coding strand corresponding to the reverse complement of GenBank Accession AP001918.1, location 3747 to 3839 (SEQ ID NO: 21, nucleotides 1-93); and (5) sequence of *E. coli* strain NCM3722 F-like plasmid, which apparently corresponds to inc RNA, encoded by a DNA coding strand corresponding to the reverse complement of GenBank Accession CP011496.1, location 37765 to 37862 (SEQ ID NO: 19).

FIG. 2 shows differences in the aligned DNA sequences of coding strands corresponding to the sequences shown in FIG. 1, with the coding strand of inc RNA of RepFIC of plasmid P307 provided in full and the coding strands of the other sequences provided showing differences, and also shows the central domain of the coding strand for wild-type inc RNA (SEQ ID NO: 23, nucleotides 43-65) provided in full.

FIG. 3 shows a sequence alignment of DNA sequences of coding strands for the following:

(1) sequence of *E. coli* strain NCM3722 F-like plasmid, which apparently corresponds to inc RNA, encoded by a DNA coding strand corresponding to the reverse complement of GenBank Accession CP011496.1, location 37765 to 37862 (SEQ ID NO: 19); and (2) sequence of a variant inc coding strand (SEQ ID NO: 17) including a C to T substitution in the central domain and thus comprising SEQ ID NO: 15.

FIG. 4 shows differences in the aligned DNA sequences of coding strands corresponding to the sequences shown in FIG. 3, with the coding strand of the sequence of *E. coli* strain NCM3722 F-like plasmid provided in full and the variant inc coding strand provided showing differences, and also shows the central domain of the coding strand for the variant inc RNA (SEQ ID NO: 15) provided in full.

Figure 5A:
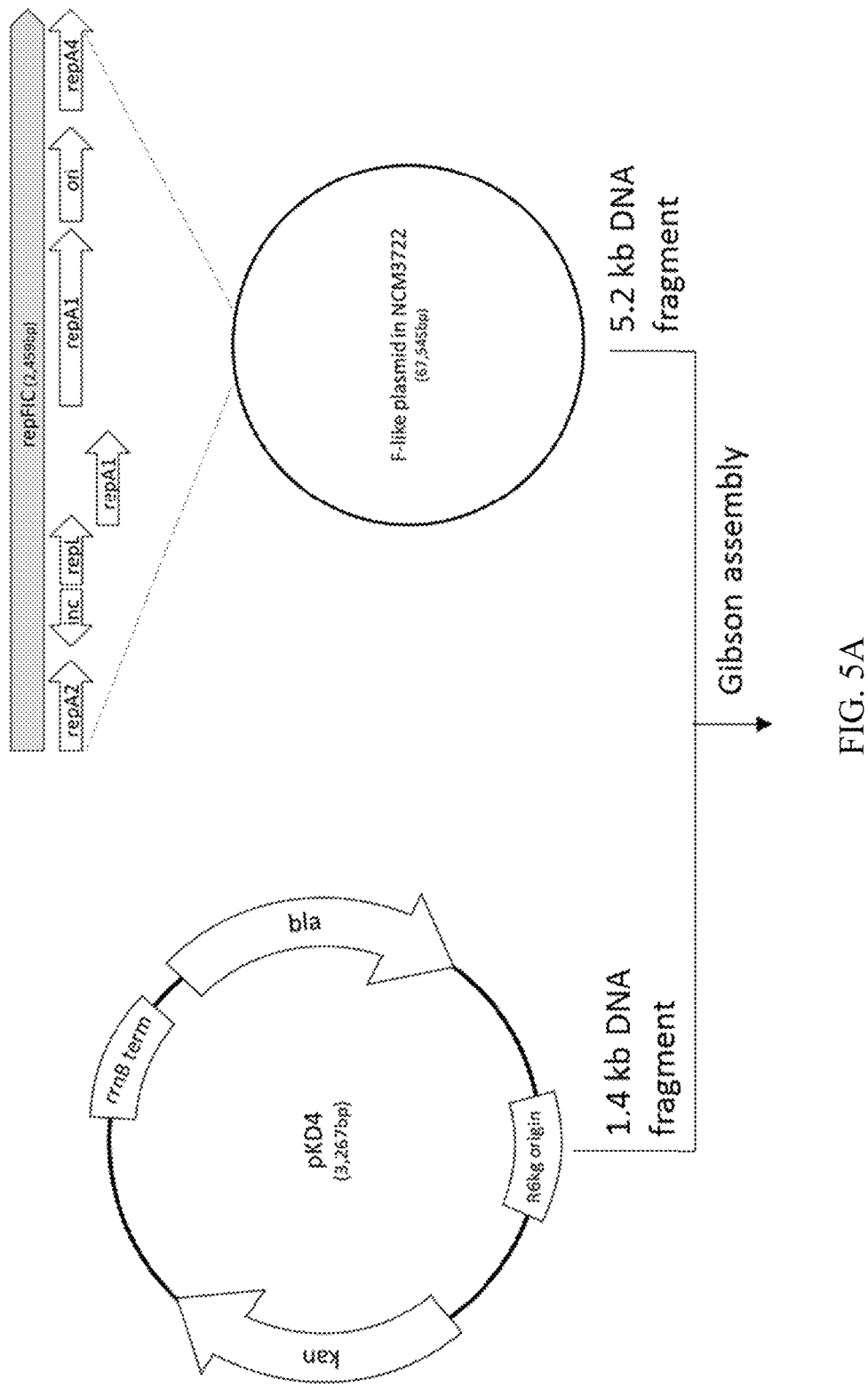
Figure 5B:
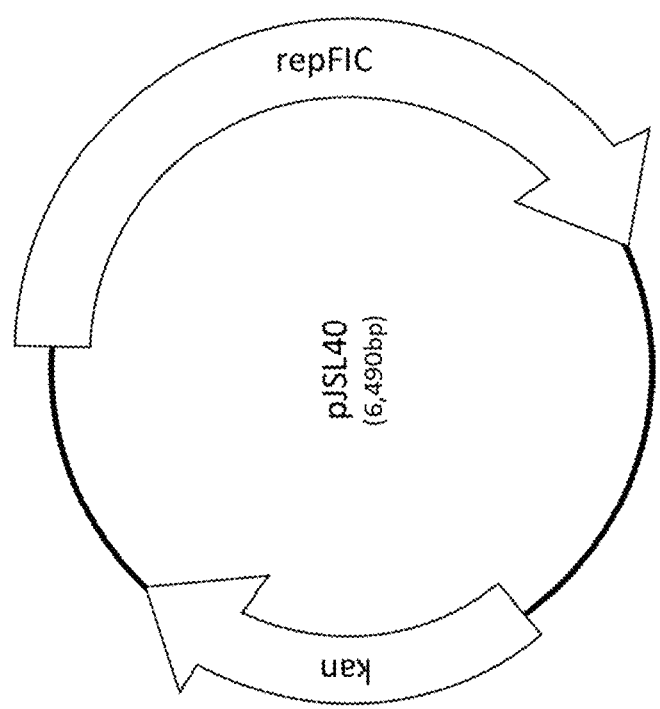

FIG. 5A-B illustrates the process of constructing a recombinant plasmid, termed pJSL40, which includes wildtype RepFIC identical to that of *E. coli* strain NCM3722 F-like plasmid (SEQ ID NO: 19).

Figure 6A:
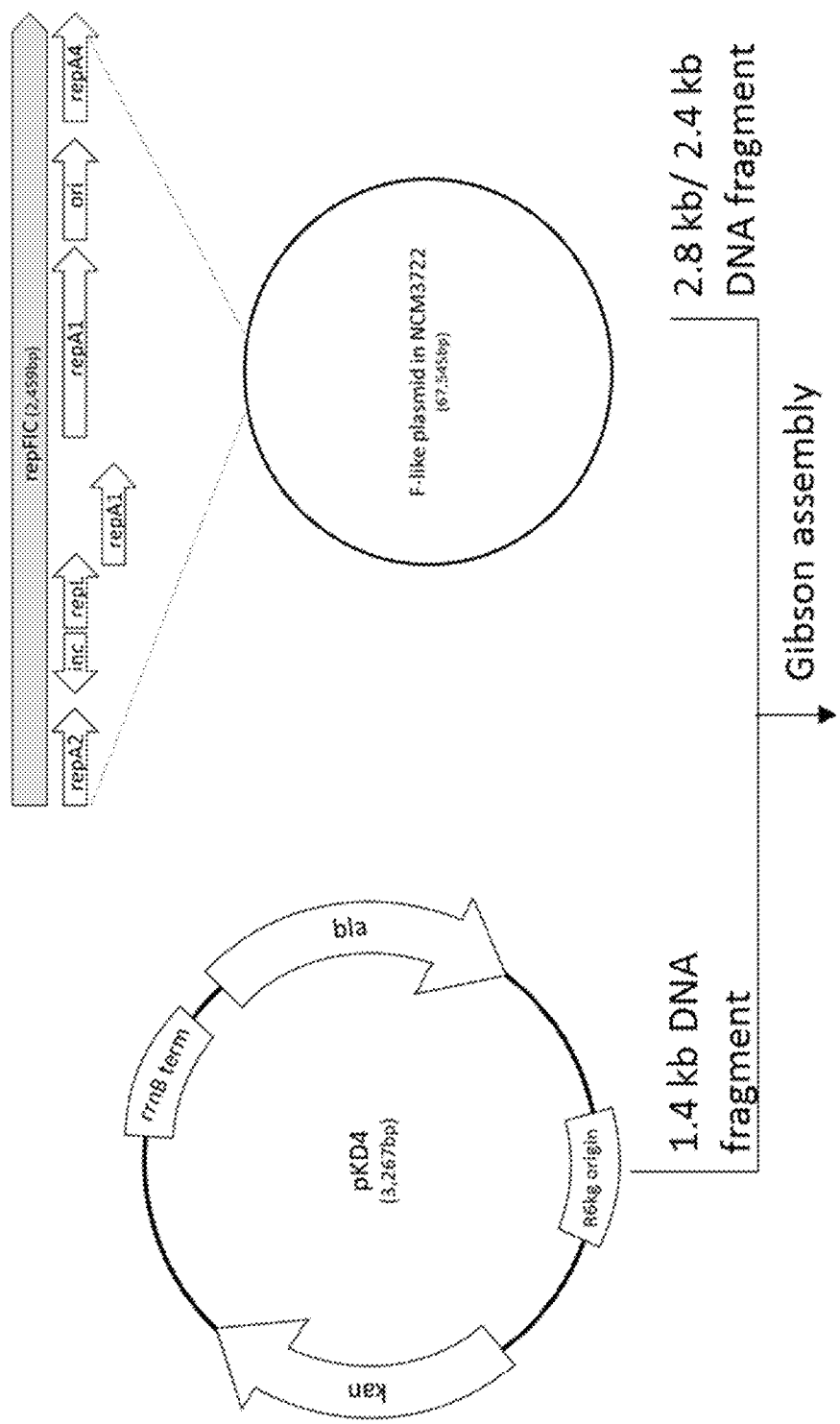
Figure 6B:
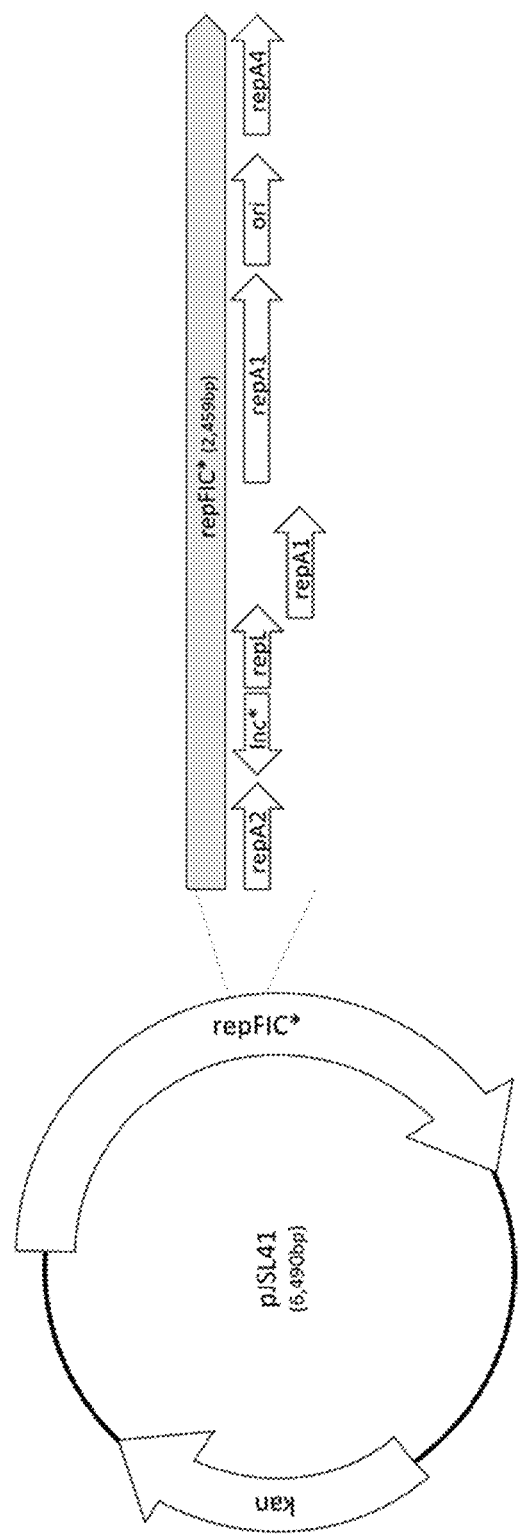

FIG. 6A-B illustrates the process of constructing a recombinant plasmid, termed pJSL41, which includes a modified DNA sequence of RepFIC, corresponding to the sequence of the variant inc coding strand (SEQ ID NO: 17) including a C to T substitution in the central domain and thus comprising SEQ ID NO: 15.

FIG. 7 shows a multiple sequence alignment, by CLUSTAL O(1.2.4), of an N-terminal domain of *Thermus thermophilus* RpoC (Q8RQE8) (SEQ ID NO: 34), *Acetobacter pasteurianus* RpoC (BAH99075.1) (SEQ ID NO: 35), *Neisseria gonorrhoeae* RpoC (Q5F5R6) (SEQ ID NO: 36), *Legionella pneumophila* RpoC (Q5X865) (SEQ ID NO: 37), *Pseudomonas aeruginosa* RpoC (Q9HWC9) (SEQ ID NO: 38), *Vibrio cholerae* RpoC (Q9KV29) (SEQ ID NO: 39), *Escherichia coli* (P0A8T7) (SEQ ID NO: 26), *Salmo-* nella enterica serovar Typhimurium RpoC (P0A2R4) (SEQ ID NO: 40), Actinomyces odontolyticus RpoC (EDN79927.1) (SEQ ID NO: 41), Streptomyces coelicolor RpoC (Q8CJT1) (SEQ ID NO: 42), Corynebacterium diphtheriae RpoC (Q6NJF6) (SEQ ID NO: 43), Mycobacterium tuberculosis RpoC (A5U053) (SEQ ID NO: 44), Rhodococcus equi RpoC (CBH49656.1) (SEQ ID NO: 45), Chlamydia trachomatis RpoC (O84316) (SEQ ID NO: 46), Clostridium botulinum RpoC (A7FZ76) (SEQ ID NO: 47), Bacillus subtilis RpoC (P37871) (SEQ ID NO: 48), Streptococcus pneumoniae RpoC (Q97NQ8) (SEQ ID NO: 49), Enterococcus faecalis RpoC (Q82Z41) (SEQ ID NO: 50), and Lactobacillus brevis RpoC (Q03PV0) (SEQ ID NO: 51).

FIG. 8 shows a multiple sequence alignment, by CLUSTAL O(1.2.4), of a central domain of the RpoC proteins as shown in FIG. 7 (SEQ ID NOS: 34-39, 26, and 40-51, respectively).

FIG. 9A-B shows a multiple sequence alignment, by CLUSTAL O(1.2.4), of a C-terminal domain of the RpoC proteins as shown in FIG. 7 (SEQ ID NOS: 34-39, 26, and 40-51, respectively).

FIG. 10 shows a sequence alignment of an N-terminal domain of RpoC protein of *E. coli* (SEQ ID NO: 26) and a variant RpoC (SEQ ID NO: 27).

FIG. 11 shows differences in the aligned N-terminal domain of RpoC protein of *E. coli* (SEQ ID NO: 26) and a variant RpoC (SEQ ID NO: 27), with the sequence of the N-terminal domain of RpoC of *E. coli* provided in full and the sequence of the variant RpoC provided showing differences.

Figure 12A:
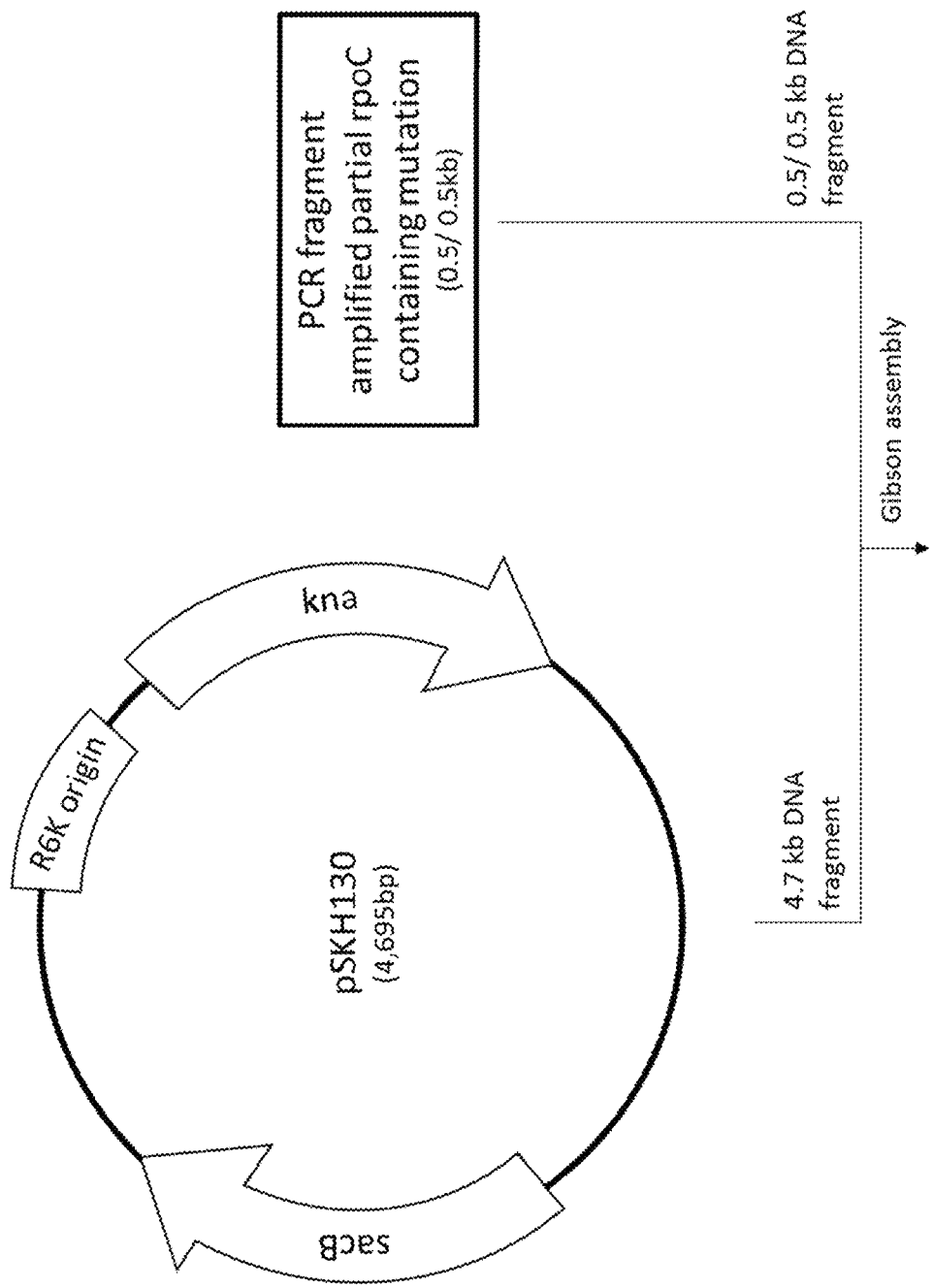
Figure 12B:
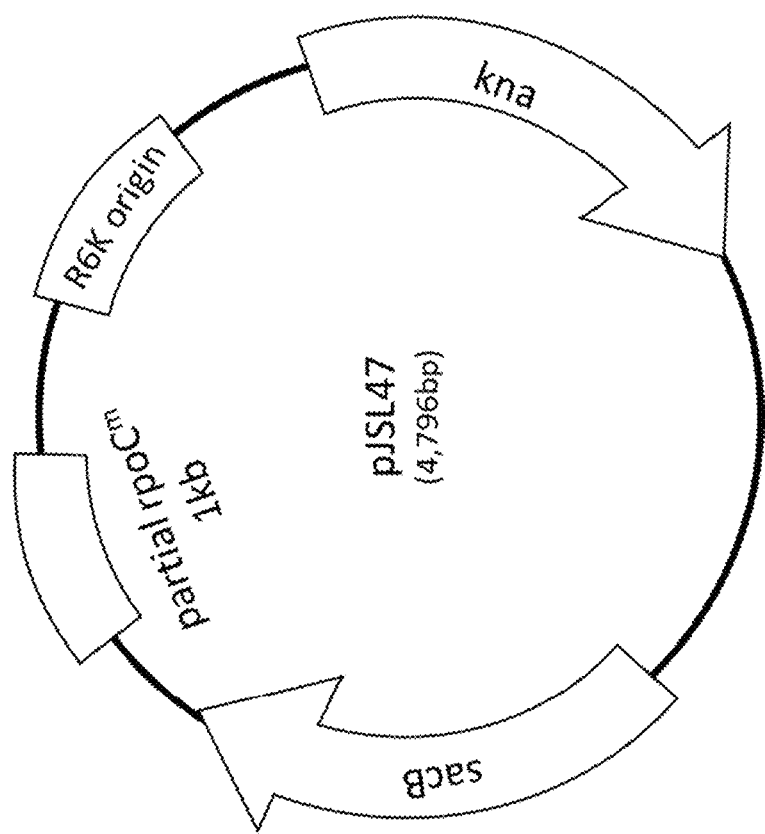

FIG. 12A-B illustrates the process of constructing a recombinant plasmid, termed pJSL47, which is for replacing an rpoC sequence on a chromosome.

Figure 13B:
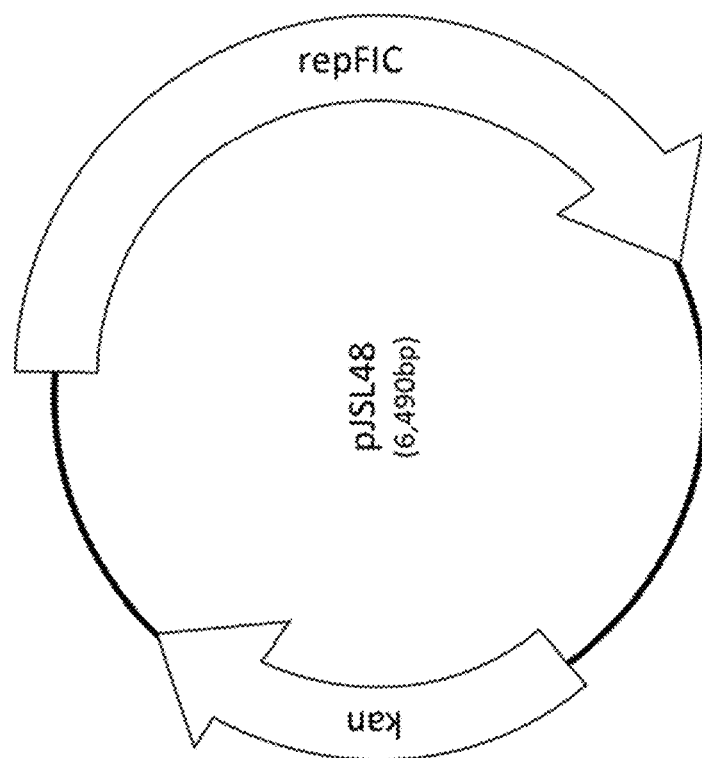

FIG. 13A-B illustrates the process of constructing a recombinant plasmid, termed pJSL48, which includes wild-type RepFIC replicon.

Figure 14A:
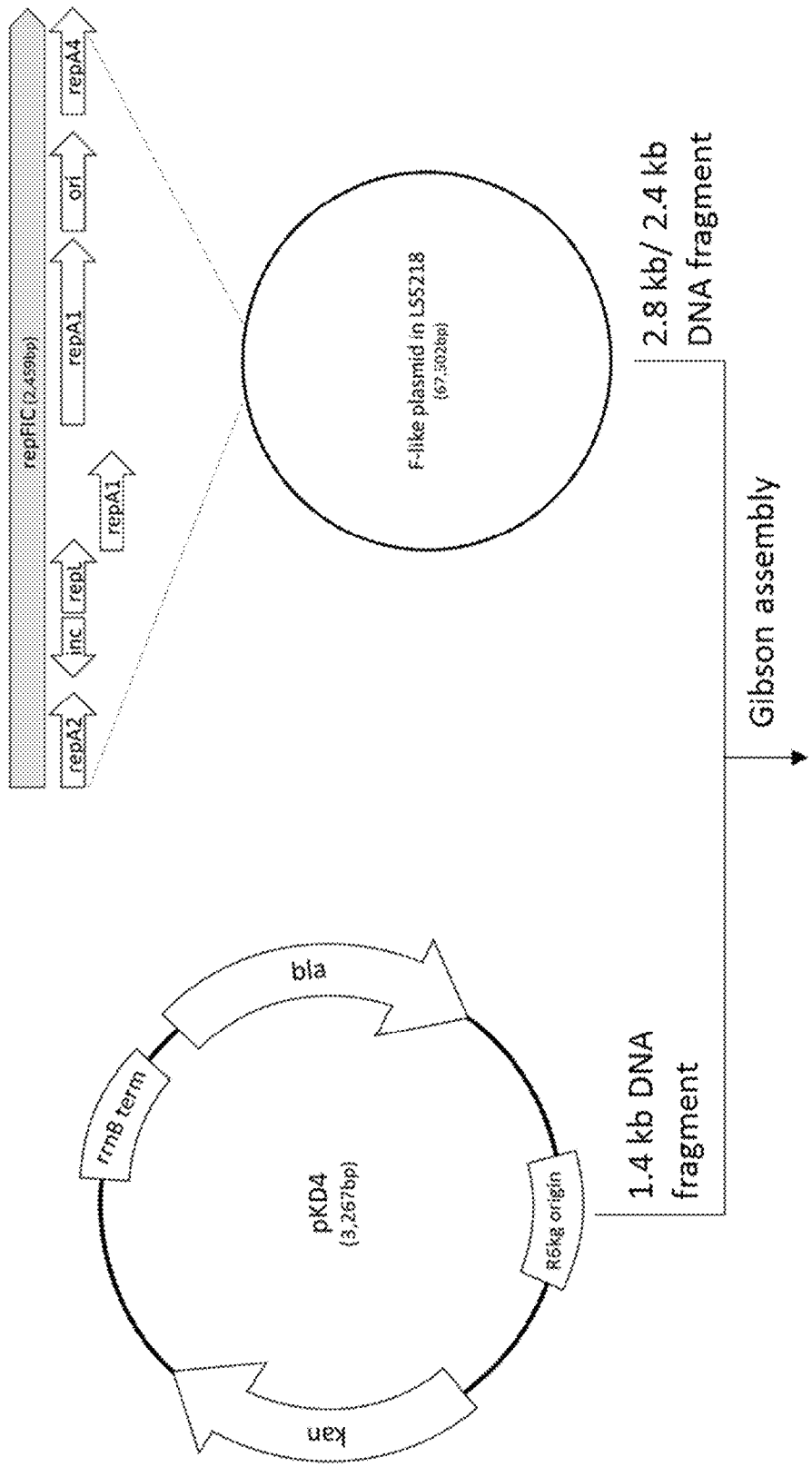
Figure 14B:
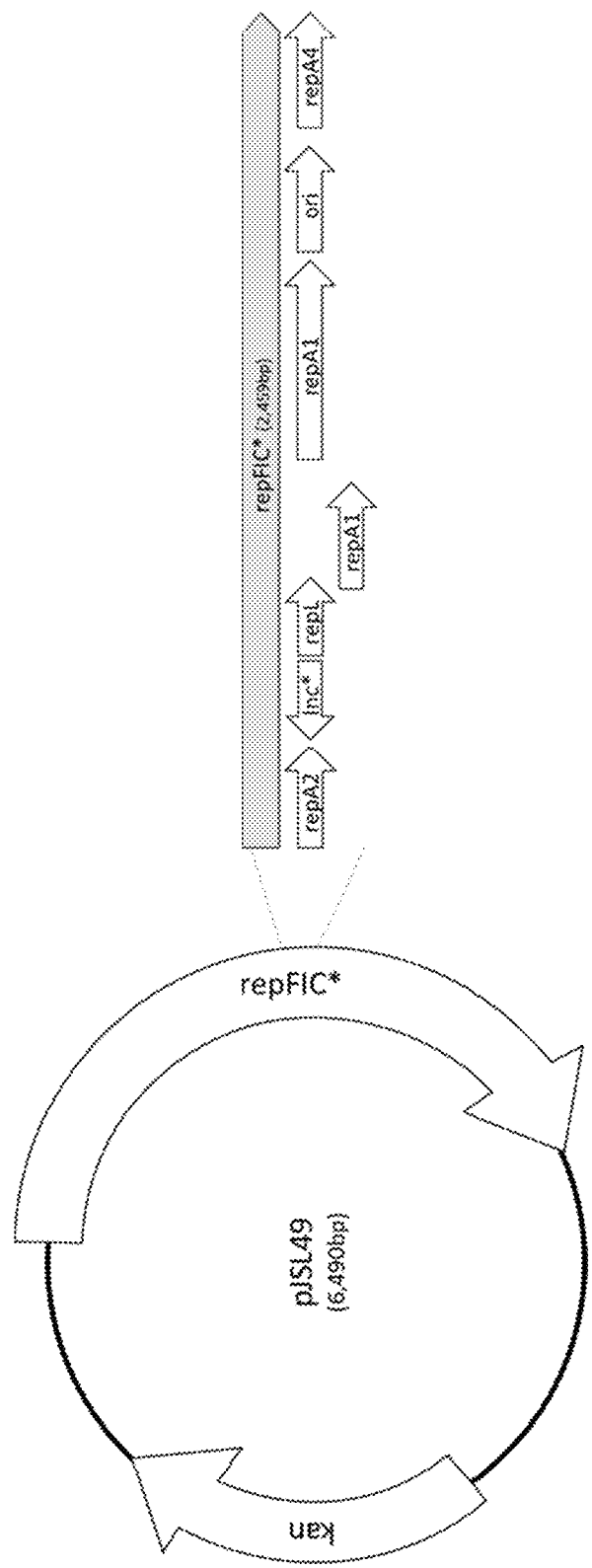

FIG. 14A-B illustrates the process of constructing a recombinant plasmid, termed pJSL49, which includes a modified RepFIC replicon.

DETAILED DESCRIPTION OF THE INVENTION

A nucleic acid molecule comprising a variant inc coding strand that comprises SEQ ID NO: 15 is disclosed. The variant inc coding strand encodes a variant inc RNA. The variant inc RNA is a regulator of plasmid copy number.

Surprisingly, it has been determined that a nucleic acid molecule comprising a variant inc coding strand that comprises SEQ ID NO: 15, wherein the variant inc coding strand encodes a variant inc RNA, and the variant inc RNA is a regulator of plasmid copy number, can be used to accomplish a substantial increase in copy number of a plasmid comprising the nucleic acid molecule.

Without wishing to be bound by theory, it is believed that the coding strand for inc RNA includes a central domain that is conserved among wild-type sequences. The wild-type central domain corresponds to nucleotides 43-65 of SEQ ID NO: 19. As shown in FIG. 1 and FIG. 2, this sequence is conserved among each of five previously disclosed coding strands for inc RNA, namely those of RepFIC of plasmid P307, RepFIC of plasmid F as disclosed by Saadi et al., copA of *E. coli* strain to1C, RepFIC of *E. coli* strain K-12, and F-like plasmid of *E. coli* strain NCM3722. As shown in FIG. 1 and FIG. 2, the coding strands can vary with respect to their sequences, e.g. at nucleotide positions 42 (C or T), 66 (C or A), and 89 (T or G), with positions numbered according to SEQ ID NO: 19. As noted above, according to Saadi et al., the sequence of the coding strand of inc RNA of plasmid F differs from that of inc RNA of plasmid P307 by two bases, and this difference has no demonstrable effect on incompatibility. Thus, the coding strands also can maintain incompatibility despite such variation. Also, as can be seen, the coding sequence of the inc RNA of plasmid F according to Saadi et al. differs from that of F-like plasmid of *E. coli* strain NCM3722 by a single substitution. This suggests that this substitution also has no demonstrable effect. As shown in FIG. 2, the central domain corresponds to a 23 nucleotide sequence, from nucleotide position 43 to nucleotide position 65, with positions numbered according to SEQ ID NO: 19. The central domain is located between two of the nucleotide positions that can vary, namely nucleotide positions 42 and 66. Given that the sequence of the central domain is conserved among each of the five previously disclosed coding strands for inc RNA, and that the variations elsewhere in the coding strands appear to be without demonstrable effect, the central domain sequence corresponding to nucleotides 43-65 of SEQ ID NO: 19 may be considered wild-type.

Also without wishing to be bound by theory, it is believed that the central domain of inc RNA plays an important role in determining copy number of plasmids including the RepFIC replicon. As shown in FIG. 3 and FIG. 4, the variant inc coding strand includes a central domain that comprises SEQ ID NO: 15 and that differs from the wild-type central domain by a single substitution, namely C to T at nucleotide position 60, with positions numbered according to SEQ ID NO: 17. A variant inc coding strand that includes this substitution and that is otherwise identical to the coding strand for inc RNA of *E. coli* NCM3722 exhibits an increase in plasmid copy number of, for example, about 5 to 15 fold, with the precise increase apparently depending on factors such as plasmid size and strain. Because the C to T substitution in the central domain is the only difference between the variant inc coding strand and the coding strand for inc RNA of *E. coli* NCM3722, and because the central domain is located between two of the nucleotide positions that can vary without apparent demonstrable effect, and further because no other substitutions occur within the central domain among the five previously disclosed coding strands for inc RNA, the central domain appears to be important in determining plasmid copy number.

As used herein, the term nucleic acid molecule means a molecule of DNA and/or RNA, including for example a double-stranded DNA molecule, a single-stranded DNA molecule, a double-stranded RNA molecule, a single-stranded RNA molecule, or a DNA/RNA hybrid molecule, with the structure of the nucleic acid molecule depending on whether the nucleic acid molecule includes a DNA sequence, an RNA sequence, or both.

As used herein, the term inc RNA means an RNA molecule that determines incompatibility of the RepFIC replicon of IncFI plasmids based on sequence and structure of the inc RNA. Incompatibility of the RepFIC replicon of IncFI plasmids can be measured, for example, by measuring loss of a resident plasmid from a microorganism due to introduction of an incoming plasmid into the microorganism, as discussed, for example, by Saadi et al.

As used herein, the term inc coding strand means a DNA molecule strand, or portion of a DNA molecule strand, that encodes the sequence of an inc RNA.

As used herein, the term variant inc RNA means an inc RNA that has a nucleotide sequence that differs from the sequence of a wild-type inc RNA based on addition, deletion, and/or substitution of at least one nucleotide relative to the sequence of the wild-type inc RNA.

As used herein, the term variant inc coding strand means a DNA molecule that encodes the sequence of a variant inc RNA.

As used herein, the term replicon means a region of a DNA molecule that replicates from a single origin of replication.

As used herein, the term vector means a nucleic acid molecule that can occur in a microorganism, naturally or by introduction into the microorganism, such as a plasmid, a viral vector, a cosmid, or an artificial chromosome.

As used herein, the term plasmid means a nucleic acid molecule that can occur in a microorganism, naturally or by introduction into the microorganism, that is physically separate from chromosome(s) of the microorganism, and that replicates independently of the chromosome(s). As discussed above, plasmids are typically double-stranded circular DNA molecules, but can also be linear DNA molecules and/or RNA molecules. Plasmids occur in a range of sizes, from about 1 kb to more than 2 Mb. Plasmids also occur in a range of copies per cell, from low copy number to high copy number. Plasmids can be modified to include target genes.

As used herein, the term plasmid copy number means the number of copies a plasmid in a cell of a microorganism. Plasmid copy number can be measured for a plasmid in a microorganism, for example, by using Real-time PCR to compare the number of copies of a gene that occurs in a single copy on the plasmid relative to a gene that occurs in a single copy on a chromosome of the microorganism, among other approaches.

As used herein, the term regulator of plasmid copy number means a factor, such as an RNA molecule or a protein, that causes a change in copy number of a plasmid in a microorganism, for example an increase or a decrease, when the factor is present in the microorganism versus when the factor is not present in the microorganism. By regulating plasmid copy number, it is possible to stably express the plasmid, thereby enabling the stable growth of the microorganism including the plasmid.

As noted, a nucleic acid molecule comprising a variant inc coding strand that comprises SEQ ID NO: 15 is disclosed. As also noted, SEQ ID NO: 15 corresponds to a DNA sequence. The nucleic acid molecule can be, for example, a double-stranded DNA molecule, a single-stranded DNA molecule, or a combination thereof.

The variant inc coding strand encodes a variant inc RNA. The RNA sequence of the variant inc RNA can be inferred from the DNA sequence of the variant inc coding strand. As discussed above, the variant inc coding strand includes a central domain that differs from the wild-type central domain by a single substitution, namely C to T at nucleotide position 60, with positions numbered according to SEQ ID NO: 17. Accordingly, the inferred sequence of the variant inc RNA includes a corresponding C to U substitution at this position. Like the five previously disclosed coding strands for inc RNA, the inferred sequence of the variant inc RNA also may vary depending on the source of the variant inc coding strand. The inferred sequence also may vary depending on the 5' end and the 3' end predicted for the inc RNA. Thus, for example, the variant inc coding strand may include the C to T substitution at nucleotide position 60 and otherwise be identical to the coding strand for inc RNA of *E. coli* NCM3722. Also for example, the variant inc coding strand may include one or more of the substitutions observed between the five previously disclosed coding strands for inc RNA as shown in FIG. 2, and thus at nucleotide positions 42 (C or T), 66 (C or A), and 89 (T or G), with positions numbered according to SEQ ID NO: 17. Also for example, the variant inc coding strand may vary at its 5' end and its 3' end, depending on the actual 5' end and the actual 3' end for the variant inc RNA encoded by the variant inc coding strand.

In some examples the variant inc coding strand comprises a nucleotide sequence that is at least 90% identical to SEQ ID NO: 17. For reference, SEQ ID NO: 17 corresponds to a variant inc coding strand that includes the C to T substitution at nucleotide position 60 and that is otherwise identical to the coding strand for inc RNA of *E. coli* NCM3722. Also for reference, the percentage of sequence identity between the nucleotide sequence of a variant inc coding strand and SEQ ID NO: 17 can be determined by making a pairwise sequence alignment. This can be done using EMBOSS Needle Pairwise Sequence alignment (NUCLEOTIDE) tool using default settings (matrix: DNAfull; gap open: 10; gap extend: 0.5; output format: pair; end gap penalty: false; end gap open: 10; end gap extend: 0.5) (website: ebi.ac.uk/Tools/psa/emboss_needle/nucleotide.html). This also can be done using other pairwise sequence alignment tools that are analogous. For example, the variant inc coding strand can comprise a nucleotide sequence that is at least 91%, 92%, 93%, 94%, 95%, 96%, 97%, 98%, 99%, or 100% identical to SEQ ID NO: 17.

In some examples, the variant inc coding strand comprises a nucleotide sequence that is identical to SEQ ID NO: 17 with respect to at least 90 nucleotides of SEQ ID NO: 17. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17.

In some examples, the variant inc coding strand comprises SEQ ID NO: 17. In some examples, the variant inc coding strand consists of SEQ ID NO: 17.

In some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17. For example, the variant inc coding strand can comprise a variant of SEQ ID NO: 17 that includes one substitution as follows: T to C at nucleotide position 42, A to C at nucleotide position 66, or G to T at nucleotide position 89, with positions numbered according to SEQ ID NO: 17. Also for example, the variant inc coding strand can comprise a variant of SEQ ID NO: 17 that includes a combination of any two of these substitutions. Also for example, the variant inc coding strand can comprise a variant of SEQ ID NO: 17 that includes all three of these substitutions. Also for example, the variant inc coding strand can consist of a variant of SEQ ID NO: 17 that includes one substitution as follows: T to C at nucleotide position 42, A to C at nucleotide position 66, or G to T at nucleotide position 89, with positions numbered according to SEQ ID NO: 17. Also for example, the variant inc coding strand can consist of a variant of SEQ ID NO: 17 that includes a combination of any two of these substitutions. Also for example, the variant inc coding strand can consist of a variant of SEQ ID NO: 17 that includes all three of these substitutions.

In some examples, the variant inc coding strand comprises a variant of SEQ ID NO: 17 that lacks one or more of nucleotides 1-7 of SEQ ID NO: 17. For example, the variant inc coding strand can comprise a variant of SEQ ID NO: 17 that lacks nucleotide(s) 1, 1 and 2, 1-3, 1-4, 1-5, 1-6, or 1-7 of SEQ ID NO:17. Also for example, the variant inc coding strand can consist of a variant of SEQ ID NO: 17 that lacks nucleotide(s) 1, 1 and 2, 1-3, 1-4, 1-5, 1-6, or 1-7 of SEQ ID NO:17.

In some examples, the variant inc coding strand comprises a variant of SEQ ID NO: 17 that lacks one or more of nucleotides 94-98 of SEQ ID NO: 17. For example, the variant inc coding strand can comprise a variant of SEQ ID NO: 17 that lacks nucleotide(s) 94-98, 95-98, 96-98, 97-98, or 98 of SEQ ID NO:17. Also for example, the variant inc coding strand can consist of a variant of SEQ ID NO: 17 that lacks nucleotide(s) 94-98, 95-98, 96-98, 97-98, or 98 of SEQ ID NO:17.

In some examples, the variant inc coding strand comprises a variant of SEQ ID NO: 17 that includes one or more other substitutions in addition to, or other than, at nucleotide positions 42, 66, and 89. For example, as discussed above, the inc RNA of RepFIC is predicted to have a stem-loop structure that is believed to be critical for function of the inc RNA. Accordingly, in some examples the variant inc coding strand can comprise additional substitutions that do not disrupt the stem-loop structure, e.g. pairs of substitutions that maintain the stem-loop structure.

The variant inc RNA is a regulator of plasmid copy number. More broadly, the variant inc RNA is a regulator of replicon copy number and vector copy number. As discussed above with respect to plasmids, a replicon corresponds to a region of a DNA molecule that replicates from a single origin of replication. The DNA molecule can be, for example, a vector, such as a plasmid, a viral vector, a cosmid, or an artificial chromosome. As discussed above, RepFIC is a replicon of IncFI plasmids. Also as discussed, the inc RNA of RepFIC determines incompatibility of the RepFIC replicon based on its sequence and structure. As also discussed, a variant inc coding strand that includes the C to T substitution and that is otherwise identical to the coding strand for inc RNA of E. coli NCM3722 exhibits an increase in plasmid copy number.

Thus, the variant inc RNA can be a regulator of plasmid copy number based on determining incompatibility of the replicon that encodes the variant inc RNA. For example, the variant inc RNA can affect segregational stability of a plasmid, and thus copy number of the plasmid, in a strain that includes the plasmid and another plasmid that is incompatible. Also, the variant inc RNA can be a regulator of copy number based on including the C to T substitution and thereby exhibiting an increase in plasmid copy number in a strain including the plasmid, relative to a strain including a plasmid including a replicon including a coding strand for inc RNA that does not include the C to T substitution. For example, the variant inc RNA can exhibit an increase in plasmid copy number of, for example 5 to 15 fold.

More generally, the variant inc RNA can be a regulator of replicon copy number and vector copy number. Thus, along with being a regulator of plasmid copy number, e.g. for vectors that correspond to plasmids, the variant inc RNA also can be a regulator of copy number of viral vectors, cosmids, and/or artificial chromosomes, e.g. for vectors corresponding to viral vectors, cosmids, and/or artificial chromosomes.

In some examples, expression of the variant inc RNA increases copy number of a vector relative to expression of wild-type inc RNA encoded by an inc sequence comprising SEQ ID NO: 19. For example, expression of the variant inc RNA can increase copy number of a vector relative to expression of wild-type inc RNA encoded by the coding strand for inc RNA of E. coli NCM3722. In some examples, the vector corresponds to one or more of a plasmid, a viral vector, a cosmid, or an artificial chromosome. In some examples, expression of the variant inc RNA increases copy number of a vector relative to expression of wild-type inc RNA encoded by an inc sequence comprising SEQ ID NO: 19 by 1 to 50 fold, e.g. by 2 to 40 fold, 3 to 30 fold, 4 to 20 fold, 1 to 10 fold, 5 to 15 fold, 10 to 20 fold, 15 to 25 fold, 20 to 30 fold, 25 to 35 fold, 30 to 40 fold, 35 to 45 fold, or 40 to 50 fold.

A replicon comprising the nucleic acid molecule, a promoter, and an origin of replication also is disclosed. The promoter is operably linked to the variant inc coding strand. The variant inc RNA regulates copy number of the replicon.

The nucleic acid molecule can be as described above. Thus, in some examples expression of the variant inc RNA increases copy number of a vector relative to expression of wild-type inc RNA encoded by an inc sequence comprising SEQ ID NO: 19, as discussed above. In some examples the variant inc coding strand comprises a nucleotide sequence that is at least 90% identical to SEQ ID NO: 17, as discussed above. In some examples the variant inc coding strand comprises SEQ ID NO: 17, as discussed above.

For reference, a promoter is a combination of short sequence elements to which RNA polymerase binds in order to initiate transcription of a gene. By the promoter being operably linked to the variant inc coding strand, it is meant that the promoter is a promoter for the variant inc coding strand. An origin of replication is a particular sequence at which replication is initiated.

In some examples, the replicon comprises a variant RepFIC replicon, and the nucleic acid molecule is part of the variant RepFIC replicon. As discussed above, RepFIC is a replicon of IncFI plasmids, which is present in complete form in plasmid P307, and which is present in truncated form in plasmid F. As also discussed, the inferred sequence of inc RNA of RepFIC varies depending on source and predicted ends. The variant RepFIC replicon is a variant based on including the central domain that differs from the wild-type central domain by the single C to T substitution, as discussed above. Thus, the variant RepFIC replicon can be a variant relative to another RepFIC replicon present in complete form or a RepFIC replicon present in truncated form, with the variant RepFIC replicon including the central domain that differs from the wild-type central domain by the single C to T substitution, and the other RepFIC replicon not including the single C to T substitution. Also, the variant RepFIC replicon can be a variant relative to another RepFIC replicon that includes any of the other substitutions discussed above, or other additional substitutions, with the variant RepFIC replicon including the central domain that differs from the wild-type central domain by the single C to T substitution, and the other RepFIC replicon not including the single C to T substitution.

A vector comprising the replicon also is disclosed. The replicon can be as described above. Thus, in some examples the replicon comprises a variant repFIC replicon, and the nucleic acid molecule is part of the variant repFIC replicon, as discussed above.

In some examples, the variant inc RNA increases copy number of the vector relative to expression of wild-type inc RNA encoded by an inc sequence comprising SEQ ID NO: 19, as discussed above.

In some examples, the vector comprises a plasmid. As discussed above, a vector can correspond to one or more of a plasmid, a viral vector, a cosmid, or an artificial chromosome. Thus, in some examples the vector corresponds to a plasmid.

In some examples, the vector further comprises a target gene for making a target product. The vector can be, for example, a recombinant plasmid including a target gene from an organism, such as a microorganism of the domain Bacteria, Archaea, or Eukaryota, an animal, and/or a plant, among other organisms. Regarding a microorganism of the domain Bacteria in particular, the target gene can be from, for example, a bacterium of the genus *Escherichia*, such as *Escherichia coli*, a bacterium of the genus *Corynebacterium*, such as *Corynebacterium glutamicum*, or a bacterium of the genus *Bacillus*, such as *Bacillus subtilis*, among others. Numerous techniques for genetic engineering have been developed, allowing recombinant expression of genes of diverse organisms, including microorganisms of the domain Bacteria, Archaea, and Eukaryota, as well as animals and plants, among other organisms. Such techniques can be applied to clone and express target genes from diverse organisms in a recombinant microorganism in accordance with the present disclosure, as will be apparent to a person of ordinary skill in the art.

In some examples, the target product comprises one or more of (i) a target RNA, (ii) a target protein, (iii) a target biomaterial, (iv) a target polymer, precursor thereof, and/or enzyme for production thereof, (v) a target sweetener, precursor thereof, and/or enzyme for production thereof, (vi) a target oil, precursor thereof, and/or enzyme for production thereof, (vii) a target fat, precursor thereof, and/or enzyme for production thereof, (viii) a target polysaccharide, precursor thereof, and/or enzyme for production thereof, (ix) a target amino acid, precursor thereof, and/or enzyme for production thereof, (x) a target nucleotide, precursor thereof, and/or enzyme for production thereof, (xi) a target vaccine, precursor thereof, and/or enzyme for production thereof, or (xii) a target pharmaceutical product, precursor thereof, and/or enzyme for production thereof. Thus, in some examples the target gene encodes a target RNA, and the target product corresponds to the target RNA. Also in some examples the target gene encodes a target protein, and the target product corresponds to the target protein. Also in some examples the target gene encodes a target RNA and/or a target protein, and the target RNA and/or target protein play a role in turn in producing a target biomaterial, a target polymer, precursor thereof, and/or enzyme for production thereof, a target sweetener, precursor thereof, and/or enzyme for production thereof, a target oil, precursor thereof, and/or enzyme for production thereof, a target fat, precursor thereof, and/or enzyme for production thereof, a target polysaccharide, precursor thereof, and/or enzyme for production thereof, a target amino acid, precursor thereof, and/or enzyme for production thereof, a target nucleotide, precursor thereof, and/or enzyme for production thereof, a target vaccine, precursor thereof, and/or enzyme for production thereof, or a target pharmaceutical product, precursor thereof, and/or enzyme for production thereof. For example, with respect to a target polymer, a target sweetener, a target oil, a target fat, a target polysaccharide, a target amino acid, and/or a target nucleotide, the target gene can encode a target protein that corresponds to an enzyme that produces the target polymer, the target sweetener, the target oil, the target fat, the target polysaccharide, the target amino acid, and/or the target nucleotide, either directly or through a precursor. Also for example, with respect to a vaccine, the target gene can encode a target protein that corresponds to an antigen or antigen fragment, e.g. a protein subunit, a receptor, or other protein of a pathogenic microorganism, or a fragment thereof, that can be used as a component of a vaccine against the pathogenic microorganism. Also for example, with respect to a target pharmaceutical product, the target gene can encode a target protein, such as an antibody, a receptor, or a hormone, that can be used as a component of a pharmaceutical product.

In some examples, the vector comprises a plurality of target genes, e.g. multiple target genes from a particular organism, and/or one or more target genes from each of multiple organisms. Also in some examples, the target gene is for making a plurality of target products.

In some examples, the vector, e.g. a plasmid, has a size of 3 to 120 kb. Recombinant vectors often occur in sizes of 3 to 120 kb, as these are typical sizes for vectors into which target genes have been cloned. As noted above, a variant inc coding strand that includes the C to T substitution and that is otherwise identical to the coding strand for inc RNA of *E. coli* NCM3722 exhibits an increase in plasmid copy number of, for example, about 5 to 15 fold. As discussed below, and as shown in FIG. 5 and FIG. 6, the corresponding plasmids for which the increase in plasmid copy number was observed, and F-like plasmid of *E. coli* NCM3722 from which the corresponding RepFIC replicon was obtained, occur in sizes within the range of 3 to 120 kb, demonstrating relevance of the variant inc coding strand in regulating copy number of plasmids, and thus vectors, with sizes within this range.

A recombinant microorganism comprising the replicon also is disclosed. The replicon can be as described above.

A recombinant microorganism comprising the vector also is disclosed. The vector can be as described above. Thus, in some examples expression of the variant inc RNA increases copy number of the vector relative to expression of wild-type inc RNA encoded by an inc sequence comprising SEQ ID NO: 19. Also in some examples the vector comprises a plasmid. Also in some examples the vector further comprises a target gene for making a target product. Also in some examples the target product comprises one or more of the target products as recited above.

In some examples expression of the variant inc RNA in the recombinant microorganism increases copy number of the vector relative to expression of wild-type inc RNA encoded by an inc sequence comprising SEQ ID NO: 19 in a control microorganism. The control microorganism can be, for example, derived from the same genus, species, and/or strain as the recombinant microorganism, and can include similar or identical plasmids and/or target genes, and thus can be phylogenetically similar, closely related, and/or genetically identical other than with respect to differences between the variant inc coding sequence of the recombinant microorganism and the corresponding inc sequence of the control microorganism. Similarly as discussed above, the increase can be by 1 to 50 fold, e.g. by 2 to 40 fold, 3 to 30 fold, 4 to 20 fold, 1 to 10 fold, 5 to 15 fold, 10 to 20 fold, 15 to 25 fold, 20 to 30 fold, 25 to 35 fold, 30 to 40 fold, 35 to 45 fold, or 40 to 50 fold.

In some examples, the variant inc coding strand of the recombinant microorganism comprises a nucleotide sequence that is at least 90% identical to SEQ ID NO: 17, as discussed above. For example, the variant inc coding strand can comprise a nucleotide sequence that is at least 91%, 92%, 93%, 94%, 95%, 96%, 97%, 98%, 99%, or 100% identical to SEQ ID NO: 17, as discussed. Also, in some examples, the variant inc coding strand comprises a nucleotide sequence that is identical to SEQ ID NO: 17 with respect to at least 90 nucleotides of SEQ ID NO: 17, as discussed. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17, as discussed.

In some examples, the variant inc coding strand of the recombinant microorganism comprises SEQ ID NO: 17, as discussed above. Also, in some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17, as discussed. In some examples, the variant inc coding strand comprises a variant of SEQ ID NO: 17 that lacks one or more of nucleotides 1-7 of SEQ ID NO: 17, as discussed. In some examples, the variant inc coding strand comprises a variant of SEQ ID NO: 17 that lacks one or more of nucleotides 94-98 of SEQ ID NO: 17, as discussed. In some examples, the variant inc coding strand comprises a variant of SEQ ID NO: 17 that includes one or more other substitutions in addition to, or other than, at nucleotide positions 42, 66, and 89, as discussed.

In some examples the recombinant microorganism can be prepared by introducing the vector into a precursor microorganism by one or more of transformation, conjugation, or transduction. The precursor microorganism can be a microorganism into which the vector is introduced directly, such that the recombinant microorganism is genetically identical to the precursor microorganism except that recombinant microorganism includes the vector. Transformation can be carried out by transfer of the vector in isolated form into cells of the precursor microorganism, for example, by a chemical technique, e.g. calcium chloride transformation, or by a physical technique, e.g. by electroporation. Conjugation can be carried out based on the vector including genes for synthesis of pili, and contacting cells of a donor microorganism including the vector with cells of the precursor microorganism, which will receive the vector. Transduction can be carried out based on use of a virus to accomplish transfer of the vector into cells of the precursor microorganism. Each can be carried out by standard techniques of molecular biology.

In some examples, the recombinant microorganism can be prepared from one or more of a bacterium of the genus *Escherichia* or a bacterium of the species *Escherichia coli*. As noted above, RepFIC is a replicon of IncFI plasmids. These plasmids occur naturally in *E. coli*. The RepFIC replicon functions in *E. coli*. Accordingly, the nucleic acid molecule comprising the variant inc coding strand can regulate plasmid copy number in a bacterium of the genus *Escherichia*, particularly a bacterium of the species *Escherichia coli*. Also in some examples, the recombinant microorganism can be prepared from another bacterium, i.e. from a bacterium other than of the genus *Escherichia* or the species *Escherichia coli*.

A method for regulating copy number of the vector in a recombinant microorganism also is disclosed. Use of the variant inc coding strand for regulating copy number of the vector in the recombinant microorganism also is disclosed.

The vector can be as described above. Thus, again in some examples expression of the variant inc RNA increases copy number of the vector relative to expression of wild-type inc RNA encoded by an inc sequence comprising SEQ ID NO: 19. Also in some examples the vector comprises a plasmid. Also in some examples the vector further comprises a target gene for making a target product. Also in some examples the target product comprises one or more of the target products as recited above.

The recombinant microorganism also can be as described above. Thus, again in some examples the variant inc coding strand of the recombinant microorganism comprises a nucleotide sequence that is at least 90% identical to SEQ ID NO: 17, as discussed above. Again, for example, the variant inc coding strand can comprise a nucleotide sequence that is at least 91%, 92%, 93%, 94%, 95%, 96%, 97%, 98%, 99%, or 100% identical to SEQ ID NO: 17, as discussed. Also, in some examples, the variant inc coding strand comprises a nucleotide sequence that is identical to SEQ ID NO: 17 with respect to at least 90 nucleotides of SEQ ID NO: 17, as discussed. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17, as discussed. Also again, in some examples, the variant inc coding strand of the recombinant microorganism comprises SEQ ID NO: 17, as discussed above. Also, in some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17, as discussed. In some examples, the variant inc coding strand comprises a variant of SEQ ID NO: 17 that lacks one or more of nucleotides 1-7 of SEQ ID NO: 17, as discussed. In some examples, the variant inc coding strand comprises a variant of SEQ ID NO: 17 that lacks one or more of nucleotides 94-98 of SEQ ID NO: 17, as discussed. In some examples, the variant inc coding strand comprises a variant of SEQ ID NO: 17 that includes one or more other substitutions in addition to, or other than, at nucleotide positions 42, 66, and 89, as discussed.

The method comprises a step of (1) introducing the vector into a precursor microorganism, thereby obtaining the recombinant microorganism. The vector can be introduced, for example, by one or more of transformation, conjugation, or transduction, as discussed above. The recombinant microorganism can be prepared, for example, from one or more of a bacterium of the genus *Escherichia* or a bacterium of the species *Escherichia coli*, as discussed.

The method also comprises a step of (2) cultivating the recombinant microorganism in a culture medium under conditions sufficient for replication of the vector, thereby regulating copy number of the vector. The cultivation can be carried out by standard techniques of microbiology, for example in culture tubes, flasks, and/or bioreactors, the details of which will be apparent to a person of ordinary skill in the art. The cultivation can be carried out in suitable culture media, e.g. a nutrient rich medium or a minimal medium, the details of which also will be apparent to a person of ordinary skill in the art. The cultivation can be carried out at suitable incubation temperatures, e.g. at or about 25-38° C., 28-37° C., or 37° C., the details of which also will be apparent to a person of ordinary skill in the art. As the recombinant microorganism grows and divides during cultivation, the vector will replicate. Thus, for example, regarding a recombinant microorganism prepared from *Escherichia coli*, the recombinant microorganism can be cultivated by a fermentation technique, in batch or continuously, in a bioreactor. The cultivation can be carried out in a minimal medium, e.g. a medium including defined amounts of salts such as M9 Minimal Salts Medium, and one or more carbon sources, e.g. glucose, sucrose, or lignocellulosic materials, among others. The cultivation can be carried out at about 37° C. Such conditions support growth and division of *Escherichia coli*, and thus will support replication of the vector. Other suitable conditions for cultivation of recombinant microorganisms prepared from *Escherichia coli*, as well as from other microorganisms, are known and will be apparent to a person of ordinary skill in the art.

In some examples, expression of the variant inc RNA in the recombinant microorganism increases copy number of the vector relative to expression of wild-type inc RNA encoded by an inc sequence comprising SEQ ID NO: 19 in a control microorganism, as discussed above. Thus, the control microorganism can be, for example, derived from the same genus, species, and/or strain as the recombinant microorganism, and can include similar or identical plasmids and/or target genes.

A method for making a target product by use of the vector in a recombinant microorganism also is disclosed. Use of the vector in a recombinant microorganism for making a target product also is disclosed.

The vector can be as described above. Thus, again in some examples expression of the variant inc RNA increases copy number of the vector relative to expression of wild-type inc RNA encoded by an inc sequence comprising SEQ ID NO: 19. Also in some examples the vector comprises a plasmid.

The recombinant microorganism also can be as described above. Thus, again in some examples the variant inc coding strand of the recombinant microorganism comprises a nucleotide sequence that is at least 90% identical to SEQ ID NO: 17, as discussed above. Again, for example, the variant inc coding strand can comprise a nucleotide sequence that is at least 91%, 92%, 93%, 94%, 95%, 96%, 97%, 98%, 99%, or 100% identical to SEQ ID NO: 17, as discussed. Also, in some examples, the variant inc coding strand comprises a nucleotide sequence that is identical to SEQ ID NO: 17 with respect to at least 90 nucleotides of SEQ ID NO: 17, as discussed. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17, as discussed. Also again, in some examples, the variant inc coding strand of the recombinant microorganism comprises SEQ ID NO: 17, as discussed above. Also, in some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17, as discussed. In some examples, the variant inc coding strand comprises a variant of SEQ ID NO: 17 that lacks one or more of nucleotides 1-7 of SEQ ID NO: 17, as discussed. In some examples, the variant inc coding strand comprises a variant of SEQ ID NO: 17 that lacks one or more of nucleotides 94-98 of SEQ ID NO: 17, as discussed. In some examples, the variant inc coding strand comprises a variant of SEQ ID NO: 17 that includes one or more other substitutions in addition to, or other than, at nucleotide positions 42, 66, and 89, as discussed.

The target product also can be as described above. For example, the target product can comprise one or more of (i) a target RNA, (ii) a target protein, (iii) a target biomaterial, (iv) a target polymer, precursor thereof, and/or enzyme for production thereof, (v) a target sweetener, precursor thereof, and/or enzyme for production thereof, (vi) a target oil, precursor thereof, and/or enzyme for production thereof, (vii) a target fat, precursor thereof, and/or enzyme for production thereof, (viii) a target polysaccharide, precursor thereof, and/or enzyme for production thereof, (ix) a target amino acid, precursor thereof, and/or enzyme for production thereof, (x) a target nucleotide, precursor thereof, and/or enzyme for production thereof, (xi) a target vaccine, precursor thereof, and/or enzyme for production thereof, or (xii) a target pharmaceutical product, precursor thereof, and/or enzyme for production thereof The vector further comprises a target gene for making the target product, as discussed above.

The method comprises a step of (1) introducing the vector into a precursor microorganism, thereby obtaining the recombinant microorganism, as discussed above. Again, the vector can be introduced, for example, by one or more of transformation, conjugation, or transduction, as discussed above. The recombinant microorganism can be prepared, for example, from one or more of a bacterium of the genus *Escherichia* or a bacterium of the species *Escherichia coli*, as discussed.

The method also comprises a step of (2) cultivating the recombinant microorganism in a culture medium under conditions under which the recombinant microorganism expresses the target gene, thereby making the target product, as discussed above.

The method also comprises a step of (3) recovering the target product from the recombinant microorganism and/or the culture medium. Suitable approaches for recovering the target product can be developed based on details of the target product, e.g. standard techniques of protein purification for a target product corresponding to a target protein, or standard techniques of polymer extraction and precipitation for a target product corresponding to a target polymer, among other approaches, the details of which will be apparent to a person of ordinary skill in the art, depending for example on the type of target product, e.g. RNA, protein, polymer, etc., specific details of the target product, e.g. chemical structure, molecular weight, affinity tag, etc., and desired purity, e.g. low to high. For example, regarding a target product corresponding to a target RNA, following cultivation of the recombinant microorganism, the target RNA can be recovered from the recombinant microorganism by use of an RNAsnap(™) method, as described by Stead et al., Nucleic Acids Research 40(20), e156:1-9 (2012), or by commercially available methods such as TRIzol(R) Max(™) Bacteria RNA isolation kit (ThermoFisher Scientific), RNeasy (R) Protect Bacteria isolation kit (Qiagen), or RiboPure(™) Bacteria RNA isolation (ThermoFisher Scientific), among other methods known in the art. For a target product corresponding to a target protein, the target protein can be recovered from the recombinant microorganism by extraction, ion-exchange chromatography, affinity chromatography, and/or concentration by precipitation, according to procedures well known in the art. For a target product corresponding to a target polymer, the target polymer can be recovered by extraction, washing, and concentration, with compositions for washing and precipitants for concentration chosen based on chemical structure and molecular weight, also according to procedures well known in the art. For a target product corresponding to a target sweetener, a target oil, a target fat, a target polysaccharide, a target amino acid, or a target nucleotide, if the target product accumulates within the recombinant microorganism, then similar approaches also can be used, whereas if the target product accumulates extracellularly, then the target product can be recovered, e.g. by precipitation from the culture medium, again according to procedures well known in the art. For a target product corresponding to a target vaccine or a target pharmaceutical product, the target product can be recovered, for example, as described above for a target protein, e.g. based on ion-exchange chromatography for a target vaccine corresponding to an antigen or an antigen fragment, or based on affinity chromatography for a pharmaceutical product corresponding to a monoclonal antibody, among other approaches, again according to procedures well known in the art.

In some examples expression of the variant inc RNA in the recombinant microorganism increases copy number of the vector relative to expression of wild-type inc RNA encoded by an inc sequence comprising SEQ ID NO: 19 in a control microorganism, as discussed above. Again, the control microorganism can be, for example, derived from the same genus, species, and/or strain as the recombinant microorganism, and can include similar or identical plasmids and/or target genes.

Considering the target product in more detail, in some examples the target product comprises one or more of (i) a target polymer, precursor thereof, and/or enzyme for production thereof, or (ii) a target biopolymer, precursor thereof, and/or enzyme for production thereof. Biological production of polymers, including biopolymers, can be challenging, based on a need for coordinated introduction and expression of multiple target genes in a recombinant microorganism, particularly for polymers based on monomers having complicated chemical structures and/or copolymers including two or more monomers. Similar considerations also apply regarding other target products as discussed above, particularly a target sweetener, a target fat, a target polysaccharide, a target amino acid, a target nucleotide, a target vaccine, and a target pharmaceutical product.

The method can be useful for rapidly determining suitable copy numbers for the vectors comprising multiple target genes, e.g. for production of a target polymer, a target biopolymer, a target sweetener, a target fat, a target polysaccharide, a target amino acid, or a target nucleotide, for balancing stable incorporation of the vectors in recombinant microorganisms and control of yield of products of the target genes. A first set of vectors can be prepared that include RepFIC replicons including the wild-type central domain and that cover a first range of vector copy numbers, from low to high (e.g. based on relatively large to small vector size). A second set of vectors can be prepared that is identical to the first except that the vectors of the second set include the variant central domain, and thus cover a second, higher range of vector copy numbers. A set of target genes can be cloned into each vector. The method can be carried out using each of the vectors, including the steps of (1) introducing the vectors, (2) cultivating the corresponding recombinant microorganisms, and (3) recovering the corresponding target product(s). Copy numbers can be determined for each vector during the cultivating. Yields of the target products or other relevant characteristics can be determined during the recovering. This approach can substantially increase the upper limit of copy number that can be achieved for the first set of vectors, which can be advantageous for maximizing yields in cases for which overexpression of target genes is well tolerated. This approach also can effectively double sample size with respect to testing effects of vector copy number on yields of a target product. This approach can particularly be used for vectors corresponding to plasmids, including plasmids in sizes of 3 to 120 kb and/or including multiple target genes.

Another recombinant microorganism comprising the vector, and in this case also comprising a nucleic acid molecule comprising a variant rpoC RNA-polymerase β' subunit protein coding sequence (also termed "variant rpoC coding sequence"), also is disclosed.

The vector can be as described above. Thus, again in some examples expression of the variant inc RNA increases copy number of the vector relative to expression of wild-type inc RNA encoded by an inc sequence comprising SEQ ID NO: 19. Also in some examples the vector comprises a plasmid.

The recombinant microorganism also can be as described above. Thus, again in some examples the variant inc coding strand of the recombinant microorganism comprises a nucleotide sequence that is at least 90% identical to SEQ ID NO: 17, as discussed above. Again, for example, the variant inc coding strand can comprise a nucleotide sequence that is at least 91%, 92%, 93%, 94%, 95%, 96%, 97%, 98%, 99%, or 100% identical to SEQ ID NO: 17, as discussed. Also, in some examples, the variant inc coding strand comprises a nucleotide sequence that is identical to SEQ ID NO: 17 with respect to at least 90 nucleotides of SEQ ID NO: 17, as discussed. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17, as discussed. Also again, in some examples, the variant inc coding strand of the recombinant microorganism comprises SEQ ID NO: 17, as discussed above. Also, in some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17, as discussed. In some examples, the variant inc coding strand comprises a variant of SEQ ID NO: 17 that lacks one or more of nucleotides 1-7 of SEQ ID NO: 17, as discussed. In some examples, the variant inc coding strand comprises a variant of SEQ ID NO: 17 that lacks one or more of nucleotides 94-98 of SEQ ID NO: 17, as discussed. In some examples, the variant inc coding strand comprises a variant of SEQ ID NO: 17 that includes one or more other substitutions in addition to, or other than, at nucleotide positions 42, 66, and 89, as discussed.

As noted, in this case the recombinant microorganism comprises, along with the vector, another nucleic acid molecule comprising a variant rpoC coding sequence. The variant rpoC coding sequence encodes a variant RpoC RNA-polymerase β' subunit protein (also termed "variant RpoC"). The variant RpoC comprises an R47C substitution, with numbering of the R47C substitution defined based on wild-type RpoC RNA-polymerase β' subunit protein (wild-type RpoC) of *Escherichia coli*.

Surprisingly, it has been determined that a nucleic acid molecule comprising a variant rpoC coding sequence, wherein the variant rpoC coding sequence encodes a variant RpoC, and the variant RpoC comprises an R47C substitution, can be used to cause a substantial decrease in copy number of a plasmid in a recombinant microorganism comprising the nucleotide sequence, without causing a corresponding decrease in chromosomal copy number. This is surprising, among other reasons, because the R47C substitution as disclosed herein occurs in an N-terminal domain sequence of RpoC, whereas the mutants of *E. coli* RpoC including single substitutions as described by Ederth et al. and Petersen et al. included mutations only near the 3'-terminal region of the rpoC gene, and thus in C-terminal domain sequences of RpoC. This also is surprising because the R47C substitution as disclosed herein occurs within a nine amino acid residue N-terminal domain sequence that is otherwise strictly conserved among RpoCs of diverse bacteria, whereas the single substitutions in the mutants of *E. coli* RpoC as described by Ederth et al. and Petersen et al. occur at positions within the RpoC sequence that are not surrounded by conserved residues, and thus that do not occur within conserved sequences.

Without wishing to be bound by theory, it is believed that wild-type RpoCs from diverse bacteria include an N-terminal domain sequence, corresponding to residues 40-48 of SEQ ID NO: 44, that is strictly conserved among the wild-type RpoCs. As shown in FIG. 7, this sequence is strictly conserved among 19 diverse bacteria, namely *Thermus thermophilus, Acetobacter pasteurianus, Neisseria gonorrhoeae, Legionella pneumophila, Pseudomonas aeruginosa, Vibrio cholerae, Escherichia coli, Salmonella enterica serovar Typhimurium, Actinomyces odontolyticus, Streptomyces coelicolor, Corynebacterium diphtheriae, Mycobacterium tuberculosis, Rhodococcus equi, Chlamydia trachomatis, Clostridium botulinum, Bacillus subtilis, Streptococcus pneumoniae, Enterococcus faecalis,* and *Lactobacillus brevis*, representing diverse phylogenies, metabolisms, and environments. For reference, these sequences correspond to full length RpoC sequences available from the alignment of the C-terminal domain of RpoCs of the 21 strains as provided by Lee et al. It also is believed that wild-type RpoCs from a diverse range of bacteria also include a central domain sequence, corresponding to SEQ ID NO: 47, that also is strictly conserved among the wild-type RpoCs. As shown in FIG. 8, this sequence also is strictly conserved among the 19 diverse bacteria. It also is believed that wild-type RpoCs from a diverse range of bacteria also include a C-terminal domain sequence, corresponding to SEQ ID NO: 48, that also is strictly conserved among the wild-type RpoCs. As shown in FIG. 9A-B, this sequence also is strictly conserved among the 19 diverse bacteria.

It further is believed that a longer N-terminal domain sequence, corresponding to residues 33-57 of SEQ ID NO: 44, a longer central domain sequence, corresponding to SEQ ID NO: 50, and a longer C-terminal domain sequence, corresponding to SEQ ID NO: 51, including the strictly conserved N-terminal, central, and C-terminal domain sequences, respectively, include numerous residues that are generally conserved among RpoCs of the 19 diverse bacteria. As shown in FIG. 7, FIG. 8, and FIG. 9A-B, *E. coli* RpoC includes these longer sequences. Also, the RpoCs from the other bacteria include sequences that are highly similar to these longer sequences.

Because the wild-type RpoCs from diverse bacteria include the strictly conserved N-terminal, central, and C-terminal domain sequences, it is believed that these sequences are also strictly conserved among wild-type RpoCs of other bacteria. For context, as shown in TABLE 1, results for pairwise sequence alignments of RpoC of *E. coli* compared to RpoCs of the other 18 diverse bacteria indicate a relatively high degree of sequence identity and similarity, even for RpoCs of bacteria, such as the extreme thermophile *Thermus thermophilus*, that are distant from *E. coli* phylogenetically, metabolically, and environmentally. This is consistent with the fundamental roles that RpoC plays in transcription and replication.

TABLE 1

Results for pairwise sequence alignments of RpoC of *E. coli* compared to RpoCs of other bacteria. *

| Bacterium | Accession | Length | Identity | Similarity | Gaps | Score | Sequence |
|---|---|---|---|---|---|---|---|
| Thermus thermophilus | sp\|Q8RQE8.1\|RPOC_THET8 | 1765 | 36.1% | 48.3% | 33.9% | 2851.0 | SEQ ID NO: 52 |
| Acetobacter pasteurianus | BAH99075.1 | 1439 | 59.6% | 74.6% | 5.6% | 4334.5 | SEQ ID NO: 53 |
| Neisseria gonorrhoeae | sp\|Q5F5R6.1\|RPOC_NEIG1 | 1412 | 66.1% | 80.4% | 1.8% | 4851.0 | SEQ ID NO: 54 |
| Legionella pneumophila | sp\|Q5X865.1\|RPOC_LEGPA | 1413 | 71.8% | 83.3% | 1.3% | 5223.0 | SEQ ID NO: 55 |
| Pseudomonas aeruginosa | sp\|Q9HWC9.1\|RPOC_PSEAE | 1408 | 75.4% | 85.6% | 0.7% | 5477.0 | SEQ ID NO: 56 |
| Vibrio cholerae | sp\|Q9KV29.1\|RPOC_VIBCH | 1407 | 82.4% | 89.8% | 0.4% | 5941.0 | SEQ ID NO: 57 |
| Escherichia coli | sp\|P0A8T7.1\|RPOC_ECOLI | 1407 | 100.0% | 100.0% | 0.0% | 7139.0 | SEQ ID NO: 44 |
| Salmonella enterica serovar Typhimurium | sp\|P0A2R4.1\|RPOC_SALTY | 1407 | 98.6% | 99.3% | 0.0% | 7057.0 | SEQ ID NO: 58 |
| Actinomyces odontolyticus | EDN79927.1 | 1529 | 40.9% | 54.7% | 23.0% | 2883.5 | SEQ ID NO: 59 |
| Streptomyces coelicolor | sp\|Q8CJT1.1\|RPOC_STRCO | 1539 | 42.6% | 55.7% | 24.2% | 3048.0 | SEQ ID NO: 60 |
| Corynebacterium diphtheriae | sp\|Q6NJF6.1\|RPOC_CORDI | 1566 | 40.9% | 54.1% | 24.8% | 2933.0 | SEQ ID NO: 61 |
| Mycobacterium tuberculosis | sp\|A5U053.1\|RPOC_MYCTA | 1552 | 41.0% | 55.0% | 24.5% | 2944.0 | SEQ ID NO: 62 |
| Rhodococcus equi | CBH49656.1 | 1542 | 41.6% | 55.6% | 23.2% | 2986.5 | SEQ ID NO: 63 |
| Chlamydia trachomatis | sp\|O84316.1\|RPOC_CHLTR | 1468 | 47.8% | 65.6% | 9.1% | 3447.0 | SEQ ID NO: 64 |
| Clostridium botulinum | sp\|A7FZ76.1\|RPOC_CLOB1 | 1420 | 47.5% | 62.7% | 18.0% | 3344.5 | SEQ ID NO: 65 |
| Bacillus subtilis | sp\|P37871.4\|RPOC_BACSU | 1451 | 45.7% | 59.4% | 20.4% | 3248.5 | SEQ ID NO: 66 |
| Streptococcus pneumoniae | sp\|Q97NQ8.1\|RPOC_STRPN | 1460 | 44.5% | 58.4% | 19.7% | 3111.0 | SEQ ID NO: 67 |

TABLE 1-continued

Results for pairwise sequence alignments of RpoC of *E. coli* compared to RpoCs of other bacteria. *

| Bacterium | Accession | Length | Identity | Similarity | Gaps | Score | Sequence |
|---|---|---|---|---|---|---|---|
| *Enterococcus faecalis* | sp|Q82Z41.1|RPOC_ENTFA | 1454 | 44.8% | 59.8% | 19.5% | 3199.0 | SEQ ID NO: 68 |
| *Lactobacillus brevis* | sp|Q03PV0.1|RPOC_LACBA | 1449 | 44.4% | 59.4% | 19.0% | 3174.5 | SEQ ID NO: 69 |

* Pairwise sequence alignments were made using EMBOSS Needle Pairwise Sequence Alignment (PROTEIN) tool using default settings (matrix: BLOSUM62; gap open: 10; gap extend: 0.5; output format: pair; end gap penalty: false; end gap open: 10;, end gap extend: 0.5) (website: ebi.ac.uk/Tools/psa/emboss_needle/).

Also, because the wild-type RpoCs from diverse bacteria include sequences that are highly similar to the longer N-terminal, central, and C-terminal domain sequences, it is believed that wild-type RpoCs of other bacteria include sequences that are highly similar to these sequences too. In addition, based on the various sequences being strictly or generally conserved, it is believed that the corresponding N-terminal, central, and C-terminal domain sequences make important contributions, structurally and/or functionally, in the roles that RpoC plays in transcription and in replication of chromosomes and plasmids.

Also without wishing to be bound by theory, it is believed that in RpoC the N-terminal domain in particular plays an important role in determining copy number of plasmids. As shown in FIG. 10 and FIG. 11, the variant rpoC coding sequence includes an N-terminal domain that includes SEQ ID NO: 46, which differs from the strictly conserved sequence of the wild-type N-terminal domain by a single substitution, namely R (i.e. arginine) to C (i.e. cysteine), at amino acid position 47 (also termed "R47C"), with numbering defined based on wild-type RpoC of *E. coli*. A variant RpoC that includes this R47C substitution and that is otherwise identical to wild-type RpoC of *E. coli* exhibits a decrease in plasmid copy number of, for example, about 25% to 75%. Because the R47C substitution in the N-terminal domain is the only difference between the variant RpoC and wild-type RpoC of *E. coli*, and because the R47C substitution is located within the longer N-terminal domain sequence that includes numerous residues that are generally conserved among the 19 diverse bacteria, and because no other substitutions occur within the strictly conserved N-terminal domain sequence corresponding to residues 40-48 of SEQ ID NO: 44 among the wild-type RpoCs from the 19 diverse bacteria, the N-terminal domain appears to be important in determining plasmid copy number.

As used herein, the term RNA-polymerase β' subunit protein means an RNA polymerase β' subunit of an RNA polymerase. As discussed above, RNA polymerase plays a role in transcription. RNA polymerase also plays a role in replication of chromosomes and plasmids. An RNA-polymerase β' subunit protein can be identified based on structural and/or functional similarity to known RNA-polymerase β' subunit proteins, e.g. based on sequence alignments as shown by Lee et al., and/or structural features, as discussed by Mukhopadhyay et al. RNA polymerase activity can be measured, for example, as described by Chamberlin et al., The Journal of Biological Chemistry 254(20):10061-10069 (1979).

As used herein, the term rpoC RNA-polymerase β' subunit protein coding sequence means a DNA molecule strand, or portion of a DNA molecule strand, that encodes the sequence of an RNA-polymerase β' subunit protein.

As used herein, the term wild-type RNA-polymerase β' subunit protein means an RNA-polymerase β' subunit protein that occurs among individuals of a species under natural conditions.

As used herein, the term N-terminal domain means a portion of a protein occurring at or near the N-terminus of the protein, for example within the beginning third of the amino acid sequence of the protein.

As used herein, the term central domain means a portion of a protein occurring at or near the center of the protein, for example within the middle third of the amino acid sequence of the protein.

As used herein, the term C-terminal domain means a portion of a protein occurring at or near the C-terminus of the protein, for example within the last third of the amino acid sequence of the protein.

As noted, a nucleic acid molecule comprising a variant rpoC coding sequence is disclosed. The nucleic acid molecule can be, for example, a double-stranded DNA molecule, such as chromosomal DNA into which the variant rpoC coding sequence has been introduced, or a plasmid into which the variant rpoC coding sequence has been cloned.

As also noted, the variant rpoC coding sequence encodes a variant RpoC. The variant RpoC is a variant based on comprising an R47C substitution, with numbering of the R47C substitution defined based on wild-type RpoC of *E. coli*. The variant RpoC is an RpoC, and thus plays roles in transcription, replication of chromosomes, and replication of plasmids. Just as the wild-type RpoCs of the 19 diverse bacteria vary with respect to each other, e.g. at amino acid positions that are not conserved, the variant RpoC also may vary depending on the source of the variant rpoC coding sequence. Thus, for example, the variant RpoC may include the R47C substitution and otherwise be at least 90% identical to wild-type RpoC of *E. coli*. Also for example, the variant RpoC may include the R47C substitution and otherwise be at least 90% identical to wild-type RpoC of any of the other 18 diverse bacteria, i.e. *Thermus thermophilus, Acetobacter pasteurianus, Neisseria gonorrhoeae, Legionella pneumophila, Pseudomonas aeruginosa, Vibrio cholerae, Salmonella enterica serovar Typhimurium, Actinomyces odontolyticus, Streptomyces coelicolor, Corynebacterium diphtherias, Mycobacterium tuberculosis, Rhodococcus equi, Chlamydia trachomatis, Clostridium botulinum, Bacillus subtilis, Streptococcus pneumoniae, Enterococcus faecalis,* or *Lactobacillus brevis*. Also for example, the variant RpoC may include the R47C substitution and one or more portions of one or more of wild-type RpoC of *E. coli* or the other 18 diverse bacteria.

In some examples, the variant RpoC further comprises: (1) an N-terminal domain comprising SEQ ID NO: 46, (2) a central domain comprising SEQ ID NO: 47, and (3) a C-terminal domain comprising SEQ ID NO: 48, wherein the R47C substitution is present within the N-terminal domain. In these examples, the variant RpoC comprises the N-terminal domain sequence corresponding to SEQ ID NO: 46, including the R47C substitution. The variant RpoC also includes the strictly conserved central domain sequence corresponding to SEQ ID NO: 47 and the strictly conserved C-terminal domain sequence corresponding to SEQ ID NO: 48, consistent with the roles that RpoC plays in transcription and in replication of chromosomes and plasmids.

In some examples, the variant RpoC further comprises: (1) an N-terminal domain comprising SEQ ID NO: 49, (2) a central domain comprising SEQ ID NO: 50, and (3) a C-terminal domain comprising SEQ ID NO: 51, wherein the R47C substitution is present within the N-terminal domain. In these examples, the variant RpoC comprises the N-terminal domain sequence corresponding to SEQ ID NO: 49, including the R47C substitution. The variant RpoC also includes the generally conserved longer central domain sequence corresponding to SEQ ID NO: 50 and the generally conserved longer C-terminal domain sequence corresponding to SEQ ID NO: 51, also consistent with the roles that RpoC plays in transcription and in replication of chromosomes and plasmids.

In some examples, the variant RpoC comprises an amino acid sequence that is at least 90% identical to SEQ ID NO: 45. For reference, SEQ ID NO: 45 corresponds to a variant RpoC that includes the R47C substitution and otherwise is identical to wild-type RpoC of E. coli. Also for reference, the percentage of sequence identity between the amino acid sequence of a variant RpoC and SEQ ID NO: 45 can be determined by making a pairwise sequence alignment. This can be done using EMBOSS Needle Pairwise Sequence Alignment (PROTEIN) tool using default settings (matrix: BLOSUM62; gap open: 10; gap extend: 0.5; output format: pair; end gap penalty: false; end gap open: 10; end gap extend: 0.5) (website: ebi.ac.uk/Tools/psa/emboss_needle/). This also can be done using other pairwise sequence alignment tools that are analogous.

The amino acid sequence of a variant RpoC can differ from SEQ ID NO: 45, for example, predominantly or entirely based on substitutions of amino acid residues that are not conserved between wild-type RpoC of E. coli and RpoCs of the other 18 diverse bacteria. With reference to TABLE 1, although results for pairwise sequence alignments of RpoC of E. coli compared to RpoCs of the other 18 diverse bacteria indicate a relatively high degree of sequence identity and similarity, the results also indicate that RpoCs of 17 of the diverse bacteria have sequence identities ranging from 36.1% to 82.4% in comparison to wild-type RpoC of E. coli, and thus well below 90%. Substitutions of amino acid residues that are not conserved between similar proteins are generally more likely to be tolerated, e.g. to not disrupt structure and/or function, in comparison to substitutions of amino acid residues that are conserved. The results of TABLE 1 indicate that RpoCs include many amino acids residues that are not conserved and that thus may be amenable to substitution.

The amino acid sequence of a variant RpoC also can differ from SEQ ID NO: 45, for example, based on including some or many conservative substitutions, meaning replacement of an amino acid residue with another structurally similar amino acid residue, relative to SEQ ID NO: 45. Conservative substitutions typically include substitutions within the following groups: (1) glycine and alanine, (2) valine, isoleucine, and leucine, (3) aspartic acid and glutamic acid, (4) asparagine and glutamine, (5) serine and threonine, (6) lysine and arginine, and (7) phenylalanine and tyrosine. Conservative substitutions are generally more likely to be tolerated in comparison to substitutions that are not conservative.

Thus, in these examples the variant RpoC includes the R47C substitution. The variant RpoC also comprises an amino acid sequence that is at least 90% identical to SEQ ID NO: 45. For example, the variant RpoC can comprise an amino acid sequence that is at least 91%, 92%, 93%, 94%, 95%, 96%, 97%, 98%, 99%, or 100% identical to SEQ ID NO: 45.

In some examples, the variant RpoC comprises SEQ ID NO: 45.

In some examples, expression of the variant RpoC decreases copy number of a plasmid relative to expression of wild-type RpoC comprising SEQ ID NO: 44. For reference, SEQ ID NO: 44 corresponds to wild-type RpoC of E. coli. As noted above, the variant RpoC is an RpoC, and thus plays roles in transcription, replication of chromosomes, and replication of plasmids. Also as noted, a variant RpoC that includes the R47C substitution and that is otherwise identical to wild-type RpoC of E. coli exhibits a decrease in plasmid copy number of, for example, about 25% to 75%.

Importantly, in the context of the recombinant microorganism, which as discussed above also comprises the vector that comprises the variant inc coding strand that comprises SEQ ID NO: 15, the presence of the variant RpoC can cause a decrease in copy number of the vector. The decrease can be, for example, to a copy number intermediate between (i) the copy number of the vector comprising a variant RepFIC replicon including the central domain that differs from the wild-type central domain by the single C to T substitution, as present in a microorganism that is expressing wild-type RpoC, and (ii) the copy number of a corresponding vector comprising the RepFIC replicon not including the single C to T substitution, also as present in a microorganism that is expressing wild-type RpoC. Thus, the presence of the variant RpoC can be used to modulate plasmid copy number, e.g. between levels that can be obtained with variant inc coding strands versus levels obtained with wild-type inc coding strands.

In some examples, expression of the variant RpoC decreases copy number of a plasmid relative to expression of wild-type RpoC comprising SEQ ID NO: 44 by 10% to 80%, e.g. by 25% to 75%, 30% to 70%, 35% to 65%, 40% to 60%, 45% to 55%, 10% to 40%, 20% to 50%, 30% to 60%, 40% to 70%, or 50% to 80%.

The recombinant microorganism comprising the nucleic acid molecule comprising the variant rpoC coding sequence can be obtained, for example, by introducing a complete variant rpoC coding sequence, e.g. cloned in a vector, into a precursor microorganism, e.g. by transformation, conjugation, or transduction, to obtain the recombinant microorganism, and then maintaining the complete variant rpoC coding sequence in the recombinant microorganism, e.g. by selection of the vector. This can be accomplished by standard techniques of molecular biology. In some examples the recombinant microorganism can be prepared by introducing an rpoC coding sequence vector, e.g. a plasmid, comprising the nucleic acid sequence into a precursor microorganism by one or more of transformation, conjugation, or transduction.

The recombinant microorganism comprising the nucleic acid molecule comprising the variant rpoC coding sequence also can be obtained, for example, by introducing a portion of a variant rpoC coding sequence, e.g. cloned in a vector, and using the portion to replace a corresponding portion of an endogenous chromosomal wild-type rpoC coding sequence, e.g. by gene replacement by homologous recombination, e.g. by using a sacB vector. This also can be accomplished by standard techniques of molecular biology. Thus, in some examples, the recombinant microorganism comprises a chromosome, and the variant rpoC coding sequence is present in the chromosome based on replacement of an endogenous rpoC coding sequence by the variant rpoC coding sequence.

As noted above, a variant RpoC that includes the R47C substitution and that is otherwise identical to wild-type RpoC of E. coli exhibits a decrease in plasmid copy number of, for example, about 25% to 75%. As discussed below, this has been achieved in various E. coli strains. Accordingly, the nucleic acid molecule comprising the variant rpoC coding strand can regulate plasmid copy number specifically in a bacterium of the genus Escherichia, particularly a bacterium of the species Escherichia coli.

Another method for regulating copy number of the vector in a recombinant microorganism also is disclosed, in this case with the recombinant microorganism comprising the nucleic acid molecule comprising a variant rpoC coding sequence as described above.

The vector can be as described above. Thus, again in some examples expression of the variant inc RNA increases copy number of the vector relative to expression of wild-type inc RNA encoded by an inc sequence comprising SEQ ID NO: 19. Also in some examples the vector comprises a plasmid.

The recombinant microorganism also can be as described above. Thus, again in some examples the variant inc coding strand of the recombinant microorganism comprises a nucleotide sequence that is at least 90% identical to SEQ ID NO: 17, as discussed above. Again, for example, the variant inc coding strand can comprise a nucleotide sequence that is at least 91%, 92%, 93%, 94%, 95%, 96%, 97%, 98%, 99%, or 100% identical to SEQ ID NO: 17, as discussed. Also, in some examples, the variant inc coding strand comprises a nucleotide sequence that is identical to SEQ ID NO: 17 with respect to at least 90 nucleotides of SEQ ID NO: 17, as discussed. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17, as discussed. Also again, in some examples, the variant inc coding strand of the recombinant microorganism comprises SEQ ID NO: 17, as discussed above. Also, in some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17, as discussed. In some examples, the variant inc coding strand comprises a variant of SEQ ID NO: 17 that lacks one or more of nucleotides 1-7 of SEQ ID NO: 17, as discussed. In some examples, the variant inc coding strand comprises a variant of SEQ ID NO: 17 that lacks one or more of nucleotides 94-98 of SEQ ID NO: 17, as discussed. In some examples, the variant inc coding strand comprises a variant of SEQ ID NO: 17 that includes one or more other substitutions in addition to, or other than, at nucleotide positions 42, 66, and 89, as discussed.

The method comprises a step of (1) introducing the vector into a precursor microorganism, thereby obtaining the recombinant microorganism.

The method also comprises a step of (2) cultivating the recombinant microorganism in a culture medium under conditions sufficient for replication of the vector, thereby regulating copy number of the vector. Again, the cultivation can be carried out by standard techniques of microbiology, for example in culture tubes, flasks, and/or bioreactors, in suitable culture media, e.g. a nutrient rich medium or a minimal medium, at suitable incubation temperatures, e.g. at or about 25-38° C., 28-37° C., or 37° C., the details of which will be apparent to a person of ordinary skill in the art.

As noted, the recombinant microorganism also comprises the nucleic acid molecule comprising a variant rpoC coding sequence as described above. Again, the variant rpoC coding sequence encodes a variant RpoC. The variant RpoC comprises an R47C substitution, with numbering of the R47C substitution defined based on wild-type RpoC of Escherichia coli. Thus, in some examples, the variant RpoC further comprises: (1) an N-terminal domain comprising SEQ ID NO: 46, (2) a central domain comprising SEQ ID NO: 47, and (3) a C-terminal domain comprising SEQ ID NO: 48, wherein the R47C substitution is present within the N-terminal domain. In some examples, the variant RpoC further comprises: (1) an N-terminal domain comprising SEQ ID NO: 49, (2) a central domain comprising SEQ ID NO: 50, and (3) a C-terminal domain comprising SEQ ID NO: 51, wherein the R47C substitution is present within the N-terminal domain. In some examples, the variant RpoC comprises an amino acid sequence that is at least 90% identical to SEQ ID NO: 45, e.g. at least 91%, 92%, 93%, 94%, 95%, 96%, 97%, 98%, 99%, or 100% identical to SEQ ID NO: 45. In some examples, the variant RpoC comprises SEQ ID NO: 45. In some examples, expression of the variant RpoC decreases copy number of a plasmid relative to expression of wild-type RpoC comprising SEQ ID NO: 44, e.g. by 10% to 80%, e.g. by 25% to 75%, 30% to 70%, 35% to 65%, 40% to 60%, 45% to 55%, 10% to 40%, 20% to 50%, 30% to 60%, 40% to 70%, or 50% to 80%.

Another method for making a target product by use of the vector in a recombinant microorganism also is disclosed, in this case with the recombinant microorganism comprising the nucleic acid molecule comprising a variant rpoC coding sequence as described above.

The vector can be as described above. Thus, again in some examples expression of the variant inc RNA increases copy number of the vector relative to expression of wild-type inc RNA encoded by an inc sequence comprising SEQ ID NO: 19. Also in some examples the vector comprises a plasmid.

The recombinant microorganism also can be as described above. Thus, again in some examples the variant inc coding strand of the recombinant microorganism comprises a nucleotide sequence that is at least 90% identical to SEQ ID NO: 17, as discussed above. Again, for example, the variant inc coding strand can comprise a nucleotide sequence that is at least 91%, 92%, 93%, 94%, 95%, 96%, 97%, 98%, 99%, or 100% identical to SEQ ID NO: 17, as discussed. Also, in some examples, the variant inc coding strand comprises a nucleotide sequence that is identical to SEQ ID NO: 17 with respect to at least 90 nucleotides of SEQ ID NO: 17, as discussed. For example, the variant inc coding strand can comprise a nucleotide sequence that is identical to SEQ ID NO: 17 with respect to at least 91, 92, 93, 94, 95, 96, 97, or 98 nucleotides of SEQ ID NO: 17, as discussed. Also again, in some examples, the variant inc coding strand of the recombinant microorganism comprises SEQ ID NO: 17, as discussed above. Also, in some examples, the variant inc coding strand comprises a variant of SEQ ID NO: 17 that includes one or more substitutions as follows: T to C at nucleotide position 42, A to C at nucleotide position 66, or G to T at nucleotide position 89, with positions numbered according to SEQ ID NO: 17, as discussed. In some examples, the variant inc coding strand comprises a variant of SEQ ID NO: 17 that lacks one or more of nucleotides 1-7 of SEQ ID NO: 17, as discussed. In some examples, the variant inc coding strand comprises a variant of SEQ ID NO: 17 that lacks one or more of nucleotides 94-98 of SEQ ID NO: 17, as discussed. In some examples, the variant inc coding strand comprises a variant of SEQ ID NO: 17 that includes one or more other substitutions in addition to, or other than, at nucleotide positions 42, 66, and 89, as discussed.

In accordance with this method, the vector further comprises a target gene for making the target product, as discussed above.

The method comprises a step of (1) introducing the vector into a precursor microorganism, thereby obtaining the recombinant microorganism. The method also comprises a step of (2) cultivating the recombinant microorganism in a culture medium under conditions under which the recombinant microorganism expresses the target gene, thereby making the target product. The method also comprises a step of (3) recovering the target product from the recombinant microorganism and/or the culture medium.

As noted, the recombinant microorganism also comprises the nucleic acid molecule comprising a variant rpoC coding sequence as described above. Again, the variant rpoC coding sequence encodes a variant RpoC. The variant RpoC comprises an R47C substitution, with numbering of the R47C substitution defined based on wild-type RpoC of Escherichia coli. Thus, in some examples, the variant RpoC further comprises: (1) an N-terminal domain comprising SEQ ID NO: 46, (2) a central domain comprising SEQ ID NO: 47, and (3) a C-terminal domain comprising SEQ ID NO: 48, wherein the R47C substitution is present within the N-terminal domain. In some examples, the variant RpoC further comprises: (1) an N-terminal domain comprising SEQ ID NO: 49, (2) a central domain comprising SEQ ID NO: 50, and (3) a C-terminal domain comprising SEQ ID NO: 51, wherein the R47C substitution is present within the N-terminal domain. In some examples, the variant RpoC comprises an amino acid sequence that is at least 90% identical to SEQ ID NO: 45, e.g. at least 91%, 92%, 93%, 94%, 95%, 96%, 97%, 98%, 99%, or 100% identical to SEQ ID NO: 45. In some examples, the variant RpoC comprises SEQ ID NO: 45. In some examples, expression of the variant RpoC decreases copy number of a plasmid relative to expression of wild-type RpoC comprising SEQ ID NO: 44, e.g. by 10% to 80%, e.g. by 25% to 75%, 30% to 70%, 35% to 65%, 40% to 60%, 45% to 55%, 10% to 40%, 20% to 50%, 30% to 60%, 40% to 70%, or 50% to 80%.

The method can be useful for further rapidly determining suitable copy numbers for the vectors comprising multiple target genes, e.g. for production of a target polymer, a target biopolymer, a target sweetener, a target fat, a target polysaccharide, a target amino acid, a target nucleotide, a target vaccine, or a target pharmaceutical product, for balancing stable incorporation of the vectors in recombinant microorganisms and control of yield of products of the target genes. As discussed above, a first set of vectors can be prepared that include RepFIC replicons including the wild-type central domain and that cover a first range of vector copy numbers, from low to high (e.g. based on relatively large to small vector size). A second set of vectors can be prepared that is identical to the first except that the vectors of the second set include the variant central domain, and thus cover a second, higher range of vector copy numbers. A set of target genes can be cloned into each vector. The first and second sets of vectors can be introduced into a first bacterial strain, e.g. an E. coli strain, comprising a wild-type rpoC coding sequence, which thus expresses a wild-type RpoC, to obtain a first set of E. coli strains including the first and second sets vectors and expressing the wild-type RpoC. The first and second set of vectors also can be introduced into a corresponding second recombinant bacterial strain, e.g. a recombinant E. coli strain that comprises a variant rpoC coding sequence that encodes a variant RpoC comprising the R47C substitution, which thus expresses a variant RpoC, the second strain otherwise being identical to the first strain, to obtain a second set of corresponding E. coli strains including the first and second sets of vectors and expressing the variant RpoC. The method can be carried out using each of the vectors, including the steps of (1) introducing the vectors, (2) cultivating the corresponding recombinant microorganisms, and (3) recovering the corresponding target product(s). Copy numbers can be determined for each vector during the cultivating. Yields of the target products or other relevant characteristics can be determined during the recovering. Along with substantially increasing the upper limit of copy number that can be achieved for the first set of vectors relating to use of the variant central domain of the RepFIC replicon, as discussed above, this approach also can substantially decrease the lower limit of copy number that can be achieved for the first set of vectors based on expression of the variant RpoC, which can be advantageous for maintaining viability of cells of the strains in cases in which expression of target genes is deleterious, e.g. for target genes that encode target RNAs and/or target proteins that are toxic to cells when expressed above certain levels in the cells. This approach also can effectively quadruple sample size with respect to testing effects of vector copy number on yields of a target product. Again, this approach can particularly be used for vectors corresponding to plasmids, including plasmids in sizes of 3 to 120 kb and/or including multiple target genes.

EXAMPLES

Example 1

Construction of Plasmids Containing a Modified DNA Sequence of the RepFIC Replicon (1) Preparation of RepFIC fragment and kanamycin-resistance gene fragment.

In order to amplify the 5.2 kb DNA fragment containing the RepFIC replicon (SEQ ID NO: 1), the genomic DNA (gDNA) of Escherichia coli strain NCM3722, which is a prototrophic K-12 strain and was obtained from the Coli Genetic Stock Center (CGSC) (strain 12355), was extracted using a QIAGEN Genomic-tip system, and a polymerase chain reaction (PCR) was performed using the gDNA as a template with a PfuUltra II Fusion HS DNA Polymerase (manufactured by Agilent). The PCR was performed using primers of SEQ ID NO: 2 and SEQ ID NO: 3 as follows: 30 cycles of denaturation at 95° C. for 30 seconds, annealing at 56° C. for 30 seconds, and elongation at 72° C. for 5 minutes.

In order to amplify the 1.4 kb DNA fragment containing the kanamycin resistance gene, PCR was performed using the plasmid pKD4 as a template with a PfuUltra II Fusion HS DNA Polymerase. PCR was performed using primers of SEQ ID NO: 4 and SEQ ID NO: 5 as follows: 30 cycles of denaturation at 94° C. for 30 seconds, annealing at 56° C. for 30 seconds, and elongation at 72° C. for 1 minute 30 seconds.

After PCR reactions were completed, 1.3 $\mu$L of DpnI and 5.7 µl of 10× buffer Tango from Thermo Fisher Scientific (Cat No. ER1701) were added to the 50 µL PCR mixtures, which were then incubated at 37° C. for 1 hour to remove the template DNA. The mixtures were purified with a QIAGEN purification kit and then eluted to obtain a 5.2 kb DNA fragment (also termed "RepFIC fragment") and a 1.4 kb DNA fragment (also termed "KanR fragment").

(2) Preparation of RepFIC fragment containing a modified sequence.

In order to amplify a 5.2 kb DNA fragment containing the RepFIC replicon that has a modified sequence (SEQ ID NO: 17, reverse complement SEQ ID NO: 6), PCR was performed using the gDNA of *E. coli* NCM3722 as a template with a PfuUltra II Fusion HS DNA Polymerase. A PCR was performed using primers of SEQ ID NO: 2 and SEQ ID NO: 7 as follows: 30 cycles of denaturation at 95° C. for 30 seconds, annealing at 56° C. for 30 seconds, and elongation at 72° C. for 3 minutes. Another PCR was performed using primers of SEQ ID NO: 8 and SEQ ID NO: 3 for elongation at 72° C. for 2 minutes and 30 seconds.

After PCR reactions were completed, 1.3 $\mu$L of DpnI and 5.7 µl of 10× buffer Tango were added to the 50 µL PCR reaction mixtures, which were then incubated at 37° C. for 1 hour to remove the template DNA. The mixtures were purified with a QIAGEN purification kit and then eluted to obtain a 2.8 kb DNA fragment and a 2.4 kb DNA fragment.

(3) Construction of plasmids containing wildtype or modified sequence of RepFIC replicon.

The RepFIC and KanR fragments described in Example: 1-(1) were used for the construction of a plasmid, termed pJSL40, as shown in FIG. 5A-B. The pJSL40 plasmid was constructed using a NEBuilder HiFi DNA Assembly Master Mix (manufactured by NEB).

The 2.8 kb and 2.4 kb DNA fragments described in Example: 1-(2) and the KanR fragment described in Example: 1-(1) were used for the construction of another plasmid, termed pJSL41, as shown in FIG. 6A-B. Gibson assembly of the three fragments was performed with a NEBuilder HiFi DNA Assembly Master Mix.

(4) Construction of the F-like plasmid containing the modified sequence of RepFIC replicon.

In order to examine the effect of the modified sequence of the RepFIC replicon on the copy number of large plasmids ranging in size from ten thousand base pairs to more than 100 kilobases (kb), the RepFIC sequence on F-like plasmid in *E. coli* NCM3722 was replaced with the modified sequence described above (SEQ ID NO: 6) by using a known one-step inactivation method (Warner et al., Proc. Natl. Acad. Sci. U.S.A. 97(12):6640-6645, (2000)). At first, a linear DNA fragment to introduce the modified sequence of RepFIC by using a Cre-loxP recombinase system was prepared by PCR that was performed with plasmid pKD3 as a template by using primers of SEQ ID NO: 9 and SEQ ID NO: 10 as follows: 30 cycles of denaturation at 94° C. for 30 seconds, annealing at 56° C. for 30 seconds, and elongation at 72° C. for 1 minute to obtain a 1.2 kb PCR fragment. The PCR mixture was treated with DpnI as described above and the amplified DNA fragment was purified with a QIAGEN purification kit.

The linear DNA fragment was introduced by electroporation into *E. coli* NCM3722/pKD46, which was constructed by introducing pKD46 plasmid into *E. coli* NCM3722 (Warner et al.), and then single colonies were isolated on a Luria-Bertani (LB) plate containing 15 µg/mL of chloramphenicol. The RepFIC regions in the isolated strains were sequenced and a strain containing the modified sequence of RepFIC that replaced wildtype sequence of the F-like plasmid was selected. Plasmid pJW168 (BMG Biotechnol. 2001; 1:7. Epub 2001 Sep. 26) was introduced into the selected strain to prepare the recombinant pJSL42, in which the wildtype RepFIC was substituted with the modified sequence of RepFIC. The *E. coli* NCM3722 isolate containing pJSL42 plasmid was designated as *E. coli* strain CC06-9612.

Example 2

Measurement of Plasmid Copy Number

To measure plasmid copy number, plasmids pJSL40 and pJSL41 were introduced into *E. coli* strain MG1655, which was obtained from the Coli Genetic Stock Center (CGSC No. 6300). The constructed strains MG1655 harboring pJSL40 and pJSL41 were designated as *E. coli* strain CC06-9614 and CC06-9615, respectively.

The copy numbers of the plasmids in the *E. coli* strains CC06-9614, CC06-9615, NCM3722, and CC06-9612 were measured using Real-time PCR (also termed "qPCR") method. The method involves use of SYBR (R) Green I dye to detect PCR products by binding double-stranded DNA formed during PCR. The protocol employs a Fast SYBR (R) Green Cells-to-Ct (™) Kit to perform cell lysis and PCR reactions in "one-pot" on an Applied Biosystems 7500 Fast real-time PCR system.

To prepare cell lysate, the overnight culture of each strain in LB broth was diluted with a cold (4° C.) 1× PBS buffer followed by addition of a lysis solution, a stop solution (Fast SYBR (R) Green Cells-to-Ct (TM) kit, Cat. # 4402956) and an RNase A (Life Technologies, Cat. # 12091-021, 20 mg/ml).

The qPCR reaction mixture was prepared by adding 4 µL of cell lysate to 16 µL of PCR cocktail, the composition of which is shown in TABLE 2.

TABLE 2

| PCR cocktail composition | |
|---|---|
| Component | Volume |
| Fast SYBR (R) Green PCR Master Mix | 10 µL |
| Forward primer (50 µM stock) | 0.12 µL |
| Reverse primer (50 µM stock) | 0.12 µL |
| Nuclease-free water | 5.76 µL |
| Finial volume of PCR cocktail for 20 µL qPCR reaction mixture | 16 µL |

The copy numbers of plasmids in the cell samples were estimated from the relative abundance of a marker DNA sequence on the plasmids, RepFIC, relative to that of a single copy chromosomal gene lacZ encoding β-galactosidase. The primers used for RepFIC were SEQ ID NO: 11 and SEQ ID NO: 12 and for lacZ were SEQ ID NO: 13 and SEQ ID NO: 14. As an internal control for each sample, the copy number of 16S rDNA (rrsH) was measured relative to lacZ. The relative abundance of rrsH to lacZ would be predicted to be about 7, based on the presence of seven chromosomal copies of rrsH. The primers used for rrsH were SEQ ID NO: 25 and SEQ ID NO: 26.

Real-time PCR reactions were performed using the 7500 Fast real-time PCR default program as follows: 1 cycle of enzyme activation at 95° C. for 20 seconds, 40 cycles of denaturation at 95° C. for 3 seconds, annealing and extension at 60° C. for 30 seconds, and dissociation curve.

The plasmid copy number was measured by calculating $2^{\Delta Ct}$, where $\Delta Ct$ was calculated by subtracting RepFIC Ct value from lacZ gene Ct value ($\Delta Ct=Ct_{lacZ}-Ct_{repFIC}$).

TABLE 3 qPCR copy number measurement results

| strain | rrsH relative abundance to lacZ | RepFIC relative abundance to lacZ |
|---|---|---|
| CC06-9614 | 8.4 | 23.5 |
| CC06-9615 | 8.1 | 282.4 |
| NCM3722 | 7.8 | 21.8 |
| CC06-9612 | 7.4 | 214.9 |

As shown in TABLE 3, the plasmid copy number for E. coli strain CC06-9615 was about 14 times higher than that of the control strain CC06-9614. Also, the plasmid copy number of E. coli strain CC06-9612 was about 10 times higher than the F-like plasmid copy number in strain NCM3722. Thus, it was confirmed that the modified sequence of RepFIC resulted in an increase of plasmid copy number independent of the plasmid size, e.g. for both a small plasmid and a large plasmid, and of E. coli background strains, e.g. for both MG1655 and NCM3722.

Example 3

Construction of the Modified RepFIC Replicon Containing F-like Plasmid in E. coli LS5218 and Measurement of Plasmid Copy Numbers In order to re-examine the effect of the modified sequence of RepFIC replicon on plasmid copy number, and to test for the effect in a different strain of E. coli, the RepFIC sequence on F-like plasmid in E. coli LS5218 (CGSC strain #6966) was replaced with the modified sequence described above (SEQ ID NO: 6) by using the same method and materials as described in Example 1-(4). The RepFIC sequence of E. coli LS5218 is the same as that of E. coli NCM3722. The recombinant plasmid pJSL33, in which the wildtype RepFIC was substituted with the modified sequence of RepFIC, was created to re-examine the effect of the modified RepFIC. The E. coli strain LS5218 containing the pJSL33 plasmid was designated as E. coli strain CC06-9667.

The copy numbers of the plasmid in the E. coli strains LS5218 and CC06-9667 were measured using the Real-time PCR, as described in Example 2. qPCR was carried out to clarify the increase in plasmid copy number. RepFIA is another replicon present on the plasmid. The primers used for RepFIA were SEQ ID NO: 27 and SEQ ID NO: 28. Again, as an internal control for each sample, the copy number of 16S rDNA (rrsH) was measured relative to lacZ.

TABLE 4 qPCR copy number measurement results

| Strain | rrsH relative abundance to lacZ | RepFIA relative abundance to lacZ | RepFIC relative abundance to lacZ |
|---|---|---|---|
| LS5218 | 5 | 9.2 | 8.9 |
| CC06-9667 | 6 | 54.5 | 49.4 |

As shown in TABLE 4, the plasmid copy number of E. coli strain CC06-9667 was about 5.5 times higher than the F-like plasmid copy number in strain LS5218. Thus, it was reconfirmed that the modified sequence of RepFIC resulted in an increase of plasmid copy number independent of which background strains were used.

Example 4

Construction of Plasmids for Replacing the rpoC Sequence on a Chromosome (1) Preparation of rpoC fragment and sacB vector.

In order to amplify two 0.5 kb DNA fragments containing a partial variant rpoC sequence that has a modified sequence (SEQ ID NO: 33), the genomic DNA (gDNA) of Escherichia coli strain LS5218, which was obtained from the Coli Genetic Stock Center (CGSC) (strain 6966), was extracted using a QIAGEN Genomic-tip system, and a polymerase chain reaction (PCR) was performed using the gDNA as a template with a PfuUltra II Fusion HS DNA Polymerase (manufactured by Agilent). The corresponding modified RpoC protein, as deduced from the nucleotide sequence, is SEQ ID NO: 45. The modified RpoC protein sequence takes into account that the rpoC nucleotide sequence includes an alternative start codon GTG, instead of ATG. Although GTG generally codes for valine, GTG as an alternative start codon codes for methionine. A PCR was performed using primers of SEQ ID NO: 35 and SEQ ID NO: 36 as follows: 30 cycles of denaturation at 95° C. for 30 seconds, annealing at 56° C. for 30 seconds, and elongation at 72° C. for 30 seconds. Another PCR was performed using primers of SEQ ID NO: 5 and SEQ ID NO: 6 for elongation at 72° C. for 30 seconds. The mixtures were purified with a QIAGEN purification kit and then eluted to obtain two different 0.5 kb DNA fragments.

In order to prepare a gene replacement vector (FIG. 12A-B) containing the sacB gene and R6K origin, pSKH130 was digested with a restriction enzyme EcoRV. The PCR mixture and the reaction mixture of EcoRV digestion were purified with a QIAGEN purification kit and then eluted to obtain a first 0.5 kb DNA fragment, a second 0.5 kb DNA fragment, and a 4.7 kb vector DNA fragment (also termed "sacB vector cut").

(2) Construction of plasmids for replacing the rpoC sequence.

The first 0.5 kb DNA fragment, the second 0.5 kb DNA fragment, and the sacB vector cut described in Example: 4-(1) were used for the construction of pJSL47. The pJSL47 plasmid was constructed using a NEBuilder HiFi DNA Assembly Master Mix (manufactured by NEB) and BW25113, which is strain 7636 of the Coli Genetic Stock Center (CGSC).

(3) Preparation of recombinant E. coli CC06-9642.

In order to substitute the rpoC on the chromosome of Escherichia coli LS5218 (SEQ ID NO: 39) with the variant rpoC sequence (SEQ ID NO: 33), pJSL47 plasmid was introduced by electroporation into E. coli strain LS5218 followed by selection of single colonies grown on a Luria-Bertani (LB) agar plate containing 50 µg/L of kanamycin. Insertion of pJSL47 into the chromosome of the selected colonies was confirmed by PCR using primers of SEQ ID NO: 40 and SEQ ID NO: 41. The selected strains were grown on LB agar plates lacking NaCl but containing 10% sucrose in order to "pop out" the sacB gene and the R6K origin. The transformants were verified for the replacement of LS5218 rpoC (SEQ ID NO: 39) with the variant rpoC sequence (SEQ ID NO: 33) by PCRs and sequence confirmations. The resulting strain that has a correct genotype was designated as E. coli CC06-9642.

Example 5

Measurement of the Plasmid Copy Number

Both LS5218, a wild type strain, and strain CC06-9642 contain an F-like plasmid (67,502 bp). After CC06-9642 was created, the presence of the F-like plasmid was confirmed by a PCR method. The primers used were, for example, of SEQ ID NOS: 11 and 12. When CC06-9642 was created, CC06-9637 was also created. The difference between them is that CC06-9642 contains the F-like plasmid, whereas CC06-9637 does not contain it. RpoC of CC06-9637 is also a variant rpoC.

The plasmid copy number of the two strains was measured using a real-time PCR (also termed "qPCR") method that used SYBR (R) Green I dye to detect PCR products by binding double-stranded DNA formed during the PCR. The protocol employed a Fast SYBR (R) Green Cells-to-Ct (TM) kit to perform cell lysis and PCR reaction in "one-pot" on an Applied Biosystems 7500 Fast real-time PCR system.

To prepare cell lysate, the overnight culture of each strain in LB broth was diluted with a cold (4° C.) 1× PBS buffer followed by addition of a lysis Solution, stop solution (Fast SYBR (R) Green Cells-to-Ct kit, Cat. # 4402956) and an RNase A (Life Technologies, Cat. # 12091-021, 20 mg/ml). The qPCR reaction mixture was prepared by adding 4 µL of cell lysate to 16 µL of PCR cocktail, the composition of which is shown in TABLE 5.

TABLE 5

| PCR cocktail composition | |
|---|---|
| Component | Volume |
| Fast SYBR (R) Green PCR Master Mix | 10 µL |
| Forward primer (50 µM stock) | 0.12 µL |
| Reverse primer (50 µM stock) | 0.12 µL |
| Nuclease-free water | 5.76 µL |
| Final volume of PCR cocktail for 20 µL qPCR reaction mixture | 16 µL |

The copy numbers of the F-like plasmid in the LS5218 and CC06-9642 cell samples were estimated from the relative abundance of marker DNA sequences, specifically RepFIA and RepFIC, on the plasmids relative to that of a single copy chromosomal lacZ gene encoding β-galactosidase. The primers used for RepFIA were SEQ ID NO: 27 and SEQ ID NO: 28. The primers used for RepFIC were SEQ ID NO: 11 and SEQ ID NO: 12. The primers used for lacZ were SEQ ID NO: 13 and SEQ ID NO: 14.

The real-time PCR reactions were performed using the 7500 Fast real-time PCR default program as follows: 1 cycle of enzyme activation at 95° C. for 20 seconds, 40 cycles of denaturation at 95° C. for 3 seconds, annealing and extension at 60° C. for 30 seconds, and dissociation curve.

The plasmid copy number was measured by calculating $2^{\Delta Ct}$, where $\Delta Ct$ was calculated by subtracting RepFIC Ct value from lacZ gene Ct value ($\Delta Ct = Ct_{lacZ} - Ct_{repFIC}$).

TABLE 6

| Copy number measurement results using qPCR. | | |
|---|---|---|
| Strain | RepFIA relative abundance to lacZ | RepFIC relative abundance to lacZ |
| LS5218 | 9.2 | 11.5 |
| CC06-9642 | 6.2 | 4.3 |

As shown in TABLE 6, the copy number of F-like plasmid of CC06-9642 was lower than that of the control LS5218. Thus, it was confirmed that the variant rpoC sequence resulted in a decrease of copy number of F-like plasmid. When the plasmid copy number is excessive, metabolic burdens may be exerted in the cells of a microorganism. The above results indicate that the variant rpoC can have a function of regulating plasmid copy number, and thus it can be known from the results above that the strain can be stably grown and the plasmid can be stably expressed.

Example 6

Construction of Plasmids Containing a Modified DNA Sequence of RepFIC Replicon (1) Preparation of RepFIC fragment and kanamycin-resistance gene fragment.

In order to amplify the 5.2 kb DNA fragment containing the RepFIC replicon (SEQ ID NO: 1), the genomic DNA (gDNA) of *E. coli* LS5218, which is a prototrophic K-12 strain and was obtained from the Coli Genetic Stock Center (CGSC) (strain 12355), was extracted using a QIAGEN Genomic-tip system, and a polymerase chain reaction (PCR) was performed using the gDNA as a template with a PfuUltra II Fusion HS DNA Polymerase (manufactured by Agilent). The PCR was performed using primers of SEQ ID NO: 2 and SEQ ID NO: 3 as follows: 30 cycles of denaturation at 95° C. for 30 seconds, annealing at 56° C. for 30 seconds, and elongation at 72° C. for 5 minutes.

In order to amplify the 1.4 kb DNA fragment containing the kanamycin-resistance gene, PCR was performed using the plasmid pKD4 as a template with a PfuUltra II Fusion HS DNA Polymerase. PCR was performed using primers of SEQ ID NO: 4 and SEQ ID NO: 5 as follows: 30 cycles of denaturation at 94° C. for 30 seconds, annealing at 56° C. for 30 seconds, and elongation at 72° C. for 1 minute 30 seconds.

After PCR reactions were completed and then mixed, 1.3 µL of DpnI and 5.7 µl of 10× buffer Tango were added to the each of 50 µL PCR mixtures, which were then incubated at 37° C. for 1 hour to remove the template DNA. The mixtures were purified with a QIAGEN purification kit and then eluted to obtain a 5.2 kb DNA fragment (also termed "RepFIC fragment") and a 1.4 kb DNA fragment (also termed "KanR fragment").

(2) Preparation of RepFIC fragment containing a modified sequence.

In order to amplify a 5.2 kb DNA fragment containing the RepFIC replicon that has a modified sequence (SEQ ID NO: 6), PCR was performed using the gDNA of *E. coli* NCM3722 as a template with a PfuUltra II Fusion HS DNA Polymerase. A PCR was performed using primers of SEQ ID NO: 2 and SEQ ID NO: 7 as follows: 30 cycles of denaturation at 95° C. for 30 seconds, annealing at 56° C. for 30 seconds, and elongation at 72° C. for 3 minutes. Another PCR was performed using primers of SEQ ID NO: 8 and SEQ ID NO: 3 for elongation at 72° C. for 2 minutes and 30 seconds.

After PCR reactions were completed, 1.3 µAL of DpnI and 5.7 µl of 10× buffer Tango were added to the 50 µL PCR reaction mixtures that were then incubated at 37° C. for 1 hour to remove the template DNA. The mixtures were purified with a QIAGEN purification kit and then eluted to obtain a 2.8 kb DNA fragment and a 2.4 kb DNA fragment.

(3) Construction of plasmids containing wildtype or modified sequence of RepFIC replicon.

The RepFIC fragment and the KanR fragment described in Example: 6-(1) were used for the construction of a plasmid, termed pJSL48. The pJSL48 plasmid was constructed using a NEBuilder HiFi DNA Assembly Master Mix (manufactured by NEB), as shown in FIG. 13A-B.

The 2.8 kb and 2.4 kb DNA fragments described in Example: 6-(2) and the KanR fragment described in Example: 6-(1) were used for the construction of another plasmid, termed pJSL49. Gibson assembly of the three fragments was performed with a NEBuilder HiFi DNA Assembly Master Mix, as shown in FIG. 14A-B.

Example 7

Measurement of Plasmid Copy Number

To measure plasmid copy numbers, plasmids pJSL48 and pJSL49 were introduced into *E. coli* LS5218, resulting in *E. coli* strains CC06-9665 and CC06-9666. Plasmids pJSL48 and pJSL49 also were introduced into CC06-9642, resulting in *E. coli* strains CC06-9638 and CC06-9639, respectively.

The copy numbers of the plasmids in the *E. coli* strains CC06-9665, 9666, 9638 and 9639 were measured using the real-time PCR method, as described in Example 5.

The copy numbers of plasmids in the cell samples were estimated from the relative abundance of a marker DNA sequence on the plasmids, RepFIC replicon, relative to that of a single copy chromosomal lacZ gene encoding β-galactosidase. The primers used for RepFIC were SEQ ID NO: 11 and SEQ ID NO: 12. The primers used for lacZ were SEQ ID NO: 13 and SEQ ID NO: 14. The primers used for the kanamycin-resistance gene were SEQ ID NO: 42 and SEQ ID NO: 43.

TABLE 7 qPCR copy number measurement results

| Strain | KanR relative abundance to lacZ | repFIC relative abundance to lacZ |
| --- | --- | --- |
| CC06-9665 | 5.4 | 8.8 |
| CC06-9666 | 51.7 | 71.0 |
| CC06-9638 | 4.0 | 4.8 |
| CC06-9639 | 18.4 | 19.6 |

As shown in TABLE 7, the plasmid copy numbers of strains CC06-9666 and 9639, which are the strains containing the variant RepFIC sequence that was introduced into the plasmid pJSL49, were higher than those of strains CC06-9665 and 9638. The plasmid copy number of strain CC06-9665 was higher than that of CC06-9638, and the plasmid copy number of strain CC06-9666 was higher than that of CC06-9639. Thus, it was confirmed that the replaced rpoC sequence resulted in a decrease of plasmid copy number independent of which RepFIC replicon, wild-type or variant, was used.

INDUSTRIAL APPLICABILITY

The nucleic acid molecules comprising the variant inc coding strand that comprises SEQ ID NO: 15 disclosed herein are useful for regulating copy numbers of vectors, such as plasmids, comprising replicons comprising the nucleic acid molecules, particularly for increasing the copy numbers of the vectors, and thus are useful for improving commercial production of target products by use of the vectors.

Information Regarding Biological Deposit

An *E. coli* strain transformed to include a nucleic acid molecule comprising a variant inc coding strand (SEQ ID NO: 6) was prepared as described above, was designated as *Escherichia coli* CC06-9612, and was deposited on Jun. 15, 2018 at the Korean Culture Center of Microorganisms, which is an International Depositary Authority under the Budapest Treaty, under Accession No. KCCM12275P. This strain is deposited by an International Depository Authority under the Budapest Treaty.

An *E. coli* strain transformed to include a nucleic acid molecule comprising a variant rpoC coding sequence that encodes a variant RpoC that includes an R47C substitution was prepared as described above, was designated as *Escherichia coli* CC06-9637, and was deposited on Jun. 15, 2018 at the Korean Culture Center of Microorganisms, which is an International Depositary Authority under the Budapest Treaty, under Accession No. KCCM12276P. This strain is deposited by an International Depository Authority under the Budapest Treaty.

Reference to a "Sequence Listing," a Table, or a Computer Program Listing Appendix Submitted as an ASCII Text File The material in the ASCII text file, named "CJCJ-585561.1-51-Sequences_ST25.txt", created Aug. 3, 2019, file size of 274,432 bytes, is hereby incorporated by reference.

What is claimed is:

1. A nucleic acid molecule comprising a variant inc coding strand that comprises SEQ ID NO: 15, wherein:
   the variant inc coding strand encodes a variant inc RNA; and
   the variant inc RNA is a regulator of plasmid copy number.

2. The nucleic acid molecule according to claim 1, wherein expression of the variant inc RNA increases copy number of a vector relative to expression of wild-type inc RNA encoded by an inc sequence comprising SEQ ID NO: 19.

3. The nucleic acid molecule according to claim 1, wherein the variant inc coding strand comprises a nucleotide sequence that is at least 90% identical to SEQ ID NO: 17.

4. A replicon comprising the nucleic acid molecule of claim 1, a promoter, and an origin of replication, wherein:
   the promoter is operably linked to the variant inc coding strand; and
   the variant inc RNA regulates copy number of the replicon.

5. The replicon according to claim 4, wherein the replicon comprises a variant repFIC replicon, and the nucleic acid molecule is part of the variant repFIC replicon.

6. A vector comprising the replicon of claim 4.

7. The vector according to claim 6, wherein expression of the variant inc RNA increases copy number of the vector relative to expression of wild-type inc RNA encoded by an inc sequence comprising SEQ ID NO: 19.

8. The vector according to claim 6, wherein the vector comprises a plasmid.

9. The vector according to claim 6, further comprising a target gene for making a target product.

10. The vector according to claim 9, wherein the target product comprises one or more of (i) a target RNA, (ii) a target protein, (iii) a target biomaterial, (iv) a target polymer, precursor thereof, and/or enzyme for production thereof, (v) a target sweetener, precursor thereof, and/or enzyme for production thereof, (vi) a target oil, precursor thereof, and/or enzyme for production thereof, (vii) a target fat, precursor thereof, and/or enzyme for production thereof, (viii) a target polysaccharide, precursor thereof, and/or enzyme for production thereof, (ix) a target amino acid, precursor thereof, and/or enzyme for production thereof, (x) a target nucleotide, precursor thereof, and/or enzyme for production thereof, (xi) a target vaccine, precursor thereof, and/or enzyme for production thereof, or (xii) a target pharmaceutical product, precursor thereof, and/or enzyme for production thereof.

11. A recombinant microorganism comprising the replicon of claim 4.

12. A recombinant microorganism comprising the vector of claim 6.

13. The recombinant microorganism according to claim 12, wherein expression of the variant inc RNA in the recombinant microorganism increases copy number of the vector relative to expression of wild-type inc RNA encoded by an inc sequence comprising SEQ ID NO: 19 in a control microorganism.

14. The recombinant microorganism according to claim 12, wherein the variant inc coding strand comprises a nucleotide sequence that is at least 90% identical to SEQ ID NO: 17.

15. The recombinant microorganism according to claim 12, wherein the recombinant microorganism was prepared by introducing the vector into a precursor microorganism by one or more of transformation, conjugation, or transduction.

16. The recombinant microorganism according to claim 12, wherein the recombinant microorganism was prepared from one or more of a bacterium of the genus *Escherichia* or a bacterium of the species *Escherichia coli*.

17. The recombinant microorganism according to claim 12, wherein the recombinant microorganism further comprises another nucleic acid molecule comprising a variant rpoC RNA-polymerase β' subunit protein coding sequence (variant rpoC coding sequence), wherein:
    the variant rpoC coding sequence encodes a variant RpoC RNA-polymerase β' subunit protein (variant RpoC); and
    the variant RpoC comprises an R47C substitution, with numbering of the R47C substitution defined based on wild-type RpoC RNA-polymerase β' subunit protein (wild-type RpoC) of *Escherichia coli* of SEQ ID NO: 44.

18. A method for regulating copy number of the vector of claim 6 in a recombinant microorganism, the method comprising the steps of:
    (1) introducing the vector into a precursor microorganism, thereby obtaining the recombinant microorganism; and
    (2) cultivating the recombinant microorganism in a culture medium under conditions sufficient for replication of the vector, thereby regulating copy number of the vector.

19. The method according to claim 18, wherein expression of the variant inc RNA in the recombinant microorganism increases copy number of the vector relative to expression of wild-type inc RNA encoded by an inc sequence comprising SEQ ID NO: 19 in a control microorganism.

20. A method for making a target product by use of the vector of claim 7 in a recombinant microorganism, wherein the vector further comprises a target gene for making the target product, the method comprising the steps of:
    (1) introducing the vector into a precursor microorganism, thereby obtaining the recombinant microorganism;
    (2) cultivating the recombinant microorganism in a culture medium under conditions under which the recombinant microorganism expresses the target gene, thereby making the target product; and
    (3) recovering the target product from the recombinant microorganism and/or the culture medium.

21. The method according to claim 20, wherein expression of the variant inc RNA in the recombinant microorganism increases copy number of the vector relative to expression of wild-type inc RNA encoded by an inc sequence comprising SEQ ID NO: 19 in a control microorganism.

22. The method according to claim 20, wherein the variant inc coding strand comprises a nucleotide sequence that is at least 90% identical to SEQ ID NO: 17.

23. The method according to claim 20, wherein the target product comprises one or more of (i) a target RNA, (ii) a target protein, (iii) a target biomaterial, (iv) a target polymer, precursor thereof, and/or enzyme for production thereof, (v) a target sweetener, precursor thereof, and/or enzyme for production thereof, (vi) a target oil, precursor thereof, and/or enzyme for production thereof, (vii) a target fat, precursor thereof, and/or enzyme for production thereof, (viii) a target polysaccharide, precursor thereof, and/or enzyme for production thereof, (ix) a target amino acid, precursor thereof, and/or enzyme for production thereof, (x) a target nucleotide, precursor thereof, and/or enzyme for production thereof, (xi) a target vaccine, precursor thereof, and/or enzyme for production thereof, or (xii) a target pharmaceutical product, precursor thereof, and/or enzyme for production thereof.

24. The method according to claim 18, wherein: the recombinant microorganism further comprises another nucleic acid molecule comprising a variant rpoC coding sequence; the variant rpoC coding sequence encodes a variant RpoC; and the variant RpoC comprises an R47C substitution, with numbering of the R47C substitution defined based on wild-type RpoC of *Escherichia coli* of SEQ ID NO: 44.

25. The method according to claim 20, wherein: the recombinant microorganism further comprises another nucleic acid molecule comprising a variant rpoC coding sequence; the variant rpoC coding sequence encodes a variant RpoC; and the variant RpoC comprises an R47C substitution, with numbering of the R47C substitution defined based on wild-type RpoC of *Escherichia coli* of SEQ ID NO: 44.

* * * * *